United States Patent
Von Nussbaum et al.

(10) Patent No.: US 8,889,700 B2
(45) Date of Patent: *Nov. 18, 2014

(54) 4-(4-CYANO-2-THIOARYL) DIHYDROPYRIMIDINONES AND THEIR USE

(75) Inventors: Franz Von Nussbaum, Düsseldorf (DE); Dagmar Karthaus, Solingen (DE); Sonja Anlauf, Wuppertal (DE); Martina Delbeck, Heiligenhaus (DE); Volkhart Min-Jian Li, Velbert (DE); Daniel Meibom, Leverkusen (DE); Klemens Lustig, Wuppertal (DE); Jens Schamberger, Wuppertal (DE)

(73) Assignee: Bayer Intellectual Property GmbH, Monheim (DE)

(*) Notice: Subject to any disclaimer, the term of this patent is extended or adjusted under 35 U.S.C. 154(b) by 0 days.

This patent is subject to a terminal disclaimer.

(21) Appl. No.: 13/612,435

(22) Filed: Sep. 12, 2012

(65) Prior Publication Data

US 2014/0045802 A1    Feb. 13, 2014

Related U.S. Application Data

(62) Division of application No. 12/809,781, filed as application No. PCT/EP2008/010411 on Dec. 9, 2008, now Pat. No. 8,288,402.

(30) Foreign Application Priority Data

Dec. 20, 2007  (DE) .......................... 10 2007 061 766
May 7, 2008    (DE) .......................... 10 2008 022 521
Oct. 17, 2008  (DE) .......................... 10 2008 052 013

(51) Int. Cl.
| | |
|---|---|
| *A01N 43/54* | (2006.01) |
| *A61K 31/505* | (2006.01) |
| *C07D 413/06* | (2006.01) |
| *C07D 401/06* | (2006.01) |
| *C07D 403/06* | (2006.01) |
| *A61K 31/541* | (2006.01) |
| *C07D 403/12* | (2006.01) |
| *C07D 405/12* | (2006.01) |
| *C07D 487/04* | (2006.01) |
| *C07D 239/22* | (2006.01) |
| *A61K 31/513* | (2006.01) |
| *C07D 401/14* | (2006.01) |
| *A61K 31/5377* | (2006.01) |
| *C07D 417/12* | (2006.01) |
| *A61K 31/519* | (2006.01) |
| *C07D 401/12* | (2006.01) |
| *A61K 45/06* | (2006.01) |
| *C07D 413/12* | (2006.01) |
| *C07D 409/12* | (2006.01) |

(52) U.S. Cl.
CPC ............ *C07D 239/22* (2013.01); *C07D 413/06* (2013.01); *C07D 401/06* (2013.01); *C07D 403/06* (2013.01); *A61K 31/541* (2013.01); *C07D 403/12* (2013.01); *C07D 405/12* (2013.01); *C07D 487/04* (2013.01); *A61K 31/513* (2013.01); *C07D 401/14* (2013.01); *A61K 31/5377* (2013.01); *C07D 417/12* (2013.01); *A61K 31/519* (2013.01); *C07D 401/12* (2013.01); *A61K 45/06* (2013.01); *C07D 413/12* (2013.01); *C07D 409/12* (2013.01)
USPC ............................. 514/274; 544/296; 544/315

(58) Field of Classification Search
USPC .................................... 544/296, 315; 514/274
See application file for complete search history.

(56) References Cited

PUBLICATIONS

A.T. Hill et al., 15 European Respiratory Journal, 886-890 (2000).*
K. Fujie et al., Inflammation Research, 160-167 (1999).*
K. Kazuhito et al., 451 European Journal of Pharmacology, 1-10 (2002).*
H. Nakamura et al., 89 The Journal of Clinical Investigation, Inc., 1478-1484 (1992).*
M. Rabinovitch, 122 The Journal of Clinical Investigation, 4306-4313 (2012).*

* cited by examiner

*Primary Examiner* — James O Wilson
*Assistant Examiner* — Alexander R Pagano
(74) *Attorney, Agent, or Firm* — Karen B. King

(57) ABSTRACT

The present invention relates to novel 4-(4-cyano-2-thioaryl) dihydropyrimidin-2-one derivatives, to processes for their preparation, to their use alone or in combination for the treatment and/or prevention of diseases and also to their use for preparing medicaments for the treatment and/or prevention of diseases, in particular for the treatment and/or prevention of disorders of the lung and the cardiovascular system.

14 Claims, No Drawings

4-(4-CYANO-2-THIOARYL) DIHYDROPYRIMIDINONES AND THEIR USE

The present invention relates to novel 4-(4-cyano-2-thioaryl)dihydropyrimidin-2-one derivatives, to processes for their preparation, to their use alone or in combination for the treatment and/or prevention of diseases and also to their use for preparing medicaments for the treatment and/or prevention of diseases, in particular for the treatment and/or prevention of disorders of the lung and the cardiovascular system.

Human leukocyte elastase (HLE, EC 3.4.21.37), also called human neutrophil elastase (HNE, hNE), belongs to the family of the serine proteases. The proteolytic enzyme is found in the azurophilic granules of polymorphonuclear leukocytes (PMN leukocytes). Intracellular elastase performs an important function in defense against pathogens by breaking down the foreign particles taken by phagocytosis. Activated neutrophilic cells release the HNE from the granules into the extracellular space (extracellular HNE), with some of the released HNE remaining on the outside of the neutrophilic cell membrane (membrane-associated HNE). The highly active enzyme is able to break down a large number of connective tissue proteins, for example the proteins elastin, collagen and fibronectin. Elastin occurs in high concentrations in all tissue types showing high elasticity, for example in the lung and the arteries. HNE is involved in the tissue breakdown and transformation (tissue remodeling) associated with a large number of pathological processes (for example tissue injuries). HNE is also an important modulator of inflammatory processes. HNE induces for example increased interleukin-8 (IL-8) gene expression.

Accordingly, it is presumed that HNE plays an important role in many disorders, injuries and pathological changes whose formation and/or progression are/is associated with inflammatory events and/or proliferative and hypertrophic tissue and vessel transformation. This can be in particular disorders and/or injuries of the lung or the cardiovascular system, or it may be sepsis, cancerous disorders or other inflammatory disorders.

Disorders and injuries of the lung which may be mentioned in this context are in particular chronic obstructive pulmonary disease (COPD), acute respiratory distress syndrome (ARDS), cystic fibrosis (CF; also referred to as mucoviscidosis), lung emphysema and acute lung injury (ALI). Disorders and injuries of the cardiovascular system where HNE is involved are, for example, tissue transformations during heart failure and reperfusion damage after acute myocardial infarction (AMI), cardiogenic shock, acute coronary syndrome (ACS), and also aneurysms. Disorders associated with sepsis are, for example, systemic inflammatory response syndrome (SIRS), severe sepsis, septic shock and multi-organ failure (MOF; multi-organ dysfunction, MODS) and also disseminated intravascular coagulation (DIC). Examples of tissue breakdown and transformation in cancerous processes are the migration of cancer cells into healthy tissue (formation of metastases) and the formation of new supply blood vessels (neo-angiogenesis). Other inflammatory diseases where HNE plays a role are rheumatoid disorders, for example rheumatoid arthritis, inflammatory bowel disease (IBD), Crohn's disease (CD), ulcerative colitis (UC) and arteriosclerosis.

It is generally assumed that elastase-mediated pathological processes are based on a displaed equilibrium between free elastase and endogenous elastase inhibitor protein (mainly alpha-1 antitrypsin, AAT) [Neutrophils and protease/antiprotease imbalance, Stockley, Am. J. Respir. Crit. Care Med. 160, 49-52 (1999)]. AAT is present in large excess in the plasma and thus very rapidly neutralizes free HNE.

The concentration of free elastase is elevated in various pathological processes, so that there is a local shift in the balance between protease and protease inhibitor in favor of the protease. In addition, membrane-associated elastase of the activated PMN cells is very substantially protected from inhibition by AAT. The same applies to free elastase, which is located in a microcompartment which is difficult to access between the neutrophilic cell and the adjoining tissue cell (for example endothelial cell). In addition, strong oxidizing conditions prevail in the vicinity of activated leukocytes (oxidative burst), and thus AAT is oxidized and loses several orders of magnitude in the inhibitory effect.

Novel elastase-inhibiting active compounds (exogenously administered inhibitors of HNE) ought accordingly to have a low molecular weight in order to be able also to reach and inhibit the membrane-associated HNE and the HNE present in the protected microcompartment (see above). Also necessary for this purpose is good in vivo stability of the substances (low in vivo clearance). In addition, these compounds ought to be stable under oxidative conditions in order not to lose inhibitory power in the pathological process.

Pulmonary arterial hypertension (PAH) is a progressive lung disorder which, untreated, leads to death on average within 2.8 years after being diagnosed. An increasing constriction of the pulmonary circulation leads to increased stress on the right heart, which may develop into right heart failure. By definition, the main pulmonary aterial pressure (mPAP) in case of chronic pulmonary hypertension is >25 mmHg at rest or >30 mmHg during exertion (normal value <20 mmHg). The pathophysiology of pulmonary arterial hypertension is characterized by vasoconstriction and remodeling of the pulmonary vessels. In chronic PAH there is neomuscularization of initially unmuscularized pulmonary vessels, and the vascular muscles of the already muscularized vessels increase in circumference. This increasing obliteration of the pulmonary circulation results in progressive stress on the right heart, which leads to a reduced output from the right heart and eventually ends in right heart failure (M. Humbert et al., J. Am. Coll. Cardiol. 2004, 43, 13S-24S). PAH is an extremely rare disorder, with a prevalence of 1-2 per million. The average age of the patients has been estimated to be 36 years, and only 10% of the patients were over 60 years of age. Distinctly more women than men are affected (G. E. D'Alonzo et al., Ann. Intern. Med. 1991, 115, 343-349).

Despite all the advances in the therapy of pulmonary arterial hypertension there is as yet no prospect of cure of this serious disorder. Standard therapies available on the market (for example prostacyclin analogs, endothelin receptor antagonists, phosphodiesterase inhibitors) are able to improve the quality of life, the exercise tolerance and the prognosis of the patients. The principles of these therapies are primarily hemodynamic, influencing vessel tone but having no direct influence on the pathogenic remodeling processes. In addition, the possibility of using these medicaments is restricted through the sometimes serious side effects and/or complicated types of administration. The period over which the clinical situation of the patients can be improved or stabilized by specific monotherapy is limited (for example owing to the development of tolerance). Eventually the therapy escalates and thus a combination therapy is applied, where a plurality of medicaments must be given concurrently.

Novel combination therapies are one of the most promising future therapeutic options for the treatment of pulmonary arterial hypertension. In this connection, the finding of novel pharmacological mechanisms for the treatment of PAH is of particular interest (Ghofrani et al., Herz 2005, 30, 296-302; E. B. Rosenzweig, Expert Opin. Emerging Drugs 2006, 11, 609-

619; T. Ito et al., Curr. Med. Chem. 2007, 14, 719-733). Therapeutic options which intervene directly in the remodeling event (antiremodeling mechanisms) in particular might form the basis for a more causal treatment and thus be of great advantage for the patients. In this connection, it will be possible to combine known and novel therapies. In order to minimize the risk of interfering medicament-medicament interactions in such a combination therapy, these novel active compounds ought inhibit metabolizing P450 CYP enzymes only to a very small extent or not at all.

These days, one proceeds on the assumption that elastase plays a central role in pathological remodeling. It has been possible to find a fragmentation of connective tissue (internal elastic lamina) in animal models and in patients with elevated pulmonary arterial blood pressure (pulmonary arterial hypertension) [Rabinovitch et al., Lab. Invest. 55, 632-653 (1986)], and it was possible to show in animal models of pulmonary arterial hypertension (hypoxic rat and mouse model, monocrotaline rat model) that elastase activity was increased and was associated with a fragmentation of connective tissue [Todorovich-Hunter et al., Am. Rev. Respir. Dis. 146, 213-223 (1992)]. It is suspected that the tissue remodeling to be observed during the disease process of pulmonary arterial hypertension is induced by an elastase-mediated release of connective tissue-associated growth factors, for example of basic fibroblast growth factor (bFGF) [Rabinovitch, Am. J. Physiol. 277, L5-L12 (1999)]. It was possible to show a positive effect with an overexpressed elastase inhibitor protein in the hypoxic mouse model of pulmonary arterial hypertension [Zaidi et al., Circulation 105, 516-521 (2002)]. It was possible to show a positive effect with synthetic low-molecular-weight elastase inhibitors in the monocrotaline rat model of pulmonary arterial hypertension; in this case there was also a beneficial effect on tissue remodeling to be noted [Cowan et al., Nature Med. 6, 698-702 (2000)]. However, all previously disclosed low-molecular-weight elastase inhibitors have low selectivity, are chemically reactive and/or have only limited oral availability, thus to date thwarting clinical development of an oral elastase inhibitor for these indications. The term "pulmonary arterial hypertension" includes particular types of pulmonary hypertension as have been specified for example by the World Health Organization (WHO) (Clinical Classification of Pulmonary Hypertension, Venedig 2003; G. Simonneau et al., J. Am. Coll. Cardiol. 2004, 43, 5S-12S).

According to this classification, pulmonary arterial hypertension includes idiopathic pulmonary arterial hypertension (IPAH, formerly also called primary pulmonary hypertension, PPH), familial pulmonary arterial hypertension (FPAH), persistent pulmonary hypertension in neonates and also associated pulmonary arterial hypertension (APAH) which is associated with collagenoses, congenital systemic-pulmonary shunt vitiae, portal hypertension, HIV infections, intake of particular drugs and medicaments (for example anorectics), with disorders having a significant venous/capillary involvement, such as pulmonary venal-occlusive disease and pulmonary capillary hemangiomatosis, or with other disorders such as thyroid disorders, glycogen storage diseases, Gaucher's disease, hereditary teleangiectasia, hemoglobinopathies, myeloproliferative disorders and splenectomy.

Other types of pulmonary hypertension include, for example, the pulmonary hypertension associated with left heart disorders, for example with ventricular or valvular disorders, the pulmonary hypertension associated with disorders of the respiratory tract and/or of the lungs, for example with chronic obstructive lung disease, interstitial lung disease or pulmonary fibrosis, the pulmonary hypertension attributable to chronic thrombotic and/or embolic disorders, for example associated with thromboembolic obstruction of pulmonary arteries, and the pulmonary hypertension caused by generally inflammatory disease processes or by special causes (for example associated with schistosomiasis, sarcoidosis, neoplastic diseases).

Chronic obstructive pulmonary disease (COPD) is a pulmonary disease which progresses slowly and is characterized by obstruction of breathing caused by pulmonary emphysema and/or chronic bronchitis. First symptoms of the disorder generally appear from the fourth to the fifth decade of life onwards. In the years that follow, the short breath frequently worsens and cough, associated with extensive and sometimes prolonged discharge and obstructed breathing up to breathlessness (dyspnea), manifests itself. COPD is primarily a smoker's disease: smoking is responsible for 90% of all cases of COPD and 80-90% of all deaths caused by COPD. COPD is a major medical problem and represents the sixth most frequent cause of death world-wide. About 4-6% of people over the age of 45 are affected. Although the obstruction of breathing may only be partial and temporal, COPD cannot be cured. Accordingly, the target of the treatment is to improve the quality of life, to ameliorate the symptoms, to prevent acute worsening and to slow the progressive impairment of pulmonary function. Existing pharmacotherapies, which have hardly changed over the last two to three decades, are the use of bronchodilators to open up blocked respiratory paths, and in certain situations corticosteroids to control the inflammation of the lung [P. J. Barnes, N. Engl. J. Med. 343, 269-280 (2000)]. The chronic inflammation of the lung, caused by cigarette smoke or other irritants, is the force behind the development of the disease. The mechanism on which it is based involves immune cells which, during the course of the inflammatory reaction of the lung, secrete various chemokines. This attracts neutrophilic cells and subsequently alveolar macrophages to the connective tissue of the lung and the lumen. Neutrophilic cells secrete a protease cocktail which contains mainly HNE and protease 3. This causes the local protease/antiprotease balance to shift in favor of the proteases, resulting inter alia in an unchecked elastase activity and as a consequence thereof an excess degradation of the alveolar cells [J. E. Gadek et al., J. Clin. Invest. 68, 889-898 (1981); Z. Werb et al., J. Invest. Dermatol. 79, 154-159 (1982); A. Janoff, Am. Rev. Respir. Dis. 132, 417-433 (1985); P. J. Barnes, N. Engl. J. Med. 343, 269-280 (2000)]. This tissue degradation causes the bronchii to collapse. This is associated with a reduced elasticity of the lung, which leads to obstructed breathing and impaired respiration. In addition, frequent and persistent inflammation of the lung may lead to remodeling of the bronchii and as a consequence to the formation of lesions. Such lesions contribute to chronic cough, which characterizes chronic bronchitis.

Alpha-1 antitrypsin (AAT) is a small endogenous protein and represents, as mentioned above, the most important endogenous elastase inhibitor. In patients having a genetic deficiency of this protein (AADT), the protease/antiprotease balance is shifted. Accordingly, in AADT patients, the effective radius and the duration of action of HNE is increased by a factor of 2.5 and 6.5, respectively [T. G. Liou and E. J. Campbell, Biochemistry 1995, 16171-16177]. AADT patients have an increased risk of developing pulmonary emphysema or COPD, and in many AADT patients a lung transplant is indicated.

Acute lung injury (ALI) and the more pronounced form thereof, acute respiratory distress syndrome (ARDS), are serious disorders associated with a mortality of 50-60%. According to the definition of the North American-European Consensus Conference (NAECC) of 1994, ALI and ARDS are defined by an acute onset, bilateral radiologically visible infiltrates, a $PaO_2/FiO_2$ index of ≤300 mmHg (ALI) or ≤200 mmHg (ARDS), a pulmonary capillary wedge pressure of <18 mmHg and no clinical evidence of left atrial hypertension.

The development of acute lung injury may be preceded both by pulmonary and extrapulmonary disorders. Aspiration of stomach content, pneumonias, smoke poisoning, pulmonary contusion and near-drowning are considered to be lung-specific predisposing factors. In particular the aspiration of stomach content and pneumonias are frequently seen as initial disorders of ALI/ARDS of pulmonary origin. The most frequent indirect events are polytrauma, sepsis, repeated blood transfusions, acute pancreatitis and burns. The incidence is 17.9 cases of ALI and 13.5 cases of ARDS per 100 000 inhabitants and year [Luhr et al., Am. J. Respir. Crit. Care Med. 159, 1849-1861 (1999)].

A central role in the development of these disorders is played by the massive inflammatory changes in the lung, which are triggered by a widely branched system of mediators. An important role in the development of lung injury is also played by neutrophilic granulocytes, the number of which increases permanently during the inflammatory process [Chollet-Martin et al., Am. J. Respir. Crit. Care Med. 154, 594-601 (1996)]. The action of the mediators causes damage to the alveolocapillary membranes, and this results in an increased permeability of the alveolar capillary barrier. Owing to the increased permeability, protein-rich fluid can permeate into the alveolae and also into the interstitial space; a low-pressure pulmonary edema develops. Characteristic for ALI/ARDS, this is a noncardiogenic edema. The edema fluid contains mainly fibrin, erythrocytes, leukocytes, hyaline membranes and other proteins. Together with the products of activated neutrophils, the protein-rich exudate leads to dysfunction of the surfactant. The inflammatory processes cause damage and loss of pneumocytes of type II, which form surfactant, resulting in a reduced surfactant production. The surfactant deficit increases the surface tension in the alveolae; the alveolae collapse and atelectases are formed. With perfusion being maintained, there is thus a ventilation/perfusion imbalance resulting in an increase of the pulmonary right-left shunt. Furthermore, compliance is reduced, and in contrast the alveolar dead space is increased because there are areas which are ventilated but, owing to pulmonary hypertension, no longer sufficiently perfused.

An increased elastase activity, which correlates to the severity of the lung injury, could be measured in the bronchoalveolar lavage fluid (BALF) of ARDS patients. In animal models where the lung is injured (for example by administration of LPS), this effect can be reproduced. Here, treatment with elastase inhibitors (for example sivelestat or elafin, vide infra,) reduces the elastase activity in the BALF considerably and improves lung function.

In Japan and South Korea, an elastase inhibitor (sivelestat, Elaspol®) is approved for the treatment of acute lung injury associated with SIRS. The reversible, but reactive compound has only a relatively weak effect on HNE ($K_i$ 200 nM) and also acts on the pancreas elastase ($IC_{50}$ 5.6 µM). The active compound is administered intravenously, oral administration is not possible.

Elafin and structural analogs are also investigated as therapeutically useful elastase inhibitors. Elafin is an endogenous small protein which inhibits both elastase and proteinase 3. However, owing to the proteinergic character, oral administration of elafin is not possible.

WO 2004/024700, WO 2004/024701, WO 2005/082863 and WO 2005/082864 disclose various 1,4-diaryldihydropyrimidin-2-one derivatives as HNE inhibitors for the treatment of chronic obstructive pulmonary disease, acute coronary syndrome, myocardial infarction and heart failure. Di- and multimers of such compounds for the treatment of respiratory disorders are claimed in WO 2006/082412, WO 2006/136857 and WO 2007/042815. 4-Aryldihydropyrimidin-2-one derivatives as inhibitors of the calcium channel function for the treatment of hypertension are described in WO 2005/009392. WO 2007/129060 discloses tetrahydropyrrolopyrimidinediones and multimers thereof as HNE inhibitors. Meanwhile, WO 2008/003412 describes the use of 1,4-diaryldihydropyrimidin-2-one derivatives for the treatment of pulmonary arterial hypertension.

It has now been found that 1,4-diaryldihydropyrimidin-2-one derivatives are particularly suitable for the treatment and/or prevention of disorders. These compounds described below are low-molecular-weight, non-reactive and selective inhibitors of human neutrophil elastase (HNE) which, surprisingly, show considerably better inhibition of this protease than the compounds known from the prior art. In addition, the compounds according to the invention have unexpectedly low in vitro clearance in hepatocytes and thus improved metabolic stability. Accordingly, these substances are promising starting points for novel medicaments for the treatment and/or prevention of in particular disorders of the lung and the cardiovascular system.

Compared to the compounds of the prior art, the 1,4-diaryldihydropyrimidin-2-one derivatives of the present invention have a structure which is distinguished by an ortho-sulfanyl, ortho-sulfinyl or ortho-sulfonyl substituent in the 4-aryl head group of the dihydropyrimidinone which, surprisingly, results in the above-described improved properties of the compounds.

Specifically, the present invention relates to compounds of the general formula (I)

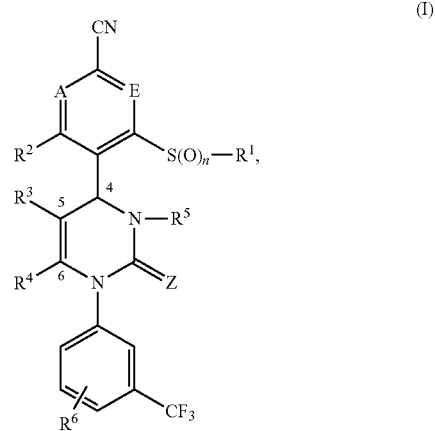

in which
A and E both represent C—$R^7$ or one of the two ring members A and E represents N and the other represents C—$R^7$, in which
$R^7$ represents in each case hydrogen, fluorine or chlorine,
Z represents O or S,
n represents the number 0, 1 or 2,
$R^1$ represents ($C_1$-$C_6$)-alkyl which may be substituted by hydroxyl, ($C_1$-$C_4$)-alkoxy, amino, mono- or di-($C_1$-$C_4$)-alkylamino, hydroxycarbonyl, aminocarbonyl, ($C_3$-$C_6$)-cycloalkyl, phenyl or 5- or 6-membered heteroaryl or up to five times by fluorine, or represents $(C_2-C_6)$-alkenyl, $(C_3-C_6)$-cycloalkyl, phenyl or 5- or 6-membered heteroaryl, where the $(C_3-C_6)$-cycloalkyl groups mentioned may be substituted up to two times by identical or different substituents from the group consisting of $(C_1-C_4)$-alkyl, hydroxyl and $(C_1-C_4)$-alkoxy and the phenyl and heteroaryl groups mentioned may be substituted up to two times by identical or different substituents from the group consisting of fluorine, chlorine, cyano, $(C_1-C_4)$-alkyl, difluoromethyl, trifluoromethyl, $(C_1-C_4)$-alkoxy, difluoromethoxy and trifluoromethoxy, $R^2$ represents hydrogen, fluorine or chlorine, $R^3$ represents cyano or a group of the formula —C(=O)—$R^8$, —C(=O)—O—$R^8$, —C(=O)—NH$_2$ or —C(=O)—NH—$R^8$, in which $R^8$ represents $(C_1-C_6)$-alkyl, $(C_3-C_6)$-alkenyl or $(C_3-C_6)$-cycloalkyl, where $(C_1-C_6)$-alkyl and $(C_3-C_6)$-cycloalkyl for their part may be substituted up to two times by identical or different substituents from the group consisting of hydroxyl, $(C_1-C_4)$-alkoxy, hydroxycarbonyl, $(C_1-C_4)$-alkoxycarbonyl, amino, mono- and di-$(C_1-C_4)$-alkylamino and in $(C_1-C_6)$-alkyl and $(C_3-C_6)$-cycloalkyl in each case one CH$_2$ group may be replaced by an oxygen atom, if this results in a chemically stable compound, $R^4$ represents methyl or ethyl or $R^3$ and $R^4$ are attached to one another and together form a fused group of the formula

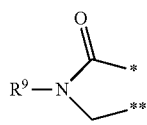

in which

\* denotes the point of attachment to the 5-position, shown in formula (I), of the dihydropyrimidine ring and \*\* denotes the point of attachment to the 6-position, shown in formula (I), of the dihydropyrimidine ring and $R^9$ represents hydrogen, $(C_1-C_6)$-alkyl or $(C_3-C_6)$-cycloalkyl, where $(C_1-C_6)$-alkyl may be substituted by hydroxyl, $(C_1-C_4)$-alkoxy, aminocarbonyl, aminocarbonylamino, $(C_1-C_4)$-acylamino or $(C_3-C_6)$-cycloalkyl, $R^5$ represents hydrogen or $(C_1-C_6)$-alkyl which may be substituted by cyano, hydroxyl, $(C_1-C_4)$-alkoxy, amino, mono- or di-$(C_1-C_4)$-alkylamino or $(C_3-C_6)$-cycloalkyl or up to three times by fluorine, or represents phenyl, pyridyl or pyrimidinyl, where phenyl, pyridyl and pyrimidinyl for their part may be substituted up to two times by identical or different substituents from the group consisting of fluorine, chlorine, cyano, $(C_1-C_4)$-alkyl, trifluoromethyl, $(C_1-C_4)$-alkoxy and trifluoromethoxy, or $R^5$ represents a group of the formula —C(=O)—O—$R^{10}$, -L$^1$-C(=O)—O—$R^{11}$, -L$^2$-C(=O)—NR$^{12}$R$^{13}$, -L$^2$-SO$_2$—NR$^{12}$R$^{13}$, -L$^2$-C(=O)—NR$^{14}$—NR$^{12}$R$^{13}$ or -L$^2$-SO$_2$—R$^{15}$, in which $L^1$ represents $(C_1-C_6)$-alkanediyl, $L^2$ represents a bond or $(C_1-C_6)$-alkanediyl, $R^{10}$ represents $(C_1-C_6)$-alkyl which may be substituted by $(C_3-C_6)$-cycloalkyl or phenyl, $R^{11}$ represents hydrogen or $(C_1-C_6)$-alkyl which may be substituted by $(C_3-C_6)$-cycloalkyl or phenyl, $R^{12}$ and $R^{13}$ are identical or different and independently of one another represent hydrogen, $(C_1-C_6)$-alkyl, $(C_3-C_6)$-cycloalkyl or 4- to 6-membered heterocyclyl, where $(C_1-C_6)$-alkyl, $(C_3-C_6)$-cycloalkyl and 4- to 6-membered heterocyclyl for their part may be substituted up to two times by identical or different substituents from the group consisting of fluorine, hydroxyl, $(C_1-C_4)$-alkoxy, oxo, amino, mono- or di-$(C_1-C_4)$-alkylamino, hydroxycarbonyl, $(C_1-C_4)$-alkoxycarbonyl and aminocarbonyl and in $(C_1-C_6)$-alkyl a OH$_2$ group may be replaced by an oxygen atom, if this results in a chemically stable compound, and $(C_3-C_6)$-cycloalkyl and 4- to 6-membered heterocyclyl may additionally be substituted up to two times by identical or different $(C_1-C_4)$-alkyl radicals, which for their part may be substituted by hydroxyl, $(C_1-C_4)$-alkoxy or hydroxycarbonyl, or $R^{12}$ and $R^{13}$ together with the nitrogen atom to which they are attached form a 4- to 6-membered heterocycle which may contain a further ring heteroatom from the group consisting of N, O, S, SO and SO$_2$ and which may be substituted up to two times by identical or different substituents from the group consisting of $(C_1-C_4)$-alkyl, hydroxyl, $(C_1-C_4)$-alkoxy, oxo, amino, mono- or di-$(C_1-C_4)$-alkylamino, hydroxycarbonyl, aminocarbonyl, $(C_3-C_6)$-cycloalkyl, 4- to 6-membered heterocyclyl and 5- or 6-membered heteroaryl, where $(C_1-C_4)$-alkyl for its part may be substituted by hydroxyl, $(C_1-C_4)$-alkoxy or hydroxycarbonyl, $R^{14}$ represents hydrogen or $(C_1-C_4)$-alkyl and $R^{15}$ represents $(C_1-C_6)$-alkyl, $(C_3-C_6)$-cycloalkyl, phenyl or 5- or 6-membered heteroaryl, where $(C_1-C_6)$-alkyl may be substituted by chlorine, hydroxyl, $(C_1-C_4)$-alkoxy, mono- or di-$(C_1-C_4)$-alkylamino or $(C_3-C_6)$-cycloalkyl or up to three times by fluorine and phenyl and 5- or 6-membered heteroaryl for their part may be substituted up to two times by identical or different substituents from the group consisting of fluorine, chlorine, cyano, $(C_1-C_4)$-alkyl, difluoromethyl, trifluoromethyl, $(C_1-C_4)$-alkoxy and trifluoromethoxy, and $R^6$ represents hydrogen, fluorine or chlorine, and their salts, solvates and solvates of the salts.

Compounds according to the invention are the compounds of the formula (I) and the salts, solvates and solvates of the salts thereof, the compounds of the formulae mentioned hereinafter and encompassed by formula (I) and the salts, solvates and solvates of the salts thereof, and the compounds which are mentioned hereinafter as exemplary embodiments and encompressed by formula (I) and the salts, solvates and solvates of the salts thereof, insofar as the compounds encompassed by formula (I) and mentioned hereinafter are not already salts, solvates and solvates of the salts.

The compounds according to the invention may, depending on their structure, exist in various stereoisomeric forms, i.e. in the form of configurational isomers or, if appropriate, also as conformational isomers (enantiomers and/or diastereomers, including atropisomers). The present invention therefore relates to the enantiomers and diastereomers and to their respective mixtures. The stereoisomerically pure constituents can be isolated in a known manner from such mixtures of enantiomers and/or diastereomers.

If the compounds according to the invention may occur in tautomeric forms, the present invention encompasses all tautomeric forms.

Salts which are preferred for the purposes of the present invention are physiologically acceptable salts of the compounds according to the invention. Also encompassed are salts which are themselves unsuitable for pharmaceutical uses but can be used for example for isolating or purifying the compounds according to the invention.

Physiologically acceptable salts of the compounds according to the invention include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid. Physiologically acceptable salts of the compounds according to the invention also include salts of conventional bases such as, by way of example and preferably, alkali metal salts (for example sodium salts and potassium salts), alkaline earth metal salts (for example calcium salts and magnesium salts) and ammonium salts derived from ammonia or organic amines having 1 to 16 carbon atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine. Solvates refers for the purposes of the invention to those forms of the compounds according to the invention which form, in the solid or liquid state, a complex by coordination with solvent molecules. Hydrates are a specific form of solvates in which the coordination takes place with water. Hydrates are preferred solvates in the context of the present invention.

The present invention additionally encompasses prodrugs of the compounds of the invention. The term "prodrugs" encompasses compounds which themselves may be biologically active or inactive, but are converted during their residence time in the body into compounds according to the invention (for example by metabolism or hydrolysis).

In the context of the present invention, the substituents have the following meaning, unless specified otherwise:

$(C_1-C_6)$-Alkyl and $(C_1-C_4)$-alkyl stand for the purposes of the invention for a straight-chain or branched alkyl radical having respectively 1 to 6 and 1 to 4 carbon atoms. A straight-chain or branched alkyl radical having 1 to 4 carbon atoms is preferred. Examples which may be preferably mentioned are: methyl, ethyl, n-propyl, isopropyl, n-butyl, isobutyl, sec-butyl, tert-butyl, 1-ethylpropyl, n-pentyl, neopentyl and n-hexyl.

$(C_1-C_6)$-Alkanediyl stands for the purpose of the invention for a straight-chain or branched divalent alkyl radical having 1 to 6 carbon atoms. A straight-chain or branched alkanediyl radical having 1 to 4 carbon atoms is preferred. Examples which may be preferably mentioned are: methylene, ethane-1,2-diyl (1,2-ethylene), ethane-1,1-diyl, propane-1,3-diyl (1,3-propylene), propane-1,1-diyl, propane-1,2-diyl, propane-2,2-diyl, butane-1,4-diyl (1,4-butylene), butane-1,2-diyl, butane-1,3-diyl, butane-2,3-diyl, pentane-1,5-diyl (1,5-pentylene), pentane-2,4-diyl, 3-methylpentane-2,4-diyl and hexane-1,6-diyl (1,6-hexylene).

$(C_2-C_6)$-Alkenyl and $(C_3-C_6)$-alkenyl stand for the purposes of the invention for a straight-chain or branched alkenyl radical having respectively 2 to 6 and 3 to 6 carbon atoms and one or two double bonds. A straight-chain or branched alkenyl radical having 3 to 6 carbon atoms and one double bond is preferred. Examples which may be preferably mentioned are: allyl, isopropenyl, n-but-2-en-1-yl, n-but-3-en-1-yl, n-pent-2-en-1-yl, n-pent-3-en-1-yl, n-pent-4-en-1-yl, 3-methylbut-2-en-1-yl and 4-methylpent-3-en-1-yl.

$(C_1-C_4)$-Alkoxy stands for the purposes of the invention for a straight-chain or branched alkoxy radical having 1 to 4 carbon atoms. Examples which may be preferably mentioned are: methoxy, ethoxy, n-propoxy, isopropoxy, n-butoxy and tert-butoxy.

$(C_1-C_4)$-Alkoxycarbonyl stands for the purposes of the invention for a straight-chain or branched alkoxy radical having 1 to 4 carbon atoms which is attached via a carbonyl group. Examples which may be preferably mentioned are: methoxycarbonyl, ethoxycarbonyl, n-propoxycarbonyl, isopropoxycarbonyl, n-butoxycarbonyl and tert-butoxycarbonyl.

Mono-$(C_1-C_4)$-alkylamino stands for the purposes of the invention for an amino group having a straight-chain or branched alkyl substituent which has 1 to 4 carbon atoms. Examples which may be preferably mentioned are: methylamino, ethylamino, n-propylamino, isopropylamino, n-butylamino and tert-butylamino.

Di-$(C_1-C_4)$-alkylamino stands for the purposes of the invention for an amino group having two identical or different straight-chain or branched alkyl substituents having in each case 1 to 4 carbon atoms. Examples which may be preferably mentioned are: N,N-dimethylamino, N,N-diethylamino, N-ethyl-N-methylamino, N-methyl-N-n-propylamino, N-isopropyl-N-methylamino, N-isopropyl-N-n-propylamino, N,N-diisopropylamino, N-n-butyl-N-methylamino and N-tert-butyl-N-methylamino.

$(C_1-C_4)$-Acyl [$(C_1-C_4)$-alkanoyl] stands for the purposes of the invention for a straight-chain or branched alkyl radical having 1 to 4 carbon atoms which has a doubly attached oxygen atom in the 1-position and is attached via the 1-position. Examples which may be preferably mentioned are: formyl, acetyl, propionyl, n-butyryl and isobutyryl.

$(C_1-C_4)$-Acylamino stands for the purposes of the invention for an amino group having a straight-chain or branched acyl substituent which has 1 to 4 carbon atoms and is attached via the carbonyl group to the nitrogen atom. Examples which may be preferably mentioned are: formylamino, acetylamino, propionylamino, n-butyrylamino and isobutyrylamino.

$(C_3-C_6)$-Cycloalkyl stands for the purposes of the invention for a monocyclic saturated cycloalkyl group having 3 to 6 ring carbon atoms. Examples which may be preferably mentioned are: cyclopropyl, cyclobutyl, cyclopentyl and cyclohexyl. 4- to 6-membered heterocyclyl stands for the purposes of the invention for a monocyclic saturated heterocycle having a total of 4 to 6 ring atoms which contains one or two ring heteroatoms from the group consisting of N, O, S, SO and $SO_2$ and is attached via a ring carbon atom or, if appropriate, a ring nitrogen atom. Preference is given to a 5- or 6-membered heterocycle having one or two ring heteroatoms from the group consisting of N, O and S. Examples which may be mentioned are:
azetidinyl, oxetanyl, pyrrolidinyl, pyrazolidinyl, tetrahydrofuranyl, thiolanyl, piperidinyl, piperazinyl, tetrahydropyranyl, tetrahydrothiopyranyl, morpholinyl and thiomorpholinyl. Preference is given to pyrrolidinyl, tetrahydrofuranyl, piperidinyl, piperazinyl, tetrahydropyranyl and morpholinyl.

5- or 6-membered heteroaryl stands for the purposes of the invention for an aromatic heterocycle (heteroaromatic) having a total of 5 or 6 ring atoms which contains one or two ring heteroatoms from the group consisting of N, O and S and is attached via a ring carbon atom or, if appropriate, a ring nitrogen atom. Examples which may be mentioned are: furyl, pyrrolyl, thienyl, pyrazolyl, imidazolyl, oxazolyl, thiazolyl, isoxazolyl, isothiazolyl, pyridyl, pyrimidinyl, pyridazinyl and pyrazinyl. Preference is given to thienyl, thiazolyl, pyridyl, pyrimidinyl, pyridazinyl and pyrazinyl.

When radicals in the compounds according to the invention are substituted, the radicals may be mono- or polysubstituted, unless specified otherwise. For the purposes of the present invention, the meanings of all radicals which occur more than once are independent of one another. Preference is given to substitution by one or two identical or different substituents. Very particularly preferred is substitution by one substituent.

In a particular embodiment, the present invention embraces compounds of the formula (I) in which A and E both represent C—$R^7$ or one of the two ring members A and E represents N and the other represents C—$R^7$, in which $R^7$ represents in each case hydrogen, fluorine or chlorine, Z represents O or S, n represents the number 0, 1 or 2, $R^1$ represents ($C_1$-$C_6$)-alkyl which may be substituted by hydroxyl, ($C_1$-$C_4$)-alkoxy, amino, mono- or di-($C_1$-$C_4$)-alkylamino, hydroxycarbonyl, aminocarbonyl, ($C_3$-$C_6$)-cycloalkyl or phenyl, or represents ($C_2$-$C_6$)-alkenyl, ($C_3$-$C_6$)-cycloalkyl or phenyl, where the ($C_3$-$C_6$)-cycloalkyl groups mentioned may be substituted up to two times by identical or different substituents from the group consisting of ($C_1$-$C_4$)-alkyl, hydroxyl and ($C_1$-$C_4$)-alkoxy and the phenyl groups mentioned may be substituted up to two times by identical or different substituents from the group consisting of fluorine, chlorine, cyano, ($C_1$-$C_4$)-alkyl, difluoromethyl, trifluoromethyl, ($C_1$-$C_4$)-alkoxy, difluoromethoxy and trifluoromethoxy, $R^2$ represents hydrogen, fluorine or chlorine, $R^3$ represents cyano or a group of the formula —C(=O)—$R^8$, —C(=O)—O—$R^8$, —C(=O)—$NH_2$ or —C(=O)—NH—$R^8$, in which $R^8$ represents ($C_1$-$C_6$)-alkyl, ($C_3$-$C_6$)-alkenyl or ($C_3$-$C_6$)-cycloalkyl, where ($C_1$-$C_6$)-alkyl and ($C_3$-$C_6$)-cycloalkyl for their part may be substituted up to two times by identical or different substituents from the group consisting of hydroxyl, ($C_1$-$C_4$)-alkoxy, hydroxycarbonyl, ($C_1$-$C_4$)-alkoxycarbonyl, amino, mono- and di-($C_1$-$C_4$)-alkylamino and in ($C_1$-$C_6$)-alkyl and ($C_3$-$C_6$)-cycloalkyl in each case one $CH_2$ group may be replaced by an oxygen atom, if this results in a chemically stable compound, $R^4$ represents methyl or ethyl or $R^3$ and $R^4$ are attached to one another and together form a fused group of the formula

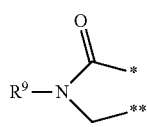

in which

\* denotes the point of attachment to the 5-position, shown in formula (I), of the dihydropyrimidine ring and \*\* denotes the point of attachment to the 6-position, shown in formula (I), of the dihydropyrimidine ring and $R^9$ represents hydrogen, ($C_1$-$C_6$)-alkyl or ($C_3$-$C_6$)-cycloalkyl, where ($C_1$-$C_6$)-alkyl may be substituted by hydroxyl, ($C_1$-$C_4$)-alkoxy, aminocarbonyl, ($C_1$-$C_4$)-acylamino or ($C_3$-$C_6$)-cycloalkyl, $R^5$ represents hydrogen or ($C_1$-$C_6$)-alkyl which may be substituted up to three times by fluorine, or represents phenyl, pyridyl or pyrimidinyl, where phenyl, pyridyl and pyrimidinyl for their part may be substituted up to two times by identical or different substituents from the group consisting of fluorine, chlorine, cyano, ($C_1$-$C_4$)-alkyl, trifluoromethyl, ($C_1$-$C_4$)-alkoxy and trifluoromethoxy, or $R^5$ represents a group of the formula —C(=O)—O—$R^{10}$, -$L^1$-C(=O)—O—$R^{11}$, -$L^2$-C(=O)—$NR^{12}R^{13}$, -$L^2$-$SO_2$—$NR^{12}R^{13}$, -$L^2$-C(=O)—$NR^{14}$—$NR^{12}R^{13}$ or -$L^2$-$SO_2$—$R^{15}$, in which $L^1$ represents ($C_1$-$C_6$)-alkanediyl, $L^2$ represents a bond or ($C_1$-$C_6$)-alkanediyl, $R^{10}$ represents ($C_1$-$C_6$)-alkyl, $R^{11}$ represents hydrogen or ($C_1$-$C_6$)-alkyl, $R^{12}$ and $R^{13}$ are identical or different and independently of one another represent hydrogen, ($C_1$-$C_6$)-alkyl, ($C_3$-$C_6$)-cycloalkyl or 4- to 6-membered heterocyclyl, where ($C_1$-$C_6$)-alkyl, ($C_3$-$C_6$)-cycloalkyl and 4- to 6-membered heterocyclyl for their part may be substituted up to two times by identical or different substituents from the group consisting of fluorine, hydroxyl, ($C_1$-$C_4$)-alkoxy, oxo, amino, mono- or di-($C_1$-$C_4$)-alkylamino, hydroxycarbonyl, ($C_1$-$C_4$)-alkoxycarbonyl and aminocarbonyl and in ($C_1$-$C_6$)-alkyl a $OH_2$ group may be replaced by an oxygen atom, if this results in a chemically stable compound, or $R^{12}$ and $R^{13}$ together with the nitrogen atom to which they are attached form a 4- to 6-membered heterocycle which may contain a further ring heteroatom from the group consisting of N, O, S, SO and $SO_2$ and may be substituted up to two times by identical or different substituents from the group consisting of ($C_1$-$C_4$)-alkyl, hydroxyl, ($C_1$-$C_4$)-alkoxy, oxo, amino, mono- and di-($C_1$-$C_4$)-alkylamino, where ($C_1$-$C_4$)-alkyl for its part may be substituted by hydroxyl or ($C_1$-$C_4$)-alkoxy, $R^{14}$ represents hydrogen or ($C_1$-$C_4$)-alkyl and $R^{15}$ represents ($C_1$-$C_6$)-alkyl, ($C_3$-$C_6$)-cycloalkyl, phenyl or 5- or 6-membered heteroaryl, where ($C_1$-$C_6$)-alkyl may be substituted by fluorine, chlorine, hydroxyl, ($C_1$-$C_4$)-alkoxy, mono- or di-($C_1$-$C_4$)-alkylamino and phenyl and 5- or 6-membered heteroaryl for their part may be substituted up to two times by identical or different substituents from the group consisting of fluorine, chlorine, cyano, ($C_1$-$C_4$)-alkyl, trifluoromethyl, ($C_1$-$C_4$)-alkoxy and trifluoromethoxy, and $R^6$ represents hydrogen, fluorine or chlorine, and their salts, solvates and solvates of the salts.

Preferred for the purposes of the present invention are compounds of the formula (I) in which A and E both represent CH and $R^2$ represents hydrogen, and their salts, solvates and solvates of the salts.

Preference is likewise given to compounds of the formula (I) in which

Z represents O, and to their salts, solvates and solvates of the salts.

Particularly preferred for the purposes of the present invention are compounds of the formula (I) in which A and E both represent CH, Z represents O, n represents the number 0 or 2, $R^1$ represents ($C_1$-$C_4$)-alkyl which may be substituted by hydroxyl, ($C_1$-$C_4$)-alkoxy, hydroxycarbonyl, aminocarbonyl, ($C_3$-$C_6$)-cycloalkyl, phenyl or 5-membered heteroaryl or up to three times by fluorine, or represents $(C_3-C_6)$-cycloalkyl, phenyl or 5-membered heteroaryl,
where the phenyl and heteroaryl groups mentioned may be substituted up to two times by identical or different substituents from the group consisting of fluorine, chlorine, cyano, methyl, trifluoromethyl, methoxy and trifluoromethoxy, $R^2$ represents hydrogen, $R^3$ represents cyano, acetyl or (2-hydroxyethoxy)carbonyl, $R^4$ represents methyl or $R^3$ and $R^4$ are attached to one another and together form a fused group of the formula

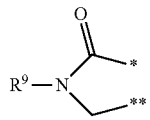

in which

* denotes the point of attachment to the 5-position, shown in formula (I), of the dihydropyrimidine ring and

** denotes the point of attachment to the 6-position, shown in formula (I), of the dihydropyrimidine ring and $R^9$ represents hydrogen, $(C_1-C_4)$-alkyl or $(C_3-C_6)$-cycloalkyl, where $(C_1-C_4)$-alkyl may be substituted by hydroxyl or $(C_1-C_4)$-alkoxy, $R^5$ represents hydrogen or $(C_1-C_4)$-alkyl which may be substituted by cyano or di-$(C_1-C_4)$-alkylamino, or represents a group of the formula -$L^2$-C(=O)—$NR^{12}R^{13}$, -$L^2$-C(=O)—NH—$NR^{12}R^{13}$ or -$L^2$-$SO_2$—$R^{15}$, in which $L^2$ represents a bond, —$CH_2$—, —$CH_2CH_2$— or —CH($CH_3$)—, $R^{12}$ represents hydrogen or $(C_1-C_4)$-alkyl which may be substituted by hydroxyl or $(C_1-C_4)$-alkoxy, $R^{13}$ represents hydrogen, $(C_1-C_6)$-alkyl or $(C_3-C_6)$-cycloalkyl, where $(C_1-C_6)$-alkyl may be substituted up to two times by identical or different substituents from the group consisting of hydroxyl, $(C_1-C_4)$-alkoxy, hydroxycarbonyl, $(C_1-C_4)$-alkoxycarbonyl and aminocarbonyl and in $(C_1-C_6)$-alkyl a $CH_2$ group may be replaced by an oxygen atom, if this results in a chemically stable compound, or $R^{12}$ and $R^{13}$ together with the nitrogen atom to which they are attached form a 5- or 6-membered heterocycle which may contain a further ring heteroatom from the group consisting of N, O and S and may be substituted by $(C_1-C_4)$-alkyl, hydroxyl, $(C_1-C_4)$-alkoxy, oxo, hydroxycarbonyl, aminocarbonyl, 4- to 6-membered heterocyclyl or 5- or 6-membered heteroaryl, where $(C_1-C_4)$-alkyl for its part may be substituted by hydroxyl, $(C_1-C_4)$-alkoxy or hydroxycarbonyl, and $R^{15}$ represents $(C_1-C_4)$-alkyl, $(C_3-C_6)$-cycloalkyl or phenyl, where $(C_1-C_4)$-alkyl may be substituted by $(C_3-C_6)$-cycloalkyl and phenyl may be substituted up to two times by identical or different substituents from the group consisting of fluorine, chlorine, cyano, methyl, trifluoromethyl, methoxy and trifluoromethoxy, and $R^6$ represents hydrogen or fluorine, and their salts, solvates and solvates of the salts.

In a further particularly preferred embodiment, the present invention embraces compounds of the formula (I) in which A and E both represent CH, Z represents O, n represents the number 0 or 2, $R^1$ represents $(C_1-C_4)$-alkyl which may be substituted by hydroxyl, $(C_1-C_4)$-alkoxy, hydroxycarbonyl, aminocarbonyl, $(C_3-C_6)$-cycloalkyl or phenyl, or represents $(C_3-C_6)$-cycloalkyl or phenyl, where the phenyl groups mentioned may be substituted up to two times by identical or different substituents from the group consisting of fluorine, chlorine, cyano, methyl, trifluoromethyl, methoxy and trifluoromethoxy, $R^2$ represents hydrogen, $R^3$ represents cyano or acetyl, $R^4$ represents methyl or $R^3$ and $R^4$ are attached to one another and together form a fused group of the formula

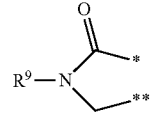

in which

* denotes the point of attachment to the 5-position, shown in formula (I), of the dihydropyrimidine ring and

** denotes the point of attachment to the 6-position, shown in the formula (I), of the dihydropyrimidine ring and $R^9$ represents hydrogen, $(C_1-C_4)$-alkyl or $(C_3-C_6)$-cycloalkyl, where $(C_1-C_4)$-alkyl may be substituted by hydroxyl or $(C_1-C_4)$-alkoxy, $R^5$ represents hydrogen, $(C_1-C_4)$-alkyl or a group of the formula -$L^2$-C(=O)—$NR^{12}R^{13}$, -$L^2$-C(=O)—NH—$NR^{12}R^{13}$ or -$L^2$-$SO_2$—$R^{15}$, in which $L^2$ represents a bond, —$CH_2$—, —$CH_2CH_2$— or —CH($CH_3$)—, $R^{12}$ represents hydrogen or $(C_1-C_4)$-alkyl which may be substituted by hydroxyl or $(C_1-C_4)$-alkoxy, $R^{13}$ represents hydrogen, $(C_1-C_6)$-alkyl or $(C_3-C_6)$-cycloalkyl, where $(C_1-C_6)$-alkyl may be substituted up to two times by identical or different substituents from the group consisting of hydroxyl, $(C_1-C_4)$-alkoxy, hydroxycarbonyl, $(C_1-C_4)$-alkoxycarbonyl and aminocarbonyl and in $(C_1-C_6)$-alkyl a $CH_2$ group may be replaced by an oxygen atom, if this results in a chemically stable compound, or $R^{12}$ and $R^{13}$ together with the nitrogen atom to which they are attached form a 5- or 6-membered heterocycle which may contain a further ring heteroatom from the group consisting of N, O and S and may be substituted by $(C_1-C_4)$-alkyl, hydroxyl, $(C_1-C_4)$-alkoxy or oxo, where $(C_1-C_4)$-alkyl for its part may be substituted by hydroxyl or $(C_1-C_4)$-alkoxy, and $R^{15}$ represents $(C_1-C_4)$-alkyl, $(C_3-C_6)$-cycloalkyl or phenyl, where phenyl may be substituted up to two times by identical or different substituents from the group consisting of fluorine, chlorine, cyano, methyl, trifluoromethyl, methoxy and trifluoromethoxy, and $R^6$ represents hydrogen or fluorine, and their salts, solvates and solvates of the salts.

Especially preferred for the purposes of the present invention are compounds of the formula (I) in which A and E both represent CH,
Z represents O,
n represents the number 2,
$R^1$ represents $(C_1-C_4)$-alkyl which may be substituted by hydroxyl, $(C_1-C_4)$-alkoxy, cyclopropyl, cyclobutyl or phenyl or up to three times by fluorine,
$R^2$ represents hydrogen,
$R^3$ represents cyano or (2-hydroxyethoxy)carbonyl,
$R^4$ represents methyl,
$R^5$ represents hydrogen, $(C_1-C_4)$-alkyl or a group of the formula $-L^2-C(=O)-NH-R^{13}$ or $-SO_2-R^{15}$, in which
$L^2$ represents a bond or $-CH_2-$,
$R^{13}$ represents hydrogen or $(C_1-C_4)$-alkyl which may be substituted by hydroxyl or $(C_1-C_4)$-alkoxy, or $(C_3-C_6)$-cycloalkyl
and
$R^{15}$ represents $(C_1-C_4)$-alkyl or $(C_3-C_6)$-cycloalkyl,
and
$R^6$ represents hydrogen,
and their salts, solvates and solvates of the salts.

Very particularly preferred for the purposes of the present invention are compounds of the formula (I) in which A and E both represent CH,
Z represents O,
n represents the number 2,
$R^1$ represents $(C_1-C_4)$-alkyl which may be substituted by hydroxyl or $(C_1-C_4)$-alkoxy,
$R^2$ represents hydrogen,
$R^3$ represents cyano,
$R^4$ represents methyl,
$R^5$ represents hydrogen, $(C_1-C_4)$-alkyl or a group of the formula $-CH_2-C(=O)-NH-R^{13}$ or $-SO_2-R^{15}$, in which
$R^{13}$ represents hydrogen or $(C_1-C_4)$-alkyl which may be substituted by hydroxyl or $(C_1-C_4)$-alkoxy
and
$R^{15}$ represents $(C_1-C_4)$-alkyl or $(C_3-C_6)$-cycloalkyl,
and
$R^6$ represents hydrogen,
and their salts, solvates and solvates of the salt.

Of particular relevance are compounds according to formula (I) having the configuration shown in formula (I-ent) at the 4-position of the dihydropyrimidine ring

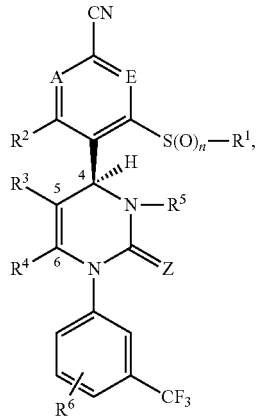
(I-ent)

in which A, E, Z, n, $R^1$, $R^2$, $R^3$, $R^4$, $R^5$ and $R^6$ each have the meanings given above, and their salts, solvates and solvates of the salts.

Specific radical definitions given in the respective combinations or preferred combinations of radicals are, independently of the combinations of radicals given in each case, also replaced by any radical definitions of other combinations.

Very particular preference is given to combinations of two or more of the preferred ranges mentioned above.

The invention furthermore provides a process for preparing the compounds of the formula (I) according to the invention, characterized in that a compound of the formula (II)

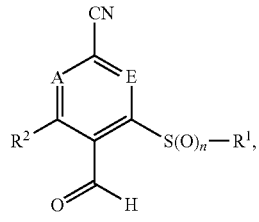
(II)

in which A, E, n, $R^1$ and $R^2$ each have the meanings given above, is reacted in the presence of an acid or an acid anhydride in a 3-component one-pot reaction or sequentially with a compound of the formula (III)

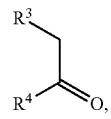
(III)

in which $R^3$ and $R^4$ have the meanings given above,
and a compound of the formula (IV)

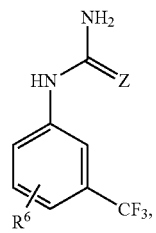
(IV)

in which Z and $R^6$ have the meanings given above, is reacted to give a compound of the formula (I-A)

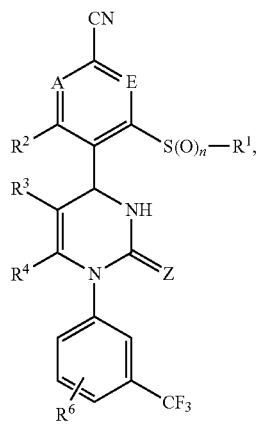

(I-A)

in which A, E, Z, n, R¹, R², R³, R⁴ and R⁶ each have the meanings given above, and this compound is, in the case that R⁵ in formula (I) does not represent hydrogen, reacted in the presence of a base with a compound of the formula (V)

$$R^{5A}-X \qquad (V),$$

in which $R^{5A}$ has the meaning of $R^5$ given above, but does not represent hydrogen, and X represents a leaving group, such as, for example, halogen, mesylate, tosylate or triflate, to give a compound of the formula (I-B)

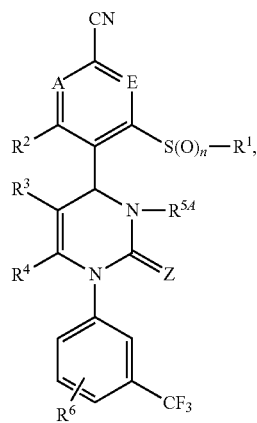

(I-B)

in which A, E, Z, n, R¹, R², R³, R⁴, $R^{5A}$ and R⁶ each have the meanings given above, and the compound of the formula (I-A) or (I-B) obtained in this manner is, if appropriate, separated by methods known to the person skilled in the art into its enantiomers and/or diastereomers and/or converted with the appropriate (i) solvents and/or (ii) bases or acids into its solvates, salts and/or solvates of the salts. Suitable solvents for the process step (II)+(III)+(IV)→(I-A) are usual organic solvents which are not altered under the reaction conditions. These include, for example, ethers, such as diethyl ether, diisopropyl ether, methyl tert-butyl ether, 1,2-dimethoxyethane, dioxane or tetrahydrofuran, alcohols, such as methanol, ethanol, n-propanol, isopropanol, n-butanol or tert-butanol, hydrocarbons, such as pentane, hexane, cyclohexane, benzene, toluene or xylene, halogenated hydrocarbons, such as dichloromethane, 1,2-dichloroethane, trichloromethane or chlorobenzene, or other solvents, such as ethyl acetate, acetonitrile, dimethyl sulfoxide or N,N-dimethylformamide. It is also possible to use mixtures of the solvents mentioned. Preference is given to using methyl tert-butyl ether, tetrahydrofuran or dioxane. Suitable as acid for the process step (II)+(III)+(IV)→(I-A) are usual inorganic or organic acids or acid anhydrides. These include preferably carboxylic acids, such as, for example, acetic acid or trifluoroacetic acid, sulfonic acids, such as methanesulfonic acid, trifluoromethanesulfonic acid or p-toluenesulfonic acid, hydrochloric acid, sulfuric acid, phosphoric acid, phosphonic acids, or phosphoric or phosphonic anhydrides or esters, such as polyphosphoric acid, phosphoric acid triethyl ester, polyphosphoric acid ethyl ester, phosphorus pentoxide or propanephosphonic anhydride. Preference is given to using phosphoric acid triethyl ester in combination with phosphorus pentoxide. The acid is generally employed in an amount of from 0.25 mol to 100 mol based on 1 mol of the compound (III). Process step (II)+(III)+(IV)→(I-A) is generally carried out in a temperature range from +20° C. to +150° C., preferably at +50° C. to +100° C. The reaction can be carried out under atmospheric, elevated or reduced pressure (for example from 0.5 to 5 bar). It is generally carried out under atmospheric pressure.

Solvents suitable for process step (I-A)+(V)→(I-B) are usual organic solvents which are not altered under the reaction conditions. These include, for example, ethers, such as diethyl ether, diisopropyl ether, methyl tert-butyl ether, 1,2-dimethoxyethane, dioxane or tetrahydrofuran, hydrocarbons, such as pentane, hexane, cyclohexane, benzene, toluene or xylene, halogenated hydrocarbons, such as dichloromethane, 1,2-dichloroethane, trichloromethane or chlorobenzene, or other solvents, such as ethyl acetate, acetone, methyl ethyl ketone, methyl tert-butyl ketone, acetonitrile, dimethyl sulfoxide, N,N-dimethylformamide, N,N'-dimethylpropyleneurea (DMPU) or N-methylpyrrolidone (NMP). It is also possible to use mixtures of the solvents mentioned. Preference is given to using tetrahydrofuran, acetonitrile or dimethylformamide.

Suitable as base for the process step (I-A)+(V)→(I-B) are usual inorganic or organic bases. These include in particular alkali metal or alkaline earth metal carbonates, such as lithium carbonate, sodium carbonate, potassium carbonate, calcium carbonate or cesium carbonate, alkali metal alkoxides, such as sodium tert-butoxide or potassium tert-butoxide, alkali metal hydrides, such as sodium hydride or potassium hydride, amides, such as lithium bis(trimethylsilyl)amide or potassium bis(trimethylsilyl)amide or lithium diisopropylamide (LDA), organic amines, such as triethylamine, N-methylmorpholine, N-methylpiperidine, N,N-diisopropylethylamine, 1,5-diazabicyclo[4.3.0]non-5-ene (DBN), 1,8-diazabicyclo[5.4.0]undec-7-ene (DBU), pyridine or 4-N,N-dimethylaminopyridine, or phosphazine bases ("Schwesinger bases"), such as, for example, P1-t-Bu, P2-t-Bu or P4-t-Bu. Preference is given to using potassium carbonate, cesium carbonate, sodium hydride, triethylamine, N,N-diisopropylethylamine or lithium bis(trimethylsilyl)amide; sodium hydride and lithium bis(trimethylsilyl)amide are particularly preferred. The base is generally employed in an amount of from 0.1 mol to 10 mol, preferably from 1 mol to 3 mol, based on 1 mol of the compound (I-A).

Process step (I-A)+(V)→(I-B) is generally carried out in a temperature range from −78° C. to +100° C., preferably at −78° C. to +80° C., particularly preferably at −78° C. to +25° C. The reaction can be carried out under atmospheric, elevated or reduced pressure (for example from 0.5 to 5 bar). It is generally carried out under atmospheric pressure.

Compounds according to the invention of the formula (I) in which R³ and R⁴ are attached to one another, and, together, form a fused group of the formula

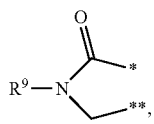

in which * and ** are the points of attachment described above and R⁹ has the meaning given above
can also be prepared by brominating a compound of the formula (I-C)

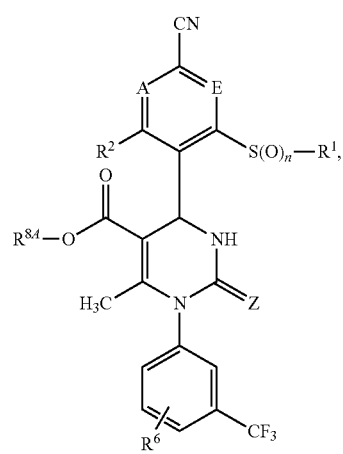
(I-C)

in which A, E, Z, n, R¹, R² and R⁶ each have the meanings given above and
R$^{8A}$ represents $(C_1-C_6)$-alkyl, $(C_3-C_6)$-alkenyl or $(C_3-C_6)$-cycloalkyl,
in an inert solvent to give a compound of the formula (VI)

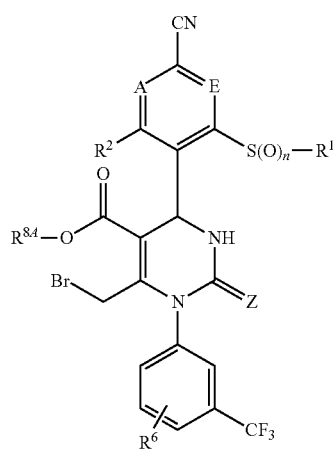
(VI)

in which A, E, Z, n, R¹, R², R⁶ and R$^{8A}$ each have the meanings given above
and then cyclizing it with a compound of the formula (VII)

R⁹—NH₂ (VII)

in which R⁹ has the meaning given above to give a compound of the formula (I-D)

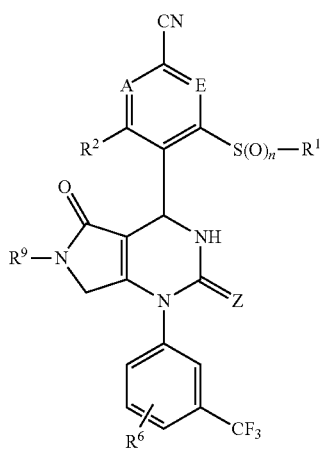
(I-D)

in which A, E, Z, n, R¹, R², R⁶ and R⁹ each have the meanings given above, which is subsequently, if appropriate, converted with a compound of the formula (V), as described above, into a compound of the formula (I-E)

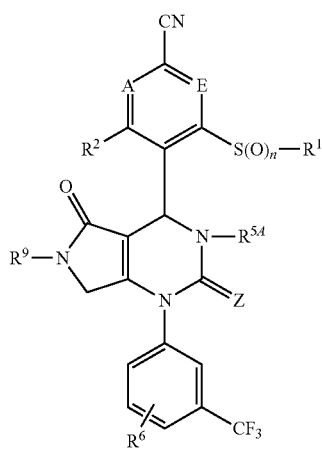
(I-E)

in which A, E, Z, n, R¹, R², R$^{5A}$, R⁶ and R⁹ each have the meanings given above.

The bromination in process step (I-C)→(VI) is preferably carried out using elemental bromine in a usual inert solvent, such as chloroform, at a temperature from −20° C. to +40° C. A CC double bond, which may optionally be present in the radical R$^{8A}$[R$^{8A}$=(C₃-C₆)-alkenyl], may also be brominated under these reaction conditions; however, this does not interfere with the subsequent ring-closure reaction with the compound (VII).

The lactam formation in process step (VI)+(VII)→(I-D) is preferably carried out in an ether such as tetrahydrofuran or dioxane as inert solvent at a temperature from −20° C. to +60° C. If appropriate, it may be advantageous to use a tertiary amine, such as triethylamine, N-methylmorpholine, N-methylpiperidine or N,N-diisopropylethylamine as auxiliary base.

For its part, the compound of the formula (I-C) can be obtained according to the reaction (II)+(III)+(IV)→(I-A) described above.

If expedient, further compounds of the formula (I) according to the invention can also be prepared by transformations of functional groups of individual substituents, in particular those listed under $R^1$, $R^3$ and $R^5$, starting with other compounds of the formula (I) obtained by the above process. These transformations are carried out according to customary methods known to the person skilled in the art and include, for example, reactions such as nucleophilic or electrophilic substitution reactions, transition metal-mediated coupling reactions (for example Suzuki or Heck reaction), oxidation, reduction, hydrogenation, alkylation, acylation, amination, hydroxylation, etherification, esterification, ester cleavage and ester hydrolysis, formation of nitriles, carboxamides, sulfonamides, carbamates and ureas, and also the introduction and removal of temporary protective groups [cf. also the reaction schemes 2-5 below and the exemplary embodiments].

Separation of the compounds according to the invention into the corresponding enantiomers and/or diastereomers is possible, as expedient, at the stage of the compounds (I-B) or (I-E) or else at the stage of the compounds (I-A), (I-C) or (I-D), where the latter can then, in separated form, be reacted further according to the process steps described above. Such a separation of stereoisomers can be carried out by customary methods known to the person skilled in the art; preference is given to chromatographic methods, in particular to HPLC chromatography on a chiral phase.

The compounds of the formulae (III), (IV), (V) and (VII) are commercially available, known per se from the literature or can be prepared by customary methods described in the literature.

Some of the compounds of the formula (II) are known from the literature, or they can be prepared analogously to processes described in the literature [cf. also reaction schemes 6-9 below and the literature cited therein].

In the process described above, it may, if appropriate, be synthetically expedient to employ, instead of the compound of the formula (II), initially a compound of the formula (II-A)

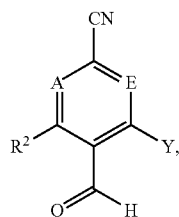

(II-A)

in which A, E and $R^2$ have the meanings given above
and

Y represents an exchangeable group, such as, for example, fluorine, chlorine, bromine, iodine, nitro or amino,
in the reaction sequence described and then to introduce the ortho-thio substituent $R^1$—$S(O)_n$— of the aryl head group at the stage of the dihydropyrimidinone—which corresponds to the compound (I-A) or (I-B)—in exchange for the radical Y [cf. reaction scheme 10 below]. Some of the compounds of the formula (II-A) are likewise known from the literature, or they can be prepared analogously to methods known from the literature.

The processes described above can be illustrated by the reaction schemes below:

Scheme 1

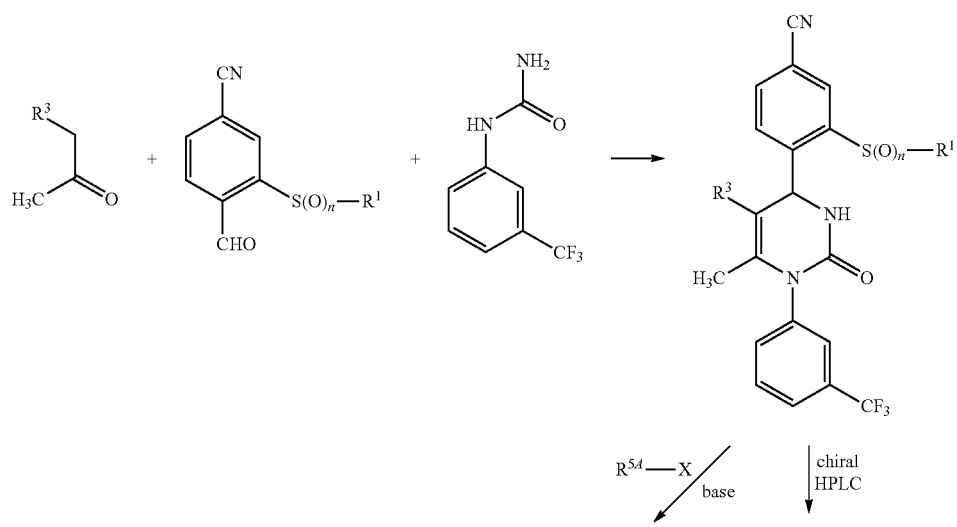

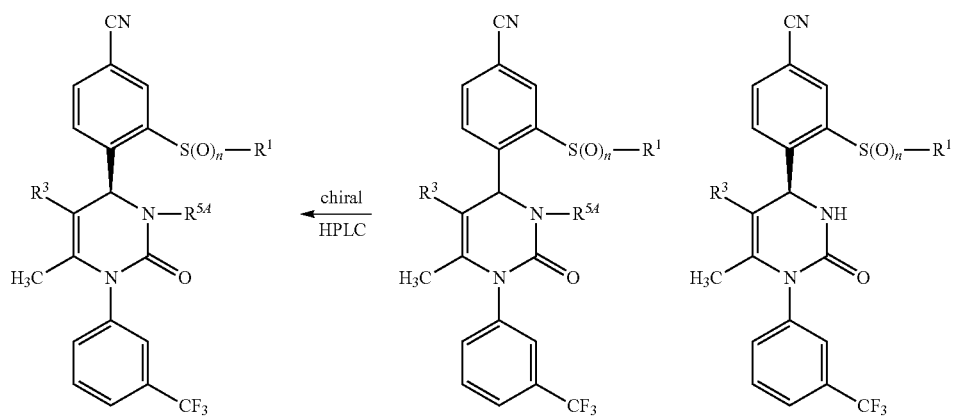
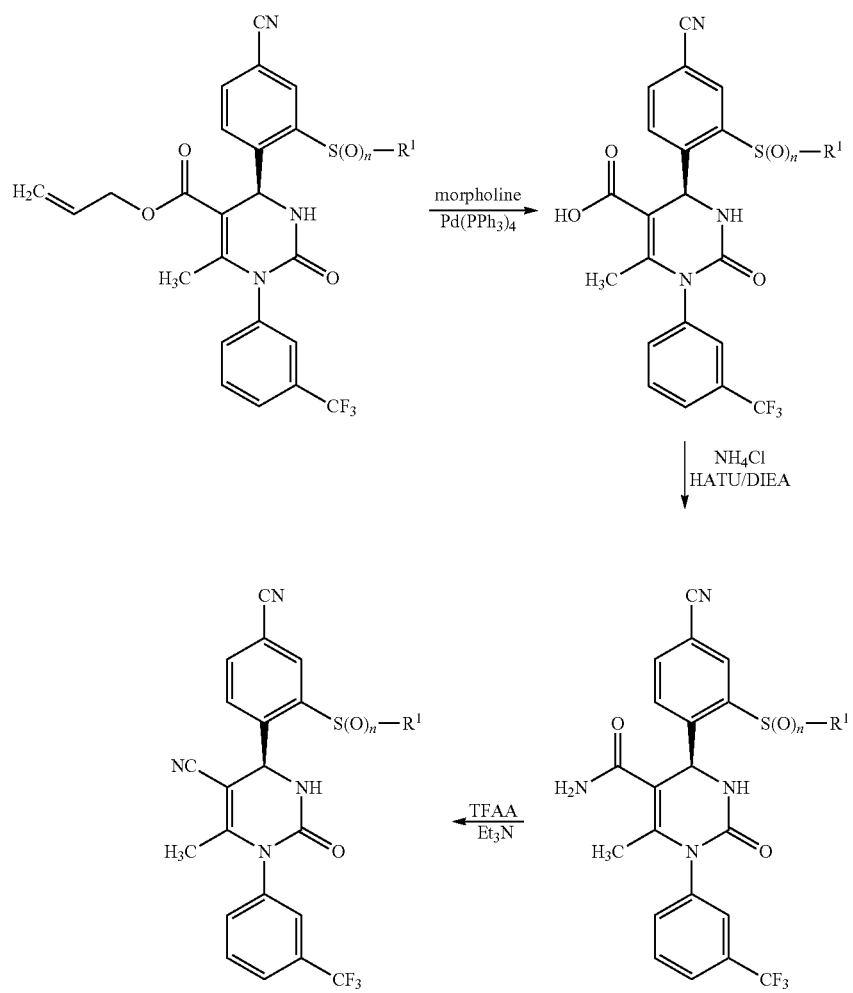
Scheme 2

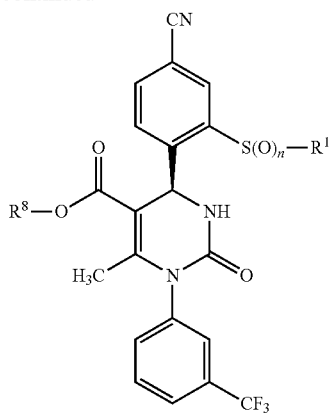
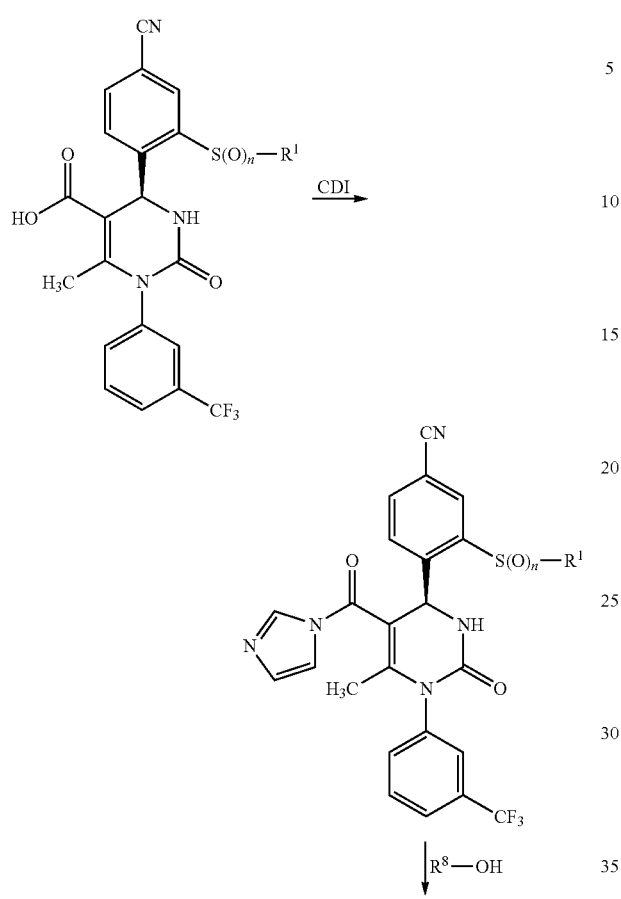
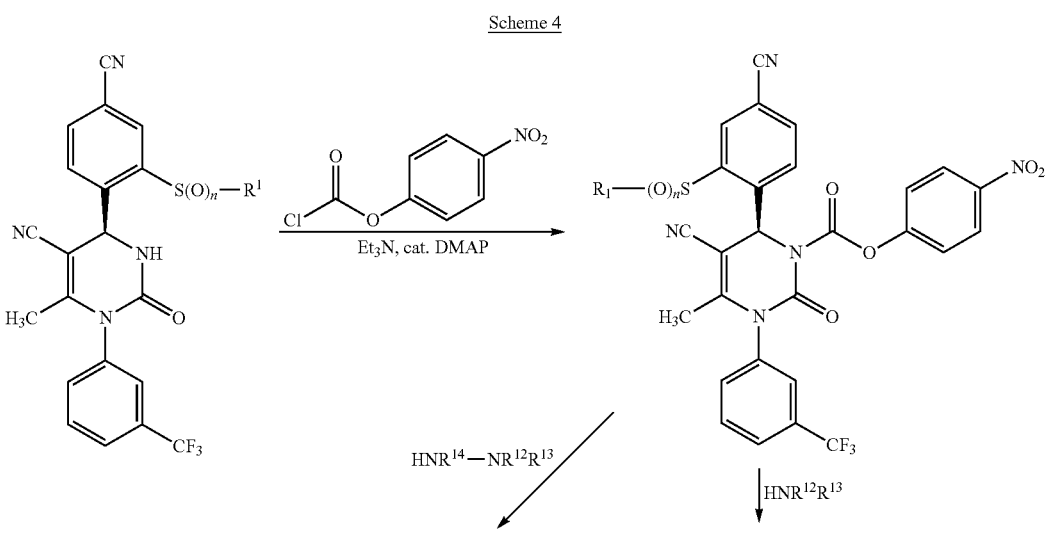

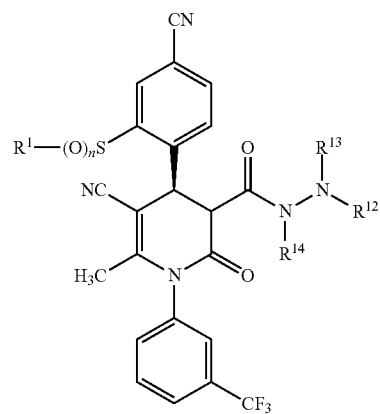
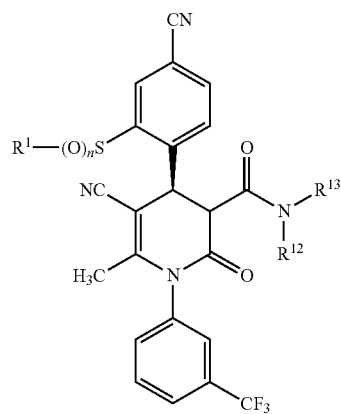
Scheme 5
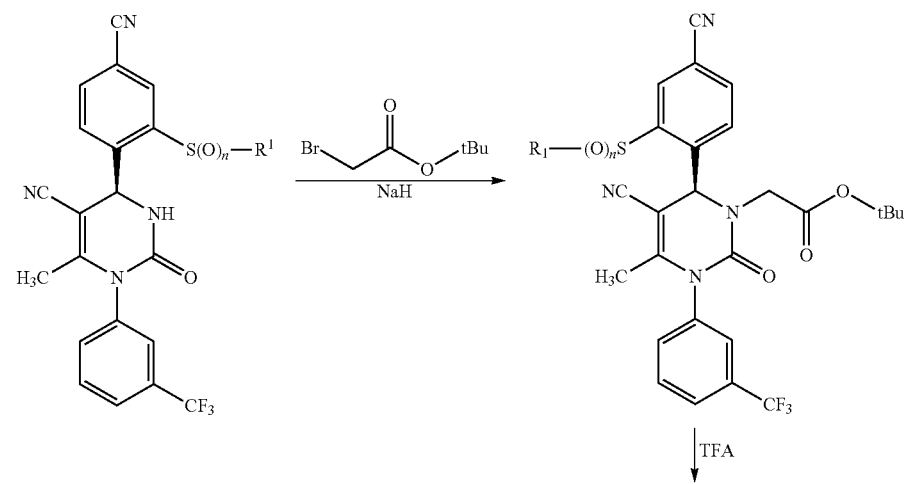
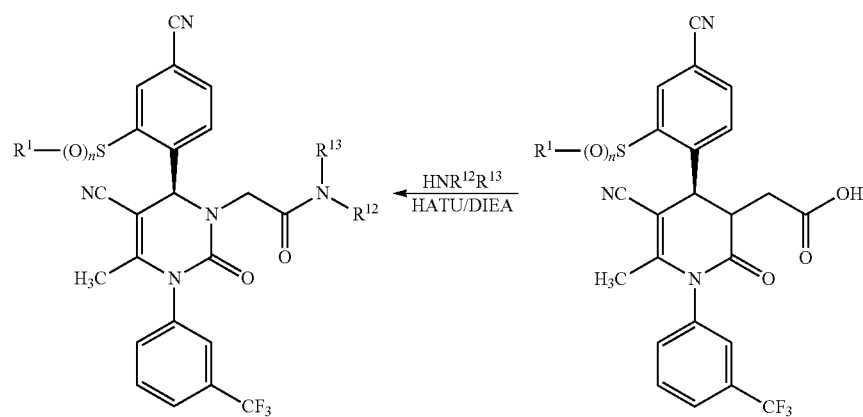

Scheme 6
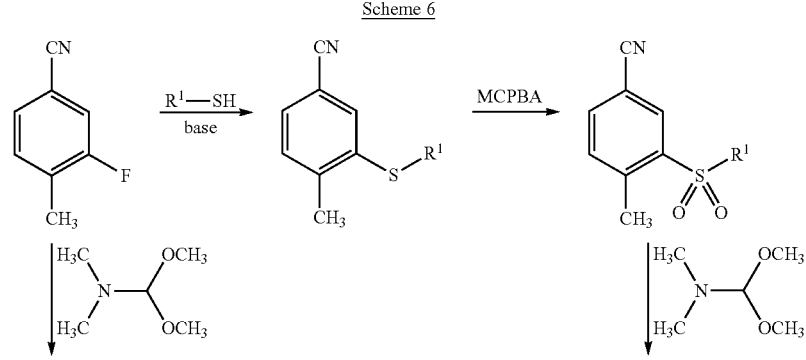
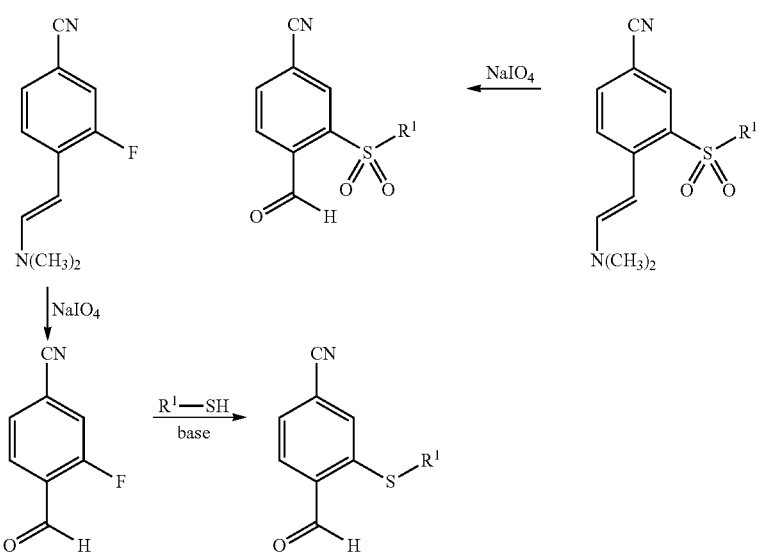
Scheme 7
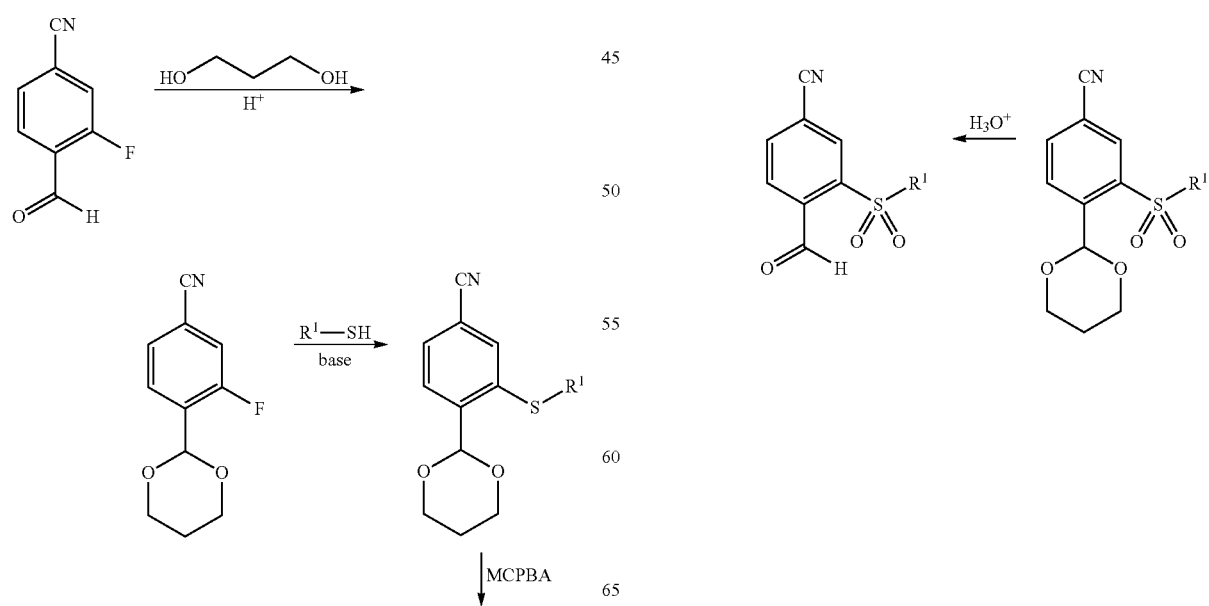

Scheme 8
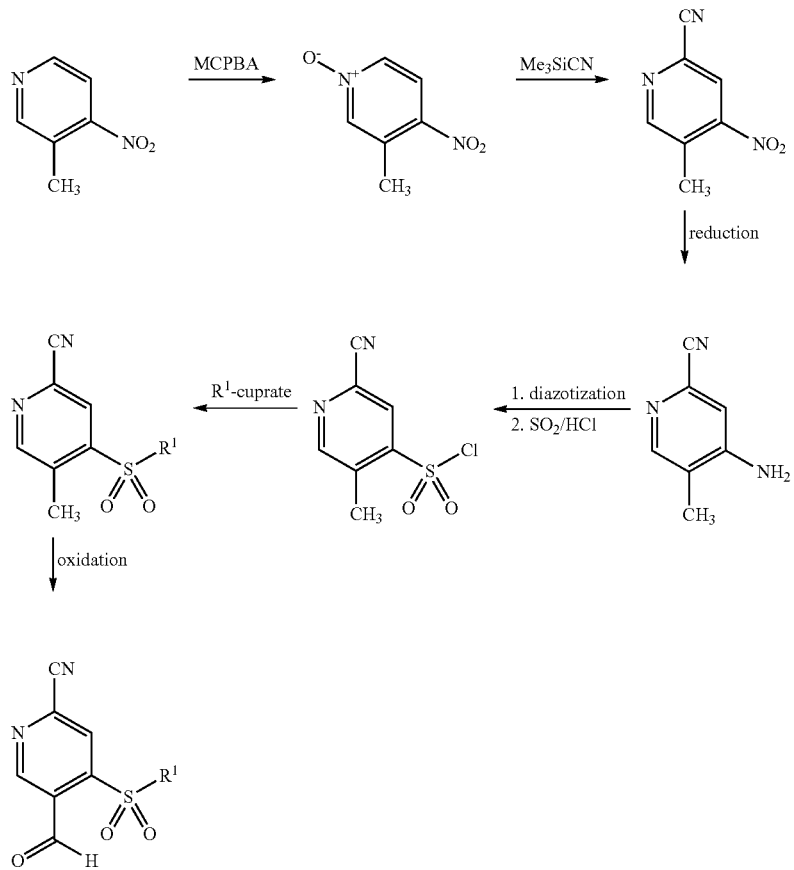
[cf., for example, W. K. Fife, J. Org. Chem. 48, 1375 (1983); H. Vorbruiggen and K. Krolikiewicz, Synthesis, 316 (1983); R. T. Shuman et al., J. Org. Chem. 55, 738 (1990); C. S. Burgey et al., J. Med. Chem. 46 (4), 461 (2003); V. M. Naidan et al., J. Gen. Chem. USSR (Engl. Transl.) 55 (2), 346 (1985)].
Scheme 9
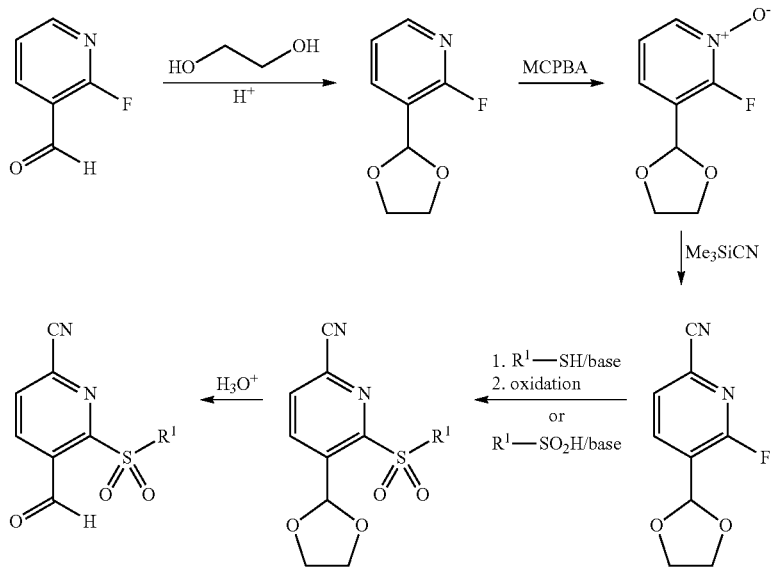

[cf., for example, W. K. Fife, J. Org. Chem. 48, 1375 (1983); H. Vorbruiggen and K. Krolikiewicz, Synthesis, 316 (1983); R. T. Shuman et al., J. Org. Chem. 55, 738 (1990); C. S. Burgey et al., J. Med. Chem. 46 (4), 461 (2003); J. J. L¹ et al., J. Med. Chem. 39, 1846 (1996); K. N. Dack et al., Bioorg. Med. Chem. Lett. 8 (16), 2061 (1998)].
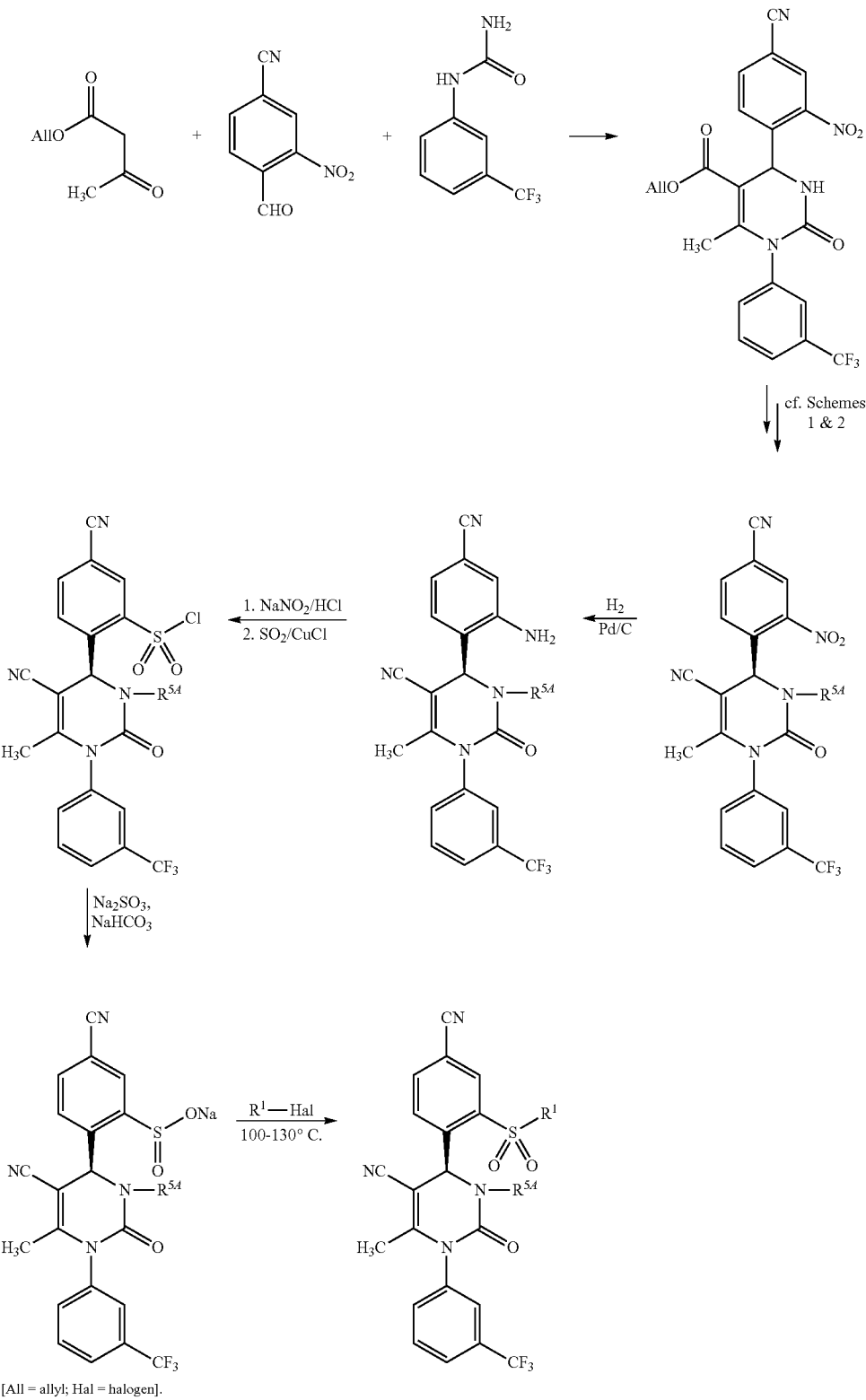
Scheme 10
[All = allyl; Hal = halogen].

The compounds according to the invention have useful pharmacological properties and can be used for prevention and treatment of disorders in humans and animals. The compounds according to the invention are low-molecular-weight, unreactive and selective inhibitors of human neutrophil elastase which, surprisingly, show a considerably more pronounced inhibition of this protease than the compounds known from the prior art. In addition, the compounds according to the invention unexpectedly have lower in vitro clearance by hepatocytes and thus improved metabolic stability.

Accordingly, the compounds according to the invention are particularly suitable for the treatment and/or prevention of disorders and pathological processes, in particular those where neutrophil elastase (HNE) is involved in an inflammatory event and/or a tissue or vessel remodeling.

For the purposes of the present invention, this includes in particular disorders such as pulmonary arterial hypertension (PAH) and other forms of pulmonary hypertension (PH), chronic obstructive pulmonary disease (COPD), acute respiratory distress syndrome (ARDS), acute lung injury (ALI), alpha-1-antitrypsin deficiency (AATD), pulmonary fibrosis, pulmonary emphysema, cystic fibrosis, acute coronary syndrome (ACS), inflammations of the heart muscle (myocarditis) and other autoimmune heart disorders (pericarditis, endocarditis, valvolitis, aortitis, cardiomyopathies), myocardial infarction, cardiogenic shock, heart failure, aneurysms, sepsis (SIRS), multi-organ failure (MODS, MOF), arteriosclerosis, inflammatory disorders of the kidney, chronic inflammations of the intestine (IBD, CD, UC), pancreatitis, peritonitis, rheumatoid disorders, inflammatory skin disorders and also inflammatory eye disorders.

The compounds according to the invention can furthermore be used for the treatment and/or prevention of asthmatic disorders of various severity with intermittent or persistent progression (refractive asthma, bronchial asthma, allergic asthma, intrinsic asthma, extrinsic asthma, asthma induced by medicaments or by dust), of multifarious forms of bronchitis (chronic bronchitis, infectious bronchitis, eosinophilic bronchitis), of bronchiolitis obliterans, bronchiectasia, pneumonia, farmer's lung and related diseases, cough and cold diseases (chronic inflammatory cough, iatrogenic cough), inflammations of the nasal mucosa (including medicament-induced rhinitis, vasomotoric rhinitis and seasonal allergic rhinitis, for example hayfever) and of polyps.

In addition, the compounds according to the invention can also be used for the treatment and/or prevention of micro- and macrovascular injuries (vasculitis), reperfusion damage, arterial and venous thromboses, diabetic and non-diabetic nephropathy, glomerulonephritis, glomerulosclerosis, nephrotic syndrome, hypertensive nephrosclerosis, microalbuminuria, acute and chronic renal insufficiency, acute and chronic renal failure, cystitis, urethritis, prostatitis, epidymititis, oophoritis, salpingitis, vulvovaginitis, erectile dysfunction, Hunner's altsa, Peyronie's disease, arterial hypertension, shock, atrial and ventricular arrhythmias, transitory and ischemic attacks, heart failure, stroke, endothelial dysfunction, peripheral and cardiovascular disorders, impaired peripheral perfusion, edema formation such as, for example, pulmonary edema, brain edema, renal edema and heart failure-related edema, restenoses, for example after thrombolysis therapies, percutaneous transluminal angioplasties (PTA), transluminal coronary angioplasties (PTCA), heart transplants and bypass operations, for increased levels of fibrinogen and low-density LDL and also for increased concentrations of plasminogen activator inhibitor 1 (PAI-1), of dyslipidemias (hypercholesterolemia, hypertriglyceridemia, increased concentrations of postprandial plasma triglycerides, hypoalpha-lipoproteinemia, combined hyperlipidemias) and also metabolic disorders (metabolic syndrome, hyperglycemia, insulin-dependent diabetes, non-insulin-dependent diabetes, gestational diabetes, hyperinsulinemia, insulin resistance, glucose intolerance, adipositas and diabetic sequelae, such as retinopathy, nephropathy and neuropathy), neoplastic disorders (skin cancer, brain tumors, breast cancer, bone marrow tumors, leukemias, liposarcomas, carcinomas of the gastrointestinal tract, the liver, the pancreas, the lungs, the kidneys, the urethra, the prostate and the genital tract and also malignant tumors of the lymphoproliferative system, such as, for example, Hodgkin's and non-Hodgkin's lymphoma), of disorders of the gastrointestinal tract and the abdomen (glossitis, gingivitis, periodontitis, esophagitis, eosinophilic gastroenteritis, mastocytosis, Crohn's disease, colitis, proctitis, pruritis ani, diarrhea, celiac disease, hepatitis, hepatic fibrosis, cirrhosis of the liver, pancreatitis and cholecystitis), of disorders of the central nervous system and neurodegenerative disorders (stroke, Alzheimer's disease, Parkinson's disease, dementia, epilepsy, depressions, multiple sclerosis), immune disorders, thyroid disorders (hyperthyreosis), skin disorders (psoriasis, acne, eczema, neurodermitis, multifarious forms of dermatitis, such as, for example, dermatitis abacribus, dermatitis actinica, dermatitis allergica, dermatitis ammoniacalis, dermatitis artefacta, dermatitis autogenica, dermatitis atrophicans, dermatitis calorica, dermatitis combustionis, dermatitis congelationis, dermatitis cosmetica, dermatitis escharotica, dermatitis exfoliativa, dermatitis gangraenose, dermatitis haemostatica, dermatitis herpetiformis, dermatitis lichenoides, dermatitis linearis, dermatitis maligna, dermatitis medimencatosa, dermatitis palmaris et plantaris, dermatitis parasitaria, dermatitis photoallergica, dermatitis phototoxica, dermatitis pustularis, dermatitis seborrhoica, dermatitis solaris, dematitis toxica, dermatitis ulcerosa, dermatitis veneata, infectious dermatitis, pyogenic dermatitis and rosacea-like dermatitis, and also keratitis, bullosis, vasculitis, cellulitis, panniculitis, lupus erythematosus, erythema, lymphomas, skin cancer, Sweet syndrome, Weber-Christian syndrome, scar formation, wart formation, chilblains), of inflammatory eye diseases (saccoidosis, blepharitis, conjunctivitis, iritis, uveitis, chorioiditis, ophthalmitis), viral diseases (caused by influenza, adeno and corona viruses, such as, for example, HPV, HCMV, HIV, SARS), of disorders of the skeletal bone and the joints and also the skeletal muscle (multifarious forms of arthritis, such as, for example, arthritis alcaptonurica, arthritis ankylosans, arthritis dysenterica, arthritis exsudativa, arthritis fungosa, arthritis gonorrhoica, arthritis mutilans, arthritis psoriatica, arthritis purulenta, arthritis rheumatica, arthritis serosa, arthritis syphilitica, arthritis tuberculosa, arthritis urica, arthritis villonodularis pigmentosa, atypical arthritis, hemophilic arthritis, juvenile chronic arthritis, rheumatoid arthritis and metastatic arthritis, furthermore Still syndrome, Felty syndrome, Sjörgen syndrome, Clutton syndrome, Poncet syndrome, Pott syndrome and Reiter syndrome, multifarious forms of arthropathias, such as, for example, arthropathie deformans, arthropathie neuropathica, arthropathie ovaripriva, arthropathie psoriatica and arthropathie tabica, systemic scleroses, multifarious forms of inflammatory myopathies, such as, for example, myopathie epidemica, myopathie fibrosa, myopathie myoglobinurica, myopathie ossificans, myopathie ossificans neurotica, myopathie ossificans progressiva multiplex, myopathie purulenta, myopathie rheumatica, myopathie trichinosa, myopathie tropica and myopathie typhosa, and also the Ginther syndrome and the Mnchmeyer syndrome), of inflammatory changes of the arteries (multifarious forms of arteritis, such as, for example, endarteritis, mesarteritis, periarteritis, panarteritis, arteritis rheumatica, arteritis deformans, arteritis temporalis, arteritis cranialis, arteritis gigantocellularis and arteritis granulomatosa, and also Horton syndrome, Churg-Strauss syndrome and Takayasu arteritis), Muckle-Well syndrome, Kikuchi disease, of polychondritis, dermatosclerosis and also other disorders having an inflammatory or immunological component, such as, for example, cataract, cachexia, osteoporosis, gout, incontinence, lepra, Sezary syndrome and paraneoplastic syndrome, for rejection reactions after organ transplants and for wound healing and angiogenesis in particular in the case of chronic wounds.

By virtue of their property profile, the compounds according to the invention are suitable in particular for the treatment and/or prevention of pulmonary arterial hypertension (PAH) and other forms of pulmonary hypertension (PH), chronic obstructive lung disease (COPD), acute lung injury (ALI), acute respiratory distress syndrome (ARDS), pulmonary emphysema, alpha-1-antitrypsin deficiency (AATD), cystic fibrosis (CF), sepsis and systemic-inflammatory response syndrome (SIRS), multiple organ failure (MOF, MODS), inflammatory intestinal disorders (IBD, Crohn's disease, colitis), chronic bronchitis, bronchiolitis, asthma, rhinitis, rheumatoid arthritis, inflammatory skin and eye diseases, arteriosclerosis and neoplastic disorders.

The present invention furthermore provides the use of the compounds according to the invention for the treatment and/or prevention of disorders, in particular the disorders mentioned above.

The present invention furthermore provides the use of the compounds according to the invention for preparing a medicament for the treatment and/or prevention of disorders, in particular the disorders mentioned above.

The present invention furthermore provides the use of the compounds according to the invention in a method for the treatment and/or prevention of disorders, in particular the disorders mentioned above.

The present invention furthermore provides a method for the treatment and/or prevention of disorders, in particular the disorders mentioned above, using an effective amount of at least one of the compounds according to the invention.

The compounds according to the invention can be employed alone or, if required, in combination with other active compounds. Accordingly, the present invention furthermore provides medicaments comprising at least one of the compounds according to the invention and one or more further active compounds, in particular for the treatment and/or prevention of the disorders mentioned above. Suitable active compounds for combinations are, by way of example and preferably:

compounds which inhibit the signal transduction cascade, for example and preferably from the group of the kinase inhibitors, in particular from the group of the tyrosine kinase and/or serine/threonine kinase inhibitors;

compounds which inhibit the degradation and remodeling of the extracellular matrix, by way of example and preferably inhibitors of matrix metalloproteases (MMPs), in particular inhibitors of stromelysin, collagenases, gelatinases and aggrecanases (here in particular of MMP-1, MMP-3, MMP-8, MMP-9, MMP-10, MMP-11 and MMP-13) and of metalloelastase (MMP-12);

organic nitrates and NO donors, such as, for example, sodium nitroprusside, nitroglycerin, isosorbide mononitrate, isosorbide dinitrate, molsidomine or SIN-1, and also inhaled NO;

NO-independent but hem-dependent stimulators of soluble guanylate cyclase, such as, in particular, the compounds described in WO 00/06568, WO 00/06569, WO 02/42301 and WO 03/095451;

NO- and hem-independent activators of soluble guanylate cyclase, such as, in particular, the compounds described in WO 01/19355, WO 01/19776, WO 01/19778, WO 01/19780, WO 02/070462 and WO 02/070510; prostacycline analogs, such as, by way of example and preferably, iloprost, beraprost, treprostinil or epoprostenol;

compounds which inhibit soluble epoxide hydrolase (sEH), such as, for example, N,N'-dicyclohexylurea, 12-(3-adamantan-1-ylureido)dodecanoic acid or 1-adamantan-1-yl-3-{5-[2-(2-ethoxyethoxy)ethoxy]pentyl}urea;

compounds which influence the energy metabolism of the heart, such as, by way of example and preferably, etomoxir, dichloroacetate, ranolazine or trimetazidine; compounds which inhibit the degradation of cyclic guanosine monophosphate (cGMP) and/or cyclic adenosine monophosphate (cAMP), such as, for example, inhibitors of phosphodiesterases (PDE) 1, 2, 3, 4 and/or 5, in particular PDE 5 inhibitors, such as sildenafil, vardenafil and tadalafil;

agents having antithrombotic action, by way of example and preferably from the group of the platelet aggregation inhibitors, of anticoagulants or of profibrinolytic substances;

active compounds which lower blood pressure, by way of example and preferably from the group of the calcium antagonists, angiotensin AII antagonists, ACE inhibitors, vasopeptidase inhibitors, endothelin antagonists, renin inhibitors, alpha-receptor blockers, beta-receptor blockers, mineralocorticoid receptor antagonists, Rho kinase inhibitors and diuretics;

agents having a bronchodilatory effect, by way of example and preferably from the group of the beta-adrenergic receptor agonists, such as, in particular, albuterol, isoproterenol, metaproterenol, terbutalin, formoterol or salmeterol, or from the group of the anticholinergics, such as, in particular, ipratropium bromide;

agents having antiinflammatory action, by way of example and preferably from the group of the glucocorticoids, such as, in particular, prednisone, prednisolone, methylprednisolone, triamcinolone, dexamethasone, beclomethasone, betamethasone, flunisolide, budesonide or futicasone; and/or active ingredients which alter lipid metabolism, for example and preferably from the group of the thyroid receptor agonists, cholesterol synthesis inhibitors, such as, by way of example and preferably, HMG-CoA reductase inhibitors or squalene synthesis inhibitors, of ACAT inhibitors, CETP inhibitors, MTP inhibitors, PPAR-alpha, PPAR-gamma and/or PPAR-delta agonists, cholesterol absorption inhibitors, lipase inhibitors, polymeric bile adsorbents, bile acid reabsorption inhibitors and lipoprotein(a) antagonists.

In a preferred embodiment of the invention, the compounds according to the invention are employed in combination with a kinase inhibitor such as by way of example and preferably bortezomib, canertinib, erlotinib, gefitinib, imatinib, lapatinib, lestaurtinib, lonafarnib, pegaptinib, pelitinib, semaxanib, sorafenib, sunitinib, tandutinib, tipifarnib, vatalanib, fasudil, lonidamine, leflunomide, BMS-3354825 or Y-27632.

Agents having an antithrombotic effect preferably mean compounds from the group of platelet aggregation inhibitors, of anticoagulants or of profibrinolytic substances.

In a preferred embodiment of the invention, the compounds according to the invention are administered in combination with a platelet aggregation inhibitor such as by way of example and preferably aspirin, clopidogrel, ticlopidine or dipyridamole.

In a preferred embodiment of the invention, the compounds according to the invention are administered in combination with a thrombin inhibitor such as by way of example and preferably ximelagatran, melagatran, bivalirudin or clexane.

In a preferred embodiment of the invention, the compounds according to the invention are administered in combination with a GPIIb/IIIa antagonist such as by way of example and preferably tirofiban or abciximab.

In a preferred embodiment of the invention, the compounds according to the invention are administered in combination with a factor Xa inhibitor such as by way of example and preferably rivaroxaban, DU-176b, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or a low molecular weight (LMW) heparin derivative.

In a preferred embodiment of the invention, the compounds according to the invention are administered in combination with a vitamin K antagonist such as by way of example and preferably coumarin.

Agents which lower blood pressure preferably mean compounds from the group of calcium antagonists, angiotensin AII antagonists, ACE inhibitors, endothelin antagonists, renin inhibitors, alpha-receptor blockers, beta-receptor blockers, mineralocorticoid receptor antagonists, Rho kinase inhibitors, and diuretics.

In a preferred embodiment of the invention, the compounds according to the invention are administered in combination with a calcium antagonist such as by way of example and preferably nifedipine, amlodipine, verapamil or diltiazem.

In a preferred embodiment of the invention, the compounds according to the invention are administered in combination with an alpha-1 receptor blocker such as by way of example and preferably prazosin.

In a preferred embodiment of the invention, the compounds according to the invention are administered in combination with a beta-receptor blocker such as by way of example and preferably propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII antagonist such as by way of example and preferably losartan, candesartan, valsartan, telmisartan or embusartan.

In a preferred embodiment of the invention, the compounds according to the invention are administered in combination with an ACE inhibitor such as by way of example and preferably enalapril, captopril, lisinopril, ramipril, delapril, fosinopril, quinopril, perindopril or trandopril.

In a preferred embodiment of the invention, the compounds according to the invention are administered in combination with an endothelin antagonist such as by way of example and preferably bosentan, darusentan, ambrisentan or sitaxsentan.

In a preferred embodiment of the invention, the compounds according to the invention are administered in combination with a renin inhibitor such as by way of example and preferably aliskiren, SPP-600 or SPP-800.

In a preferred embodiment of the invention, the compounds according to the invention are administered in combination with a mineralocorticoid receptor antagonist such as by way of example and preferably spironolactone or eplerenone.

In a preferred embodiment of the invention, the compounds according to the invention are administered in combination with a Rho kinase inhibitor such as by way of example and preferably fasudil, Y-27632, SLx-2119, BF-66851, BF-66852, BF-66853, KI-23095, SB-772077, GSK-269962A or BA-1049.

In a preferred embodiment of the invention, the compounds according to the invention are administered in combination with a diuretic such as by way of example and preferably furosemide.

Agents which alter lipid metabolism preferably mean compounds from the group of CETP inhibitors, thyroid receptor agonists, cholesterol synthesis inhibitors such as HMG-CoA reductase inhibitors or squalene synthesis inhibitors, of ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and lipoprotein(a) antagonists.

In a preferred embodiment of the invention, the compounds according to the invention are administered in combination with a CETP inhibitor such as by way of example and preferably torcetrapib (CP-529 414), JJT-705 or CETP vaccine (Avant).

In a preferred embodiment of the invention, the compounds according to the invention are administered in combination with a thyroid receptor agonist such as by way of example and preferably D-thyroxine, 3,5,3'-triiodothyronine (T3), CGS 23425 or axitirome (CGS 26214).

In a preferred embodiment of the invention, the compounds according to the invention are administered in combination with an HMG-CoA reductase inhibitor from the class of statins such as by way of example and preferably lovastatin, simvastatin, pravastatin, fluvastatin, atorvastatin, rosuvastatin, cerivastatin or pitavastatin.

In a preferred embodiment of the invention, the compounds according to the invention are administered in combination with a squalene synthesis inhibitor such as by way of example and preferably BMS-188494 or TAK-475.

In a preferred embodiment of the invention, the compounds according to the invention are administered in combination with an ACAT inhibitor such as by way of example and preferably avasimibe, melinamide, pactimibe, eflucimibe or SMP-797.

In a preferred embodiment of the invention, the compounds according to the invention are administered in combination with an MTP inhibitor such as by way of example and preferably implitapide, BMS-201038, R-103757 or JTT-130.

In a preferred embodiment of the invention, the compounds according to the invention are administered in combination with a PPAR-gamma agonist such as by way of example and preferably pioglitazone or rosiglitazone.

In a preferred embodiment of the invention, the compounds according to the invention are administered in combination with a PPAR-delta agonist such as by way of example and preferably GW-501516 or BAY 68-5042.

In a preferred embodiment of the invention, the compounds according to the invention are administered in combination with a cholesterol absorption inhibitor such as by way of example and preferably ezetimibe, tiqueside or pamaqueside.

In a preferred embodiment of the invention, the compounds according to the invention are administered in combination with a lipase inhibitor such as by way of example and preferably orlistat.

In a preferred embodiment of the invention, the compounds according to the invention are administered in combination with a polymeric bile acid adsorbent such as by way of example and preferably cholestyramine, colestipol, colesolvam, CholestaGel or colestimide.

In a preferred embodiment of the invention, the compounds according to the invention are administered in combination with a bile acid reabsorption inhibitor such as by way of example and preferably ASBT (=IBAT) inhibitors such as, for example, AZD-7806, S-8921, AK-105, BARI-1741, SC-435 or SC-635.

In a preferred embodiment of the invention, the compounds according to the invention are administered in combination with a lipoprotein(a) antagonist such as by way of example and preferably gemcabene calcium (CI-1027) or nicotinic acid.

The present invention further provides medicaments comprising at least one compound according to the invention, usually in combination with one or more inert, non-toxic, pharmaceutically suitable excipients, and their use for the purposes mentioned above.

The compounds according to the invention may have systemic and/or local effects. For this purpose, they can be administered in a suitable way such as, for example, by the oral, parenteral, pulmonary, nasal, sublingual, lingual, buccal, rectal, dermal, transdermal, conjunctival or otic route or as implant or stent.

The compounds according to the invention can be administered in administration forms suitable for these administration routes.

Suitable for oral administration are administration forms which function according to the prior art and deliver the compounds according to the invention rapidly and/or in a modified manner, and which contain the compounds of the invention in crystalline and/or amorphized and/or dissolved form, such as, for example, tablets (uncoated and coated tablets, for example having coatings which are resistant to gastric juice or are insoluble or dissolve with a delay and control the release of the compound of the invention), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g inhalative, intramuscular, subcutaneous, intracutaneous, percutaneous, or intraperitoneal). Administration forms suitable for parenteral administration are, inter alia, preparations for injection and infusion in the form of solutions, suspensions, emulsions, lyophilizates or sterile powders.

Suitable for the other routes of administration are, for example, pharmaceutical forms for inhalation (inter alia powder inhalers, nebulizers, aerosols), nasal drops, solutions, sprays; tablets for lingual, sublingual or buccal administration, films/wafers or capsules, suppositories, preparations for the ears and eyes, vaginal capsules, aqueous suspensions (lotions, shaking mixtures), lipophilic suspensions, ointments, creams, transdermal therapeutic systems (for example patches), milk, pastes, foams, dusting powders, implants or stents.

Oral or parenteral administration are preferred, especially oral and intravenous administration and administration by inhalation.

The compounds according to the invention can be converted into the stated administration forms. This can take place in a manner known per se by mixing with inert, non-toxic, pharmaceutically suitable excipients. These excipients include inter alia carriers (for example microcrystalline cellulose, lactose, mannitol), solvents (e.g. liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (e.g. antioxidants such as, for example, ascorbic acid), colorings (e.g. inorganic pigments such as, for example, iron oxides) and masking flavors and/or odors.

It has generally proved to be advantageous on parenteral administration to administer amounts of about 0.001 to 1 mg/kg, preferably about 0.01 to 0.5 mg/kg of body weight per day to achieve effective results. On oral administration, the dosage is about 0.01 to 100 mg/kg, preferably about 0.01 to 20 mg/kg, and very particularly preferably about 0.1 to 10 mg/kg of body weight.

It may nevertheless be necessary where appropriate to deviate from the stated amounts, in particular as a function of body weight, administration route, individual response to the active ingredient, type of preparation and time or interval over which administration takes place. Thus, in some cases it may be sufficient to make do with less than the aforementioned minimum amount, whereas in other cases the upper limit mentioned must be exceeded. Where relatively large amounts are administered, it may be advisable to distribute these in a plurality of single doses over the day.

The following exemplary embodiments illustrate the invention. The invention is not restricted to the examples.

The percentage data in the following tests and examples are, unless indicated otherwise, percentages by weight; parts are parts by weight. Solvent ratios, dilution ratios and concentration data of liquid/liquid solutions are based in each case on the volume.

A. EXAMPLES

Abbreviations aq. aqueous, aqueous solution
c concentration
cat. catalytic
CDI N,N'-carbonyldiimidazole
TLC thin-layer chromatography
DCI direct chemical ionization (in MS)
dist. distilled
DIEA N,N-diisopropylethylamine
DMAP 4-N,N-dimethylaminopyridine
DMF dimethylformamide
DMSO dimethyl sulfoxide
ee enantiomeric excess
ent enantiomerically pure enantiomer
eq. equivalent(s)
ESI electrospray ionization (in MS)
Et ethyl
GC-MS gas chromatography-coupled mass spectrometry
h hour(s)
HATU O-(7-azabenzotriazol-1-yl)-N,N,N',N'-tetramethyluronium-hexafluorophosphate
HPLC high-pressure, high-performance liquid chromatography
conc. concentrated
LC-MS liquid chromatography-coupled mass spectrometry
MCPBA meta-chloroperbenzoic acid
Me methyl
min minute(s)
MPLC medium-pressure liquid chromatography
MS mass spectrometry
MTBE methyl tert-butyl ether
NMR nuclear magnetic resonance spectrometry
Ph phenyl PyBOP benzotriazol-1-yloxytris(pyrrolidino)phosphonium hexafluorophosphate
quant. quantitative (in yield)
rac racemic, racemate
RT room temperature
$R_t$ retention time (in HPLC)
m.p. melting point
tBu tert-butyl
TFA trifluoroacetic acid
TFAA trifluoroacetic anhydride
THF tetrahydrofuran
UV ultraviolet spectrometry
v/v volume to volume ratio (of a solution)
HPLC, GC-MS and LC-MS Methods:
Method 1 (GC-MS):
  Instrument: Micromass GCT, GC 6890; column: Restek RTX-35, 15 m×200 μm×0.33 μm; constant helium flow: 0.88 ml/min; oven: 70° C.; inlet: 250° C.; gradient: 70° C., 30° C./min→310° C. (maintained for 3 min).
Method 2 (Analytical HPLC):
  Instrument: HP 1100 with DAD detection; column: Kromasil 100 RP-18, 60 mm×2.1 mm, 3.5 μm; mobile phase A: 5 ml of HClO₄ (70% strength)/liter of water, mobile phase B: acetonitrile; gradient: 0 min 2% B→0.5 min 2% B→4.5 min 90% B→9.0 min 90% B→9.2 min 2% B→10 min 2% B; flow rate: 0.75 ml/min; column temperature: 30° C.; UV detection: 210 nm.
Method 3 (Analytical HPLC):
  Instrument: HP 1100 with DAD detection; column: Kromasil 100 RP-18, 60 mm×2.1 mm, 3.5 μm; mobile phase A: 5 ml of HClO₄ (70% strength)/liter of water, mobile phase B: acetonitrile; gradient: 0 min 2% B→0.5 min 2% B→4.5 min 90% B→6.5 min 90% B→6.7 min 2% B→7.5 min 2% B; flow rate: 0.75 ml/min; column temperature: 30° C.; UV detection: 210 nm.
Method 4 (LC-MS):
  Instrument: Micromass QuattroPremier with Waters UPLC Acquity; column: Thermo Hypersil GOLD 1.9μ 50 mm×1 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→1.5 min 10% A→2.2 min 10% A; flow rate: 0.33 ml/min; oven: 50° C.; UV detection: 210 nm.
Method 5 (LC-MS):
  MS instrument type: Micromass ZQ; HPLC instrument type: Waters Alliance 2795; column: Phenomenex Synergi 2.5μ MAX-RP 100A Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→3.0 min 5% A→4.0 min 5% A→4.01 min 90% A; flow rate: 2 ml/min; oven: 50° C.; UV detection: 210 nm.
Method 6 (LC-MS):
  MS instrument type: Micromass ZQ; HPLC instrument type: HP 1100 Series; UV DAD; column: Phenomenex Gemini 3μ 30 mm×3.0 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.
Method 7 (Preparative HPLC/MS):
  MS instrument: Waters ZQ 2000; HPLC instrument: Agilent 1100, 2-column system; autosampler: HTC PAL; column: YMC-ODS-AQ, 50 mm×4.6 mm, 3.0 μm; mobile phase A: water+0.1% formic acid, mobile phase B: acetonitrile+0.1% formic acid; gradient: 0.0 min 100% A→0.2 min 95% A→1.8 min 25% A→1.9 min 10% A→2.0 min 5% A→3.2 min 5% A→3.21 min 100% A→3.35 min 100% A; oven: 40° C.; flow rate: 3.0 ml/min; UV detection: 210 nm.
Method 8 (LC-MS):
  MS instrument type: Waters ZQ; HPLC instrument type: Waters Alliance 2795; column: Phenomenex Onyx Monolithic C18, 100 mm×3 mm; mobile phase A: 1 l of water+0.5 ml of 50% strength formic acid, mobile phase B: 1 l of acetonitrile+0.5 ml of 50% strength formic acid; gradient: 0.0 min 90% A→2 min 65% A→4.5 min 5% A→6 min 5% A; flow rate: 2 ml/min; oven: 40° C.; UV detection: 210 nm.
Method 9 (LC-MS):
  Instrument: Waters Acquity SQD UPLC System; column: Waters Acquity UPLC HSS T3 1.8μ, 50 mm×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; flow rate: 0.40 ml/min; oven: 50° C.; UV detection: 210-400 nm.
Method 10 (LC-MS):
  Instrument: Micromass Quattro Micro MS with HPLC Agilent Series 1100; column: Thermo Hypersil GOLD 3μ 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→3.0 min 10% A→4.0 min 10% A→4.01 min 100% A (flow rate 2.5 ml/min)→5.00 min 100% A; oven: 50° C.; flow rate: 2 ml/min; UV detection: 210 nm.
Starting Materials and Intermediates:

Example 1A

4-Methyl-3-(methylsulfanyl)benzonitrile

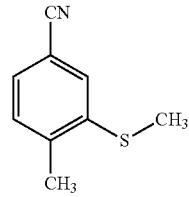

Method A:
  The reaction was carried out under argon. 3-Fluoro-4-methylbenzonitrile (3000 mg, 22.2 mmol) and sodium methanethiolate (1572 mg, 20.2 mmol) were initially charged in DMF (30 ml), potassium carbonate (6973 mg, 50.5 mmol) was added and the mixture was stirred under reflux overnight. The reaction was then concentrated, the residue was suspended in methylene chloride/methanol (10:1) and the insoluble potassium carbonate was filtered off. The filtrate was reconcentrated and the residue was chromatographed on silica gel (mobile phase: cyclohexane/ethyl acetate 10:1). This gave 2.51 g (64% of theory) of the desired compound.
Method B:
  The reaction was carried out with the aid of a washer filled with sodium hypochlorite solution. 3-Fluoro-4-methylbenzonitrile (200 g, 1479.9 mmol) was initially charged in DMF (1.5 liters) and warmed to 40° C., and sodium methanethiolate (altogether 126.8 g, 1627.9 mmol) was added a little at a time (about 25 g per portion). During the addition, the temperature increased to 100° C. The reaction mixture was stirred initially at a bath temperature of 175° C. for 1.5 h and then at room temperature overnight. The reaction mixture was then poured into water (7.5 liters) and extracted twice with ethyl acetate (1875 ml each). The combined organic phases were washed with saturated sodium chloride solution (1875 ml) and concentrated on a rotary evaporator, and the residue was chromatographed on silica gel (mobile phase: petroleum ether/ethyl acetate 95:5, about 30 liters). Removal of the solvent on a rotary evaporator and drying under high vacuum gave 172 g (71% of theory) of the desired compound.

GC-MS (Method 1): $R_t$=5.25 min; MS (ESIpos): m/z (%)=163.0 (100) $[M]^+$ $^1$H-NMR (400 MHz, DMSO-$d_6$): δ=2.30 (s, 3H), 2.54 (s, 3H), 7.38 (d, 1H), 7.52 (dd, 1H), 7.58 (br. s, 1H).

Example 2A

4-Methyl-3-(methylsulfonyl)benzonitrile

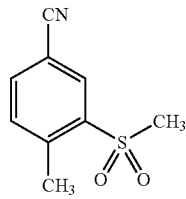

Method A:

4-Methyl-3-(methylsulfanyl)benzonitrile (14 050 mg, 80.1 mmol; Example 1A) was dissolved in dichloromethane (700 ml) and cooled to 0° C., and 3-chloroperbenzoic acid (50 923 mg, 206.6 mmol) was added slowly. The mixture was then stirred initially at 0° C. for 40 min and then at room temperature overnight. The precipitated 3-chlorobenzoic acid was filtered off, the filtrate was washed with 1N aqueous sodium hydroxide solution and the organic phase was dried over sodium sulfate and concentrated. The residue was purified by silica gel chromatography (mobile phase: cyclohexane/ethyl acetate 1:1, 1:2). This gave 13.65 g (81% of theory) of the desired compound.

Method B:

3-Chloroperbenzoic acid (2501 g, 10 144.4 mmol) was dissolved in 27.2 liters of dichloromethane and cooled to 10° C., and 4-methyl-3-(methylsulfanyl)benzonitrile (552 g, 3381.5 mmol; Example 1A) was added a little at a time. After the addition had ended, the mixture was stirred at RT for 5 h. The precipitated 3-chlorobenzoic acid was filtered off with suction and the solid was washed with dichloromethane (3 liters). The combined filtrates were stirred with 1N aqueous sodium hydroxide solution (15 liters), the mixture was filtered and the organic phase was separated off. The latter was once more stirred with 1N aqueous sodium hydroxide solution (15 liters), separated from the sodium hydroxide solution, dried and concentrated on a rotary evaporator. The residue was suspended in diethyl ether (4 liters), stirred for 10 min and then filtered. The solid was washed with a little diethyl ether and dried under high vacuum. This gave 613 g (93% of theory) of the desired compound.

GC-MS (Method 1): $R_t$=6.59 min; MS (ESIpos): m/z (%)=195.0 (100) $[M]^+$ $^1$H-NMR (400 MHz, DMSO-$d_6$): δ=2.30 (s, 3H), 2.54 (s, 3H), 7.38 (d, 1H), 7.52 (dd, 1H), 7.58 (br. s, 1H).

Example 3A

4-[2-(Dimethylamino)ethenyl]-3-(methylsulfonyl)benzonitrile

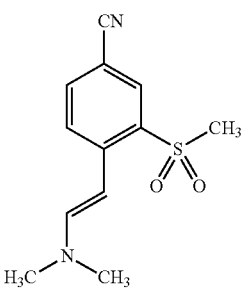

Method A:

The reaction was carried out under argon. At 140° C., 4-methyl-3-(methylsulfonyl)benzonitrile (13 000 mg, 66.6 mmol; Example 2A) and 1,1-dimethoxy-N,N-dimethylmethanamine (10 315 mg, 86.6 mmol) were stirred in DMF (200 ml) for 14 h. To bring the reaction to completion, more 1,1-dimethoxy-N,N-dimethylmethanamine (3967 mg, 33.3 mmol) was then added, and the mixture was stirred at 140° C. for a further 24 h. The DMF was then removed on a rotary evaporator, and the residue was reacted without further purification in the next step.

Method B:

The reaction was carried out under argon. 4-Methyl-3-(methylsulfonyl)benzonitrile (612 g, 3134.6 mmol; Example 2A) was initially charged in DMF (6.12 liters), 1,1-dimethoxy-N,N-dimethylmethanamine (859 g, 7209.5 mmol) was added and the mixture was stirred at 140° C. for 7 h. The reaction mixture was then poured into 35 liters of 10% strength sodium chloride solution and extracted twice with in each case 10 liters of ethyl acetate. The combined organic phases were washed with saturated sodium chloride solution (5 liters), dried and concentrated on a rotary evaporator, and the residue was dried under high vacuum overnight. This gave 1098 g (98% of theory) of the desired compound.

GC-MS (Method 1): $R_t$=8.95 min; MS (ESIpos): m/z (%)=250.0 (10) $[M]^+$.

Example 4A

4-Formyl-3-(methylsulfonyl)benzonitrile

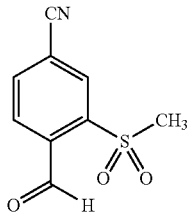

Method A:

4-[2-(Dimethylamino)ethenyl]-3-(methylsulfonyl)benzonitrile (16 666 mg, 66.6 mmol; Example 3A) was initially charged in water/THF (1:1, 500 ml), sodium periodate (42 722 mg, 199.7 mmol) was added and the mixture was stirred at room temperature overnight. The precipitated solid was filtered off and washed with ethyl acetate. The combined organic phases were washed with saturated sodium bicarbonate solution and saturated sodium chloride solution, dried over sodium sulfate, filtered and concentrated. The residue was purified by silica gel chromatography (mobile phase: cyclohexane/ethyl acetate 1:1). This gave 4.6 g (33% of theory) of the desired compound.

Method B:

4-[2-(Dimethylamino)ethenyl]-3-(methylsulfonyl)benzonitrile (1098 g, 3070.5 mmol; Example 3A) was initially charged in THF/water (1:1, 13.8 liters), sodium periodate (1970 g, 9211.4 mmol) was added and the mixture was stirred at room temperature for 1 h. The precipitated solid was filtered off with suction and washed with ethyl acetate (17 liters). Water (17 liters) was added to the combined filtrates, and after the extraction the aqueous phase was removed. The organic phase was washed with saturated sodium bicarbonate solution (8.5 liters) and saturated sodium chloride solution (8.5 liters), and then dried and concentrated on a rotary evaporator. The residue was purified by silica gel chromatography (mobile phase: dichloromethane/ethyl acetate 9:1, 60 liters). The product fractions were concentrated, the residue was suspended in petroleum ether and then filtered off with suction and the solid was dried under high vacuum overnight. This gave 436 g (65% of theory) of the desired compound.

GC-MS (Method 1): $R_t$=6.89 min; MS (ESIpos): m/z (%)=191.1 (15) [M-18]$^+$, 161.0 (100).

$^1$H-NMR (400 MHz, DMSO-$d_6$): δ=3.57 (s, 3H), 8.10 (d, 1H), 8.39 (dd, 1H), 8.45 (d, 1H), 10.63 (s, 1H).

Example 5A (4S)-4-[4-Cyano-2-(methylsulfonyl)phenyl]-6-methyl-2-oxo-1-[3-(trifluoromethyl)phenyl]-1,2,3,4-tetrahydropyrimidine-5-carboxylic acid

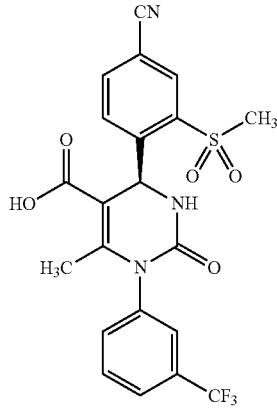 [SMILES: CC1=C(C(=O)O)[C@@H](c2ccc(C#N)cc2S(C)(=O)=O)NC(=O)N1c1cccc(C(F)(F)F)c1]

The reaction was carried out under argon. Allyl (4S)-4-[4-cyano-2-(methylsulfonyl)phenyl]-6-methyl-2-oxo-1-[3-(trifluoromethyl)phenyl]-1,2,3,4-tetrahydropyrimidine-5-carboxylate (800 mg, 1.54 mmol; Example 4) and morpholine (1.5 eq., 201 mg, 2.31 mmol) were initially charged in dry THF (25 ml) at RT. The reaction mixture was degassed repeatedly (evacuation followed by venting with argon). Under protective gas, tetrakis(triphenylphosphine)palladium(0) (0.05 eq., 89 mg, 0.077 mmol) was added, and the reaction mixture was stirred at RT for 90 min (HPLC control). The reaction mixture was then concentrated and the residue was taken up in ethyl acetate (500 ml). The organic phase was washed with saturated ammonium chloride solution (50 ml), with water (50 ml) and with conc. sodium chloride solution (50 ml), dried over sodium sulfate, filtered and concentrated under reduced pressure. The residue was purified by preparative HPLC (column: Gromsil C-18 10 μm; mobile phase: acetonitrile/water+0.1% TFA 10:90→90:10). This gave a colorless amorphous solid (696 mg, purity 86%, 81% of theory).

LC-MS (Method 6): $R_t$=2.15 min; MS (ESIpos): m/z (%)=480.1 (100) [M+H]$^+$; MS (ESIneg): m/z (%)=478.1 (100) [M–H]$^-$ $^1$H-NMR (400 MHz, DMSO-$d_6$): δ=2.14 (s, 3H), 3.45 (s, 3H), 6.35 (d, 1H), 7.14 (d, 1H), 7.72 (m, 2H), 7.80 (m, 1H), 7.86 (s, 1H), 8.11 (d, 1H), 8.27 (d, 1H), 8.36 (s, 1H), 12.64 (br. s, 1H).

Example 6A

4-Nitrophenyl (6S)-5-cyano-6-[4-cyano-2-(methylsulfonyl)phenyl]-4-methyl-2-oxo-3-[3-(trifluoromethyl)phenyl]-3,6-dihydropyrimidine-1(2H)-carboxylate

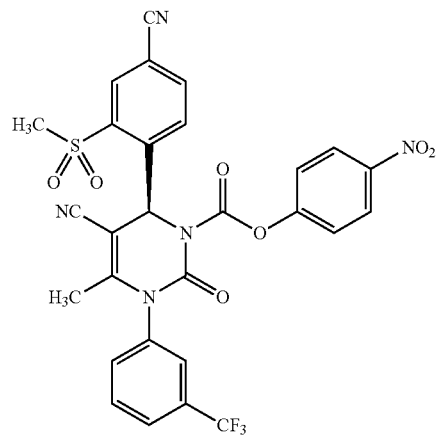 [SMILES: CC1=C(C#N)[C@@H](c2ccc(C#N)cc2S(C)(=O)=O)N(C(=O)Oc2ccc([N+](=O)[O-])cc2)C(=O)N1c1cccc(C(F)(F)F)c1]

(4S)-4-[4-Cyano-2-(methylsulfonyl)phenyl]-6-methyl-2-oxo-1-[3-(trifluoromethyl)phenyl]-1,2,3,4-tetrahydropyrimidine-5-carbonitrile (1.00 g, 2.17 mmol; Example 6) and triethylamine (659 mg, 6.52 mmol) were, together with a spatula tip of 4-N,N-dimethylaminopyridine, suspended in dichloromethane (8.3 ml). 4-Nitrophenyl chloroformate (875 mg, 4.34 mmol) was then added. The resulting solution was stirred at room temperature for 5 min, and water (1 ml) was then added. Furthermore, toluene (7 ml) was added to the contents of the flask, and the mixture was concentrated under reduced pressure. The residue was subjected to flash chromatography on silica gel (mobile phase: dichloromethane). The concentrated product fractions were triturated with ethanol (20 ml), and the resulting solid was filtered off with suction. This gave the target compound (559 mg, 39% of theory).

HPLC (Method 3): $R_t$=4.92 min (94%); MS (ESIpos): m/z (%)=626.3 (18) [M+H]$^+$ $^1$H-NMR (400 MHz, DMSO-$d_6$): δ=1.88 (s, 3H), 3.39 (s, 3H), 7.31 (s, 1H), 7.37 (d, 2H), 7.78-8.22 (m, 5H), 8.24 (d, 2H), 8.41 (d, 1H), 8.51 (s, 1H).

Example 7A (rac)-2,3-Dibromopropyl 6-(bromomethyl)-4-[4-cyano-2-(methylsulfonyl)phenyl]-2-oxo-1-[3-(trifluoromethyl)phenyl]-1,2,3,4-tetrahydropyrimidine-5-carboxylate

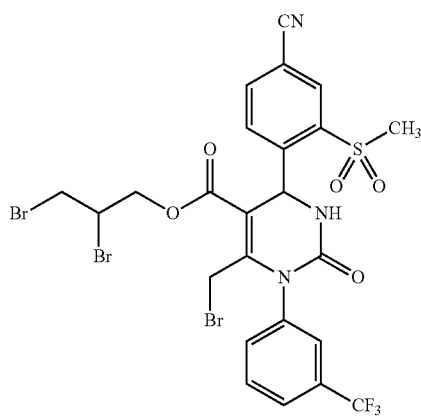 [SMILES: CS(=O)(=O)c1cc(C#N)ccc1C1NC(=O)N(c2cccc(C(F)(F)F)c2)C(CBr)=C1C(=O)OCC(Br)CBr]

At 0° C., a solution of bromine (335.6 mg, 2.1 mmol, 2.1 eq.) in chloroform (2 ml) was added dropwise to a solution of allyl (rac)-4-[4-cyano-2-(methylsulfonyl)phenyl]-6-methyl-2-oxo-1-[3-(trifluoromethyl)phenyl]-1,2,3,4-tetrahydropyrimidine-5-carboxylate (Example 3; 519 mg, 1.0 mmol) in chloroform (10 ml). The reaction mixture was stirred at RT overnight. HPLC control then showed complete conversion. The mixture was diluted with dichloromethane (50 ml) and then washed with 10% strength aqueous sodium sulfite solution (2×50 ml) and saturated aqueous sodium chloride solution (30 ml). The organic phase was dried over sodium sulfate, filtered and concentrated under reduced pressure, and the residue was dried under high vacuum. This gave a solid as crude product (880 mg, quant., purity according to LC-MS about 94%) which was reacted further without further purification.

LC-MS (Method 6): $R_t$=2.79 min; MS (ESIpos): m/z (%)=759.8 (100) [M+H]$^+$; MS (ESIneg): m/z (%)=714.9 (90), 758.0 (100) [M−H]$^-$.

Example 8A

3-Fluoro-4-formylbenzonitrile

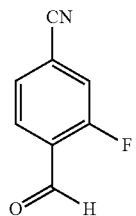 [SMILES: N#Cc1ccc(C=O)c(F)c1]

The reaction was carried out under argon. 3-Fluoro-4-methylbenzonitrile (121 g, 895 mmol) and N,N-dimethylformamide dimethyl acetal (245 g, 2.06 mol) were dissolved in DMF (1.8 liters) and stirred under reflux overnight. The contents of the flask was then poured into water (2 liters), the mixture was extracted twice with ethyl acetate and the combined organic phases were washed with saturated sodium chloride solution. The organic phase was concentrated, and the residue was dissolved again in THF/water (1:1, 2.7 liters). Sodium periodate (503 g, 2.35 mol) was added, and the mixture was stirred at room temperature for one hour. The precipitate was then separated off, and the filtrate was recovered and extracted repeatedly with ethyl acetate. The combined organic phases were washed once with saturated sodium bicarbonate solution and once with saturated sodium chloride solution, dried and concentrated to give an oil. This was purified by column chromatography on silica gel (mobile phase: petroleum ether/dichloromethane 6:4, then 4:6, finally pure dichloromethane). The product fractions were concentrated. This gave 28.0 g (20% of theory) of the target compound as a white crystalline solid.

GC-MS (Method 1): $R_t$=3.63 min; MS (ESIpos): m/z (%)=149.0 (48) [M]$^+$, 150.0 (5) [M+H]$^+$ $^1$H-NMR (400 MHz, DMSO-d$_6$): δ=7.89 (d, 1H), 8.00 (t, 1H), 8.11 (d, 1H), 10.24 (s, 1H).

Example 9A

4-Formyl-3-(methylsulfanyl)benzonitrile

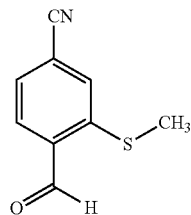

3-Fluoro-4-formylbenzonitrile (2.00 g, 13.4 mmol; Example 8A) was dissolved in DMSO (27 ml), and sodium methanethiolate (1.50 g, 21.5 mmol) was added with ice-bath cooling. The mixture was stirred for 45 min and then diluted with water (100 ml). The resulting precipitated product was filtered off with suction, washed with water and dried under reduced pressure. This gave 1.36 g (51% of theory) of the target compound as a yellow crystalline solid.

GC-MS (Method 1): $R_t$=5.90 min; MS (ESIpos): m/z (%)=177.0 (100) [M]$^+$, 178.0 (11) [M+H]$^+$.

Example 10A (rac)-4-[4-Cyano-2-(methylsulfanyl)phenyl]-6-methyl-2-oxo-1-[3-(trifluoromethyl)phenyl]-1,2,3,4-tetrahydropyrimidine-5-carboxylic acid

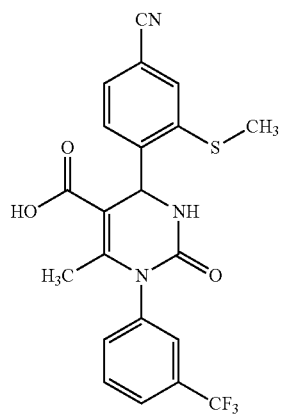 [SMILES: CSc1cc(C#N)ccc1C1NC(=O)N(c2cccc(C(F)(F)F)c2)C(C)=C1C(=O)O]

Allyl (rac)-4-[4-cyano-2-(methylsulfanyl)phenyl]-6-methyl-2-oxo-1-[3-(trifluoromethyl)phenyl]-1,2,3,4-tetrahydropyrimidine-5-carboxylate (750 mg, 1.54 mmol; Example 39) was dissolved in THF (10 ml), and morpholine (201 mg, 2.308 mmol) was added. The reaction solution was saturated with argon (argon was bubbled through the solution for 30 min). Tetrakis(triphenylphosphine)palladium(0) (7.47 mg, 0.006 mmol) was then added, and the mixture was stirred at RT overnight. Since, by HPLC control, only little conversion could be observed, more tetrakis(triphenylphosphine)palladium(0) (7.47 mg, 0.006 mmol) was added, and the mixture was stirred at RT for a further 3 h. The contents of the flask was then filtered through kieselguhr, and the residue was washed with THF. The filtrate was concentrated under reduced pressure and the residue was recrystallized from diethyl ether (15 ml). The crystals were filtered off with suction and dried under high vacuum. This gave 663 mg (96% of theory) of the target compound.

LC-MS (Method 4): $R_t$=1.10 min; MS (ESIpos): m/z (%)=448.0 (100) [M+H]$^+$; MS (ESIneg): m/z (%)=446.3 (100) [M−H]$^−$.

Example 11A (4S)-4-[4-Cyano-2-(methylsulfanyl)phenyl]-6-methyl-2-oxo-1-[3-(trifluoromethyl)phenyl]-1,2,3,4-tetrahydropyrimidine-5-carboxylic acid

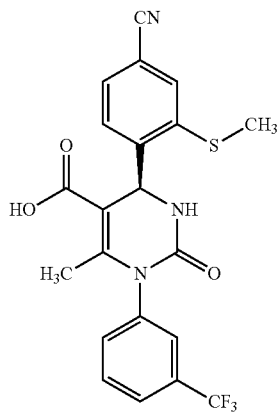 [SMILES: CSc1cc(C#N)ccc1[C@H]1NC(=O)N(c2cccc(C(F)(F)F)c2)C(C)=C1C(=O)O]

(rac)-4-[4-Cyano-2-(methylsulfanyl)phenyl]-6-methyl-2-oxo-1-[3-(trifluoromethyl)phenyl]-1,2,3,4-tetrahydropyrimidine-5-carboxylic acid (663 mg, 1.48 mmol; Example 10A) was separated into the enantiomers by preparative HPLC chromatography on a chiral phase [column: chiral silica gel phase based on the selector poly(N-methacryloyl-D-leucine-dicyclopropylmethylamide); column dimensions: 670 mm×40 mm; sample preparation: the sample was dissolved in 20 ml of methanol/ethyl acetate 1:3; injection volume: 15 ml; gradient elution: ethyl acetate (100%)→methanol (100%); flow rate: 80 ml/min; temperature: 25° C.; detection: 260 nm]. This gave 279 mg (84% of theory, 96% ee) of the 4S-enantiomer as a colorless amorphous solid.

HPLC (Method 2): $R_t$=4.15 min.

MS (DCI/NH$_3$): m/z=448.1 [M+H]$^+$ $^1$H-NMR (400 MHz, DMSO-d$_6$): δ=2.07 (s, 3H), 2.57 (s, 3H), 5.80 (d, 1H), 7.62-7.83 (m, 7H), 8.02 (d, 1H).

Optical rotation: $[α]^{20}_{Na}$=+14.0° (c=0.210 in DMF).

Example 12A tert-Butyl [(3R)-1-{[(6S)-5-cyano-6-[4-cyano-2-(methylsulfonyl)phenyl]-4-methyl-2-oxo-3-[3-(trifluoromethyl)phenyl]-3,6-dihydropyrimidin-1(2H)-yl]carbonyl}piperidin-3-yl]carbamate

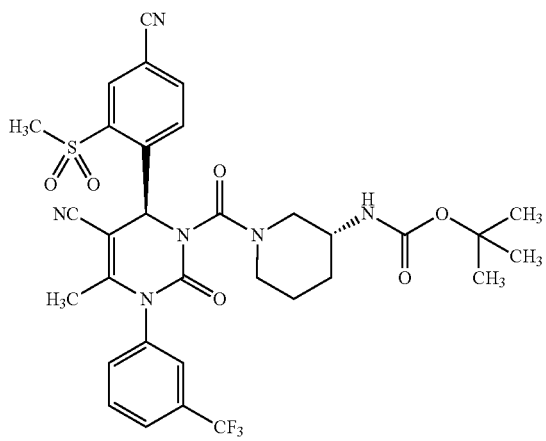 [SMILES: CC1=C(C#N)[C@@H](c2ccc(C#N)cc2S(C)(=O)=O)N(C(=O)N2CCC[C@@H](NC(=O)OC(C)(C)C)C2)C(=O)N1c1cccc(C(F)(F)F)c1]

4-Nitrophenyl (6S)-5-cyano-6-[4-cyano-2-(methylsulfonyl)phenyl]-4-methyl-2-oxo-3-[3-(trifluoromethyl)phenyl]-3,6-dihydropyrimidine-1(2H)-carboxylate (Example 6A; 100 mg, 0.16 mmol) was dissolved in acetonitrile (1.25 ml), and tert-butyl (3R)-piperidin-3-ylcarbamate (96.1 mg, 0.48 mmol) was added with stirring. The mixture was stirred at RT overnight. The reaction mixture was then purified directly by preparative HPLC (column: Kromasil C18, 125 mm×20 mm, 5 μm; mobile phase A: water with 0.01% formic acid, mobile phase B: acetonitrile; gradient: 0 min 10% B→2 min 10% B→9 min 90% B→12 min 90% B→12.1 min 10% B→15 min 10% B; flow rate: 0.35 ml/min; UV detection: 254 nm). The product fractions were combined and concentrated under reduced pressure. This gave 81 mg (74% of theory) of the target compound.

HPLC (Method 2): $R_t$=4.90 min.

MS (ESIpos): m/z (%)=709.1 (35) [M+Na]$^+$.

Example 13A (rac)-Ethyl 6-(bromomethyl)-4-[4-cyano-2-(methylsulfonyl)phenyl]-2-oxo-1-[3-(trifluoromethyl)phenyl]-1,2,3,4-tetrahydropyrimidine-5-carboxylate

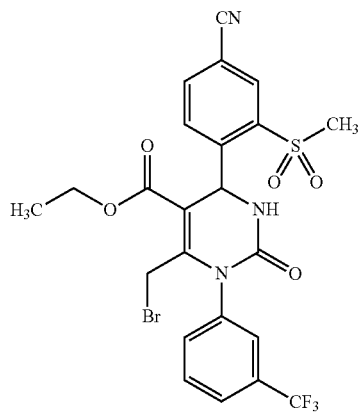 [SMILES: CCOC(=O)C1=C(CBr)N(c2cccc(C(F)(F)F)c2)C(=O)NC1c1ccc(C#N)cc1S(C)(=O)=O]

(rac)-Ethyl 4-[4-cyano-2-(methylsulfonyl)phenyl]-6-methyl-2-oxo-1-[3-(trifluoromethyl)phenyl]-1,2,3,4-tetrahydropyrimidine-5-carboxylate (Example 115; 3.00 g, 5.62 mmol) was dissolved in chloroform (49.9 ml), and the solution was cooled to 0° C. on an ice bath. Bromine (987 mg, 6.18 mmol) was then added dropwise. Subsequently, the ice bath was removed and the reaction mixture was stirred at RT for 1 h. Sodium thiosulfate solution (50 ml) was then added, and the organic phase was separated off, dried over sodium sulfate and concentrated under reduced pressure. The residue was triturated with diethyl ether, and the solid was filtered off with suction and washed with diethyl ether. This gave 2.96 g (90% of theory) of the target compound as a yellow crystalline solid.

HPLC (Method 2): $R_t$=4.73 min.

MS (ESIpos): m/z (%)=586 (57), 588 (62) $[M+H]^+$ $^1$H-NMR (400 MHz, DMSO-$d_6$): δ=0.97 (t, 3H), 3.50 (s, 3H), 3.94-4.09 (q, 2H), 4.18 (d, 1H), 4.70 (d, 1H), 6.48 (s, 1H), 7.47 (s, 1H), 7.70-7.95 (m, 4H), 8.07 (br. s, 1H), 8.31 (d, 1H), 8.42 (s, 1H).

Example 14A 2,3-Dibromopropyl (4S)-6-(bromomethyl)-4-[4-cyano-2-(methylsulfonyl)phenyl]-3-methyl-2-oxo-1-[3-(trifluoromethyl)phenyl]-1,2,3,4-tetrahydropyrimidine-5-carboxylate

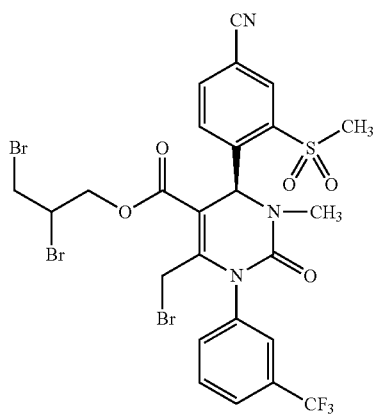 [SMILES: CN1C(=O)N(c2cccc(C(F)(F)F)c2)C(CBr)=C(C(=O)OCC(Br)CBr)[C@H]1c1ccc(C#N)cc1S(C)(=O)=O]

At 0° C., a solution of bromine (320.8 mg, 2.0 mmol, 2.1 eq.) in chloroform (5 ml) was added dropwise to a solution of allyl (4S)-4-[4-cyano-2-(methylsulfonyl)phenyl]-3,6-dimethyl-2-oxo-1-[3-(trifluoromethyl)phenyl]-1,2,3,4-tetrahydropyrimidine-5-carboxylate (510 mg, 0.96 mmol) in chloroform (15 ml). The reaction mixture was stirred at RT for 2 h. HPLC control then showed complete conversion. The mixture was diluted with dichloromethane (100 ml) and subsequently washed with 10% strength aqueous sodium sulfite solution (2×50 ml) and saturated aqueous sodium chloride solution (30 ml). The organic phase was dried over sodium sulfate, filtered and concentrated under reduced pressure, and the residue was dried under high vacuum. This gave a solid as a crude product (803 mg, quant.) which was reacted further without further purification.

LC-MS (Method 4): $R_t$=1.50 min; MS (ESIpos): m/z (%)=773.7 (100) $[M+H]^+$.

Example 15A 4-(1,3-Dioxan-2-yl)-3-fluorobenzonitrile

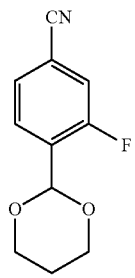 [SMILES: N#Cc1ccc(C2OCCCO2)c(F)c1]

4-Cyano-2-fluorobenzaldehyde (65 g, 436 mmol) and 1,3-propanediol (36.5 g, 479 mmol; 1.1 eq.) were, together with 4-toluenesulfonic acid monohydrate (1.66 g, 8.72 mmol; 0.02 eq.), initially charged in toluene (1000 ml) and stirred at boiling point on a water separator for 6 h. The reaction mixture was then washed with saturated sodium bicarbonate solution (3×300 ml) and saturated sodium chloride solution (3×300 ml). The organic phase was dried over sodium sulfate and concentrated. The title compound was obtained as a solid (92 g, quant.).

GC-MS (Method 1): $R_t$=5.49 min; MS (ESIpos): m/z (%)=206.1 (100) $[M-H]^+$ $^1$H-NMR (400 MHz, DMSO-$d_6$): δ=1.46 (d, 1H), 2.00 (m, 1H), 4.00 (t, 2H), 4.15 (dd, 2H), 5.80 (s, 1H), 7.70 (m, 2H), 7.90 (m, 1H).

Example 16A 4-(1,3-Dioxan-2-yl)-3-(ethylsulfanyl)benzonitrile

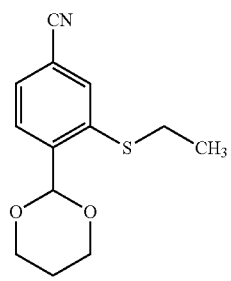 [SMILES: CCSc1cc(C#N)ccc1C1OCCCO1]

The reaction was carried out under argon. 4-(1,3-Dioxan-2-yl)-3-fluorobenzonitrile (4.14 g, 20 mmol) and sodium ethanethiolate (1.68 g, 20 mmol; 1 eq.) were initially charged in DMF (100 ml). Potassium carbonate (6.91 g, 50 mmol; 2.5 eq.) was added at RT, and the mixture was stirred at 100° C. for 5 h. TLC control then showed complete conversion. The mixture was concentrated and the residue was subjected to flash chromatography on silica gel (mobile phase: cyclohexane→cyclohexane/ethyl acetate 4:1). The title compound was obtained as a solid (4.8 g, 97% of theory).

MS (DCI/NH$_3$): m/z=266.1 $[M+NH_3]^+$

¹H-NMR (400 MHz, DMSO-d₆): δ=1.25 (t, 3H), 1.45 (d, 1H), 2.00 (m, 1H), 3.10 (q, 2H), 4.00 (m, 2H), 4.15 (m, 2H), 5.70 (s, 1H), 7.65 (m, 2H), 7.85 (m, 1H).

Example 17A 4-(1,3-Dioxan-2-yl)-3-(ethylsulfonyl)benzonitrile

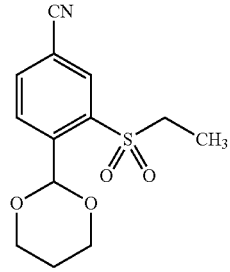 [SMILES: CCS(=O)(=O)c1cc(C#N)ccc1C1OCCCO1]

4-(1,3-Dioxan-2-yl)-3-(ethylsulfanyl)benzonitrile (1060 mg, 4.25 mmol) was initially charged in dichloromethane (45 ml). At 0° C., MCPBA (2641 mg, 15.3 mmol; 3.6 eq.) was added a little at a time. The mixture was slowly warmed to RT and then stirred for 16 h. The reaction mixture was then diluted with dichloromethane (200 ml), subsequently washed with 5% strength aqueous sodium carbonate solution (6×50 ml) and saturated sodium chloride solution (50 ml), dried over solid sodium sulfate, filtered and concentrated. The resulting product (1230 mg, quant., purity according to LC-MS 100%) was reacted further as such.

LC-MS (Method 4): $R_t$=0.97 min; MS (ESIpos): m/z (%)=208.0 (100), 282.1 (20) [M+H]⁺

MS (DCI/NH₃): m/z (%)=282.0 (15) [M+H]⁺, 299.1 (100) [M+NH₄]⁺

¹H-NMR (400 MHz, DMSO-d₆): δ=1.13 (t, 3H), 1.50 (d, 1H), 2.05 (m, 1H), 3.40 (q, 2H), 4.00 (m, 2H), 4.20 (m, 2H), 6.30 (s, 1H), 8.00 (m, 2H), 8.25 (m, 1H).

Example 18A 3-(Ethylsulfonyl)-4-formylbenzonitrile

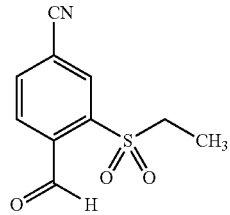

In an Emrys microwave, 4-(1,3-dioxan-2-yl)-3-(ethylsulfonyl)benzonitrile (1230 mg, 4.4 mmol) and pyridinium 4-toluenesulfonate (814 mg, 3.3 mmol; 0.75 eq.) in acetone/water (1:1, 20 ml) were heated with stirring at 165° C. for 7 min. The reaction mixture was then added to water (150 ml) and extracted with ethyl acetate (6×50 ml). The combined organic phases were then washed with saturated sodium chloride solution (30 ml), dried over sodium sulfate, filtered and concentrated under reduced pressure. The crude product was subjected to flash chromatography on silica gel (mobile phase: cyclohexane→cyclohexane/ethyl acetate 3:2). The title compound was isolated as a solid (0.89 g, 90% of theory).

¹H-NMR (400 MHz, DMSO-d₆): δ=1.22 (t, 3H), 3.65 (q, 2H), 8.10 (m, 2H), 8.40 (m, 1H), 10.60 (s, 1H).

Example 19A (rac)-4-[4-Cyano-2-(ethylsulfonyl)phenyl]-6-methyl-2-oxo-1-[3-(trifluoromethyl)phenyl]-1,2,3,4-tetrahydropyrimidine-5-carboxylic acid

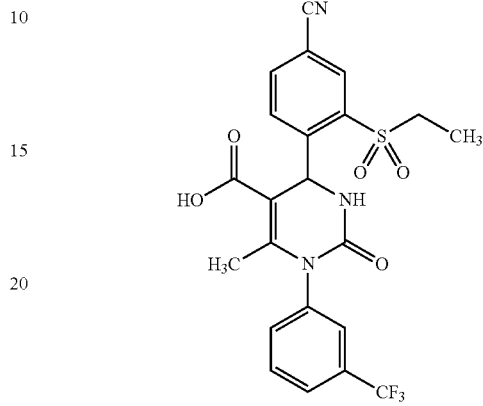

The reaction was carried out under argon. Allyl (rac)-4-[4-cyano-2-(ethylsulfonyl)phenyl]-6-methyl-2-oxo-1-[3-(trifluoromethyl)phenyl]-1,2,3,4-tetrahydropyrimidine-5-carboxylate (1300 mg, 2.44 mmol) and morpholine (1.5 eq., 318 mg, 3.66 mmol) were initially charged in dry THF (65 ml) at RT. The reaction mixture was degassed repeatedly (evacuation followed by venting with argon). Under protective gas, tetrakis(triphenylphosphine)palladium(0) (0.05 eq., 141 mg, 0.122 mmol) was added, and the reaction mixture was stirred at RT for 16 h (HPLC control). The mixture was then concentrated, and the residue was taken up in ethyl acetate (100 ml). The organic phase was washed with 0.1 N hydrochloric acid (2×40 ml) and with saturated sodium chloride solution (3×30 ml), dried over sodium sulfate, filtered and concentrated under reduced pressure. Methanol (10 ml) was added to the residue. The precipitated product was filtered off with suction and washed with methanol (2×5 ml). The title compound was isolated as a solid (1120 mg, 93% of theory).

LC-MS (Method 5): $R_t$=1.76 min; MS (ESIpos): m/z (%)=494.1 (100) [M+H]⁺; MS (ESIneg): m/z (%)=492.1 (100) [M−H]⁻

¹H-NMR (400 MHz, DMSO-d₆): δ=1.70 (t, 3H), 2.13 (s, 3H), 3.60 (m, 2H), 6.21 (br. d, 1H), 7.00 (d, 1H), 7.70-7.85 (m, 4H), 8.10 (br. d, 1H), 8.30-8.35 (m, 2H), 12.65 (br. s, 1H).

Example 20A 4-(1,3-Dioxan-2-yl)-3-[(2-hydroxyethyl)sulfanyl]benzonitrile

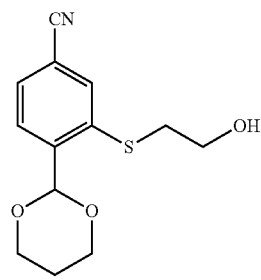 [SMILES: N#Cc1ccc(C2OCCCO2)c(SCCO)c1]

The reaction was carried out under argon. 4-(1,3-Dioxan-2-yl)-3-fluorobenzonitrile (2.07 g, 10 mmol; 1.1 eq.) and 2-mercaptoethanol (0.71 g, 9.1 mmol; 1 eq.) were initially charged in DMF (50 ml). Potassium carbonate (3.14 g, 22.7 mmol; 2.5 eq.) was added at RT, and the mixture was stirred at boiling point for 1 h. TLC control then showed complete conversion. The mixture was concentrated and the residue was subjected to flash chromatography on silica gel (mobile phase: cyclohexane→cyclohexane/ethyl acetate 1:2). The title compound was obtained as a solid (2.33 g, 88% of theory).

$^1$H-NMR (400 MHz, DMSO-$d_6$): δ=1.45 (d, 1H), 2.00 (m, 1H), 3.14 (t, 2H), 3.55 (q, 2H), 4.00 (m, 2H), 4.15 (m, 2H), 5.00 (t, 1H), 5.70 (s, 1H), 7.65 (m, 2H), 7.90 (m, 1H).

Example 21A 4-(1,3-Dioxan-2-yl)-3-[(2-hydroxyethyl)sulfonyl]benzonitrile

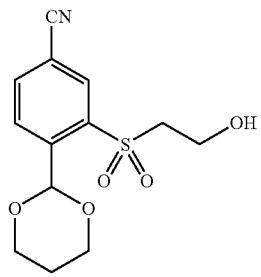 [SMILES: N#Cc1ccc(C2OCCCO2)c(S(=O)(=O)CCO)c1]

4-(1,3-Dioxan-2-yl)-3-[(2-hydroxyethyl)sulfanyl]benzonitrile (2000 mg, 7.55 mmol) was initially charged in dichloromethane (60 ml). At 0° C., MCPBA (4460 mg, 18.1 mmol; 2.4 eq.) was added a little at a time. The reaction mixture was slowly warmed to RT and then stirred for 16 h. The reaction mixture was then diluted with dichloromethane (100 ml), subsequently washed with 5% strength aqueous sodium bicarbonate solution (4×50 ml) and saturated sodium chloride solution (50 ml), dried over solid sodium sulfate, filtered and concentrated. The product obtained (2.25 g, quant., purity according to LC-MS 100%) was reacted further as such.

LC-MS (Method 5): $R_t$=1.17 min; MS (ESIpos): m/z=298 [M+H]$^+$ $^1$H-NMR (400 MHz, DMSO-$d_6$): δ=1.50 (d, 1H), 2.05 (m, 1H), 3.60 (t, 2H), 3.70 (q, 2H), 4.00 (m, 2H), 4.20 (m, 2H), 4.90 (t, 1H), 6.30 (s, 1H), 8.00 (d, 1H), 8.25 (dd, 1H), 8.30 (d, 1H).

Example 22A

3-[(2-Hydroxyethyl)sulfonyl]-4-formylbenzonitrile

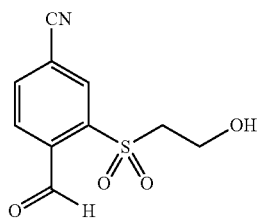 [SMILES: N#Cc1ccc(C=O)c(S(=O)(=O)CCO)c1]

In an Emrys microwave, 4-(1,3-dioxan-2-yl)-3-[(2-hydroxyethyl)sulfonyl]benzonitrile (1970 mg, 6.6 mmol) and pyridinium 4-toluenesulfonate (1249 mg, 4.97 mmol; 0.75 eq.) in acetone/water (1:1, 30 ml) were heated with stirring at 160° C. for 5 min. The reaction mixture was then added to water (200 ml) and extracted with ethyl acetate (8×50 ml). The combined organic phases were then washed with saturated sodium chloride solution (2×50 ml), dried over sodium sulfate, filtered and concentrated under reduced pressure. To increase the yield, the sodium chloride wash solution was reextracted with ethyl acetate. The title compound was obtained as a solid (1.57 g, 99% of theory).

MS (DCI/NH$_3$): m/z=257.1 [M+NH$_4$]$^+$.

Example 23A (rac)-4-[4-Cyano-2-((2-hydroxyethyl)sulfonyl)phenyl]-6-methyl-2-oxo-1-[3-(trifluoromethyl)phenyl]-1,2,3,4-tetrahydropyrimidine-5-carboxylic acid

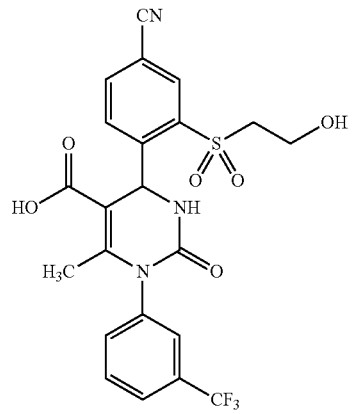 [SMILES: CC1=C(C(=O)O)C(c2ccc(C#N)cc2S(=O)(=O)CCO)NC(=O)N1c1cccc(C(F)(F)F)c1]

The reaction was carried out under argon. Allyl (rac)-4-[4-cyano-2-((2-hydroxyethyl)sulfonyl)phenyl]-6-methyl-2-oxo-1-[3-(trifluoromethyl)phenyl]-1,2,3,4-tetrahydropyrimidine-5-carboxylate (150 mg, 0.273 mmol) and morpholine (1.5 eq., 35.6 mg, 0.409 mmol) were initially charged in dry THF (4 ml) at RT. The reaction mixture was degassed repeatedly (evacuation followed by venting with argon). Under protective gas, tetrakis(triphenylphosphine)palladium(0) (0.05 eq., 15.8 mg, 0.014 mmol) was added, and the reaction mixture was stirred at RT for 1 h (HPLC control). The mixture was then concentrated, and the residue was taken up in ethyl acetate (60 ml). The organic phase was washed repeatedly with saturated ammonium chloride solution (3×20 ml), water (20 ml) and saturated sodium chloride solution (20 ml), dried over sodium sulfate, filtered and concentrated under reduced pressure. The crude product was purified by preparative HPLC (column: Gromsil C-18; mobile phase: acetonitrile/water+0.1% TFA 10:90→80:20). The title compound was obtained as a solid (60 mg, 43% of theory).

LC-MS (Method 6): $R_t$=2.04 min; MS (ESIpos): m/z (%)=510.1 (100) [M+H]$^+$; MS (ESIneg): m/z (%)=508.1 (100) [M−H]$^-$.

Example 24A (rac)-4-{2-[(2-{[tert-Butyl(dimethyl)silyl]oxy}ethyl)sulfonyl]-4-cyanophenyl}-6-methyl-2-oxo-1-[3-(trifluoromethyl)phenyl]-1,2,3,4-tetrahydropyrimidine-5-carboxamide

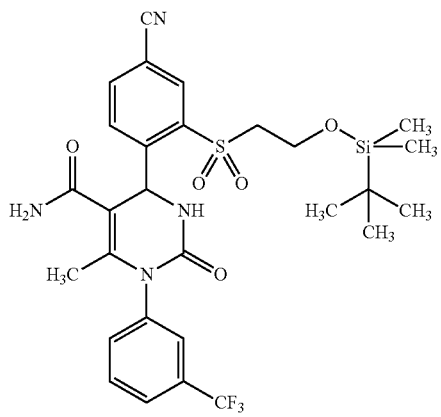 [SMILES: CC1=C(C(N)=O)C(c2ccc(C#N)cc2S(=O)(=O)CCO[Si](C)(C)C(C)(C)C)NC(=O)N1c1cccc(C(F)(F)F)c1]

The reaction was carried out under argon. (rac)-4-[4-Cyano-2-((2-hydroxyethylsulfonyl)phenyl]-6-methyl-2-oxo-1-[3-(trifluoromethyl)phenyl]-1,2,3,4-tetrahydropyrimidine-5-carboxamide (600 mg, 1.18 mmol) was initially charged in DMF (40 ml). At 0° C., imidazole (803 mg, 11.8 mmol; 10 eq.) was added, followed by tert-butyl(dimethyl)silyl chloride (1245 mg, 8.26 mmol; 7 eq.). The mixture was slowly warmed to RT and subsequently stirred for 16 h. The reaction mixture was then concentrated under high vacuum, the residue was taken up in ethyl acetate (200 ml) and the organic phase was washed with ammonium chloride solution (3×50 ml) and saturated sodium chloride solution (50 ml). The organic phase was then dried over sodium sulfate, filtered and concentrated. This gave a solid as crude product (740 mg, quant.), which was reacted without further purification.

LC-MS (Method 6): $R_t$=2.69 min; MS (ESIpos): m/z (%)=623.2 (100) [M+H]$^+$.

Example 25A (rac)-4-{2-[(2-{[tert-Butyl(dimethyl)silyl]oxy}ethyl)sulfonyl]-4-cyanophenyl}-6-methyl-2-oxo-1-[3-(trifluoromethyl)phenyl]-1,2,3,4-tetrahydropyrimidine-5-carbonitrile

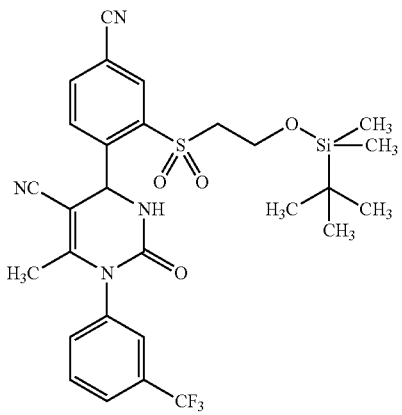

The reaction was carried out under argon. (rac)-4-{2-[(2-{[tert-Butyl(dimethyl)silyl]oxy}ethyl)sulfonyl]-4-cyanophenyl}-6-methyl-2-oxo-1-[3-(trifluoromethyl)phenyl]-1,2,3,4-tetrahydropyrimidine-5-carboxamide (740 mg, 1.18 mmol) was initially charged in dry THF (30 ml), methoxycarbonylsulfamoyltriethylammonium hydroxide (Burgess reagent; 1.699 g, 7.13 mmol; 6 eq.) was added and the mixture was stirred at RT. After 75 min, HPLC control showed complete conversion. The reaction mixture was then taken up in ethyl acetate (150 ml). The organic phase was washed with saturated sodium chloride solution (3×50 ml), dried over solid sodium sulfate, filtered and concentrated. The residue was subjected to flash chromatography on silica gel (mobile phase: cyclohexane/ethyl acetate 1:1). The title compound was obtained as a colorless solid (550 mg, 77% of theory).

LC-MS (Method 6): $R_t$=2.96 min; MS (ESIpos): m/z (%)=605.2 (100) [M+H]$^+$; MS (ESIneg): m/z (%)=560.2 (100), 603.3 (50) [M–H]$^-$.

Example 26A 4-(1,3-Dioxan-2-yl)-3-(propan-2-ylsulfanyl)benzonitrile

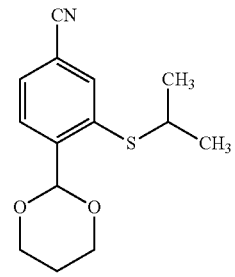 [SMILES: CC(C)Sc1cc(C#N)ccc1C1OCCCO1]

The reaction was carried out under argon. 4-(1,3-Dioxan-2-yl)-3-fluorobenzonitrile (5.51 g, 27 mmol) and sodium 2-propanethiolate (2.90 g, 26.6 mmol, purity 90%; 1 eq.) were initially charged in DMF (125 ml). Potassium carbonate (9.19 g, 66.5 mmol; 2.5 eq.) was added at RT, and the mixture was stirred at 100° C. for 4 h. TLC control then showed complete conversion. The reaction mixture was concentrated and the residue was subjected to flash chromatography on silica gel (mobile phase: cyclohexane→cyclohexane/ethyl acetate 4:1). The title compound was isolated as a solid (6.72 g, 96% of theory).

$^1$H-NMR (400 MHz, DMSO-d$_6$): δ=1.25 (d, 6H), 1.45 (d, 1H), 2.00 (m, 1H), 3.70 (m, 1H), 4.00 (m, 2H), 4.15 (m, 2H), 5.75 (s, 1H), 7.70 (m, 2H), 7.95 (m, 1H).

Example 27A 4-(1,3-Dioxan-2-yl)-3-(propan-2-ylsulfonyl)benzonitrile

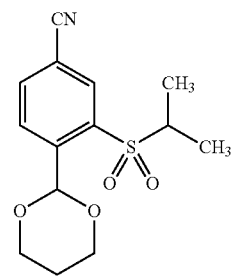 [SMILES: CC(C)S(=O)(=O)c1cc(C#N)ccc1C1OCCCO1]

4-(1,3-Dioxan-2-yl)-3-(propan-2-ylsulfanyl)benzonitrile (1090 mg, 4.14 mmol) was initially charged in dichloromethane (40 ml). At 0° C., MCPBA (2449 mg, 9.9 mmol; 2.4 eq.) was added a little at a time. The mixture was slowly warmed to RT and then stirred for 16 h. The reaction mixture was then diluted with dichloromethane, subsequently washed with saturated sodium bicarbonate solution (50 ml), 5% strength aqueous sodium carbonate solution (5×50 ml) and saturated sodium chloride solution (50 ml), dried over solid sodium sulfate, filtered and concentrated.

The product obtained in this manner (1.17 g, 96%, purity according to LC-MS 89%) was reacted without further purification.

LC-MS (Method 5): $R_t$=1.63 min; MS (ESIpos): m/z (%)=240.3 (100), 296.3 (40) [M+H]$^+$ MS (DCI/NH$_3$): m/z (%)=296.1 (25) [M+H]$^+$, 313.1 (100) [M+NH$_4$]$^+$.

Example 28A

4-Formyl-3-[(1-methylethyl)sulfonyl]benzonitrile

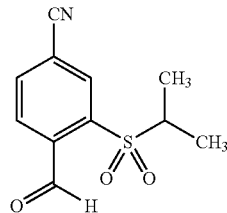 [SMILES: CC(C)S(=O)(=O)c1cc(C#N)ccc1C=O]

In an Emrys microwave, 4-(1,3-dioxan-2-yl)-3-(propan-2-ylsulfonyl)benzonitrile (1090 mg, 3.7 mmol) and pyridinium 4-toluenesulfonate (696 mg, 2.8 mmol; 0.75 eq.) in acetone/water (1:1, 15 ml) were heated with stirring at 165° C. for 7 min. The reaction mixture was then added to water (150 ml) and extracted with dichloromethane (9×30 ml). The combined organic phases were subsequently washed with saturated sodium chloride solution (30 ml), dried over sodium sulfate, filtered and concentrated under reduced pressure. The crude product was subjected to flash chromatography on silica gel (mobile phase: cyclohexane→cyclohexane/ethyl acetate 3:2). The title compound was isolated as a solid (0.764 g, 87% of theory).

$^1$H-NMR (400 MHz, DMSO-d$_6$): δ=1.25 (d, 6H), 3.80 (m, 1H), 8.10 (m, 1H), 8.40 (m, 2H), 10.60 (s, 1H).

Example 29A (rac)-4-{4-Cyano-2-[(1-methylethyl)sulfonyl]phenyl}-6-methyl-2-oxo-1-[3-(trifluoromethyl)phenyl]-1,2,3,4-tetrahydropyrimidine-5-carboxylic acid

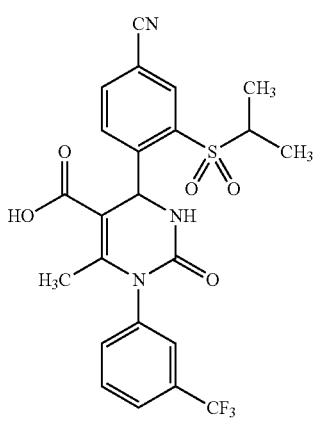 [SMILES: CC1=C(C(=O)O)C(c2ccc(C#N)cc2S(=O)(=O)C(C)C)NC(=O)N1c1cccc(C(F)(F)F)c1]

The reaction was carried out under argon. Allyl 4-{4-cyano-2-[(1-methylethyl)sulfonyl]phenyl}-6-methyl-2-oxo-1-[3-(trifluoromethyl)phenyl]-1,2,3,4-tetrahydropyrimidine-5-carboxylate (1200 mg, 2.19 mmol) and morpholine (1.5 eq., 286 mg, 3.30 mmol) were initially charged in dry THF (60 ml) at RT. The reaction mixture was degassed repeatedly (evacuation followed by venting with argon). Under protective gas, tetrakis(triphenylphosphine)palladium(0) (0.05 eq., 127 mg, 0.110 mmol) was added, and the reaction mixture was stirred at RT for 0.5 h (HPLC control). The mixture was then concentrated, and the residue was taken up in ethyl acetate (100 ml). The organic phase was washed with 0.1 N hydrochloric acid (40 ml) and with saturated sodium chloride solution (3×30 ml), dried over sodium sulfate, filtered and concentrated under reduced pressure. Methanol (10 ml) was added to the residue. The precipitated product was filtered off with suction and washed with a little methanol (2×5 ml). The title compound was isolated as a solid (1060 mg, 95% of theory).

LC-MS (Method 5): $R_t$=1.81 min; MS (ESIpos): m/z (%)=508.1 (100) [M+H]$^+$; MS (ESIneg): m/z (%)=506.1 (100) [M−H]$^−$.

Example 30A 4-(1,3-Dioxan-2-yl)-3-(phenylsulfanyl)benzonitrile

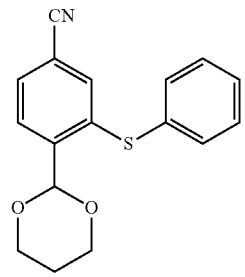 [SMILES: N#Cc1ccc(C2OCCCO2)c(Sc2ccccc2)c1]

The reaction was carried out under argon. 4-(1,3-Dioxan-2-yl)-3-fluorobenzonitrile (207 mg, 1 mmol) and thiophenol (100 mg, 0.9 mmol; 1.1 eq.) were initially charged in DMF (3 ml). Potassium carbonate (314 mg, 2.27 mmol; 2.5 eq.) was added at RT, and the mixture was stirred at 100° C. for 4 h. LC/MS control then showed complete conversion. The reaction mixture was purified directly by preparative HPLC (column: Gromsil C-18; mobile phase: acetonitrile/water+0.1% TFA 10:90→90:10). The title compound was obtained as a solid (238 mg, 80% of theory).

$^1$H-NMR (400 MHz, DMSO-d$_6$): δ=1.45 (d, 1H), 2.00 (m, 1H), 4.00 (m, 2H), 4.15 (dd, 2H), 5.85 (s, 1H), 7.35 (s, 1H), 7.45 (m, 5H), 7.75 (m, 2H).

Example 31A 4-(1,3-Dioxan-2-yl)-3-(phenylsulfonyl)benzonitrile

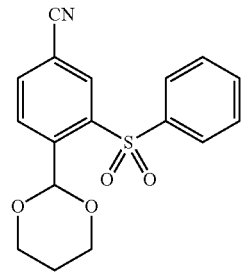 [SMILES: N#Cc1ccc(C2OCCCO2)c(S(=O)(=O)c2ccccc2)c1]

4-(1,3-Dioxan-2-yl)-3-(phenylsulfanyl)benzonitrile (230 mg, 0.773 mmol) was initially charged in dichloromethane (7 ml). At 0° C., MCPBA (458 mg, 1.85 mmol, content 70%; 2.4 eq.) was added a little at a time. The mixture was slowly warmed to RT and initially stirred for 3 h and then allowed to stand at 5° C. for a further 12 h. Water (0.5 ml) was then added, and the reaction mixture was concentrated under reduced pressure. The crude product was purified by preparative HPLC (column: Gromsil C-18; mobile phase: acetonitrile/water+0.1% TFA 10:90→75:25). The title compound was obtained as a solid (260 mg, quant.).

LC-MS (Method 5): $R_t$=1.84 min; MS (ESIpos): m/z (%)=330.2 (90) [M+H]$^+$.

Example 32A

4-Formyl-3-(phenylsulfonyl)benzonitrile

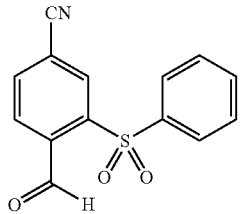 [SMILES: N#Cc1ccc(C=O)c(S(=O)(=O)c2ccccc2)c1]

In an Emrys microwave, 4-(1,3-dioxan-2-yl)-3-(phenylsulfonyl)benzonitrile (260 mg, 0.789 mmol) and pyridinium 4-toluenesulfonate (149 mg, 0.592 mmol; 0.75 eq.) in acetone/water (1:1, 3 ml) were heated with stirring at 160° C. for 6 min. The reaction mixture was then added to water (50 ml) and extracted with ethyl acetate (8×20 ml). The combined organic phases were subsequently washed with saturated sodium chloride solution (2×30 ml), dried over sodium sulfate, filtered and concentrated under reduced pressure. The title compound was obtained as a solid (0.21 g, quant.).

LC-MS (Method 6): $R_t$=2.11 min; MS (ESIpos): m/z (%)=272.2 (100) [M+H]$^+$ $^1$H-NMR (400 MHz, DMSO-$d_6$): δ=7.70 (m, 2H), 7.80 (m, 1H), 8.00 (d, 1H), 8.15 (m, 2H), 8.35 (dd, 1H), 8.70 (d, 1H), 10.65 (s, 1H).

Example 33A (rac)-4-{4-Cyano-2-[phenylsulfonyl]phenyl}-6-methyl-2-oxo-1-[3-(trifluoromethyl)phenyl]-1,2,3,4-tetrahydropyrimidine-5-carboxylic acid

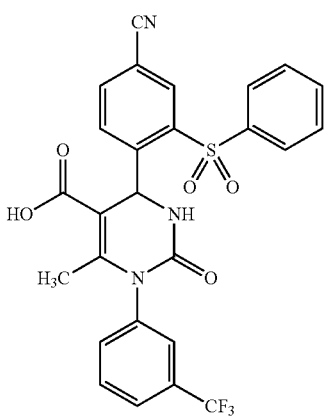 [SMILES: CC1=C(C(=O)O)C(c2ccc(C#N)cc2S(=O)(=O)c2ccccc2)NC(=O)N1c1cccc(C(F)(F)F)c1]

The reaction was carried out under argon. Allyl 4-[4-cyano-2-(phenylsulfonyl)phenyl]-6-methyl-2-oxo-1-[3-(trifluoromethyl)phenyl]-1,2,3,4-tetrahydropyrimidine-5-carboxylate (220 mg, 0.378 mmol) and morpholine (1.5 eq., 43 mg, 0.567 mmol) were initially charged in dry THF (6 ml) at RT. The reaction mixture was degassed repeatedly (evacuation followed by venting with argon). Under protective gas, tetrakis(triphenylphosphine)palladium(0) (0.05 eq., 22 mg, 0.019 mmol) was added, and the reaction mixture was stirred at RT for 16 h (HPLC control). The mixture was then concentrated, and the residue was taken up in ethyl acetate (100 ml). The organic phase was washed successively with 0.1 N hydrochloric acid (6 ml), saturated ammonium chloride solution (3×50 ml), water (30 ml) and saturated sodium chloride solution (30 ml), dried over sodium sulfate, filtered and concentrated under reduced pressure. The crude product was purified by preparative HPLC (column: Gromsil C-18; mobile phase: acetonitrile/water+0.1% TFA 10:90→80:20). The target product was obtained as a solid (104 mg, 51% of theory).

LC-MS (Method 6): $R_t$=2.35 min; MS (ESIpos): m/z (%)=542.1 (100) [M+H]$^+$; MS (ESIneg): m/z (%)=540.2 (80) [M−H]$^-$.

Example 34A (4S)-4-[4-Cyano-2-(methylsulfonyl)phenyl]-6-methyl-3-(methylsulfonyl)-2-oxo-1-[3-(trifluoromethyl)phenyl]-1,2,3,4-tetrahydropyrimidine-5-carboxylic acid

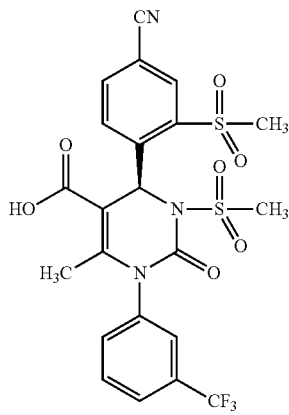 [SMILES: CC1=C(C(=O)O)[C@@H](c2ccc(C#N)cc2S(C)(=O)=O)N(S(C)(=O)=O)C(=O)N1c1cccc(C(F)(F)F)c1]

The reaction was carried out under argon. Allyl (4S)-4-[4-cyano-2-(methylsulfonyl)phenyl]-6-methyl-3-(methylsulfonyl)-2-oxo-1-[3-(trifluoromethyl)phenyl]-1,2,3,4-tetrahydropyrimidine-5-carboxylate (288 mg, 0.482 mmol) and morpholine (1.5 eq., 63 mg, 0.723 mmol) were initially charged in dry THF (5 ml) at RT. The reaction mixture was degassed repeatedly (evacuation followed by venting with argon). Under protective gas, tetrakis(triphenylphosphine)palladium(0) (0.05 eq., 28 mg, 0.024 mmol) was added, and the reaction mixture was stirred at RT for 1.5 h (HPLC control). The mixture was then concentrated under reduced pressure, and the residue was purified by preparative HPLC (column: Gromsil C-18; mobile phase: acetonitrile/water+0.1% TFA 10:90→75:25). This gave the title compound as a solid (187 mg, 70% of theory).

LC-MS (Method 5): $R_t$=1.81 min; MS (ESIpos): m/z (%)=540.1 (100), 558.1 (40) [M+H]$^+$; MS (ESIneg): m/z (%)=556.2 (10) [M−H]$^-$.

Example 35A (4S)-4-[4-Cyano-2-(methylsulfonyl)phenyl]-3,6-dimethyl-2-oxo-1-[3-(trifluoromethyl)phenyl]-1,2,3,4-tetrahydropyrimidine-5-carboxylic acid

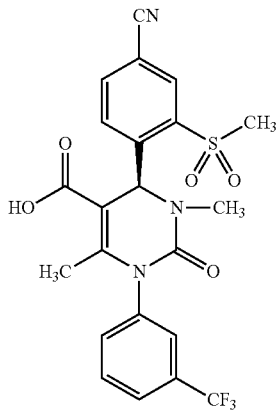 [SMILES: CC1=C(C(=O)O)[C@@H](c2ccc(C#N)cc2S(C)(=O)=O)N(C)C(=O)N1c1cccc(C(F)(F)F)c1]

The reaction was carried out under argon. Allyl (4S)-4-[4-cyano-2-(methylsulfonyl)phenyl]-3,6-dimethyl-2-oxo-1-[3-(trifluoromethyl)phenyl]-1,2,3,4-tetrahydropyrimidine-5-carboxylate (157 mg, 0.294 mmol) and morpholine (1.5 eq., 38 mg, 0.441 mmol) were initially charged in dry THF (5 ml) at RT. The reaction mixture was degassed repeatedly (evacuation followed by venting with argon). Under protective gas, tetrakis(triphenylphosphine)palladium(0) (0.05 eq., 17 mg, 0.015 mmol) was added, and the reaction mixture was stirred at RT for 16 h (HPLC control). The mixture was then concentrated under reduced pressure, and the residue was purified by preparative HPLC (column: Gromsil C-18; mobile phase: acetonitrile/water+0.1% TFA 10:90→90:10). This gave the title compound as a solid (120 mg, 83% of theory).

LC-MS (Method 5): $R_t$=1.84 min; MS (ESIpos): m/z (%)=494.1 (100) [M+H]$^+$; MS (ESIneg): m/z (%)=492.1 (100) [M−H]$^−$ $^1$H-NMR (400 MHz, DMSO-d$_6$): δ=2.05 (s, 3H), 2.75 (s, 3H), 3.45 (s, 3H), 6.70 (s, 1H), 7.75-7.80 (m, 3H), 7.90 (br. s, 1H), 8.15 (br. d, 1H), 8.30 (dd, 1H), 8.45 (d, 1H), 12.75 (br. s, 1H).

Example 36A (rac)-Allyl 4-(4-cyano-2-nitrophenyl)-6-methyl-2-oxo-1-[3-(trifluoromethyl)phenyl]-1,2,3,4-tetrahydropyrimidine-5-carboxylate

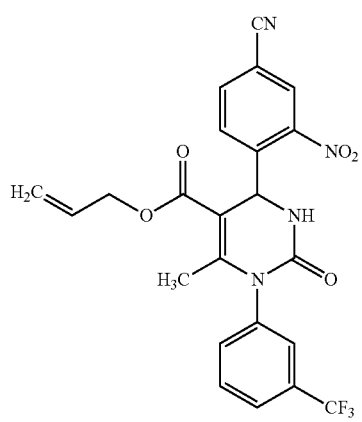 [SMILES: C=CCOC(=O)C1=C(C)N(c2cccc(C(F)(F)F)c2)C(=O)NC1c1ccc(C#N)cc1[N+](=O)[O-]]

The reaction was carried out under argon. Allyl acetoacetate (5.94 g, 41.5 mmol; 1.0 eq.) was initially charged in THF (117 ml) at RT. Subsequently, 4-cyano-2-nitrobenzaldehyde (10.45 g, 41.5 mmol, purity 70%; 1.0 eq.), 1-[3-(trifluoromethyl)phenyl]urea (8.48 g, 41.5 mmol) and triethyl phosphate (17.7 g) were added. The mixture was stirred under reflux for 16 h. For work-up, initially ice-water was added, and the mixture was then taken up in ethyl acetate (400 ml). The organic phase was dried over solid sodium sulfate, filtered and concentrated under reduced pressure. The crude product was recrystallized from hot water/isopropanol (2:1, ~400 ml). The solid obtained was triturated with diethyl ether (60 ml), once more filtered off with suction, washed with a little diethyl ether and dried under high vacuum. The title compound was obtained as a solid (16.63 g, 82% of theory).

LC-MS (Method 8): $R_t$=3.70 min; MS (ESIpos): m/z (%)=487.1 (100) [M+H]$^+$ $^1$H-NMR (400 MHz, DMSO-d$_6$): δ=2.10 (s, 3H), 4.40 (m, 2H), 4.95 (d, 1H), 5.05 (d, 1H), 5.70 (m, 1H), 6.15 (d, 1H), 6.05 (d, 1H), 7.70-7.90 (m, 4H), 8.10 (br. d, 1H), 8.25 (dd, 1H), 8.45 (d, 1H), 8.55 (d, 1H).

Example 37A (rac)-4-(4-Cyano-2-nitrophenyl)-6-methyl-2-oxo-1-[3-(trifluoromethyl)phenyl]-1,2,3,4-tetrahydropyrimidine-5-carboxylic acid

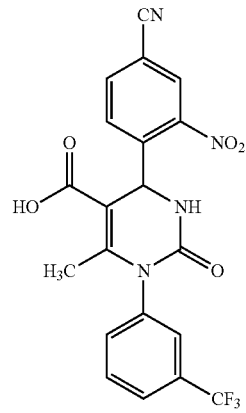 [SMILES: CC1=C(C(=O)O)C(c2ccc(C#N)cc2[N+](=O)[O-])NC(=O)N1c1cccc(C(F)(F)F)c1]

The reaction was carried out under argon. (rac)-Allyl 4-(4-cyano-2-nitrophenyl)-6-methyl-2-oxo-1-[3-(trifluoromethyl)phenyl]-1,2,3,4-tetrahydropyrimidine-5-carboxylate (15.0 g, 30.8 mmol) and morpholine (1.5 eq., 4.03 g, 46.3 mmol) were initially charged in dry THF (300 ml) at RT. The reaction mixture was degassed repeatedly (evacuation followed by venting with argon). Under protective gas, tetrakis(triphenylphosphine)palladium(0) (0.05 eq., 1.78 g, 1.54 mmol) was added, and the reaction mixture was stirred at RT for 2 h (HPLC control). The mixture was then concentrated, and the residue was taken up in ethyl acetate (700 ml). The organic phase was washed with 0.5 N hydrochloric acid (500 ml) and with saturated sodium chloride solution (300 ml), dried over sodium sulfate, filtered and concentrated under reduced pressure. The crude product was recrystallized from ethyl acetate and dried under high vacuum. The title compound was obtained as a solid (12.87 g, 93% of theory).

$^1$H-NMR (400 MHz, DMSO-d$_6$): δ=2.05 (s, 3H), 6.00 (d, 1H), 7.65-7.90 (m, 4H), 8.10 (d, 1H), 8.25 (dd, 1H), 8.40 (d, 1H), 8.50 (d, 1H), 12.5 (br. s, 1H).

Example 38A (4R)-4-(4-Cyano-2-nitrophenyl)-6-methyl-2-oxo-1-[3-(trifluoromethyl)phenyl]-1,2,3,4-tetrahydropyrimidine-5-carboxylic acid

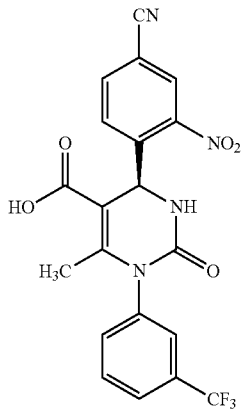 [SMILES: CC1=C(C(=O)O)[C@@H](c2ccc(C#N)cc2[N+](=O)[O-])NC(=O)N1c1cccc(C(F)(F)F)c1]

(rac)-4-(4-Cyano-2-nitrophenyl)-6-methyl-2-oxo-1-[3-(trifluoromethyl)phenyl]-1,2,3,4-tetrahydropyrimidine-5-carboxylic acid (590 g) was separated into the enantiomers by preparative HPLC chromatography on a chiral phase [column: chiral silica gel phase based on the selector poly(N-methacryloyl-L-leucine-tert-butylamide); column dimensions: 670 mm×40 mm; sample preparation: 100 g of sample dissolved in 2000 ml of THF; injection volume: 70 ml; mobile phase: ethyl acetate/methanol 100:1→1:100; flow rate: 80 ml/min; temperature: 24° C.; detection: 260 nm]. This gave 280 g (95% of theory; 99.6% ee) of the 4R enantiomer.

The enantiomeric excess (ee value) was determined chromatographically [column: chiral silica gel phase based on the selector poly(N-methacryloyl-L-leucine-tert-butylamide); column dimensions: 250 mm×4.6 mm; mobile phase: ethyl acetate/methanol 10:1; flow rate: 2 ml/min; detection: 265 nm; $R_t$=1.38 min].

Example 39A (4R)-4-(4-Cyano-2-nitrophenyl)-6-methyl-2-oxo-1-[3-(trifluoromethyl)phenyl]-1,2,3,4-tetrahydropyrimidine-5-carboxamide

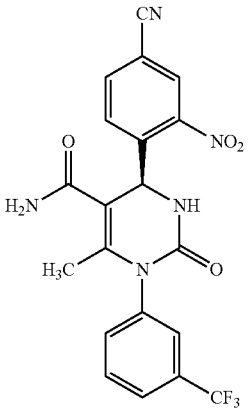 [SMILES: CC1=C(C(N)=O)[C@@H](c2ccc(C#N)cc2[N+](=O)[O-])NC(=O)N1c1cccc(C(F)(F)F)c1]

The reaction was carried out under argon. (4R)-4-(4-Cyano-2-nitrophenyl)-6-methyl-2-oxo-1-[3-(trifluoromethyl)phenyl]-1,2,3,4-tetrahydropyrimidine-5-carboxylic acid (6.0 g, 11.4 mmol, purity 85%), DMAP (140 mg, 1.143 mmol; 0.1 eq.), DIEA (1.77 g, 13.7 mmol; 1.2 eq.) and PyBOP (7.14 g, 13.71 mmol; 1.2 eq.) were initially charged in dry THF (34 ml) at RT, after brief stirring (15 min), a 0.5 M ammonia solution in THF (5 eq., 57.1 mmol) was added and the mixture was then stirred at RT for 1 h. Ethyl acetate (250 ml) was then added to the reaction mixture. The organic phase was washed successively with saturated sodium bicarbonate solution, water and saturated sodium chloride solution, dried over sodium sulfate, filtered and concentrated under reduced pressure. The crude product was subjected to flash chromatography on silica gel (mobile phase: dichloromethane/methanol 20:1). The title compound was obtained as a colorless solid (5.0 g, 98% of theory).

MS (ESIpos): m/z (%)=446.2 (100) [M+H]$^+$.

Example 40A (4R)-4-(4-Cyano-2-nitrophenyl)-6-methyl-2-oxo-1-[3-(trifluoromethyl)phenyl]-1,2,3,4-tetrahydropyrimidine-5-carbonitrile

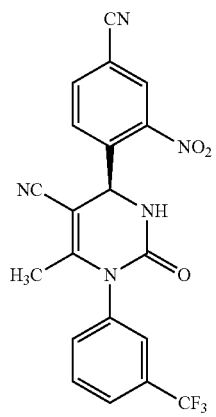 [SMILES: CC1=C(C#N)[C@@H](c2ccc(C#N)cc2[N+](=O)[O-])NC(=O)N1c1cccc(C(F)(F)F)c1]

The reaction was carried out under argon. (4R)-4-(4-Cyano-2-nitrophenyl)-6-methyl-2-oxo-1-[3-(trifluoromethyl)phenyl]-1,2,3,4-tetrahydropyrimidine-5-carboxamide (5.0 g, 10.1 mmol; purity 90%) was initially charged in dry THF (135 ml), methoxycarbonylsulfamoyltriethylammonium hydroxide (Burgess reagent; 3.85 g, 16.17 mmol; 1.6 eq.) was added and the mixture was then stirred at RT for 2 h. Ethyl acetate (300 ml) was then added to the reaction mixture. The organic phase was washed twice with water and once with saturated sodium chloride solution, dried over sodium sulfate, filtered and concentrated under reduced pressure. The crude product was recrystallized from cyclohexane/ethyl acetate. The crystals obtained were dried under high vacuum. The title compound was obtained as a solid (2.8 g, 65% of theory).

$^1$H-NMR (400 MHz, DMSO-d$_6$): δ=1.80 (s, 3H), 5.95 (s, 1H), 7.75-8.25 (m, 6H), 8.35 (dd, 1H), 8.65 (s, 1H).

Example 41A (4R)-4-(4-Cyano-2-nitrophenyl)-3,6-dimethyl-2-oxo-1-[3-(trifluoromethyl)phenyl]-1,2,3,4-tetrahydropyrimidine-5-carbonitrile

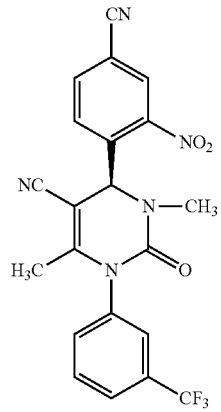

The reaction was carried out under argon. (4R)-4-(4-Cyano-2-nitrophenyl)-6-methyl-2-oxo-1-[3-(trifluoromethyl)phenyl]-1,2,3,4-tetrahydropyrimidine-5-carbonitrile (5.0 g, 11.7 mmol) was initially charged in absolute THF (500 ml), and a 1 M solution of lithium hexamethyldisilazide (LiHMDS) in THF (13.5 ml, 13.5 mmol, 1.15 eq.) was added at −78° C. After 30 min of stirring, iodomethane (8.30 g, 58.5 mmol; 5 eq.) in THF was added, and the mixture was stirred with gradual warming from −78° C. to RT for 16 h. The reaction mixture was then concentrated under reduced pressure, and initially 1N hydrochloric acid (14.0 ml), and then MTBE (500 ml) were added. The organic phase was washed successively with water (2×), saturated sodium bicarbonate solution, saturated ammonium chloride solution and saturated sodium chloride solution, dried over sodium sulfate, filtered and concentrated under reduced pressure. The title compound was obtained as a solid (4.3 g, 83% of theory).

LC-MS (Method 4): $R_t$=1.28 min; MS (ESIpos): m/z (%)=442.2 (100) [M+H]$^+$; MS (ESIneg): m/z (%)=440.2 (50) [M−H]$^-$ $^1$H-NMR (400 MHz, DMSO-d$_6$): δ=1.80 (s, 3H), 2.70 (s, 3H), 5.95 (s, 1H), 7.75-8.25 (m, 5H), 8.35 (dd, 1H), 8.65 (s, 1H).

Example 42A (4R)-4-(2-Amino-4-cyanophenyl)-3,6-dimethyl-2-oxo-1-[3-(trifluoromethyl)phenyl]-1,2,3,4-tetrahydropyrimidine-5-carbonitrile

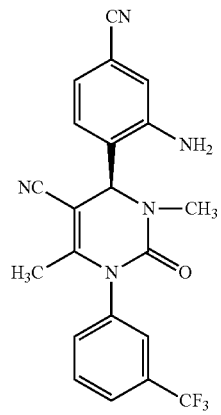

Under argon, (4R)-4-(4-cyano-2-nitrophenyl)-3,6-dimethyl-2-oxo-1-[3-(trifluoromethyl)phenyl]-1,2,3,4-tetrahydropyrimidine-5-carbonitrile (6.0 g, 11.3 mmol) was dissolved in methanol (420 ml). 10% palladium on activated carbon (5.5 g) was then added, and the mixture was hydrogenated at RT and atmospheric pressure for 5.5 h (strictly monitored by HPLC). The reaction mixture was then filtered off over kieselguhr, and the filter residue was washed with methanol (1000 ml). The filtrate was concentrated and the crude product was subjected to flash chromatography on silica gel (mobile phase: ethyl acetate/cyclohexane 2:1). The title compound was obtained as a solid (2.28 g, 40% of theory).

LC-MS (Method 9): $R_t$=1.06 min; MS (ESIpos): m/z (%)=412.3 (80) [M+H]$^+$; MS (ESIneg): m/z (%)=410.3 (100) [M−H]$^-$.

Example 43A

5-Cyano-2-{(4S)-5-cyano-3,6-dimethyl-2-oxo-1-[3-(trifluoromethyl)phenyl]-1,2,3,4-tetrahydropyrimidin-4-yl}benzenesulfonyl chloride

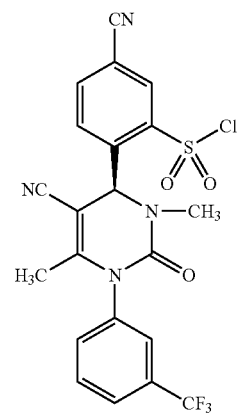 [SMILES: CC1=C(C#N)[C@@H](c2ccc(C#N)cc2S(=O)(=O)Cl)N(C)C(=O)N1c1cccc(C(F)(F)F)c1]

Under argon, (4R)-4-(2-amino-4-cyanophenyl)-3,6-dimethyl-2-oxo-1-[3-(trifluoromethyl)phenyl]-1,2,3,4-tetrahydropyrimidine-5-carbonitrile (2.1 g, 5.1 mmol) was initially charged in a 2:1:1 mixture of acetic acid/conc. hydrochloric acid/water (50 ml in total) at −10° C. A solution of sodium nitrate (371 mg, 5.38 mmol) in water (2 ml) was then slowly added dropwise, and the mixture was stirred at from −10° C. to −5° C. for 40 min. This solution was then added to 45 ml of a sulfur dioxide-saturated suspension, cooled to −10° C., of copper(I) chloride (101.4 mg, 1.0 mmol) in glacial acetic acid (44 ml). The mixture was stirred at 0° C. for about 30 min and then at +15° C. for 1 h (reaction monitored by HPLC and LC-MS). The reaction mixture was then cooled to 0° C. and subsequently added to about 300 ml of ice-cold water using a pipette. The precipitate was filtered off and taken up in ethyl acetate (150 ml). The solution was washed twice with saturated sodium chloride solution, dried over sodium sulfate, filtered and concentrated under reduced pressure. The title compound was obtained as a solid (2.13 g, 77% of theory, purity 92%) which was used without further purification in the subsequent reaction.

LC-MS (Method 4): $R_t$=1.37 min; MS (ESIpos): m/z (%)=495.1 (100) [M+H]$^+$ $^1$H-NMR (400 MHz, DMSO-d$_6$): δ=1.80 (s, 3H), 2.70 (s, 3H), 6.55 (s, 1H), 7.75-8.00 (m, 6H), 8.10 (s, 1H).

Example 44A

Sodium 5-cyano-2-{(4S)-5-cyano-3,6-dimethyl-2-oxo-1-[3-(trifluoromethyl)phenyl]-1,2,3,4-tetrahydropyrimidin-4-yl}benzenesulfinate

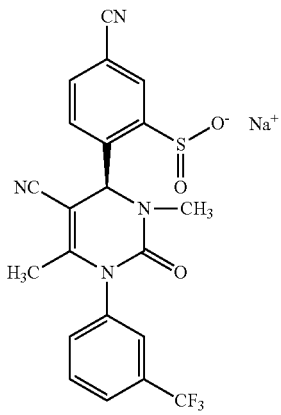 [SMILES: CC1=C(C#N)[C@@H](c2ccc(C#N)cc2S(=O)[O-])N(C)C(=O)N1c1cccc(C(F)(F)F)c1 ; [Na+]]

5-Cyano-2-{(4S)-5-cyano-3,6-dimethyl-2-oxo-1-[3-(trifluoromethyl)phenyl]-1,2,3,4-tetrahydropyrimidin-4-yl}benzenesulfonyl chloride (600 mg) was dissolved in THF (4.25 ml). Sodium sulfite (195 mg, 1.55 mmol; 1.5 eq.) and sodium bicarbonate (303 mg, 3.61 mmol; 3.5 eq.), dissolved in water (1.7 ml), were then added. The mixture was stirred at RT for 1 h. The reaction solution was then lyophilized directly. This gave a solid as product (962 mg, 58% of theory, purity 32%) which was used without further purification in the subsequent reactions.

LC-MS (Method 9): $R_t$=0.80 min; MS (ESIpos): m/z (%)=461.2 (80) [M+H]$^+$; MS (ESIneg): m/z (%)=459.2 (100) [M−H]$^−$.

Example 45A (4S)-4-(4-Cyano-2-sulfanylphenyl)-3,6-dimethyl-2-oxo-1-[3-(trifluoromethyl)phenyl]-1,2,3,4-tetrahydropyrimidine-5-carbonitrile

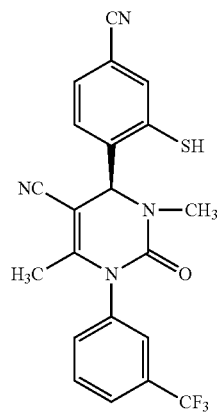

Under argon, 5-cyano-2-{(4S)-5-cyano-3,6-dimethyl-2-oxo-1-[3-(trifluoromethyl)phenyl]-1,2,3,4-tetrahydropyrimidin-4-yl}benzenesulfonyl chloride (52 mg, 105 μmol) was dissolved in dichloromethane (10 ml). Triphenylphosphine-polystyrene resin (capacity 1 mmol/g, 315 mg, 315 μmol, 3 eq.) was added, and the mixture was shaken for 15 h. More triphenylphosphine-polystyrene resin (1 mmol/g, 105 mg, 105 μmol, 1 eq.) was then added, and the mixture was shaken for a further 5 h. The reaction mixture was then filtered, the filtrate was concentrated under reduced pressure and the residue was dried under high vacuum. The title compound was obtained as a solid (90 mg, purity 50%, quant.) which was used without further purification in the subsequent reactions.

LC-MS (Method 4): $R_t$=1.25 min; MS (ESIpos): m/z (%)=429.1 (100) [M+H]$^+$; MS (ESIneg): m/z (%)=427.0 (40) [M−H]$^−$ $^1$H-NMR (400 MHz, DMSO-d$_6$): δ=1.80 (s, 3H), 2.65 (s, 3H), 3.15 (s, 1H), 5.65 (s, 1H), 7.60-7.90 (m, 7H), 8.00 (s, 1H).

Exemplary Embodiments

Example 1

(rac)-4-{5-Acetyl-6-methyl-2-oxo-1-[3-(trifluoromethyl)phenyl]-1,2,3,4-tetrahydropyrimidin-4-yl}-3-(methylsulfonyl)benzonitrile

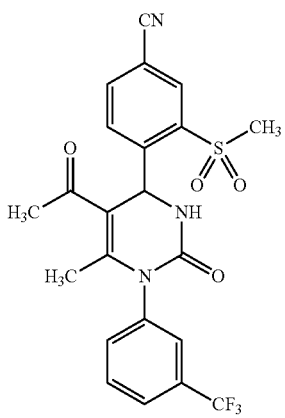 [SMILES: CC(=O)C1=C(C)N(c2cccc(C(F)(F)F)c2)C(=O)NC1c1ccc(C#N)cc1S(C)(=O)=O]

The reaction was carried out under argon. Triethyl phosphate (251 mg, 1.38 mmol) and diphosphorus pentoxide (130 mg, 0.918 mmol) were stirred at 50° C. overnight.

The mixture was then diluted with MTBE (5 ml), and 4-formyl-3-(methylsulfonyl)benzonitrile (240 mg, 1.15 mmol; Example1 4A), 1-[3-(trifluoromethyl)phenyl]urea (234 mg, 1.15 mmol) and 2,4-pentanedione (173 mg, 1.72 mmol) were added. The mixture was stirred under reflux overnight. For work-up, the solvent was removed under reduced pressure, and the residue was suspended in diethyl ether and then filtered off with suction. This gave 404 mg (73% of theory) of the target compound.

MS (DCI/NH$_3$): m/z (%)=478.2 (100) [M+H]$^+$, 495.2 (28) [M+NH$_4$]$^+$

HPLC (Method 2): $R_t$=4.38 min.

$^1$H-NMR (400 MHz, DMSO-d$_6$): δ=2.10 (s, 3H), 2.29 (s, 3H), 3.57 (s, 3H), 6.32 (s, 1H), 7.16 (s, 1H), 7.68-7.86 (m, 4H), 8.02 (d, 1H), 8.23 (d, 1H), 8.37 (s, 1H).

Example 2

4-{(4S)-5-Acetyl-6-methyl-2-oxo-1-[3-(trifluoromethyl)phenyl]-1,2,3,4-tetrahydropyrimidin-4-yl}-3-(methylsulfonyl)benzonitrile

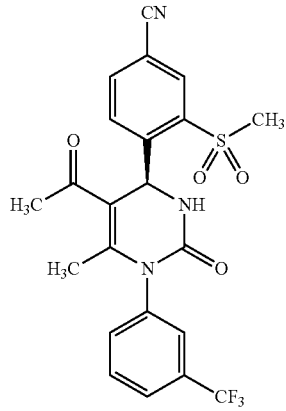

(rac)-4-{5-Acetyl-6-methyl-2-oxo-1-[3-(trifluoromethyl)phenyl]-1,2,3,4-tetrahydropyrimidin-4-yl}-3-(methylsulfonyl)benzonitrile (Example 1, 290 mg) was separated into the enantiomers by preparative HPLC chromatography on a chiral phase [column: Daicel Chiralpak IA, 250 mm×20 mm; sample preparation: the sample was dissolved in 30 ml of MTBE/methanol/acetonitrile 1:1:1; injection volume: 1.0 ml; mobile phase: MTBE/methanol 1:1; flow rate 15 ml/min; temperature: 30° C.; detection: 220 nm]. This gave 121 mg (83% of theory) of the 4S enantiomer as a colorless amorphous solid.

HPLC (Method 2): $R_t$=4.38 min.

$^1$H-NMR (400 MHz, DMSO-d$_6$): δ=2.10 (s, 3H), 2.28 (s, 3H), 3.57 (s, 3H), 6.33 (d, 1H), 7.20 (d, 1H), 7.68-7.88 (m, 4H), 8.02 (d, 1H), 8.23 (d, 1H), 8.37 (s, 1H).

Optical rotation: $[\alpha]^{20}_{Na}$=+18.7° (c=0.56 in DMF).

Example 3

Allyl (rac)-4-[4-cyano-2-(methylsulfonyl)phenyl]-6-methyl-2-oxo-1-[3-(trifluoromethyl)phenyl]-1,2,3,4-tetrahydropyrimidine-5-carboxylate

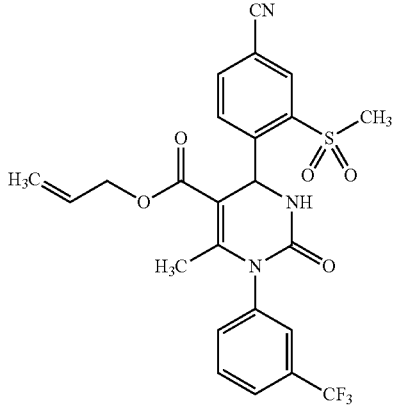 [SMILES: C=CCOC(=O)C1=C(C)N(c2cccc(C(F)(F)F)c2)C(=O)NC1c1ccc(C#N)cc1S(C)(=O)=O]

The reaction was carried out under argon. Triethyl phosphate (22.98 g, 126 mmol) and diphosphorus pentoxide (11.94 g, 84.1 mmol) were stirred at 50° C. overnight. The mixture was then diluted with MTBE (450 ml), and 4-formyl-3-(methylsulfonyl)benzonitrile (22.00 g, 105 mmol; Example 4A), 1-[3-(trifluoromethyl)phenyl]urea (21.47 g, 105 mmol) and allyl acetoacetate (22.42 g, 158 mmol) were added. The mixture was stirred under reflux overnight. Since the reaction was incomplete, the reaction mixture was concentrated by distillative removal of 350 ml of MTBE. The mixture was then heated under reflux for a further 4 h. For work-up, the solvent was removed under reduced pressure, and the residue was suspended in diethyl ether and then filtered off with suction. The solid was washed with dist. water (350 ml) and then with diethyl ether (50 ml). This gave 34.74 g (64% of theory) of the title compound.

LC-MS (Method 4): $R_t$=1.28 min; MS (ESIpos): m/z (%)=520.2 (100) [M+H]$^+$ $^1$H-NMR (400 MHz, DMSO-d$_6$): δ=2.15 (s, 3H), 3.45 (s, 3H), 4.45 (m, 2H), 4.95 (d, 1H), 5.05 (d, 1H), 5.65 (m, 1H), 6.40 (d, 1H), 7.20 (d, 1H), 7.70 (m, 2H), 7.80 (m, 1H), 7.85 (br. s, 1H), 8.10 (br. d, 1H), 8.25 (d, 1H), 8.35 (s, 1H).

Example 4

Allyl (4S)-4-[4-cyano-2-(methylsulfonyl)phenyl]-6-methyl-2-oxo-1-[3-(trifluoromethyl)phenyl]-1,2,3,4-tetrahydropyrimidine-5-carboxylate

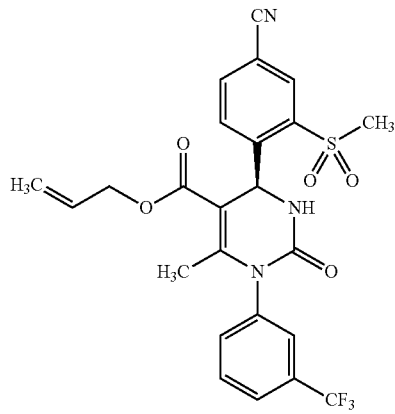 [SMILES: C=CCOC(=O)C1=C(C)N(c2cccc(C(F)(F)F)c2)C(=O)N[C@@H]1c1ccc(C#N)cc1S(C)(=O)=O]

Allyl (rac)-4-[4-cyano-2-(methylsulfonyl)phenyl]-6-methyl-2-oxo-1-[3-(trifluoromethyl)phenyl]-1,2,3,4-tetrahydropyrimidine-5-carboxylate (Example 3, 2.33 g) was separated into the enantiomers by preparative HPLC chromatography on a chiral phase [column: chiral silica gel phase based on the selector poly(N-methacryloyl-D-leucinedicyclopropylmethylamide); sample preparation: in each case 1 g of sample dissolved in 70 ml of THF/ethyl acetate/isohexane 20:25:25; injection volume: 8 ml; mobile phase: isohexane/isopropanol 1:1; flow rate: 60 ml/min; temperature: 24° C.; detection: 260 nm]. This gave 0.8 g (69% of theory, >99.5% ee) of the 4S enantiomer. The enantiomeric excess (ee value) was determined chromatographically [column: chiral silica gel phase based on the selector poly(N-methacryloyl-D-leucinedicyclopropylmethylamide), 250 mm×4.6 mm; mobile phase: isohexane/ethyl acetate 1:1; flow rate: 2 ml/min; detection: 260 nm; $R_t$=1.45 min].

LC-MS (Method 5): $R_t$=2.11 min; MS (ESIpos): m/z (%)=520.1 (100) [M+H]$^+$; MS (ESIneg): m/z (%)=475.2 (100), 518.2 (100) [M−H]$^−$ $^1$H-NMR (400 MHz, DMSO-d$_6$): δ=2.10 (s, 3H), 3.45 (s, 3H), 4.45 (m, 2H), 4.95 (d, 1H), 5.05 (d, 1H), 5.65 (m, 1H), 6.40 (d, 1H), 7.20 (d, 1H), 7.70 (m, 2H), 7.80 (m, 1H), 7.85 (br. s, 1H), 8.10 (br. d, 1H), 8.25 (d, 1H), 8.35 (s, 1H).

Example 5

(4S)-4-[4-Cyano-2-(methylsulfonyl)phenyl]-6-methyl-2-oxo-1-[3-(trifluoromethyl)phenyl]-1,2,3,4-tetrahydropyrimidine-5-carboxamide

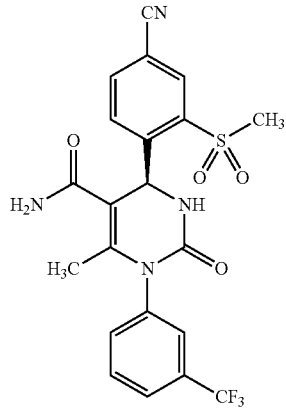

The reaction was carried out under argon. (4S)-4-[4-Cyano-2-(methylsulfonyl)phenyl]-6-methyl-2-oxo-1-[3-(trifluoromethyl)phenyl]-1,2,3,4-tetrahydropyrimidine-5-carboxylic acid (696 mg, 1.45 mmol; Example 5A) and HATU (2 eq., 1104 mg, 2.9 mmol) were initially charged in dry DMF (35 ml) at 0° C., and after brief stirring (20 min) ammonium chloride (5 eq., 388 mg, 7.26 mmol) and DIEA (7 eq., 1314 mg, 10.16 mmol) were added. The mixture was stirred at RT for 4 h (monitored by HPLC). The mixture was then concentrated, and the residue was purified by preparative HPLC (column: Gromsil C-18 10 μm; mobile phase: acetonitrile/water+0.1% TFA 10:90→90:10). This gave a colorless amorphous solid (612 mg, 88% of theory).

LC-MS (Method 6): $R_t$=1.94 min; MS (ESIpos): m/z (%)=479.1 (100) [M+H]$^+$; MS (ESIneg): m/z (%)=434.1 (100), 477 (40) [M−H]$^−$ $^1$H-NMR (400 MHz, DMSO-d$_6$): δ=1.80 (s, 3H), 3.40 (s, 3H), 6.35 (s, 1H), 7.20 (s, 1H), 7.25 (br. s, 1H), 7.45 (br. s, 1H), 7.65-7.80 (m, 4H), 8.10 (d, 1H), 8.30 (s, 1H), 8.35 (d, 1H).

Example 6

(4S)-4-[4-Cyano-2-(methylsulfonyl)phenyl]-6-methyl-2-oxo-1-[3-(trifluoromethyl)phenyl]-1,2,3,4-tetrahydropyrimidine-5-carbonitrile

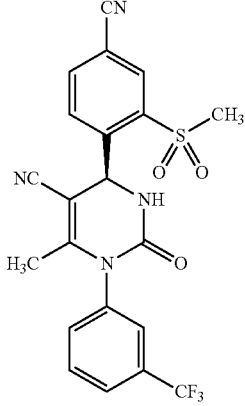

Method A:

The reaction was carried out under argon. (4S)-4-[4-Cyano-2-(methylsulfonyl)phenyl]-6-methyl-2-oxo-1-[3-(trifluoromethyl)phenyl]-1,2,3,4-tetrahydropyrimidine-5-carboxamide (560 mg, 1.17 mmol; Example 5) was initially charged in dry THF (35 ml), methoxycarbonylsulfamoyltriethylammonium hydroxide (Burgess reagent; 1115 mg, 4.68 mmol, 4 eq.) was added and the mixture was stirred at RT. After 90 min, HPLC control showed complete conversion. The reaction mixture was concentrated, and the residue was purified by preparative HPLC (column: Gromsil C-18 10 μm; mobile phase: acetonitrile/water+0.1% TFA 10:90→90:10). The title compound was obtained as a colorless amorphous solid (470 mg, 87% of theory).

Method B:

(4S)-4-[4-Cyano-2-(methylsulfonyl)phenyl]-6-methyl-2-oxo-1-[3-(trifluoromethyl)phenyl]-1,2,3,4-tetrahydropyrimidine-5-carboxamide (10.4 g, 21.7 mmol; Example 5) was, together with triethylamine, (5.63 g, 55.6 mmol) dissolved in dry THF (50 ml). Trifluoroacetic anhydride (11.69 g, 55.6 mmol) was added dropwise with slight heat tonality (up to 35° C.). After 15 min of stirring, the reaction had gone to completion (monitored by HPLC). Saturated sodium bicarbonate solution (250 ml) was added dropwise, and the mixture was extracted twice with ethyl acetate. The combined organic phases were washed with saturated sodium chloride solution, dried with magnesium sulfate, 30 g of silica gel were added and the mixture was concentrated on a rotary evaporator. The crude product, which was adsorbed in this manner to silica gel, was purified chromatographically on a further 500 g of silica gel (mobile phase: dichloromethane/ethyl acetate 2:1). This gave 6.46 g (65% of theory) of the title compound.

m.p.: 258-259° C.

Optical rotation: [α]$^{20}_{Na}$=−222.0° (c=0.48 in DMF)

LC-MS (Method 6): $R_t$=2.28 min; MS (ESIpos): m/z (%)=461.1 (100) [M+H]$^+$; MS (ESIneg): m/z (%)=352.3 (70), 416.1 (100), 459.2 (70) [M−H]$^−$ $^1$H-NMR (400 MHz, DMSO-d$_6$): δ=1.80 (s, 3H), 3.40 (s, 3H), 6.45 (s, 1H), 7.70-7.85 (m, 3H), 7.95 (br. s, 1H), 8.30-8.40 (m, 4H).

Example 7 tert-Butyl [(6R)-5-cyano-6-[4-cyano-2-(methylsulfonyl)phenyl]-4-methyl-2-oxo-3-[3-(trifluoromethyl)phenyl]-3,6-dihydropyrimidine-1(2H)-yl]acetate

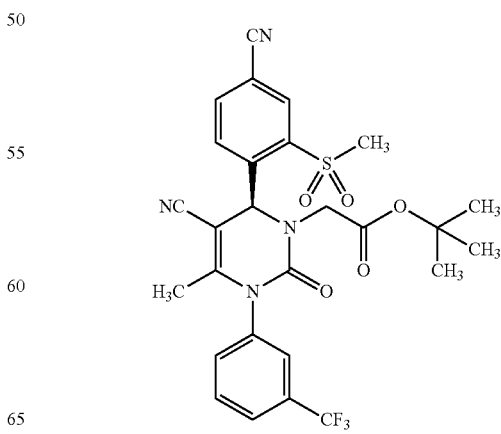

The reaction was carried out under argon. (4S)-4-[4-Cyano-2-(methylsulfonyl)phenyl]-6-methyl-2-oxo-1-[3-(trifluoromethyl)phenyl]-1,2,3,4-tetrahydropyrimidine-5-carbonitrile (290 mg, 630 µmol; Example 6) and sodium hydride (60% in mineral oil, 30.2 mg, 756 µmol, 1.2 eq.) were initially charged in THF (12 ml) at 0° C., and after brief stirring (15 min), tert-butyl bromoacetate (175 mg, 882 µmol, 1.4 eq.) was added. The reaction mixture was allowed to warm to RT. After 150 min, complete conversion was observed. The reaction mixture was then added to ethyl acetate (100 ml). The organic phase was washed with saturated sodium chloride solution (2×20 ml), dried over sodium sulfate, filtered and concentrated under reduced pressure. The crude product was purified by preparative HPLC (column: Gromsil C-18 10 µm; mobile phase: acetonitrile/water+0.1% TFA 10:90→90:10). This gave the target compound as a solid (309 mg, 85% of theory).

LC-MS (Method 4): $R_t$=1.38 min; MS (ESIpos): m/z (%)=519.1 (100); MS (ESIneg): m/z (%)=573.4 (100) [M–H]⁻.

General Procedure 1: Synthesis of N-Aminocarbonyldihydropyrimidinone Derivatives
(Process A)

4-Nitrophenyl (6S)-5-cyano-6-[4-cyano-2-(methylsulfonyl)phenyl]-4-methyl-2-oxo-3-[3-(trifluoromethyl)phenyl]-3,6-dihydropyrimidine-1(2H)-carboxylate (Example 6A, 1 eq.) was dissolved in acetonitrile, and the appropriate amine (3 eq.) was added with stirring. After the reaction had gone to completion (monitored by HPLC), the reaction mixture was purified directly by preparative HPLC (column: Kromasil C18, 125 mm×20 mm, 5 µm, 100 Å; mobile phase A: water with 0.01% formic acid, mobile phase B: acetonitrile; gradient: 0 min 10% B→2 min 10% B→9 min 90% B→12 min 90% B→12.1 min 10% B→15 min 10% B; flow rate: 0.35 ml/min; UV detection: 254 nm). The product fractions were combined and concentrated under reduced pressure.

Example 8

(6S)-5-Cyano-6-[4-cyano-2-(methylsulfonyl)phenyl]-N-[2-hydroxy-1-(hydroxymethyl)ethyl]-4-methyl-2-oxo-3-[3-(trifluoromethyl)phenyl]-3,6-dihydropyrimidine-1(2H)-carboxamide

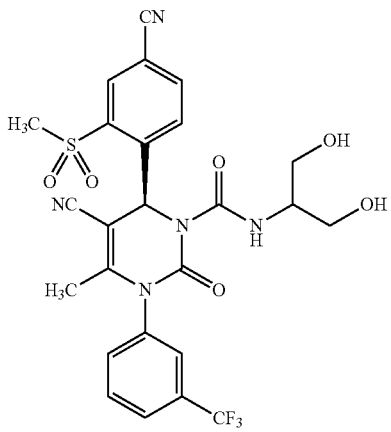 [SMILES: CC1=C(C#N)[C@@H](c2ccc(C#N)cc2S(C)(=O)=O)N(C(=O)NC(CO)CO)C(=O)N1c1cccc(C(F)(F)F)c1]

According to the General Procedure 1,4-nitrophenyl (6S)-5-cyano-6-[4-cyano-2-(methylsulfonyl)phenyl]-4-methyl-2-oxo-3-[3-(trifluoromethyl)phenyl]-3,6-dihydropyrimidine-1(2H)-carboxylate (78.0 mg, 0.125 mmol; Example 6A) was reacted with 2-amino-1,3-propanediol (34.1 mg, 0.374 mmol) in acetonitrile (1 ml) to give the target compound (50 mg, 69% of theory).

HPLC (Method 3): $R_t$=4.27 min.

MS (ESIpos): m/z (%)=578.3 (100) [M+H]⁺

¹H-NMR (400 MHz, DMSO-d₆): δ=1.78 (s, 3H), 3.20-3.57 (m, 5H), 3.50 (s, 3H), 4.70 (t, 1H), 4.76 (t, 1H), 7.27 (s, 1H), 7.74-8.23 (m, 5H), 8.29 (d, 1H), 8.44 (s, 1H), 8.90-9.02 (br. s, 1H).

Example 9

(6S)—N-(2-Amino-2-oxoethyl)-5-cyano-6-[4-cyano-2-(methylsulfonyl)phenyl]-4-methyl-2-oxo-3-[3-(trifluoromethyl)phenyl]-3,6-dihydropyrimidine-1(2H)-carboxamide

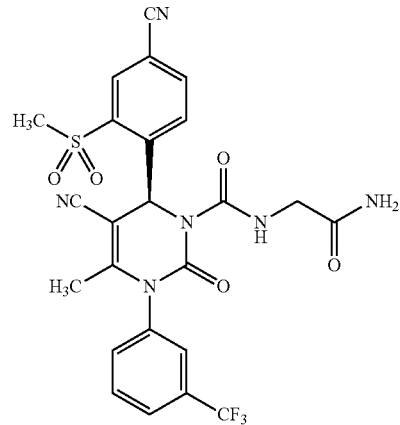 [SMILES: CC1=C(C#N)[C@@H](c2ccc(C#N)cc2S(C)(=O)=O)N(C(=O)NCC(N)=O)C(=O)N1c1cccc(C(F)(F)F)c1]

According to the General Procedure 1,4-nitrophenyl (6S)-5-cyano-6-[4-cyano-2-(methylsulfonyl)phenyl]-4-methyl-2-oxo-3-[3-(trifluoromethyl)phenyl]-3,6-dihydropyrimidine-1(2H)-carboxylate (197 mg, 0.315 mmol; Example 6A) was reacted with glycinamide hydrochloride (104 mg, 0.945 mmol) and N,N-diisopropylethylamine (122 mg, 0.945 mmol) in acetonitrile (2.5 ml) to give the target compound (72 mg, 39% of theory).

HPLC (Method 2): $R_t$=4.24 min.

MS (ESIpos): m/z (%)=561.3 (100) [M+H]⁺, 583.2 (50) [M+Na]⁺

¹H-NMR (400 MHz, DMSO-d₆): δ=1.80 (s, 3H), 3.49 (s, 3H), 3.67 (dd, 2H), 7.12 (s, 1H), 7.26 (s, 1H), 7.36 (s, 1H), 7.72-8.23 (m, 5H), 8.29 (d, 1H), 8.43 (s, 1H), 9.14 (br. s, 1H).

Example 10

(6S)-5-Cyano-6-[4-cyano-2-(methylsulfonyl)phenyl]-N-(2-hydroxyethyl)-4-methyl-2-oxo-3-[3-(trifluoromethyl)phenyl]-3,6-dihydropyrimidine-1(2H)-carboxamide

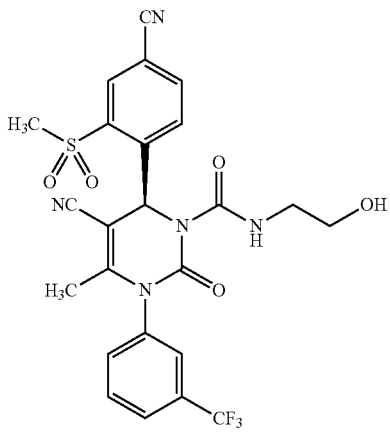 [SMILES: CC1=C(C#N)[C@@H](c2ccc(C#N)cc2S(C)(=O)=O)N(C(=O)NCCO)C(=O)N1c1cccc(C(F)(F)F)c1]

According to the General Procedure 1,4-nitrophenyl (6S)-5-cyano-6-[4-cyano-2-(methylsulfonyl)phenyl]-4-methyl-2-oxo-3-[3-(trifluoromethyl)phenyl]-3,6-dihydropyrimidine-1(2H)-carboxylate (80.0 mg, 0.128 mmol; Example 6A) was reacted with 2-aminoethanol (23.4 mg, 0.384 mmol) in acetonitrile (1 ml) to give the target compound (27 mg, 39% of theory).

HPLC (Method 2): $R_t$=4.39 min.
MS (ESIpos): m/z (%)=548.2 (100) [M+H]$^+$
$^1$H-NMR (400 MHz, DMSO-d$_6$): δ=1.78 (s, 3H), 3.03-3.45 (m, 4H), 3.50 (s, 3H), 4.74 (m, 1H), 7.26 (s, 1H), 7.74-8.22 (m, 5H), 8.29 (d, 1H), 8.43 (s, 1H), 8.94 (br. s, 1H).

Example 11

(6S)-5-Cyano-6-[4-cyano-2-(methylsulfonyl)phenyl]-4-methyl-N-morpholin-4-yl-2-oxo-3-[3-(trifluoromethyl)phenyl]-3,6-dihydropyrimidine-1(2H)-carboxamide

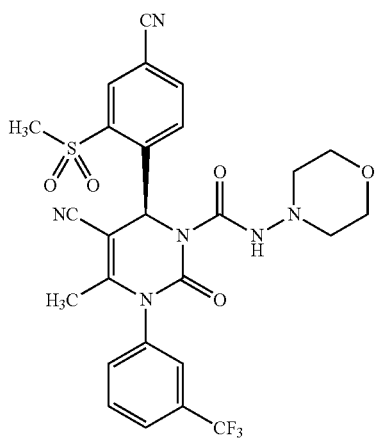 [SMILES: CC1=C(C#N)[C@@H](c2ccc(C#N)cc2S(C)(=O)=O)N(C(=O)NN2CCOCC2)C(=O)N1c1cccc(C(F)(F)F)c1]

According to the General Procedure 1,4-nitrophenyl (6S)-5-cyano-6-[4-cyano-2-(methylsulfonyl)phenyl]-4-methyl-2-oxo-3-[3-(trifluoromethyl)phenyl]-3,6-dihydropyrimidine-1(2H)-carboxylate (78.0 mg, 0.125 mmol; Example 6A) was reacted with N-aminomorpholine (38.2 mg, 0.374 mmol) in acetonitrile (1 ml) to give the target compound (46 mg, 61% of theory).

HPLC (Method 3): $R_t$=4.49 min.
MS (ESIpos): m/z (%)=589.3 (100) [M+H]$^+$
$^1$H-NMR (400 MHz, DMSO-d$_6$): δ=1.80 (s, 3H), 2.53-2.72 (m, 4H), 3.47-3.56 (m, 4H), 3.50 (s, 3H), 7.11 (s, 1H), 7.74-8.21 (m, 5H), 8.32 (d, 1H), 8.43 (s, 1H), 9.63 (s, 1H).

Example 12

(6S)-5-Cyano-6-[4-cyano-2-(methylsulfonyl)phenyl]-N',N'-bis(2-hydroxyethyl)-4-methyl-2-oxo-3-[3-(trifluoromethyl)phenyl]-3,6-dihydropyrimidine-1(2H)-carbohydrazide

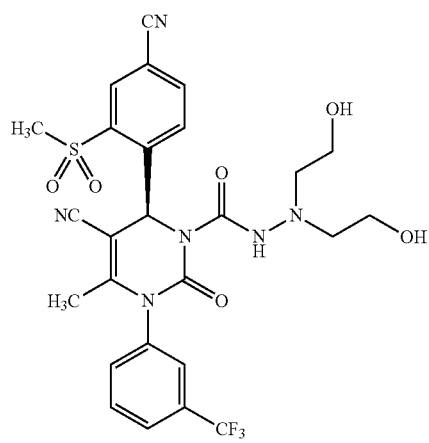 [SMILES: CC1=C(C#N)[C@@H](c2ccc(C#N)cc2S(C)(=O)=O)N(C(=O)NN(CCO)CCO)C(=O)N1c1cccc(C(F)(F)F)c1]

According to the General Procedure 1,4-nitrophenyl (6S)-5-cyano-6-[4-cyano-2-(methylsulfonyl)phenyl]-4-methyl-2-oxo-3-[3-(trifluoromethyl)phenyl]-3,6-dihydropyrimidine-1(2H)-carboxylate (78.0 mg, 0.125 mmol; Example 6A) was reacted with 2,2'-hydrazin-1,1-diyldiethanol (45.0 mg, 0.374 mmol) in acetonitrile (1 ml) to give the target compound (40 mg, 51% of theory).

HPLC (Method 3): $R_t$=4.23 min.
MS (ESIpos): m/z (%)=607.3 (100) [M+H]$^+$
$^1$H-NMR (400 MHz, DMSO-d$_6$): δ=1.80 (s, 3H), 2.70 (t, 4H), 3.20 (m, 4H), 3.46 (s, 3H), 4.15 (t, 2H), 7.11 (s, 1H), 7.74-8.37 (m, 6H), 8.44 (s, 1H), 9.60 (s, 1H).

Example 13

(6S)-5-Cyano-6-[4-cyano-2-(methylsulfonyl)phenyl]-N-(2-hydroxy-1,1-dimethylethyl)-4-methyl-2-oxo-3-[3-(trifluoromethyl)phenyl]-3,6-dihydropyrimidine-1(2H)-carboxamide

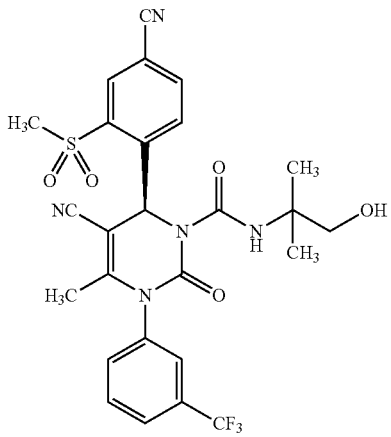 [SMILES: CC1=C(C#N)[C@@H](c2ccc(C#N)cc2S(C)(=O)=O)N(C(=O)NC(C)(C)CO)C(=O)N1c1cccc(C(F)(F)F)c1]

According to the General Procedure 1, 4-nitrophenyl (6S)-5-cyano-6-[4-cyano-2-(methylsulfonyl)phenyl]-4-methyl-2-oxo-3-[3-(trifluoromethyl)phenyl]-3,6-dihydropyrimidine-1(2H)-carboxylate (75.0 mg, 0.120 mmol; Example 6A) was reacted with 2-amino-2-methylpropanol (32.1 mg, 0.360 mmol) in acetonitrile (0.96 ml) to give the target compound (51 mg, 74% of theory).

HPLC (Method 2): $R_t$=4.65 min.

MS (ESIpos): m/z (%)=576.2 (100) [M+H]$^+$ $^1$H-NMR (400 MHz, DMSO-d$_6$): δ=1.02 (s, 3H), 1.13 (s, 3H), 1.78 (s, 3H), 3.13-3.28 (m, 2H), 3.51 (s, 3H), 4.98 (t, 1H), 7.26 (s, 1H), 7.74-8.23 (m, 5H), 8.30 (d, 1H), 8.45 (s, 1H), 8.98 (br. s, 1H).

Example 14

(6S)-5-Cyano-6-[4-cyano-2-(methylsulfonyl)phenyl]-N-[2-(2-hydroxyethoxy)ethyl]-4-methyl-2-oxo-3-[3-(trifluoromethyl)phenyl]-3,6-dihydropyrimidine-1(2H)-carboxamide

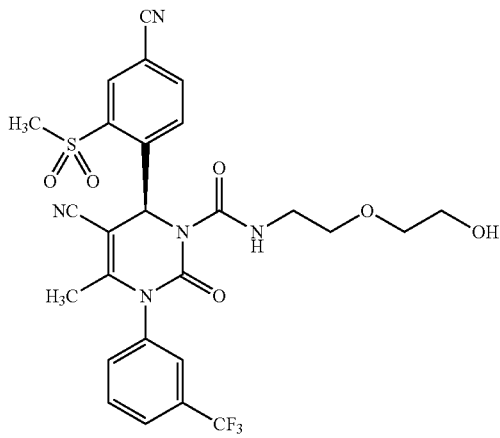 [SMILES: CC1=C(C#N)[C@@H](c2ccc(C#N)cc2S(C)(=O)=O)N(C(=O)NCCOCCO)C(=O)N1c1cccc(C(F)(F)F)c1]

According to the General Procedure 1, 4-nitrophenyl (6S)-5-cyano-6-[4-cyano-2-(methylsulfonyl)phenyl]-4-methyl-2-oxo-3-[3-(trifluoromethyl)phenyl]-3,6-dihydropyrimidine-1(2H)-carboxylate (46.5 mg, 0.074 mmol; Example 6A) was reacted with 2-(2-aminoethoxy)ethanol (23.4 mg, 0.223 mmol) in acetonitrile (1 ml) to give the target compound (30 mg, 68% of theory).

HPLC (Method 2): $R_t$=4.39 min.

MS (ESIpos): m/z (%)=592.2 (100) [M+H]$^+$ $^1$H-NMR (400 MHz, DMSO-d$_6$): δ=1.78 (s, 3H), 3.16-3.25 (m, 2H), 3.26-3.43 (m, 6H), 3.50 (s, 3H), 4.52 (m, 1H), 7.25 (s, 1H), 7.74-8.23 (m, 5H), 8.29 (d, 1H), 8.44 (s, 1H), 8.90 (br. s, 1H).

Example 15

(6S)-5-Cyano-6-[4-cyano-2-(methylsulfonyl)phenyl]-N-cyclopropyl-4-methyl-2-oxo-3-[3-(trifluoromethyl)phenyl]-3,6-dihydropyrimidine-1(2H)-carboxamide

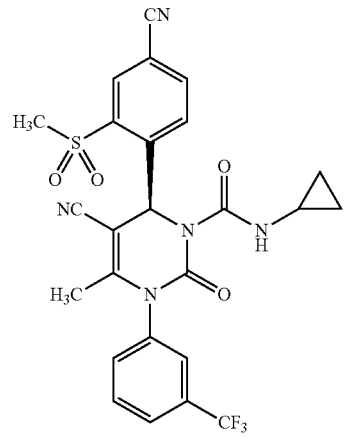 [SMILES: CC1=C(C#N)[C@@H](c2ccc(C#N)cc2S(C)(=O)=O)N(C(=O)NC2CC2)C(=O)N1c1cccc(C(F)(F)F)c1]

According to the General Procedure 1, 4-nitrophenyl (6S)-5-cyano-6-[4-cyano-2-(methylsulfonyl)phenyl]-4-methyl-2-oxo-3-[3-(trifluoromethyl)phenyl]-3,6-dihydropyrimidine-1(2H)-carboxylate (80.0 mg, 0.128 mmol; Example 6A) was reacted with cyclopropylamine (21.9 mg, 0.384 mmol) in acetonitrile (1 ml) to give the target compound (45 mg, 65% of theory).

HPLC (Method 3): $R_t$=4.83 min.

MS (ESIpos): m/z (%)=544.2 (100) [M+H]$^+$ $^1$H-NMR (400 MHz, DMSO-d$_6$): δ=0.28-0.65 (m, 4H), 1.78 (s, 3H), 2.51-2.61 (m, 1H), 3.52 (s, 3H), 7.21 (s, 1H), 7.74-8.19 (m, 5H), 8.30 (d, 1H), 8.44 (s, 1H), 8.72 (br. s, 1H).

Example 16

(6S)-5-Cyano-6-[4-cyano-2-(methylsulfonyl)phenyl]-N-(1,1-dioxidotetrahydrothiophen-3-yl)-4-methyl-2-oxo-3-[3-(trifluoromethyl)phenyl]-3,6-dihydropyrimidine-1(2H)-carboxamide

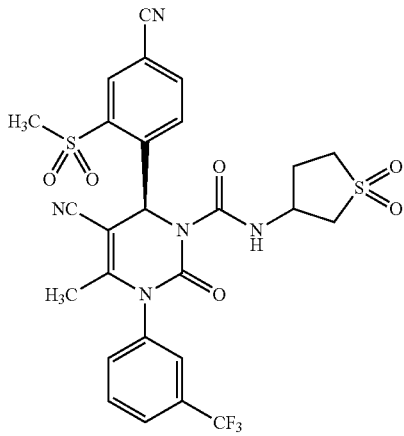 [SMILES: CC1=C(C#N)[C@@H](c2ccc(C#N)cc2S(C)(=O)=O)N(C(=O)NC2CCS(=O)(=O)C2)C(=O)N1c1cccc(C(F)(F)F)c1]

According to the General Procedure 1,4-nitrophenyl (6S)-5-cyano-6-[4-cyano-2-(methylsulfonyl)phenyl]-4-methyl-2-oxo-3-[3-(trifluoromethyl)phenyl]-3,6-dihydropyrimidine-1(2H)-carboxylate (78.0 mg, 0.125 mmol; Example 6A) was reacted with tetrahydrothiophen-3-amine 1,1-dioxide (50.6 mg, 0.374 mmol) in acetonitrile (1 ml) to give the target compound (52 mg, 66% of theory).

HPLC (Method 3): $R_t$=4.55 min.

MS (ESIpos): m/z (%)=622.3 (70) [M+H]$^+$, 639.3 (38) [M+NH$_4$]$^+$ $^1$H-NMR (400 MHz, DMSO-d$_6$): δ=1.79 (s, 3H), 1.92-2.37 (m, 2H), 2.90-3.35 (m, 4H), 3.50 (s, 3H), 4.39 (m, 1H), 7.24 (s, 1H), 7.72-8.18 (m, 5H), 8.29 (d, 1H), 8.44 (s, 1H), 9.13 (br. s, 1H).

Example 17

(6S)-5-Cyano-6-[4-cyano-2-(methylsulfonyl)phenyl]-N-(2-methoxyethyl)-4-methyl-2-oxo-3-[3-(trifluoromethyl)phenyl]-3,6-dihydropyrimidine-1(2H)-carboxamide

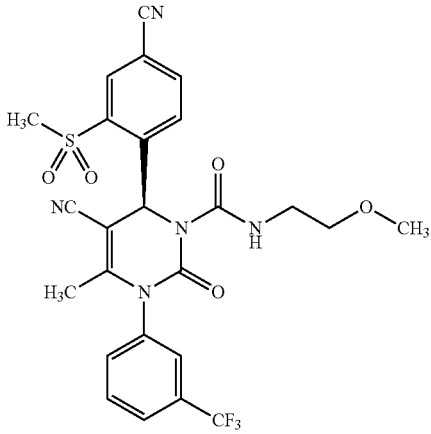

According to the General Procedure 1,4-nitrophenyl (6S)-5-cyano-6-[4-cyano-2-(methylsulfonyl)phenyl]-4-methyl-2-oxo-3-[3-(trifluoromethyl)phenyl]-3,6-dihydropyrimidine-1(2H)-carboxylate (78.0 mg, 0.125 mmol; Example 6A) was reacted with 2-methoxyethylamine (28.1 mg, 0.374 mmol) in acetonitrile (1 ml) to give the target compound (55 mg, 78% of theory).

HPLC (Method 3): $R_t$=4.72 min.

MS (ESIpos): m/z (%)=562.3 (100) [M+H]$^+$ $^1$H-NMR (400 MHz, DMSO-d$_6$): δ=1.78 (s, 3H), 3.15 (s, 3H), 3.17-3.32 (m, 4H), 3.50 (s, 3H), 7.25 (s, 1H), 7.74-8.23 (m, 5H), 8.29 (d, 1H), 8.43 (s, 1H), 8.90 (br. s, 1H).

Example 18

(4S)-4-[4-Cyano-2-(methylsulfonyl)phenyl]-3-{[(3S)-3-hydroxypyrrolidin-1-yl]carbonyl}-6-methyl-2-oxo-1-[3-(trifluoromethyl)phenyl]-1,2,3,4-tetrahydropyrimidine-5-carbonitrile

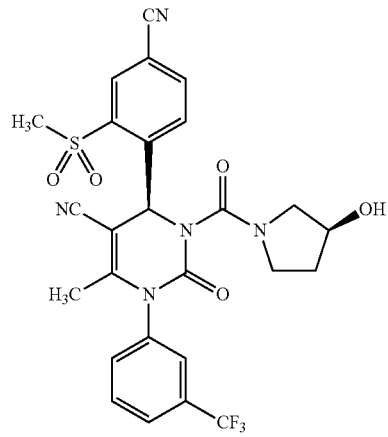 [SMILES: CC1=C(C#N)[C@@H](c2ccc(C#N)cc2S(C)(=O)=O)N(C(=O)N2CC[C@H](O)C2)C(=O)N1c1cccc(C(F)(F)F)c1]

According to the General Procedure 1,4-nitrophenyl (6S)-5-cyano-6-[4-cyano-2-(methylsulfonyl)phenyl]-4-methyl-2-oxo-3-[3-(trifluoromethyl)phenyl]-3,6-dihydropyrimidine-1(2H)-carboxylate (135 mg, 0.216 mmol; Example 6A) was reacted with (S)-(–)-3-pyrrolidinol (56.4 mg, 0.647 mmol) in acetonitrile (1.7 ml) to give the target compound (48 mg, 38% of theory).

HPLC (Method 2): $R_t$=4.21 min.

MS (DCI/NH$_3$): m/z=574 [M+H]$^+$, 591.3 [M+NH$_4$]$^+$ $^1$H-NMR (400 MHz, DMSO-d$_6$): δ=1.59-1.95 (m, 2H), 1.83 (s, 3H), 2.86-3.36 (m, 2H), 3.44-3.72 (m, 2H), 3.48 (s, 3H), 4.19 (m, 1H), 4.87 and 5.08 (in each case d, 1H), 6.82 (s, 1H), 7.73-8.43 (m, 7H).

Example 19

(4S)-4-[4-Cyano-2-(methylsulfonyl)phenyl]-3-{[(3R)-3-hydroxypyrrolidin-1-yl]carbonyl}-6-methyl-2-oxo-1-[3-(trifluoromethyl)phenyl]-1,2,3,4-tetrahydropyrimidine-5-carbonitrile

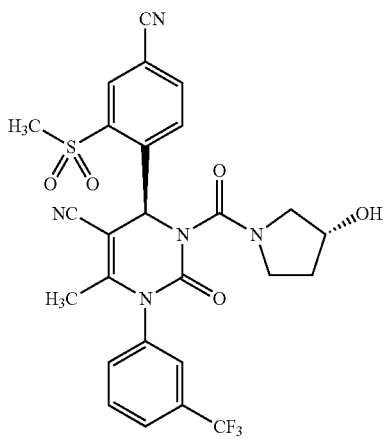 [SMILES: CC1=C(C#N)[C@@H](c2ccc(C#N)cc2S(C)(=O)=O)N(C(=O)N2CC[C@@H](O)C2)C(=O)N1c1cccc(C(F)(F)F)c1]

According to the General Procedure 1, 4-nitrophenyl (6S)-5-cyano-6-[4-cyano-2-(methylsulfonyl)phenyl]-4-methyl-2-oxo-3-[3-(trifluoromethyl)phenyl]-3,6-dihydropyrimidine-1(2H)-carboxylate (135 mg, 0.216 mmol; Example 6A) was reacted with (R)-(+)-3-pyrrolidinol (56.4 mg, 0.647 mmol) in acetonitrile (1.7 ml) to give the target compound (92 mg, 74% of theory).

HPLC (Method 2): $R_t$=4.21 min.

MS (ESI): m/z (%)=ESI$^+$ 574.2 (10) [M+H]$^+$, ESI$^-$ 618.1 (100) [M−H+HCOOH]$^-$ $^1$H-NMR (400 MHz, DMSO-d$_6$): δ=1.63-1.88 (m, 2H), 1.82 (s, 3H), 2.95-3.23 (m, 2H), 3.34-3.84 (m, 2H), 3.49 (s, 3H), 4.17 and 4.26 (in each case br. s, 1H), 4.86 and 4.91 (in each case br. s, 1H), 6.84 (s, 1H), 7.73-8.25 (m, 6H), 8.34-8.41 (m, 1H).

Example 20

(4S)-4-[4-Cyano-2-(methylsulfonyl)phenyl]-3-{[4-(2-hydroxyethyl)piperazin-1-yl]carbonyl}-6-methyl-2-oxo-1-[3-(trifluoromethyl)phenyl]-1,2,3,4-tetrahydropyrimidine-5-carbonitrile

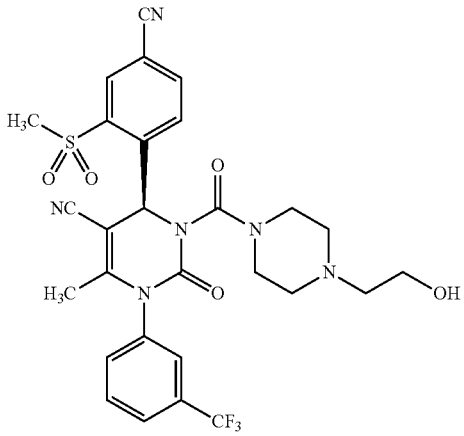 [SMILES: CC1=C(C#N)[C@@H](c2ccc(C#N)cc2S(C)(=O)=O)N(C(=O)N2CCN(CCO)CC2)C(=O)N1c1cccc(C(F)(F)F)c1]

According to the General Procedure 1,4-nitrophenyl (6S)-5-cyano-6-[4-cyano-2-(methylsulfonyl)phenyl]-4-methyl-2-oxo-3-[3-(trifluoromethyl)phenyl]-3,6-dihydropyrimidine-1(2H)-carboxylate (78 mg, 0.125 mmol; Example 6A) was reacted with N-(2-hydroxyethyl)piperazine (48.7 mg, 0.374 mmol) in acetonitrile (1.0 ml) to give the target compound (68 mg, 85% of theory).

HPLC (Method 3): $R_t$=4.18 min.

MS (ESIpos): m/z (%)=617.3 (100) [M+H]$^+$ $^1$H-NMR (400 MHz, DMSO-d$_6$): δ=1.81 (s, 3H), 2.03-2.73 (m, 4H), 2.94-3.87 (m, 11H, including t at 3.47, s at 3.51), 4.41 (br. s, 1H), 6.83 (s, 1H), 6.91-8.52 (m, 7H).

Example 21

2-[(6S)-5-Cyano-6-[4-cyano-2-(methylsulfonyl)phenyl]-4-methyl-2-oxo-3-[3-(trifluoromethyl)phenyl]-3,6-dihydropyrimidin-1(2H)-yl]acetic acid

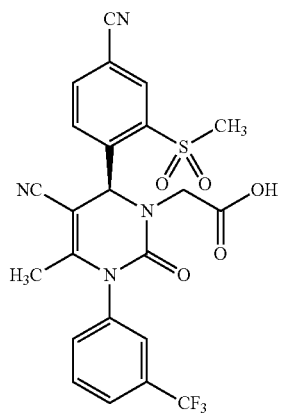 [SMILES: CC1=C(C#N)[C@@H](c2ccc(C#N)cc2S(C)(=O)=O)N(CC(=O)O)C(=O)N1c1cccc(C(F)(F)F)c1]

The reaction was carried out under argon. tert-Butyl [(6R)-5-cyano-6-[4-cyano-2-(methylsulfonyl)phenyl]-4-methyl-2-oxo-3-[3-(trifluoromethyl)phenyl]-3,6-dihydropyrimidin-1(2H)-yl]acetate (350 mg, 609 μmol; Example 7) was initially charged in dichloromethane (60 ml), and trifluoroacetic acid (20 ml) was added. The mixture was stirred at RT for 90 min. The volatile components were then removed on a rotary evaporator. The residue was taken up in toluene (50 ml) and again concentrated under reduced pressure. This procedure was repeated once more. The crude product was purified by preparative HPLC (column: Gromsil C-18 10 μm; mobile phase: acetonitrile/water+0.1% TFA 10:90→90:10). The title compound was obtained as a colorless solid (290 mg, 92% of theory).

LC-MS (Method 4): $R_t$=1.11 min; MS (ESIpos): m/z (%)=519.0 (100) [M+H]$^+$; MS (ESIneg): m/z (%)=352.1 (100), 415.9 (70), 517.0 (50) [M−H]$^-$.

Example 22

2-[(6S)-5-Cyano-6-[4-cyano-2-(methylsulfonyl)phenyl]-4-methyl-2-oxo-3-[3-(trifluoromethyl)phenyl]-3,6-dihydropyrimidin-1(2H)-yl]acetamide

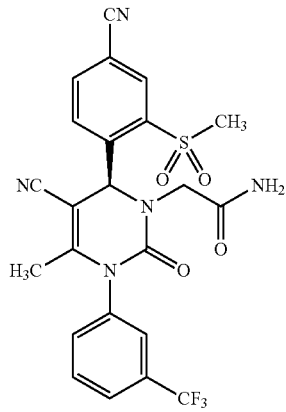 [SMILES: CC1=C(C#N)[C@@H](c2ccc(C#N)cc2S(C)(=O)=O)N(CC(N)=O)C(=O)N1c1cccc(C(F)(F)F)c1]

The reaction was carried out under argon. 2-[(6S)-5-Cyano-6-[4-cyano-2-(methylsulfonyl)phenyl]-4-methyl-2-oxo-3-[3-(trifluoromethyl)phenyl]-3,6-dihydropyrimidin-1(2H)-yl]acetic acid (90 mg, 174 µmol; Example 21) was initially charged in DMF (3 ml), HATU (330 mg, 868 µmol, 5 eq.) was added at 0° C. and the mixture was stirred for 20 min. Ammonium chloride (18.1 mg, 340 µmol, 5 eq.) and N,N-diisopropylethylamine (224 mg, 1736 µmol, 10 eq.) were then added, and the mixture was stirred at RT until complete conversion had been achieved (after a number of hours; HPLC control). The reaction mixture was then concentrated under reduced pressure, and the crude product was purified by preparative HPLC (Column: Gromsil C-18 10 µm; mobile phase: acetonitrile/water+0.1% TFA 10:90→90:10). This gave the title compound as a colorless solid (85 mg, 94% of theory).

LC-MS (Method 4): $R_t$=1.07 min; MS (ESIpos): m/z (%)=501.1 (70), 518.1 (100) [M+H]$^+$; MS (ESIneg): m/z (%)=516.7 (80) [M−H]$^−$ $^1$H-NMR (400 MHz, DMSO-d$_6$): δ=1.85 (s, 3H), 3.15 (br. d, 1H), 3.40 (s, 3H), 4.05 (d, 1H), 6.50 (s, 1H), 7.10 (s, 1H), 7.40 (s, 1H), 7.65-8.05 (m, 4H), 8.40 (m, 3H).

Example 23

2-[(6S)-5-Cyano-6-[4-cyano-2-(methylsulfonyl)phenyl]-4-methyl-2-oxo-3-[3-(trifluoromethyl)phenyl]-3,6-dihydropyrimidin-1(2H)-yl]-N-(2-hydroxyethyl)acetamide

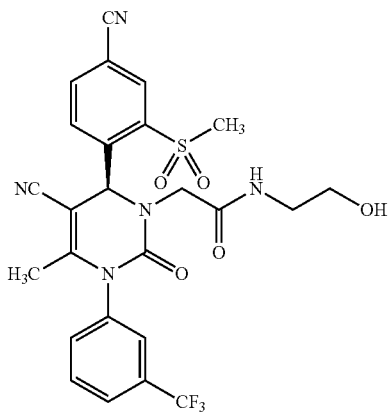 [SMILES: CC1=C(C#N)[C@@H](c2ccc(C#N)cc2S(C)(=O)=O)N(CC(=O)NCCO)C(=O)N1c1cccc(C(F)(F)F)c1]

The reaction was carried out under argon. 2-[(6S)-5-Cyano-6-[4-cyano-2-(methylsulfonyl)phenyl]-4-methyl-2-oxo-3-[3-(trifluoromethyl)phenyl]-3,6-dihydropyrimidin-1(2H)-yl]acetic acid (45 mg, 87 µmol; Example 21) was initially charged in DMF (1.5 ml), HATU (165 mg, 434 µmol, 5 eq.) was added at 0° C. and the mixture was stirred for 20 min. 2-Aminoethanol (26.5 mg, 434 µmol, 5 eq.) and N,N-diisopropylethylamine (56 mg, 434 µmol, 5 eq.) were then added, and the mixture was stirred at RT for 16 h until complete conversion had been achieved (HPLC control). The reaction mixture was then concentrated under reduced pressure, and the crude product was purified by preparative HPLC (column: Gromsil C-18 10 µm; mobile phase: acetonitrile/water+0.1% TFA 10:90→90:10). This gave the title compound as a colorless solid (40 mg, 82% of theory).

LC-MS (Method 6): $R_t$=2.05 min; MS (ESIpos): m/z (%)=562.1 (100) [M+H]$^+$ $^1$H-NMR (400 MHz, DMSO-d$_6$): δ=1.85 (s, 3H), 3.05 (m, 2H), 3.20 (d, 1H), 3.35 (m, 2H), 3.40 (s, 3H), 4.05 (d, 1H), 6.50 (s, 1H), 7.65-8.10 (m, 5H), 8.30-8.45 (m, 3H).

Example 24

(4S)-4-[4-Cyano-2-(methylsulfonyl)phenyl]-3-{2-[4-(2-hydroxyethyl)piperidin-1-yl]-2-oxoethyl}-6-methyl-2-oxo-1-[3-(trifluoromethyl)phenyl]-1,2,3,4-tetrahydropyrimidine-5-carbonitrile

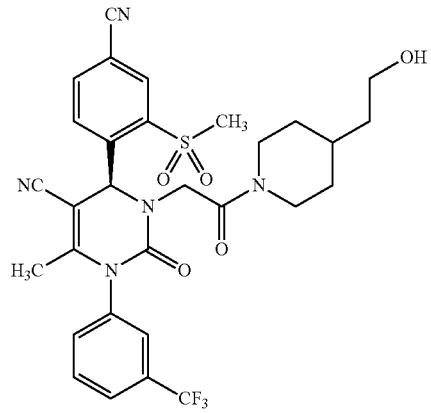 [SMILES: CC1=C(C#N)[C@@H](c2ccc(C#N)cc2S(C)(=O)=O)N(CC(=O)N2CCC(CCO)CC2)C(=O)N1c1cccc(C(F)(F)F)c1]

The reaction was carried out under argon. 2-[(6S)-5-Cyano-6-[4-cyano-2-(methylsulfonyl)phenyl]-4-methyl-2-oxo-3-[3-(trifluoromethyl)phenyl]-3,6-dihydropyrimidin-1(2H)-yl]acetic acid (45 mg, 87 µmol; Example 21) was initially charged in DMF (1.5 ml), HATU (165 mg, 434 µmol, 5 eq.) was added at 0° C. and the mixture was stirred for 20 min. 4-Piperidinethanol (33.6 mg, 260 µmol, 3 eq.) and N,N-diisopropylethylamine (56 mg, 434 µmol, 5 eq.) were then added, and the mixture was stirred at RT for 16 h until complete conversion had been achieved (HPLC control). The reaction mixture was then concentrated under reduced pressure, and the crude product was purified by preparative HPLC (column: Gromsil C-18 10 µm; mobile phase: acetonitrile/water+0.1% TFA 10:90→90:10). This gave the title compound as a colorless solid (26 mg, 48% of theory, purity about 80%).

LC-MS (Method 6): $R_t$=2.22 min; MS (ESIpos): m/z (%)=630.2 (100) [M+H]$^+$.

Example 25

(4S)-4-[4-Cyano-2-(methylsulfonyl)phenyl]-6-methyl-2-oxo-3-[2-oxo-2-(3-oxopiperazin-1-yl)ethyl]-1-[3-(trifluoromethyl)phenyl]-1,2,3,4-tetrahydropyrimidine-5-carbonitrile

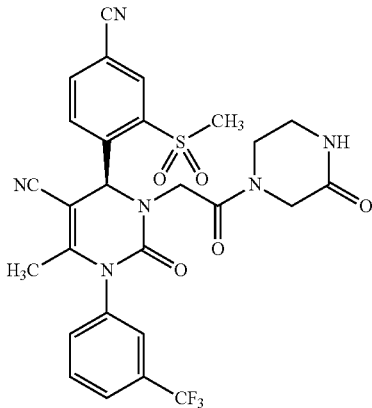 [SMILES: CC1=C(C#N)[C@@H](c2ccc(C#N)cc2S(C)(=O)=O)N(CC(=O)N2CCNC(=O)C2)C(=O)N1c1cccc(C(F)(F)F)c1]

The reaction was carried out under argon. 2-[(6S)-5-Cyano-6-[4-cyano-2-(methylsulfonyl)phenyl]-4-methyl-2-oxo-3-[3-(trifluoromethyl)phenyl]-3,6-dihydropyrimidin-1(2H)-yl]acetic acid (50 mg, 96 µmol; Example 21) was initially charged in DMF (2 ml), HATU (183 mg, 482 µmol, 5 eq.) was added at 0° C. and the mixture was stirred for 20 min. 2-Oxopiperazine (48.3 mg, 482 µmol, 5 eq.) and N,N-diisopropylethylamine (62 mg, 482 µmol, 5 eq.) were then added, and the mixture was stirred at RT for 30 min until complete conversion had been achieved (HPLC control). The reaction mixture was then concentrated under reduced pressure and the crude product was purified by preparative HPLC (column: Gromsil C-18 10 µm; mobile phase: acetonitrile/water+0.1% TFA 10:90→90:10). This gave the title compound as a colorless solid (32 mg, 55% of theory).

LC-MS (Method 6): $R_t$=2.05 min; MS (ESIpos): m/z (%)=601.2 (100) [M+H]$^+$ $^1$H-NMR (400 MHz, DMSO-d$_6$): δ=1.85 (s, 3H), 3.05 (m, 2H), 3.20-3.65 (m, 3H), 3.40 (s, 3H), 3.80-4.00 (m, 2H), 4.45 (t, 1H), 6.35 (s, 1H), 7.65-8.10 (m, 5H), 8.30-8.45 (m, 3H).

Example 26

(4S)-4-[4-Cyano-2-(methylsulfonyl)phenyl]-3-{2-[4-hydroxypiperidin-1-yl]-2-oxoethyl}-6-methyl-2-oxo-1-[3-(trifluoromethyl)phenyl]-1,2,3,4-tetrahydropyrimidine-5-carbonitrile

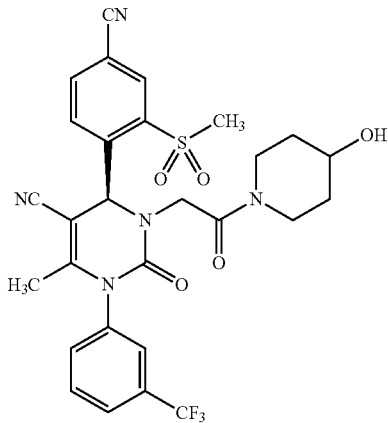 [SMILES: CC1=C(C#N)[C@@H](c2ccc(C#N)cc2S(C)(=O)=O)N(CC(=O)N2CCC(O)CC2)C(=O)N1c1cccc(C(F)(F)F)c1]

The reaction was carried out under argon. 2-[(6S)-5-Cyano-6-[4-cyano-2-(methylsulfonyl)phenyl]-4-methyl-2-oxo-3-[3-(trifluoromethyl)phenyl]-3,6-dihydropyrimidin-1(2H)-yl]acetic acid (45 mg, 87 µmol; Example 21) was initially charged in DMF (1.5 ml), HATU (165 mg, 434 µmol, 5 eq.) was added at 0° C. and the mixture was stirred for 20 min. 4-Hydroxypiperidine (43.9 mg, 434 µmol, 5 eq.) and N,N-diisopropylethylamine (56 mg, 434 µmol, 5 eq.) were then added, and the mixture was stirred at RT for 16 h until complete conversion had been achieved (HPLC control). The reaction mixture was then concentrated under reduced pressure, and the crude product was purified by preparative HPLC (column: Gromsil C-18 10 µm; mobile phase: acetonitrile/water+0.1% TFA 10:90→90:10). This gave the title compound as a colorless solid (51 mg, 98% of theory).

LC-MS (Method 6): $R_t$=2.13 min; MS (ESIpos): m/z (%)=602.1 (100) [M+H]$^+$ $^1$H-NMR (400 MHz, DMSO-d$_6$): δ=1.20 (m, 2H), 1.65 (m, 2H), 1.85 (s, 3H), 2.95 (m, 2H), 3.15 (m, 1H), 3.40 (s, 3H), 3.55-3.70 (m, 2H), 3.95 (m, 1H), 4.45 (m, 1H), 6.35 (s, 1H), 7.65-8.10 (m, 4H), 8.30-8.45 (m, 3H).

Example 27

(4S)-4-[4-Cyano-2-(methylsulfonyl)phenyl]-6-methyl-3-(methylsulfonyl)-2-oxo-1-[3-(trifluoromethyl)phenyl]-1,2,3,4-tetrahydropyrimidine-5-carbonitrile

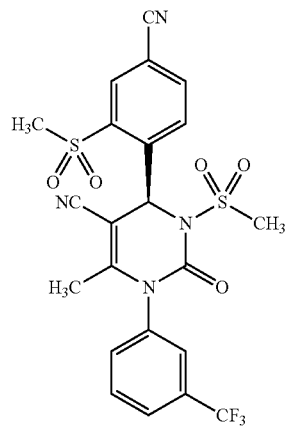

The reaction was carried out under argon. (4S)-4-[4-Cyano-2-(methylsulfonyl)phenyl]-6-methyl-2-oxo-1-[3-(trifluoromethyl)phenyl]-1,2,3,4-tetrahydropyrimidine-5-carbonitrile (69.1 mg, 150 µmol; Example 6) was initially charged in THF (2 ml), and sodium hydride (60% in mineral oil; 7.2 mg, 180 µmol) was added at 0° C. The mixture was warmed to RT and stirred for 20 min. A solution of methanesulfonyl chloride (20.6 mg, 180 µmol, 1.2 eq.) in THF (1 ml) was then slowly added dropwise. After a reaction time of 16 h, more methanesulfonyl chloride (6.7 mg, 60 µmol, 0.4 eq.) was added, and the mixture was again stirred at RT for 60 min. The reaction mixture was then concentrated, and the crude product was purified by preparative HPLC (column: Gromsil C-18 10 µm; mobile phase: acetonitrile/water+0.1% TFA 10:90→80:20). This gave the title compound as a colorless solid (47 mg, 58% of theory).

LC-MS (Method 4): $R_t$=1.22 min; MS (ESIpos): m/z (%)=539.0 (30) [M+H]$^+$; MS (ESIneg): m/z (%)=353.3 (100), 415.9 (50), 457.2 (80), 535.6 (100) [M−H]$^-$ $^1$H-NMR (400 MHz, DMSO-d$_6$): δ=1.80 (s, 3H), −3.40 (2s, 6H), 7.30 (s, 1H), 7.75-8.35 (m, 6H), 8.55 (s, 1H).

Example 28

(4S)-4-[4-Cyano-2-(methylsulfonyl)phenyl]-6-methyl-3-(isopropylsulfonyl)-2-oxo-1-[3-(trifluoromethyl)phenyl]-1,2,3,4-tetrahydropyrimidine-5-carbonitrile

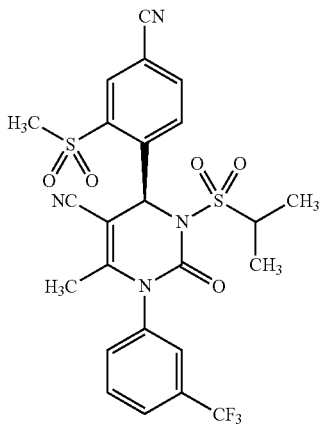 [SMILES: CC1=C(C#N)[C@@H](c2ccc(C#N)cc2S(C)(=O)=O)N(S(=O)(=O)C(C)C)C(=O)N1c1cccc(C(F)(F)F)c1]

Analogously to the preparation of Example 27, (4S)-4-[4-cyano-2-(methylsulfonyl)phenyl]-6-methyl-2-oxo-1-[3-(trifluoromethyl)phenyl]-1,2,3,4-tetrahydropyrimidine-5-carbonitrile (100 mg, 217 μmol; Example 6), sodium hydride (60%, 11.2 mg, 282 μmol) and 2-propanesulfonyl chloride (40.3 mg, 282 μmol) were reacted with one another for 16 h. This gave the title compound as a colorless solid (88 mg, 72% of theory).

LC-MS (Method 5): $R_f$=2.15 min; MS (ESIpos): m/z (%)=567.2 (100) [M+H]$^+$; MS (ESIneg): m/z (%)=565.2 (100) [M−H]$^−$ $^1$H-NMR (400 MHz, DMSO-d$_6$): δ=1.10 (d, 3H), 1.35 (d, 3H), 1.80 (s, 3H), 3.40 (s, 3H), 4.05 (m, 1H), 7.25 (s, 1H), 7.75-8.25 (m, 6H), 8.55 (s, 1H).

Example 29

(4S)-4-[4-Cyano-2-(methylsulfonyl)phenyl]-6-methyl-3-{[2-(trifluoromethoxy)phenyl]sulfonyl}-2-oxo-1-[3-(trifluoromethyl)phenyl]-1,2,3,4-tetrahydropyrimidine-5-carbonitrile

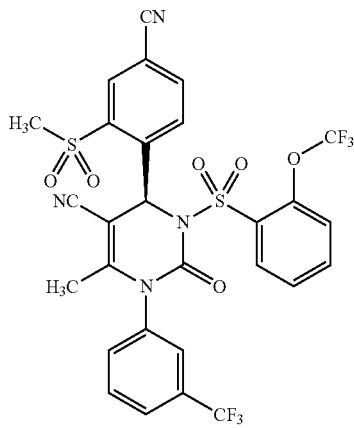 [SMILES: CC1=C(C#N)[C@@H](c2ccc(C#N)cc2S(C)(=O)=O)N(S(=O)(=O)c2ccccc2OC(F)(F)F)C(=O)N1c1cccc(C(F)(F)F)c1]

Analogously to the preparation of Example 27, (4S)-4-[4-cyano-2-(methylsulfonyl)phenyl]-6-methyl-2-oxo-1-[3-(trifluoromethyl)phenyl]-1,2,3,4-tetrahydropyrimidine-5-carbonitrile (100 mg, 217 μmol; Example 6), sodium hydride (60%, 11.2 mg, 282 μmol) and [2-(trifluoromethoxy)phenyl]sulfonyl chloride (73.6 mg, 282 μmol) were reacted with one another for 16 h. This gave the title compound as a colorless solid (115 mg, 77% of theory).

LC-MS (Method 4): $R_f$=1.39 min; MS (ESIpos): m/z (%)=685.0 (40) [M+H]$^+$; MS (ESIneg): m/z (%)=457.5 (100), 683.6 (80) [M−H]$^−$ $^1$H-NMR (400 MHz, DMSO-d$_6$): δ=1.80 (s, 3H), 3.45 (s, 3H), 7.35-8.40 (m, 11H), 8.60 (s, 1H).

Example 30

(4S)-4-[4-Cyano-2-(methylsulfonyl)phenyl]-6-methyl-3-((chloromethyl)sulfonyl)-2-oxo-1-[3-(trifluoromethyl)phenyl]-1,2,3,4-tetrahydropyrimidine-5-carbonitrile

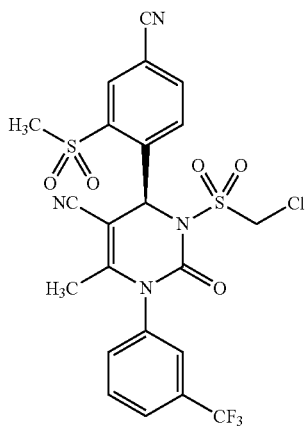 [SMILES: CC1=C(C#N)[C@@H](c2ccc(C#N)cc2S(C)(=O)=O)N(S(=O)(=O)CCl)C(=O)N1c1cccc(C(F)(F)F)c1]

Analogously to the preparation of Example 27, (4S)-4-[4-cyano-2-(methylsulfonyl)phenyl]-6-methyl-2-oxo-1-[3-(trifluoromethyl)phenyl]-1,2,3,4-tetrahydropyrimidine-5-carbonitrile (100 mg, 217 μmol; Example 6), sodium hydride (60%, 11.3 mg, 282 μmol) and chloromethanesulfonyl chloride (42 mg, 282 μmol) were reacted with one another for 3 h. This gave the title compound as a colorless solid (86 mg, 69% of theory).

LC-MS (Method 5): $R_f$=2.11 min; MS (ESIpos): m/z (%)=573.1 (100) [M+H]$^+$; MS (ESIneg): m/z (%)=571.1 (100) [M−H]$^−$ $^1$H-NMR (400 MHz, DMSO-d$_6$): δ=1.85 (s, 3H), 3.45 (s, 3H), 5.45 (d, 1H), 5.55 (d, 1H), 7.35 (s, 1H), 7.80-8.35 (m, 6H), 8.60 (s, 1H).

Example 31

(4S)-4-[4-Cyano-2-(methylsulfonyl)phenyl]-6-methyl-3-(ethylsulfonyl)-2-oxo-1-[3-(trifluoromethyl)phenyl]-1,2,3,4-tetrahydropyrimidine-5-carbonitrile

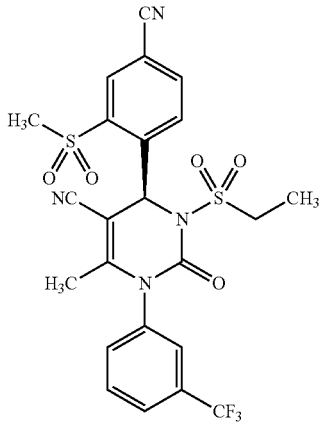 [SMILES: CCS(=O)(=O)N1C(=O)N(c2cccc(C(F)(F)F)c2)C(C)=C(C#N)[C@H]1c1ccc(C#N)cc1S(C)(=O)=O]

Analogously to the preparation of Example 27, (4S)-4-[4-cyano-2-(methylsulfonyl)phenyl]-6-methyl-2-oxo-1-[3-(trifluoromethyl)phenyl]-1,2,3,4-tetrahydropyrimidine-5-carbonitrile (100 mg, 217 µmol; Example 6), sodium hydride (60%, 11.2 mg, 282 µmol) and ethanesulfonyl chloride (36 mg, 282 µmol) were reacted with one another for 3 h. This gave the title compound as a colorless solid (99 mg, 83% of theory).

LC-MS (Method 5): $R_t$=2.06 min; MS (ESIpos): m/z (%)=553.1 (100) [M+H]$^+$; MS (ESIneg): m/z (%)=416.2 (50), 551.2 (90) [M−H]$^-$ $^1$H-NMR (400 MHz, DMSO-d$_6$): δ=1.15 (t, 3H), 1.80 (s, 3H), 3.40 (s, 3H), 3.55 (m, 1H), 3.75 (m, 1H), 7.30 (s, 1H), 7.70-8.35 (m, 6H), 8.55 (s, 1H).

Example 32

(4S)-4-[4-Cyano-2-(methylsulfonyl)phenyl]-6-methyl-3-(cyclopropylsulfonyl)-2-oxo-1-[3-(trifluoromethyl)phenyl]-1,2,3,4-tetrahydropyrimidine-5-carbonitrile

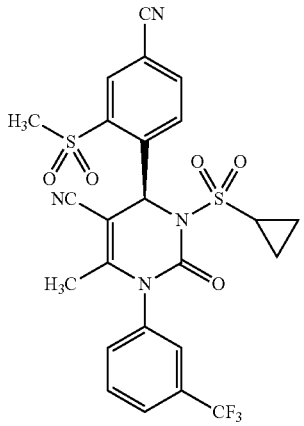 [SMILES: CC1=C(C#N)[C@@H](c2ccc(C#N)cc2S(C)(=O)=O)N(S(=O)(=O)C2CC2)C(=O)N1c1cccc(C(F)(F)F)c1]

Analogously to the preparation of Example 27, (4S)-4-[4-cyano-2-(methylsulfonyl)phenyl]-6-methyl-2-oxo-1-[3-(trifluoromethyl)phenyl]-1,2,3,4-tetrahydropyrimidine-5-carbonitrile (100 mg, 217 µmol; Example 6), sodium hydride (60%, 11.2 mg, 282 µmol) and cyclopropylsulfonyl chloride (39.7 mg, 282 µmol) were reacted with one another for 16 h. This gave the title compound as a colorless solid (57 mg, 47% of theory).

LC-MS (Method 5): $R_t$=2.07 min; MS (ESIpos): m/z (%)=565.1 (100) [M+H]$^+$; MS (ESIneg): m/z (%)=416.2 (80), 563.2 (80) [M−H]$^-$ $^1$H-NMR (400 MHz, DMSO-d$_6$): δ=0.30 (br. m, 1H), 0.85 (br. m, 1H), 1.15 (m, 2H), 1.80 (s, 3H), 3.10 (m, 1H), 3.40 (s, 3H), 7.30 (s, 1H), 7.75-8.35 (m, 6H), 8.55 (s, 1H).

Example 33

(4S)-4-[4-Cyano-2-(methylsulfonyl)phenyl]-3,6-dimethyl-2-oxo-1-[3-(trifluoromethyl)phenyl]-1,2,3,4-tetrahydropyrimidine-5-carbonitrile

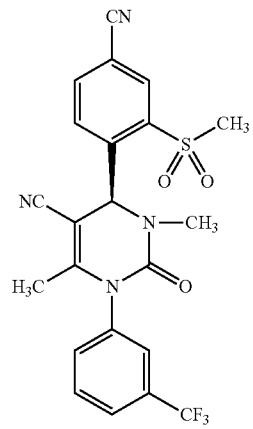

Method A:

The reaction was carried out under argon. (4S)-4-[4-Cyano-2-(methylsulfonyl)phenyl]-6-methyl-2-oxo-1-[3-(trifluoromethyl)phenyl]-1,2,3,4-tetrahydropyrimidine-5-carbonitrile (75 mg, 163 µmol; Example 6) was initially charged in THF (2 ml) and sodium hydride (60% in mineral oil; 9.2 mg, 228 µmol) was added. After 20 min of stirring, iodomethane (32.4 mg, 14.2 µl, 228 µmol) was added, and the mixture was stirred at RT for a further 120 min. The reaction mixture was then purified by preparative HPLC (column: Kromasil-100A, C-18 5 µm; mobile phase: acetonitrile/water+0.1% TFA 10:90→80:20). This gave the title compound as a colorless solid (18 mg, 23% of theory).

Method B:

The reaction was carried out under argon. (4S)-4-[4-Cyano-2-(methylsulfonyl)phenyl]-6-methyl-2-oxo-1-[3-(trifluoromethyl)phenyl]-1,2,3,4-tetrahydropyrimidine-5-carbonitrile (460.4 mg, 1 mmol; Example 6) was initially charged in absolute THF (10 ml), and at −78° C. a 1 M solution of lithium hexamethyldisilazide (LiHMDS) in THF (1 ml; 1 eq.) was added. After 20 min of stirring, iodomethane (710 mg; 5 eq.) was added, and the mixture was stirred with gradual warming from −78° C. to RT for 60 h. The reaction mixture was then purified directly by preparative HPLC (column: Gromsil, C-18 10 µm; mobile phase: acetonitrile/water+0.1% TFA 10:90→90:10). This gave the title compound as a colorless solid (454 mg, 96% of theory).

Method C:

Sodium 5-cyano-2-{(4S)-5-cyano-3,6-dimethyl-2-oxo-1-[3-(trifluoromethyl)phenyl]-1,2,3,4-tetrahydropyrimidin-4-yl}benzenesulfinate (150 mg, 65 µmol; purity about 21%)

was suspended under argon in a pressure-proof glass tube in DMF (1 ml). Molecular sieve (4 Å, 20 mg) and methyl iodide (82 µl, 1.3 mmol; 20 eq.) were added. The sealed tube was heated at 115° C. for 15 h. The reaction mixture was then filtered, and the filtrate was concentrated under reduced pressure. The residue was purified by preparative HPLC (Gromsil C18 column; mobile phase: acetonitrile/water+0.1% TFA). Lyophilization gave the title compound as a solid (29.4 mg, 95% of theory).

LC-MS (Method 4): $R_t$=1.21 min; MS (ESIpos): m/z (%)=475.0 (100) [M+H]$^+$; MS (ESIneg): m/z (%)=473.2 (100) [M−H]$^-$ $^1$H-NMR (400 MHz, DMSO-d$_6$): δ=1.80 (s, 3H), 2.65 (s, 3H), 3.40 (s, 3H), 6.45 (s, 1H), 7.65-8.40 (m, 6H), 8.45 (s, 1H).

Example 34

(rac)-4-{6-Methyl-2,5-dioxo-1-[3-(trifluoromethyl) phenyl]-2,3,4,5,6,7-hexahydro-1H-pyrrolo[3,4-d] pyrimidin-4-yl}-3-(methylsulfonyl)benzonitrile

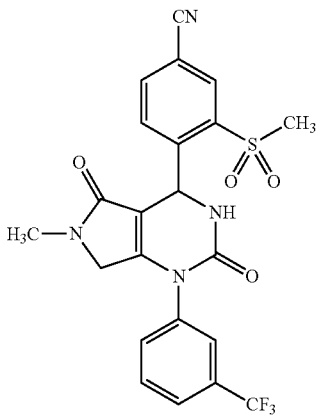

Under an argon protective gas atmosphere, (rac)-2,3-dibromopropyl 6-(bromomethyl)-4-[4-cyano-2-(methylsulfonyl)phenyl]-2-oxo-1-[3-(trifluoromethyl)phenyl]-1,2,3,4-tetrahydropyrimidine-5-carboxylate (758.2 mg, 1.0 mmol; Example 7A) was mixed with a 1 M solution of methylamine in THF (20 ml, 20.0 mmol, 20 eq.), and the mixture was stirred at RT for 30 min. The reaction mixture was then concentrated under reduced pressure, and the crude product was purified by preparative HPLC (column: Gromsil C-18 10 µm; mobile phase: acetonitrile/water+0.1% TFA 10:90→90:10). This gave the title compound as a colorless solid (328 mg, 67% of theory).

LC-MS (Method 5): $R_t$=1.61 min; MS (ESIpos): m/z (%)=491.1 (100) [M+H]$^+$; MS (ESIneg): m/z (%)=489.1 (100) [M−H]$^-$ $^1$H-NMR (400 MHz, DMSO-d$_6$): δ=2.65 (s, 3H), 3.55 (s, 3H), 3.85 (m, 2H), 6.65 (s, 1H), 7.70-7.85 (m, 3H), 8.00 (s, 1H), 8.10 (s, 1H), 8.15 (d, 1H), 8.25 (dd, 1H), 8.30 (s, 1H).

Example 35

4-{(4S)-6-Methyl-2,5-dioxo-1-[3-(trifluoromethyl) phenyl]-2,3,4,5,6,7-hexahydro-1H-pyrrolo[3,4-d] pyrimidin-4-yl}-3-(methylsulfonyl)benzonitrile

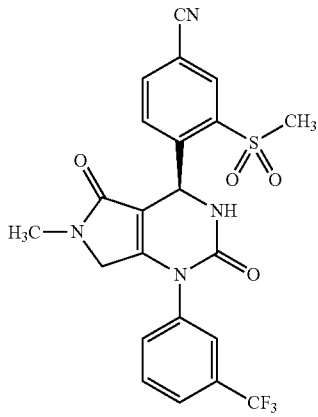

(rac)-4-{6-Methyl-2,5-dioxo-1-[3-(trifluoromethyl)phenyl]-2,3,4,5,6,7-hexahydro-1H-pyrrolo[3,4-d]pyrimidin-4-yl}-3-(methylsulfonyl)benzonitrile (Example 34, 190 mg) was separated into the enantiomers by preparative HPLC chromatography on a chiral phase [column: Daicel Chiralpak IC, 5 µm, 250 mm×20 mm; sample preparation: the sample was dissolved in 70 ml of methanol/acetonitrile/MTBE 25:10:35; injection volume: 1 ml; mobile phase: MTBE/methanol 75:25 (0-7 min); flow rate: 15 ml/min; temperature: 30° C.; detection: 220 nm]. This gave 97 mg (100% of theory, >99.0% ee) of the 4S enantiomer. The enantiomeric excess (ee value) was determined chromatographically [column: Daicel Chiralpak IC, 5 µm, 250 mm×4.6 mm; mobile phase: MTBE/methanol 75:25; flow rate: 1 ml/min; temperature: 25° C.; detection: 220 nm; $R_t$=6.62 min].

LC-MS (Method 5): $R_t$=1.59 min; MS (ESIpos): m/z (%)=491.1 (100) [M+H]$^+$; MS (ESIneg): m/z (%)=446.2 (70), 489.2 (100) [M−H]$^-$.

Example 36

4-{(4S)-6-Methyl-3-(methylsulfonyl)-2,5-dioxo-1-[3-(trifluoromethyl)phenyl]-2,3,4,5,6,7-hexahydro-1H-pyrrolo[3,4-d]pyrimidin-4-yl}-3-(methylsulfonyl)benzonitrile

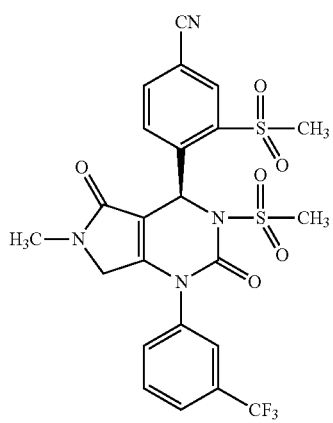

Analogously to the preparation of Example 27, 4-{(4S)-6-methyl-2,5-dioxo-1-[3-(trifluoromethyl)phenyl]-2,3,4,5,6, 7-hexahydro-1H-pyrrolo[3,4-d]pyrimidin-4-yl}-3-(methylsulfonyl)benzonitrile (20 mg, 41 μmol; Example 35), sodium hydride (60%, 2.3 mg, 57 μmol) and methanesulfonyl chloride (6.5 mg, 57 μmol) were reacted with one another for 2 h. The title compound was obtained as a colorless solid (1.7 mg, 7% of theory). In addition, 6.4 mg (32% of theory) of the starting material were recovered.

LC-MS (Method 4): $R_t$=1.10 min; MS (ESIpos): m/z (%)=569.0 (100) [M+H]$^+$; MS (ESIneg): m/z (%)=568.4 (100) [M−H]$^−$.

Example 37

(rac)-2-{4-[4-Cyano-2-(methylsulfonyl)phenyl]-6-methyl-2,5-dioxo-1-[3-(trifluoromethyl)phenyl]-1,2,4,5,6,7-hexahydro-3H-pyrrolo[3,4-d]pyrimidin-3-yl}acetamide

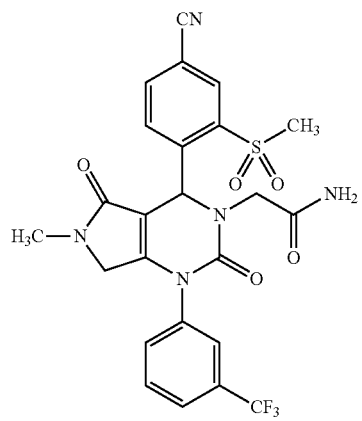 [SMILES: CN1CC2=C(C1=O)C(c1ccc(C#N)cc1S(C)(=O)=O)N(CC(N)=O)C(=O)N2c1cccc(C(F)(F)F)c1]

The title compound was obtained from (rac)-4-{6-methyl-2,5-dioxo-1-[3-(trifluoromethyl)phenyl]-2,3,4,5,6,7-hexahydro-1H-pyrrolo[3,4-d]pyrimidin-4-yl}-3-(methylsulfonyl)benzonitrile (Example 34) analogously to the multi-step preparation of 2-[(6S)-5-cyano-6-[4-cyano-2-(methylsulfonyl)phenyl]-4-methyl-2-oxo-3-[3-(trifluoromethyl)phenyl]-3,6-dihydropyrimidin-1(2H)-yl] acetamide (Example 22) from (4S)-4-[4-cyano-2-(methylsulfonyl)phenyl]-6-methyl-2-oxo-1-[3-(trifluoromethyl)phenyl]-1,2,3,4-tetrahydropyrimidine-5-carbonitrile (Example 6).

LC-MS (Method 5): $R_t$=1.44 min; MS (ESIpos): m/z (%)=548.1 (100) [M+H]$^+$; MS (ESIneg): m/z (%)=546.1 (100) [M−H]$^−$ $^1$H-NMR (400 MHz, DMSO-d$_6$): δ=2.70 (s, 3H), 3.30 (d, 1H), 3.90 (m, 2H), 3.95 (d, 1H), 6.55 (s, 1H), 6.95 (s, 1H), 7.30 (s, 1H), 7.75-7.85 (m, 3H), 8.00 (s, 1H), 8.20-8.30 (m, 2H), 8.35 (s, 1H) [a methyl group is obscured by the solvent peak].

Example 38

(rac)-4-[4-Cyano-2-(methylsulfonyl)phenyl]-N-(2-hydroxyethyl)-6-methyl-2,5-dioxo-1-[3-(trifluoromethyl)phenyl]-1,2,4,5,6,7-hexahydro-3H-pyrrolo[3,4-d]pyrimidine-3-carboxamide

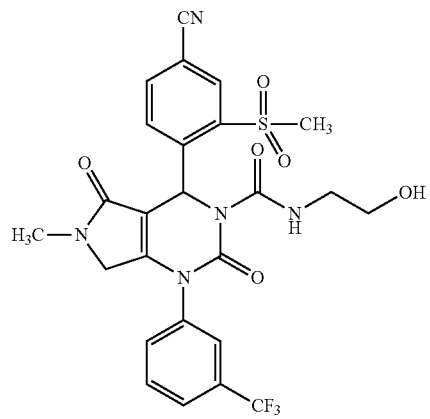 [SMILES: CN1CC2=C(C1=O)C(c1ccc(C#N)cc1S(C)(=O)=O)N(C(=O)NCCO)C(=O)N2c1cccc(C(F)(F)F)c1]

The title compound was prepared from (rac)-4-{6-methyl-2,5-dioxo-1-[3-(trifluoromethyl)phenyl]-2,3,4,5,6,7-hexahydro-1H-pyrrolo[3,4-d]pyrimidin-4-yl}-3-(methylsulfonyl)benzonitrile (Example 34) analogously to the multi-step preparation of (6S)-5-cyano-6-[4-cyano-2-(methylsulfonyl)phenyl]-N-(2-hydroxyethyl)-4-methyl-2-oxo-3-[3-(trifluoromethyl)phenyl]-3,6-dihydropyrimidine-1(2H)-carboxamide (Example 10) from (4S)-4-[4-cyano-2-(methylsulfonyl)phenyl]-6-methyl-2-oxo-1-[3-(trifluoromethyl)phenyl]-1,2,3,4-tetrahydropyrimidine-5-carbonitrile (Example 6).

LC-MS (Method 5): $R_t$=1.56 min; MS (ESIpos): m/z (%)=578.1 (100) [M+H]$^+$; MS (ESIneg): m/z (%)=489.2 (100), 576 (70) [M−H]$^−$.

Example 39

Allyl (rac)-4-[4-cyano-2-(methylsulfanyl)phenyl]-6-methyl-2-oxo-1-[3-(trifluoromethyl)phenyl]-1,2,3,4-tetrahydropyrimidine-5-carboxylate

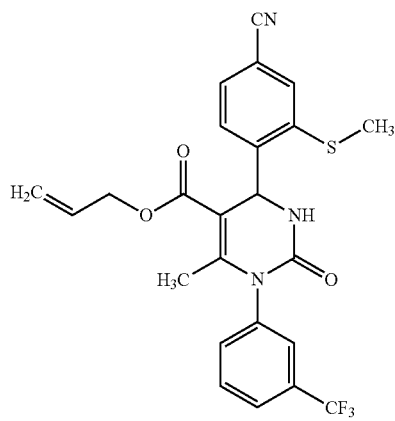 [SMILES: C=CCOC(=O)C1=C(C)N(c2cccc(C(F)(F)F)c2)C(=O)NC1c1ccc(C#N)cc1SC]

The reaction was carried out under argon. Triethyl phosphate (1.46 g, 8.04 mmol) and diphosphorus pentoxide (761 mg, 5.36 mmol) were stirred at 50° C. overnight. The mixture was then diluted with MTBE (27 ml), and 4-formyl-3-(methylsulfanyl)benzonitrile (1.18 g, 6.70 mmol; Example 9A), 1-[3-(trifluoromethyl)phenyl]urea (1.37 g, 6.70 mmol) and allyl acetoacetate (1.43 g, 10.1 mmol) were added. The mixture was stirred under reflux overnight. For work-up, the solvent was removed under reduced pressure and the residue was suspended in diethyl ether and then filtered of with suction. This gave 978 mg (19% of theory) of the title compound.

LC-MS (Method 4): $R_t$=1.37 min; MS (ESIpos): m/z (%)=488.3 (100) [M+H]$^+$; MS (ESIneg): m/z (%)=486.2 (65) [M−H]$^-$.

Example 40

(4S)-4-[4-Cyano-2-(methylsulfanyl)phenyl]-6-methyl-2-oxo-1-[3-(trifluoromethyl)phenyl]-1,2,3,4-tetrahydropyrimidine-5-carboxamide

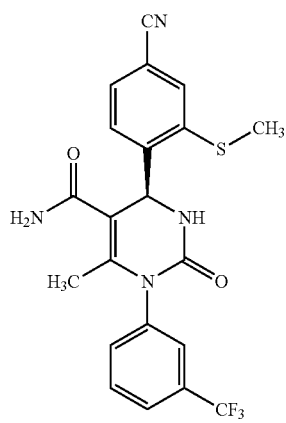 [SMILES: CSc1cc(C#N)ccc1[C@H]1NC(=O)N(c2cccc(C(F)(F)F)c2)C(C)=C1C(N)=O]

The reaction was carried out under argon. (4S)-4-[4-Cyano-2-(methylsulfanyl)phenyl]-6-methyl-2-oxo-1-[3-(trifluoromethyl)phenyl]-1,2,3,4-tetrahydropyrimidine-5-carboxylic acid (240 mg, 0.536 mmol; Example 11A) was dissolved in THF (5 ml), and PyBOP (419 mg, 0.805 mmol) and triethylamine (380 mg, 3.76 mmol) were added. After brief stirring, the mixture was cooled to 0° C. and ammonium chloride (143 mg, 2.68 mmol) was added. The reaction mixture was stirred at RT overnight, and the contents of the flask was then added to 1 N hydrochloric acid. The mixture was extracted twice with ethyl acetate, and the combined organic phases were washed with 1 N hydrochloric acid and with saturated sodium chloride solution, dried and concentrated. The residue was purified by preparative HPLC. This gave 161 mg (67% of theory) of the title compound.

LC-MS (Method 4): $R_t$=0.99 min; MS (ESIpos): m/z (%)=447.1 (100) [M+H]$^+$; MS (ESIneg): m/z (%)=445.3 (100) [M−H]$^-$.

Example 41

(4S)-4-[4-Cyano-2-(methylsulfanyl)phenyl]-6-methyl-2-oxo-1-[3-(trifluoromethyl)phenyl]-1,2,3,4-tetrahydropyrimidine-5-carbonitrile

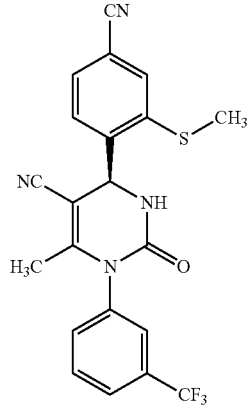

The reaction was carried out under argon. (4S)-4-[4-Cyano-2-(methylsulfanyl)phenyl]-6-methyl-2-oxo-1-[3-(trifluoromethyl)phenyl]-1,2,3,4-tetrahydropyrimidine-5-carboxamide (95.0 mg, 0.213 mmol; Example 40) was dissolved in THF (4 ml), and methoxycarbonylsulfamoyltriethylammonium hydroxide (Burgess reagent; 101 mg, 0.426 mmol) was added. After 30 min of stirring at room temperature, HPLC control showed complete conversion. The mixture was diluted with ethyl acetate (4 ml), and water (1 ml) was added. The mixture was then passed over a Merck Extrelut® NT3 column, and the filtrate was purified by preparative HPLC. Concentration of the product fractions gave 96.0 mg (quantitative) of the title compound.

HPLC (Method 3): $R_t$=4.61 min.
MS (DCI/NH$_3$): m/z=429.1 [M+H]$^+$, 446.1 [M+NH$_4$]$^+$
$^1$H-NMR (400 MHz, DMSO-d$_6$): δ=1.80 (s, 3H), 2.61 (s, 3H), 5.76 (s, 1H), 7.67-7.89 (m, 7H), 8.28 (s, 1H).

Example 42

(4S)-4-[4-Cyano-2-(methylsulfinyl)phenyl]-6-methyl-2-oxo-1-[3-(trifluoromethyl)phenyl]-1,2,3,4-tetrahydropyrimidine-5-carbonitrile

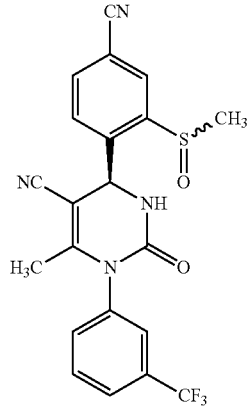

Method A:
(4S)-4-[4-Cyano-2-(methylsulfanyl)phenyl]-6-methyl-2-oxo-1-[3-(trifluoromethyl)phenyl]-1,2,3,4-tetrahydropyrimidine-5-carbonitrile (Example 41; 55 mg, 0.13 mmol) was dissolved in ethanol (5.5 ml), and methyltrioxorhenium (3.20 mg, 0.013 mmol) and hydrogen peroxide (16.0 mg, 0.14 mmol) were added. The reaction mixture was stirred at RT for 60 min and then concentrated under reduced pressure, and the residue was purified by preparative HPLC. This gave 27 mg (47% of theory) of the target compound as a mixture of diastereomers.

Method B:

(4S)-4-[4-Cyano-2-(methylsulfanyl)phenyl]-6-methyl-2-oxo-1-[3-(trifluoromethyl)phenyl]-1,2,3,4-tetrahydropyrimidine-5-carbonitrile (3.00 g, 7.00 mmol; Example 41) was initially charged in methanol/water (5:1, ~60 ml), sodium periodate (2.85 g, 13.30 mmol; 1.9 eq.) was added and the mixture was stirred at 30° C. for 16 h. The reaction mixture was then poured into saturated aqueous sodium bicarbonate solution (300 ml) and extracted with ethyl acetate (4×75 ml). The combined organic phases were dried over sodium sulfate, filtered and concentrated under reduced pressure. The crude product was subjected to flash chromatography on silica gel (gradient cyclohexane→ethyl acetate). This gave a colorless solid (1.6 g, 51% of theory).

LC-MS (Method 4): $R_t$=1.05 min; MS (ESIpos): m/z (%)=445.0 (100) [M+H]$^+$.

Example 43

(4S)-4-{4-Cyano-2-[(S)-methylsulfinyl]phenyl}-6-methyl-2-oxo-1-[3-(trifluoromethyl)phenyl]-1,2,3,4-tetrahydropyrimidine-5-carbonitrile and (4S)-4-{4-cyano-2-[(R)-methylsulfinyl]phenyl}-6-methyl-2-oxo-1-[3-(trifluoromethyl)phenyl]-1,2,3,4-tetrahydropyrimidine-5-carbonitrile (separation of diastereomers)

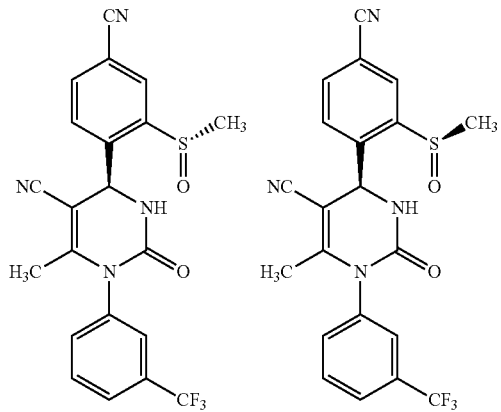

(4S)-4-[4-Cyano-2-(methylsulfinyl)phenyl]-6-methyl-2-oxo-1-[3-(trifluoromethyl)phenyl]-1,2,3,4-tetrahydropyrimidine-5-carbonitrile (Example 42; 27 mg) was separated into the enantiomerically pure diastereomers by preparative HPLC chromatography on a chiral phase [column: Daicel Chiralpak IC, 5 μm, 250 mm×20 mm; sample preparation: the sample was dissolved in 2 ml of methanol+4 ml of MTBE; injection volume: 600 μl; mobile phase: MTBE/methanol 80:20; flow rate: 15 ml/min; temperature: 30° C.; detection: 220 nm]. The enantiomeric excess (ee value) was determined chromatographically [column: Daicel Chiralpak IC, 5 μm, 250 mm×4.6 mm; mobile phase: MTBE/methanol 75:25; flow rate: 1 ml/min; temperature: 25° C.; detection: 230 nm].

Diastereomer 1:

Yield: 20 mg $R_t$=4.71 min, ee>99.0%

LC-MS (Method 6): $R_t$=2.02 min; MS (ESIpos): m/z (%)=445.0 (100) [M+H]$^+$; MS (ESIneg): m/z (%)=442.9 (80) [M−H]$^-$ $^1$H-NMR (400 MHz, CDCl$_3$): δ=1.94 (s, 3H), 2.84 (s, 3H), 5.72 (s, 1H), 7.17 (s, 1H), 7.42-7.56 (m, 2H), 7.65 (t, 1H), 7.70-7.79 (m, 2H), 7.90 (d, 1H), 8.01 (s, 1H).

Diastereomer 2:

Yield: 7 mg $R_t$=6.04 min, ee>99.0%

LC-MS (Method 6): $R_t$=2.02 min; MS (ESIpos): m/z (%)=445.0 (100) [M+H]$^+$; MS (ESIneg): m/z (%)=442.9 (100) [M−H]$^-$ $^1$H-NMR (400 MHz, CDCl$_3$): δ=1.97 (s, 3H), 2.77 (s, 3H), 5.97 (br. s, 1H), 7.06 (br. s, 1H), 7.31-7.50 (m, 2H), 7.63 (t, 1H), 7.68-7.78 (m, 2H), 7.89 (d, 1H), 8.11 (s, 1H).

Example 44

(rac)-4-{2,5-Dioxo-1-[3-(trifluoromethyl)phenyl]-2,3,4,5,6,7-hexahydro-1H-pyrrolo[3,4-d]pyrimidin-4-yl}-3-(methylsulfonyl)benzonitrile

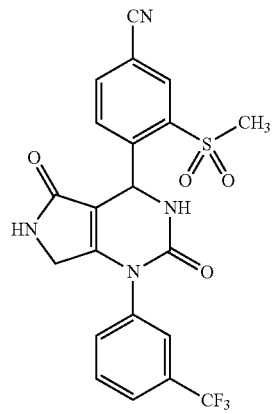 [SMILES: CS(=O)(=O)c1cc(C#N)ccc1C1NC(=O)N(c2cccc(C(F)(F)F)c2)C2=C1C(=O)NC2]

(rac)-Ethyl 6-(bromomethyl)-4-[4-cyano-2-(methylsulfonyl)phenyl]-2-oxo-1-[3-(trifluoromethyl)phenyl]-1,2,3,4-tetrahydropyrimidine-5-carboxylate (200 mg, 0.34 mmol; Example 13A) was dissolved in acetonitrile (4 ml), a 7 N solution of ammonia in methanol (5 ml) was added and the mixture was stirred at RT for 60 min. The reaction mixture was then concentrated under reduced pressure, and the residue was triturated with acetonitrile (3 ml). The crystals formed were filtered off with suction, washed with acetonitrile and water and, for further purification, separated by preparative HPLC [column: Sunfire C-18, 5 μm, 19 mm×150 mm; sample preparation: the sample was dissolved in 3 ml of acetonitrile+3 ml of 1% strength aqueous TFA solution+2 ml of THF; injection volume: 1000 μl; mobile phase: acetonitrile/water/1% aq. TFA 25:60:15 (0-12 min); flow rate: 25 ml/min; temperature: 40° C.; detection: 210 nm]. This gave 59 mg (36% of theory) of the target compound.

HPLC (Method 2): $R_t$=3.89 min.

MS (ESIpos): m/z (%)=476.9 (100) [M+H]$^+$ $^1$H-NMR (400 MHz, DMSO-d$_6$): δ=3.53 (s, 3H), 3.75 (dd, 2H), 6.61 (s, 1H), 7.70-7.86 (m, 4H), 8.01 (s, 1H), 8.08 (s, 1H), 8.16 (d, 1H), 8.27 (d, 1H), 8.34 (s, 1H).

Example 45

(rac)-4-{6-(2-Hydroxyethyl)-2,5-dioxo-1-[3-(trifluoromethyl)phenyl]-2,3,4,5,6,7-hexahydro-1H-pyrrolo[3,4-d]pyrimidin-4-yl}-3-(methylsulfonyl)benzonitrile

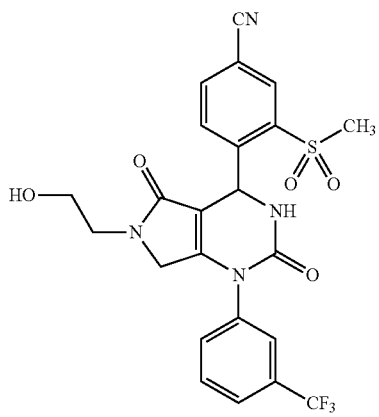 [SMILES: CS(=O)(=O)c1cc(C#N)ccc1C1NC(=O)N(c2cccc(C(F)(F)F)c2)C2=C1C(=O)N(CCO)C2]

(rac)-Ethyl 6-(bromomethyl)-4-[4-cyano-2-(methylsulfonyl)phenyl]-2-oxo-1-[3-(trifluoromethyl)phenyl]-1,2,3,4-tetrahydropyrimidine-5-carboxylate (200 mg, 0.34 mmol; Example 13A) was dissolved in acetonitrile (5 ml), 2-aminoethanol (62.5 mg, 1.02 mmol) was added and the mixture was stirred at RT overnight. The reaction mixture was then purified directly by preparative HPLC (column: Kromasil C18, 125 mm×20 mm, 5 μm, 100 Å; mobile phase A: water with 0.01% formic acid, mobile phase B: acetonitrile; gradient: 0 min 10% B→2 min 10% B→9 min 90% B→12 min 90% B→12.1 min 10% B→15 min 10% B; flow rate: 0.35 ml/min; UV detection: 254 nm). This gave 98 mg (54% of theory) of the title compound.

HPLC (Method 2): $R_t$=3.79 min.
MS (ESIpos): m/z (%)=521.1 (100) [M+H]$^+$
$^1$H-NMR (400 MHz, DMSO-d$_6$): δ=3.14-3.42 (m, 4H), 3.54 (s, 3H), 3.93 (d, 2H), 4.63 (t, 1H), 6.65 (s, 1H), 7.76 (t, 1H), 7.80-7.87 (m, 2H), 8.02 (s, 1H), 8.11 (s, 1H), 8.18 (d, 1H), 8.26 (d, 1H), 8.34 (s, 1H).

Example 46

(rac)-4-{6-Cyclopropyl-2,5-dioxo-1-[3-(trifluoromethyl)phenyl]-2,3,4,5,6,7-hexahydro-1H-pyrrolo[3,4-d]pyrimidin-4-yl}-3-(methylsulfonyl)benzonitrile

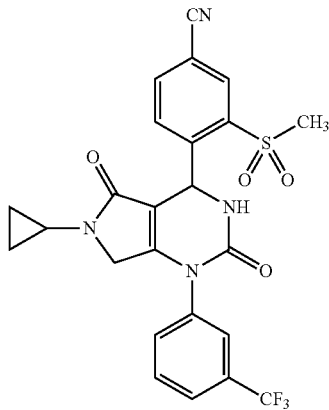 [SMILES: CS(=O)(=O)c1cc(C#N)ccc1C1NC(=O)N(c2cccc(C(F)(F)F)c2)C2=C1C(=O)N(C1CC1)C2]

(rac)-Ethyl 6-(bromomethyl)-4-[4-cyano-2-(methylsulfonyl)phenyl]-2-oxo-1-[3-(trifluoromethyl)phenyl]-1,2,3,4-tetrahydropyrimidine-5-carboxylate (200 mg, 0.34 mmol; Example 13A) was dissolved in acetonitrile (5 ml), cyclopropylamine (58.4 mg, 1.02 mmol) was added and the mixture was stirred at RT overnight. The reaction mixture was then purified directly by preparative HPLC (column: Kromasil C18, 125 mm×20 mm, 5 μm, 100 Å; mobile phase A: water with 0.01% formic acid, mobile phase B acetonitrile; gradient: 0 min 10% B→2 min 10% B→9 min 90% B→12 min 90% B→12.1 min 10% B→15 min 10% B; flow rate: 0.35 ml/min; UV detection: 254 nm). The product-containing fractions were combined and once more subjected to HPLC separation [column: Sunfire C-18, 5 μm, 19 mm×150 mm; sample preparation: the sample was dissolved in 2 ml of acetonitrile+2 ml of 1% strength aqueous TFA solution+1 ml of THF; injection volume: 1000 μl; mobile phase: acetonitrile/water/1% aq. TFA 35:52:13 (0-10 min); flow rate: 25 ml/min; temperature: 40° C.; detection: 210 nm]. This gave 38 mg (22% of theory) of the title compound.

HPLC (Method 2): $R_t$=4.24 min.
MS (ESIpos): m/z (%)=516.9 (100) [M+H]$^+$
$^1$H-NMR (400 MHz, DMSO-d$_6$): δ=0.48-0.60 (m, 4H), 2.43-2.48 (m, 1H), 3.54 (s, 3H), 3.81 (s, 2H), 6.62 (s, 1H), 7.74 (t, 1H), 7.80-7.85 (m, 2H), 7.98 (s, 1H), 8.10-8.17 (m, 2H), 8.26 (d, 1H), 8.34 (s, 1H).

Example 47

(rac)-4-{6-Ethyl-2,5-dioxo-1-[3-(trifluoromethyl)phenyl]-2,3,4,5,6,7-hexahydro-1H-pyrrolo[3,4-d]pyrimidin-4-yl}-3-(methylsulfonyl)benzonitrile

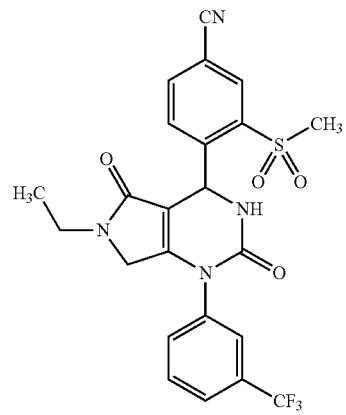 [SMILES: CCN1CC2=C(C1=O)C(c1ccc(C#N)cc1S(C)(=O)=O)NC(=O)N2c1cccc(C(F)(F)F)c1]

(rac)-Ethyl 6-(bromomethyl)-4-[4-cyano-2-(methylsulfonyl)phenyl]-2-oxo-1-[3-(trifluoromethyl)phenyl]-1,2,3,4-tetrahydropyrimidine-5-carboxylate (200 mg, 0.34 mmol; Example 13A) was dissolved in acetonitrile (5 ml), ethylamine (46.1 mg, 1.02 mmol) was added and the mixture was stirred at RT overnight. The reaction mixture was then purified directly by preparative HPLC (column: Kromasil C18, 125 mm×20 mm, 5 μm, 100 Å; mobile phase A: water with 0.01% formic acid, mobile phase B: acetonitrile; gradient: 0 min 10% B→2 min 10% B→9 min 90% B→12 min 90% B→12.1 min 10% B→15 min 10% B; flow rate: 0.35 ml/min; UV detection: 254 nm). This gave 120 mg (70% of theory) of the title compound.

HPLC (Method 2): $R_t$=4.20 min.
MS (ESIpos): m/z (%)=505.0 (100) [M+H]$^+$
$^1$H-NMR (400 MHz, DMSO-d$_6$): δ=0.94 (t, 3H), 3.11-3.26 (m, 2H), 3.54 (s, 3H), 3.86 (s, 2H), 6.64 (s, 1H), 7.75 (t, 1H), 7.80-7.88 (m, 2H), 8.02 (s, 1H), 8.10 (s, 1H), 8.17 (d, 1H), 8.26 (d, 1H), 8.34 (s, 1H).

Example 48

4-{(4S)-6-Ethyl-2,5-dioxo-1-[3-(trifluoromethyl)phenyl]-2,3,4,5,6,7-hexahydro-1H-pyrrolo[3,4-d]pyrimidin-4-yl}-3-(methylsulfonyl)benzonitrile

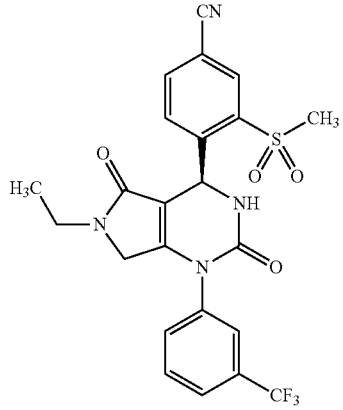 [SMILES: CCN1CC2=C(C1=O)[C@@H](c1ccc(C#N)cc1S(C)(=O)=O)NC(=O)N2c1cccc(C(F)(F)F)c1]

(rac)-4-{6-Ethyl-2,5-dioxo-1-[3-(trifluoromethyl)phenyl]-2,3,4,5,6,7-hexahydro-1H-pyrrolo[3,4-d]pyrimidin-4-yl}-3-(methylsulfonyl)benzonitrile (Example 47; 120 mg) was separated into the enantiomers by preparative HPLC chromatography on a chiral phase [column: Daicel Chiralpak IC, 5 µm, 250 mm×20 mm; sample preparation: the sample was dissolved in 1 ml of methanol+1 ml of acetonitrile+3 ml of MTBE; injection volume: 700 µl; mobile phase: MTBE/methanol 80:20; flow rate: 15 ml/min; temperature: 30° C.; detection: 220 nm]. This gave 42 mg (84% of theory, >99.0% ee) of the 4S enantiomer. The enantiomeric excess (ee value) was determined chromatographically [column: Daicel Chiralpak IC, 5 µm, 250 mm×4.6 mm; mobile phase: MTBE/methanol 80:20; flow rate: 1 ml/min; temperature: 25° C.; detection: 230 nm; $R_t$=6.83 min].

HPLC (Method 2): $R_t$=4.20 min.

MS (DCI/NH$_3$): m/z (%)=505.1 [M+H]$^+$ $^1$H-NMR (400 MHz, DMSO-d$_6$): δ=0.94 (t, 3H), 3.10-3.27 (m, 2H), 3.54 (s, 3H), 3.86 (s, 2H), 6.64 (s, 1H), 7.75 (t, 1H), 7.80-7.88 (m, 2H), 8.02 (s, 1H), 8.10 (s, 1H), 8.17 (d, 1H), 8.26 (d, 1H), 8.34 (s, 1H).

Optical rotation: $[α]^{20}_{Na}$=−107° (c=0.230 in acetone).

Example 49

(rac)-N-(2-{4-[4-Cyano-2-(methylsulfonyl)phenyl]-2,5-dioxo-1-[3-(trifluoromethyl)phenyl]-1,2,3,4,5,7-hexahydro-6H-pyrrolo[3,4-d]pyrimidin-6-yl}ethyl)acetamide

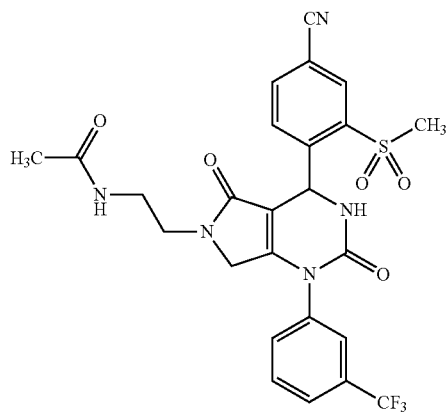

(rac)-Ethyl 6-(bromomethyl)-4-[4-cyano-2-(methylsulfonyl)phenyl]-2-oxo-1-[3-(trifluoromethyl)phenyl]-1,2,3,4-tetrahydropyrimidine-5-carboxylate (200 mg, 0.34 mmol; Example 13A) was dissolved in acetonitrile (5 ml), N-(2-aminoethyl)acetamide (105 mg, 1.02 mmol) was added and the mixture was stirred at RT overnight. The reaction mixture was then purified directly by preparative HPLC (column: Kromasil C18, 125 mm×20 mm, 5 µm, 100 Å; mobile phase A: water with 0.01% formic acid, mobile phase B: acetonitrile; gradient: 0 min 10% B→2 min 10% B→9 min 90% B→12 min 90% B→12.1 min 10% B→15 min 10% B; flow rate: 0.35 ml/min; UV detection: 254 nm). This gave 107 mg (56% of theory) of the title compound.

HPLC (Method 2): $R_t$=3.78 min.

MS (DCI/NH$_3$): m/z (%)=562.1 (25) [M+H]$^+$ $^1$H-NMR (400 MHz, DMSO-d$_6$): δ=1.66 (s, 3H), 2.97-3.24 (m, 4H), 3.54 (s, 3H), 3.91 (s, 2H), 6.64 (s, 1H), 7.73-7.86 (m, 4H), 7.98 (s, 1H), 8.11-8.17 (m, 2H), 8.27 (d, 1H), 8.34 (s, 1H).

Example 50

(rac)-1-(2-{4-[4-Cyano-2-(methylsulfonyl)phenyl]-2,5-dioxo-1-[3-(trifluoromethyl)phenyl]-1,2,3,4,5,7-hexahydro-6H-pyrrolo[3,4-d]pyrimidin-6-yl}ethyl)urea

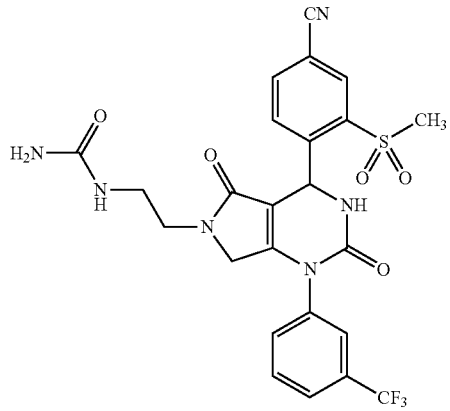 [SMILES: CC(=O)NCCN1CC2=C(C1=O)C(c1ccc(C#N)cc1S(C)(=O)=O)NC(=O)N2c1cccc(C(F)(F)F)c1]

(rac)-Ethyl 6-(bromomethyl)-4-[4-cyano-2-(methylsulfonyl)phenyl]-2-oxo-1-[3-(trifluoromethyl)phenyl]-1,2,3,4-tetrahydropyrimidine-5-carboxylate (200 mg, 0.34 mmol; Example 13A) was dissolved in acetonitrile (5 ml), 1-(2-aminoethyl)urea (106 mg, 1.02 mmol) was added and the mixture was stirred at RT overnight. The reaction mixture was then purified directly by preparative HPLC (column: Kromasil C18, 125 mm×20 mm, 5 µm, 100 Å; mobile phase A: water with 0.01% formic acid, mobile phase B: acetonitrile; gradient: 0 min 10% B→2 min 10% B→9 min 90% B→12 min 90% B→12.1 min 10% B→15 min 10% B; flow rate: 0.35 ml/min; UV detection: 254 nm). This gave 69 mg (34% of theory) of the title compound.

HPLC (Method 2): $R_t$=3.69 min.

MS (DCI/NH$_3$): m/z (%)=563.1 (100) [M+H]$^+$ $^1$H-NMR (400 MHz, DMSO-d$_6$): δ=2.90-3.24 (m, 4H), 3.54 (s, 3H), 3.94 (m, 2H), 5.42 (s, 2H), 5.85 (t, 1H), 6.63 (s, 1H), 7.73-7.86 (m, 3H), 7.98 (s, 1H), 8.10-8.14 (m, 2H), 8.27 (d, 1H), 8.34 (s, 1H).

Example 51

(4S)-4-[4-Cyano-2-(methylsulfonyl)phenyl]-3-[(3-hydroxyazetidin-1-yl)carbonyl]-6-methyl-2-oxo-1-[3-(trifluoromethyl)phenyl]-1,2,3,4-tetrahydropyrimidine-5-carbonitrile

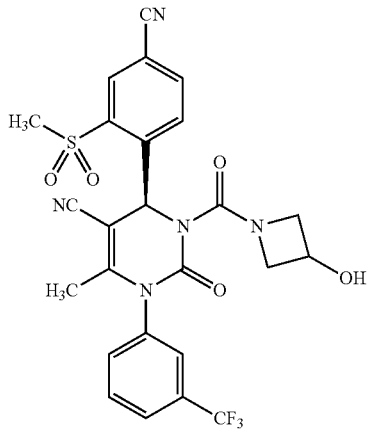 [SMILES: CC1=C(C#N)[C@@H](c2ccc(C#N)cc2S(C)(=O)=O)N(C(=O)N2CC(O)C2)C(=O)N1c1cccc(C(F)(F)F)c1]

According to the General Procedure 1, 4-nitrophenyl (6S)-5-cyano-6-[4-cyano-2-(methylsulfonyl)phenyl]-4-methyl-2-oxo-3-[3-(trifluoromethyl)phenyl]-3,6-dihydropyrimidin-1(2H)-carboxylate (80.0 mg, 0.128 mmol; Example 6A) was reacted with azetidin-3-ol hydrochloride (42.0 mg, 0.384 mmol) in acetonitrile (1 ml) to give the target compound (40 mg, 56% of theory).

HPLC (Method 2): $R_t$=4.20 min.

MS (DCI/NH$_3$): m/z (%)=560 [M+H]$^+$, 577.2 [M+NH$_4$]$^+$ $^1$H-NMR (400 MHz, DMSO-d$_6$): δ=1.81 (s, 3H), 3.38-3.61 (m, 4H), 3.79-4.08 (m, 2H), 4.22-4.45 (m, 2H), 5.74 (t, 1H), 6.83 (s, 1H), 7.74-7.90 (m, 3H), 8.00 (s, 1H), 8.12 (br. s, 1H), 8.36-8.43 (m, 2H).

Example 52

(4S)-4-[4-Cyano-2-(methylsulfonyl)phenyl]-3-[(3-hydroxypyrrolidin-1-yl)carbonyl]-6-methyl-2-oxo-1-[3-(trifluoromethyl)phenyl]-1,2,3,4-tetrahydropyrimidin-5-carbonitrile

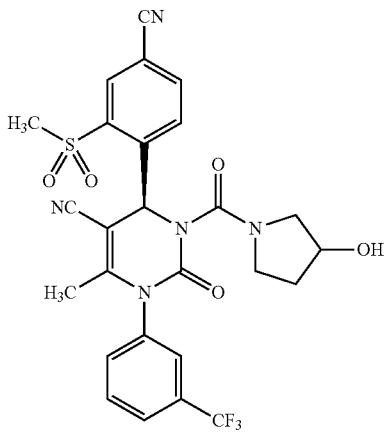 [SMILES: CC1=C(C#N)[C@@H](c2ccc(C#N)cc2S(C)(=O)=O)N(C(=O)N2CCC(O)C2)C(=O)N1c1cccc(C(F)(F)F)c1]

According to the General Procedure 1, 4-nitrophenyl (6S)-5-cyano-6-[4-cyano-2-(methylsulfonyl)phenyl]-4-methyl-2-oxo-3-[3-(trifluoromethyl)phenyl]-3,6-dihydropyrimidin-1(2H)-carboxylate (78.0 mg, 0.125 mmol; Example 6A) was reacted with pyrrolidin-3-ol (32.6 mg, 0.374 mmol) in acetonitrile (1 ml) to give the target compound (58 mg, 81% of theory).

HPLC (Method 2): $R_t$=4.31 min.

MS (ESIpos): m/z (%)=574.3 (100) [M+H]$^+$ $^1$H-NMR (400 MHz, DMSO-d$_6$): δ=1.61-1.93 (m, 5H), 2.87-3.26 (m, 2H), 3.42-3.84 (m, 5H), 4.13-4.29 (m, 1H), 4.83-5.10 (m, 1H), 6.84 (s, 1H), 7.73-7.90 (m, 3H), 7.98-8.42 (m, 4H).

Example 53

(4S)-4-[4-Cyano-2-(methylsulfonyl)phenyl]-3-[(3R)-3-methoxypiperidin-1-yl]carbonyl-6-methyl-2-oxo-1-[3-(trifluoromethyl)phenyl]-1,2,3,4-tetrahydropyrimidine-5-carbonitrile

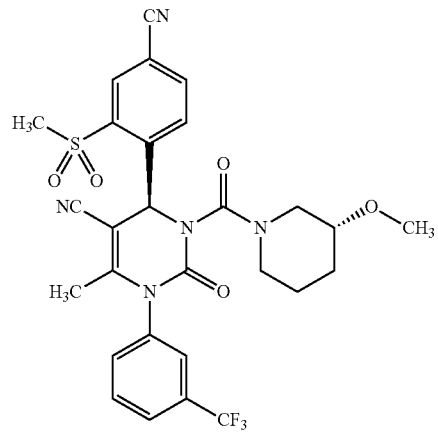

According to the General Procedure 1, 4-nitrophenyl (6S)-5-cyano-6-[4-cyano-2-(methylsulfonyl)phenyl]-4-methyl-2-oxo-3-[3-(trifluoromethyl)phenyl]-3,6-dihydropyrimidine-1(2H)-carboxylate (80.0 mg, 0.128 mmol; Example 6A) was reacted with (3R)-3-methoxypiperidine (44.2 mg, 0.384 mmol) in acetonitrile (1 ml) to give the target compound (45 mg, 57% of theory).

HPLC (Method 2): $R_t$=4.70 min.

MS (ESIpos): m/z (%)=602.0 (100) [M+H]$^+$ $^1$H-NMR (400 MHz, DMSO-d$_6$): δ=1.15-1.94 (m, 7H), 2.63-4.24 (m, 11H), 6.76-6.88 (m, 1H), 7.38-8.55 (m, 7H).

Example 54

(4S)-4-[4-Cyano-2-(methylsulfonyl)phenyl]-3-[(3-hydroxypiperidin-1-yl)carbonyl]-6-methyl-2-oxo-1-[3-(trifluoromethyl)phenyl]-1,2,3,4-tetrahydropyrimidine-5-carbonitrile

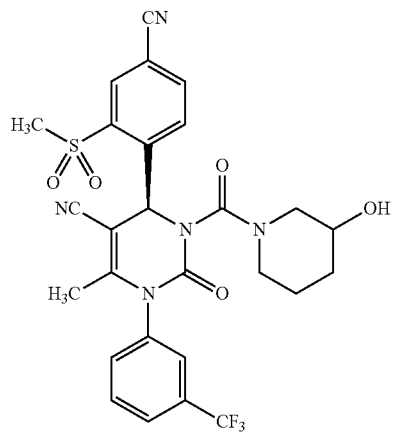 [SMILES: CC1=C(C#N)[C@@H](c2ccc(C#N)cc2S(C)(=O)=O)N(C(=O)N2CCCC(O)C2)C(=O)N1c1cccc(C(F)(F)F)c1]

According to the General Procedure 1,4-nitrophenyl (6S)-5-cyano-6-[4-cyano-2-(methylsulfonyl)phenyl]-4-methyl-2-oxo-3-[3-(trifluoromethyl)phenyl]-3,6-dihydropyrimidine-1(2H)-carboxylate (80.0 mg, 0.128 mmol; Example 6A) was reacted with piperidin-3-ol (38.8 mg, 0.384 mmol) in acetonitrile (1 ml) to give the target compound (58 mg, 77% of theory).

HPLC (Method 2): $R_t$=4.31 min.

MS (DCI/NH$_3$): m/z (%)=588 [M+H]$^+$, 605.2 [M+NH$_4$]$^+$ $^1$H-NMR (400 MHz, DMSO-d$_6$): δ=0.78-1.92 (m, 7H), 2.24-5.00 (m, 9H), 6.75-6.87 (m, 1H), 7.72-8.07 (m, 4H), 8.18-8.52 (m, 3H).

Example 55

(4S)-3-[(3R)-3-Aminopiperidin-1-yl]carbonyl-4-[4-cyano-2-(methylsulfonyl)phenyl]-6-methyl-2-oxo-1-[3-(trifluoromethyl)phenyl]-1,2,3,4-tetrahydropyrimidine-5-carbonitrile

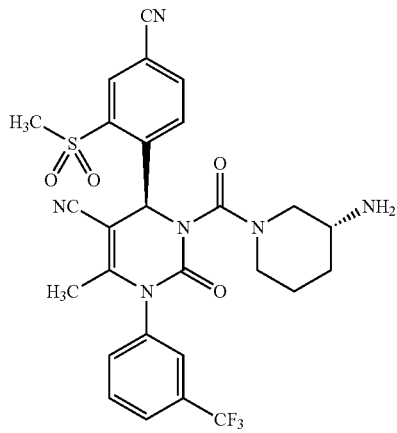 [SMILES: CC1=C(C#N)[C@@H](c2ccc(C#N)cc2S(C)(=O)=O)N(C(=O)N2CCC[C@@H](N)C2)C(=O)N1c1cccc(C(F)(F)F)c1]

tert-Butyl [(3R)-1-{[(6S)-5-cyano-6-[4-cyano-2-(methylsulfonyl)phenyl]-4-methyl-2-oxo-3-[3-(trifluoromethyl)phenyl]-3,6-dihydropyrimidin-1(2H)-yl]carbonyl}piperidin-3-yl]carbamate (Example 12A; 56.0 mg, 0.082 mmol) was dissolved in a 4 N solution of hydrogen chloride in dioxane (2.15 ml) and stirred at RT for 60 min. The contents of the flask was then concentrated under reduced pressure, and the residue was taken up in dichloromethane (15 ml) and 2 N aqueous sodium hydroxide solution (15 ml). After extraction, the organic phase was separated off, dried over sodium sulfate and concentrated under reduced pressure. This gave 47 mg (96% of theory) of the title compound.

HPLC (Method 2): $R_t$=4.17 min.

MS (ESIpos): m/z (%)=587.0 (100) [M+H]$^+$ $^1$H-NMR (400 MHz, DMSO-d$_6$): δ=1.40-1.84 (m, 7H), 2.03-2.35 (m, 2H), 2.74-2.90 (m, 1H), 3.52 (s, 3H), 3.74-4.05 (m, 1H), 6.67 (br. s, 1H), 6.80 (s, 1H), 7.27 (br. s, 1H), 7.73-8.06 (m, 4H), 8.21 (d, 1H), 8.37 (s, 1H), 8.48 (d, 1H).

General Procedure 2: Synthesis of N-Aminocarbonyldihydropyrimidinone Derivatives (Process B)

0.1 mmol of the appropriate amine was dissolved in 0.2 ml of acetonitrile, and 25.8 mg (0.2 mmol) of diisopropylethylamine and 62.5 mg (0.1 mmol) of 4-nitrophenyl (6S)-5-cyano-6-[4-cyano-2-(methylsulfonyl)phenyl]-4-methyl-2-oxo-3-[3-(trifluoromethyl)phenyl]-3,6-dihydropyrimidine-1(2H)-carboxylate (Example 6A), dissolved in 0.6 ml of acetonitrile, were added. The reaction mixture was stirred at room temperature overnight, and the acetonitrile was then evaporated in a vacuum centrifuge. The crude product was dissolved in 0.5 ml of DMSO and purified by preparative HPLC/MS (Method 7).

The exemplary embodiments shown in table 1 below were prepared according to the

General Procedure 2:

TABLE 1

| Example No. | Structure | LC/MS data (Method 7) |
|---|---|---|
| 56 | 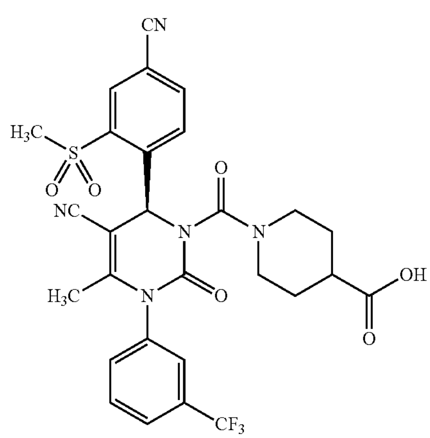 [SMILES: CC1=C(C#N)[C@@H](c2ccc(C#N)cc2S(C)(=O)=O)N(C(=O)N2CCC(C(=O)O)CC2)C(=O)N1c1cccc(C(F)(F)F)c1] | MS (ESIpos): m/z = 616 (M + H)$^+$; $R_t$ = 2.01 min |

TABLE 1-continued

| Example No. | Structure | LC/MS data (Method 7) |
|---|---|---|
| 57 | 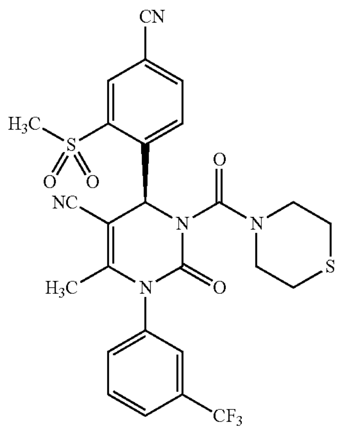 [SMILES: CC1=C(C#N)[C@@H](c2ccc(C#N)cc2S(C)(=O)=O)N(C(=O)N2CCSCC2)C(=O)N1c1cccc(C(F)(F)F)c1] | MS (ESIpos): m/z = 590 (M + H)$^+$; R$_t$ = 2.21 min |
| 58 | 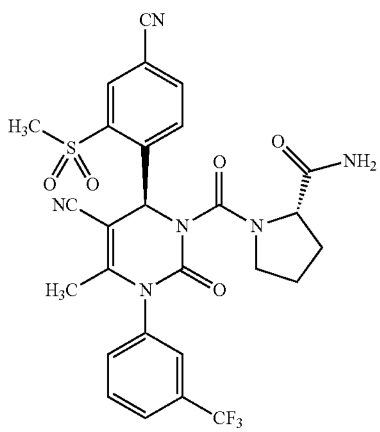 [SMILES: CC1=C(C#N)[C@@H](c2ccc(C#N)cc2S(C)(=O)=O)N(C(=O)N2CCC[C@H]2C(N)=O)C(=O)N1c1cccc(C(F)(F)F)c1] | MS (ESIpos): m/z = 601 (M + H)$^+$; R$_t$ = 1.97 min |
| 59 | 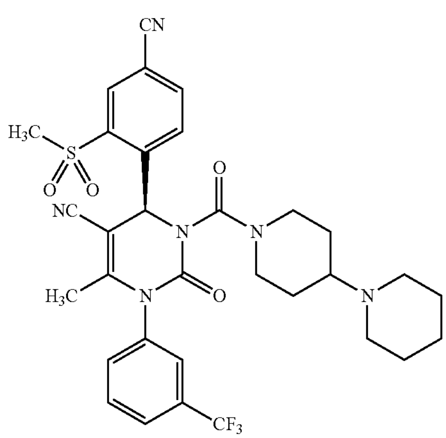 [SMILES: CC1=C(C#N)[C@@H](c2ccc(C#N)cc2S(C)(=O)=O)N(C(=O)N2CCC(N3CCCCC3)CC2)C(=O)N1c1cccc(C(F)(F)F)c1] | MS (ESIpos): m/z = 655 (M + H)$^+$; R$_t$ = 1.57 min |

TABLE 1-continued

| Example No. | Structure | LC/MS data (Method 7) |
|---|---|---|
| 60 | 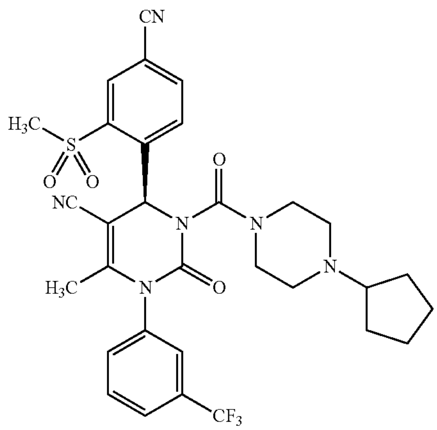 [SMILES: CC1=C(C#N)[C@@H](c2ccc(C#N)cc2S(C)(=O)=O)N(C(=O)N2CCN(C3CCCC3)CC2)C(=O)N1c1cccc(C(F)(F)F)c1] | MS (ESIpos): m/z = 641 (M + H)⁺; R_r = 1.61 min |
| 61 | 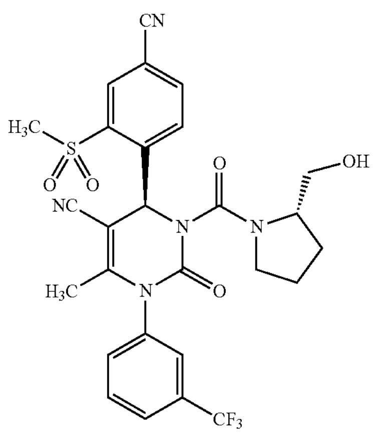 [SMILES: CC1=C(C#N)[C@@H](c2ccc(C#N)cc2S(C)(=O)=O)N(C(=O)N2CCC[C@H]2CO)C(=O)N1c1cccc(C(F)(F)F)c1] | MS (ESIpos): m/z = 588 (M + H)⁺; R_r = 2.04 min |
| 62 | 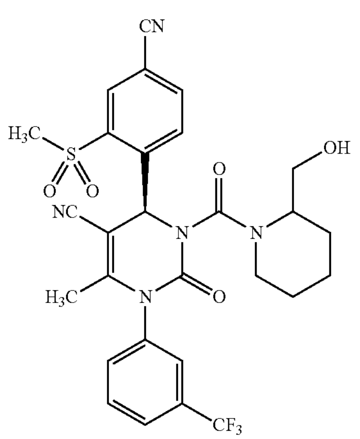 [SMILES: CC1=C(C#N)[C@@H](c2ccc(C#N)cc2S(C)(=O)=O)N(C(=O)N2CCCCC2CO)C(=O)N1c1cccc(C(F)(F)F)c1] | MS (ESIpos): m/z = 602 (M + H)⁺; R_r = 2.09 min |

TABLE 1-continued

| Example No. | Structure | LC/MS data (Method 7) |
|---|---|---|
| 63 | 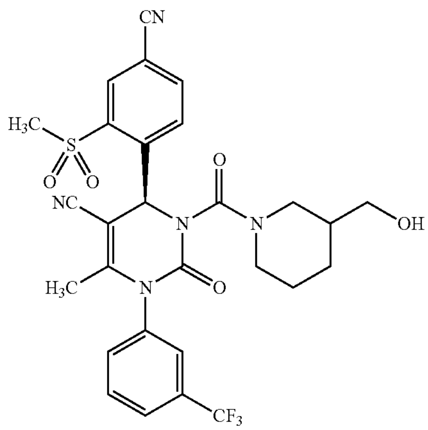 [SMILES: CC1=C(C#N)[C@@H](c2ccc(C#N)cc2S(C)(=O)=O)N(C(=O)N2CCCC(CO)C2)C(=O)N1c1cccc(C(F)(F)F)c1] | MS (ESIpos): m/z = 602 (M + H)+; R$_t$ = 2.03 min |
| 64 | 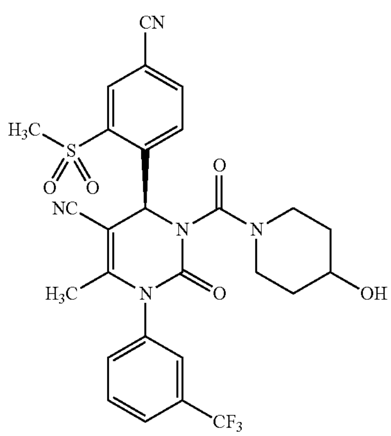 [SMILES: CC1=C(C#N)[C@@H](c2ccc(C#N)cc2S(C)(=O)=O)N(C(=O)N2CCC(O)CC2)C(=O)N1c1cccc(C(F)(F)F)c1] | MS (ESIpos): m/z = 588 (M + H)+; R$_t$ = 1.96 min |
| 65 | 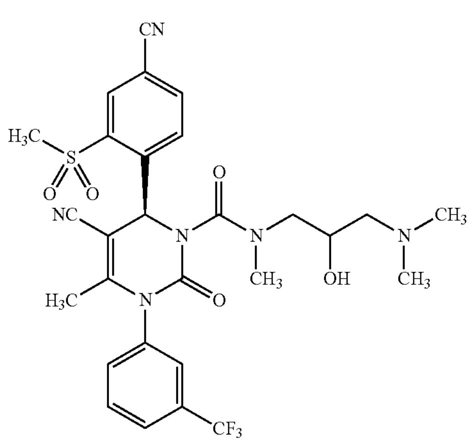 | MS (ESIpos): m/z = 619 (M + H)+; R$_t$ = 1.51 min |

TABLE 1-continued
| Example No. | Structure | LC/MS data (Method 7) |
|---|---|---|
| 66 | 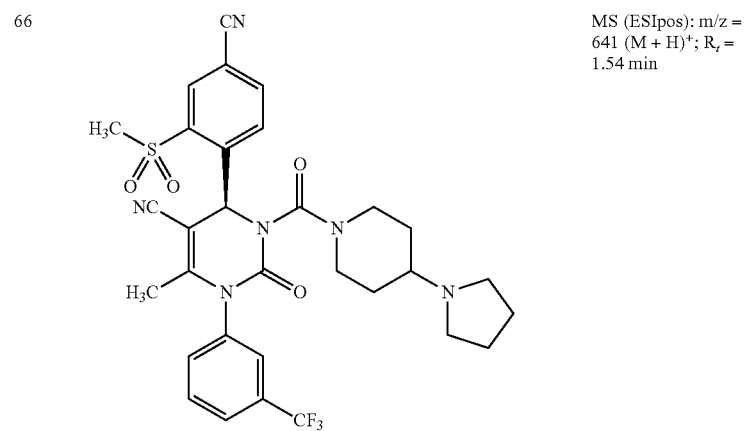 | MS (ESIpos): m/z = 641 (M + H)+; $R_t$ = 1.54 min |
| 67 | 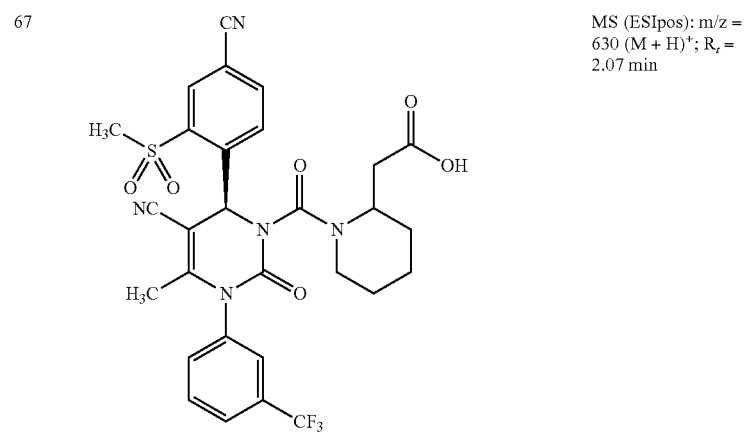 | MS (ESIpos): m/z = 630 (M + H)+; $R_t$ = 2.07 min |
| 68 | 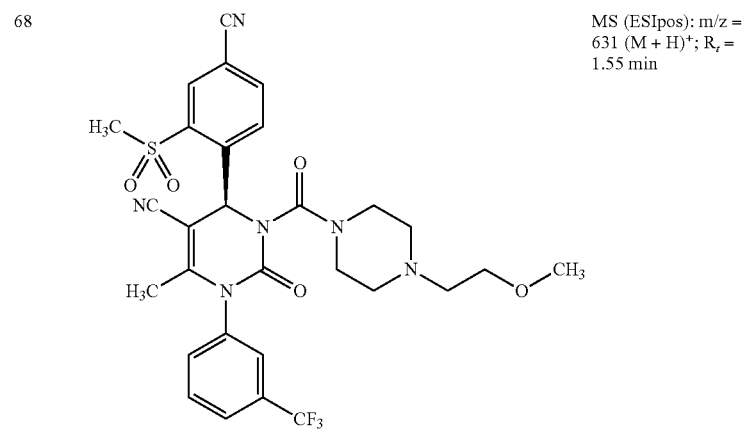 | MS (ESIpos): m/z = 631 (M + H)+; $R_t$ = 1.55 min |

TABLE 1-continued

| Example No. | Structure | LC/MS data (Method 7) |
|---|---|---|
| 69 | 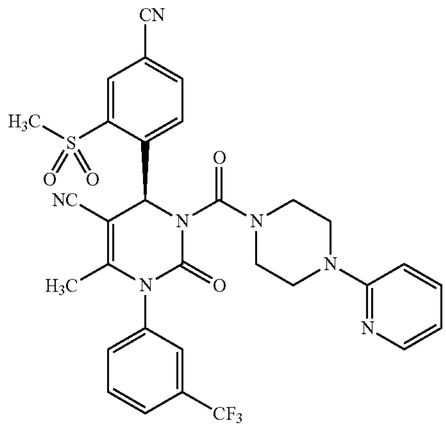 [SMILES: CC1=C(C#N)[C@@H](c2ccc(C#N)cc2S(C)(=O)=O)N(C(=O)N2CCN(c3ccccn3)CC2)C(=O)N1c1cccc(C(F)(F)F)c1] | MS (ESIpos): m/z = 650 (M + H)+; Rt = 1.74 min |
| 70 | 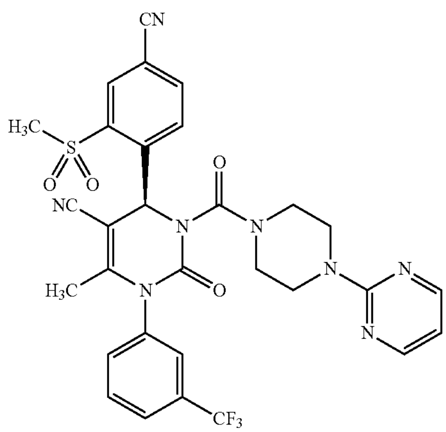 | MS (ESIpos): m/z = 651 (M + H)+; Rt = 2.18 min |
| 71 | 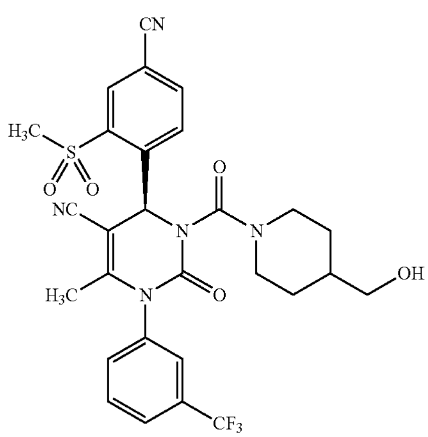 [SMILES: CC1=C(C#N)[C@@H](c2ccc(C#N)cc2S(C)(=O)=O)N(C(=O)N2CCC(CO)CC2)C(=O)N1c1cccc(C(F)(F)F)c1] | MS (ESIpos): m/z = 602 (M + H)+; Rt = 1.97 min |

TABLE 1-continued

| Example No. | Structure | LC/MS data (Method 7) |
|---|---|---|
| 72 | 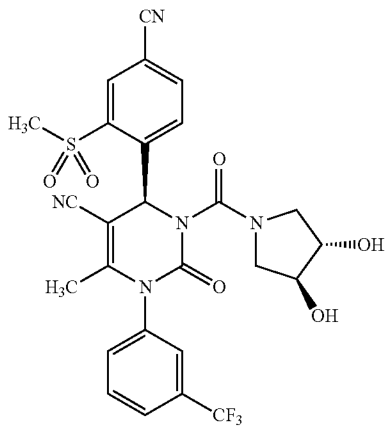 [SMILES: CC1=C(C#N)[C@@H](c2ccc(C#N)cc2S(C)(=O)=O)N(C(=O)N2C[C@H](O)[C@@H](O)C2)C(=O)N1c1cccc(C(F)(F)F)c1] | MS (ESIpos): m/z = 590 (M + H)⁺; R$_t$ = 1.84 min |
| 73 | 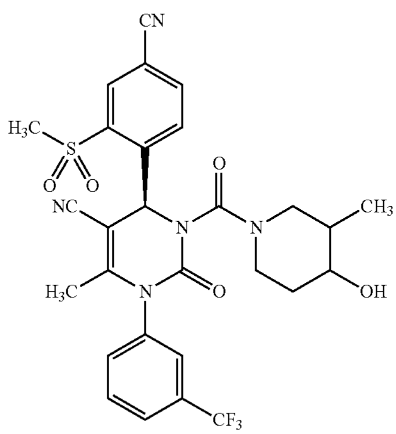 [SMILES: CC1=C(C#N)[C@@H](c2ccc(C#N)cc2S(C)(=O)=O)N(C(=O)N2CCC(O)C(C)C2)C(=O)N1c1cccc(C(F)(F)F)c1] | MS (ESIpos): m/z = 602 (M + H)⁺; R$_t$ = 2.02 min |
| 74 | 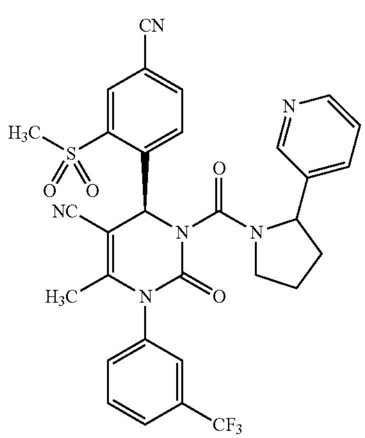 [SMILES: CC1=C(C#N)[C@@H](c2ccc(C#N)cc2S(C)(=O)=O)N(C(=O)N2CCCC2c2cccnc2)C(=O)N1c1cccc(C(F)(F)F)c1] | MS (ESIpos): m/z = 635 (M + H)⁺; R$_t$ = 1.80 min |

TABLE 1-continued

| Example No. | Structure | LC/MS data (Method 7) |
|---|---|---|
| 75 | 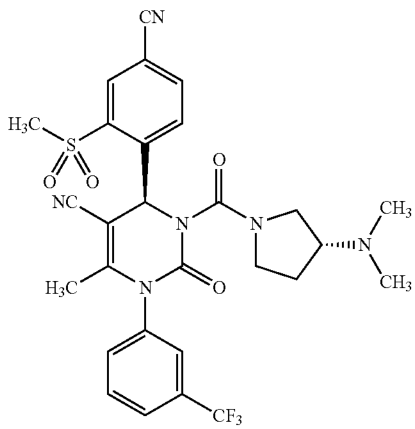 | MS (ESIpos): m/z = 601 (M + H)⁺; R$_t$ = 1.53 min |
| 76 | 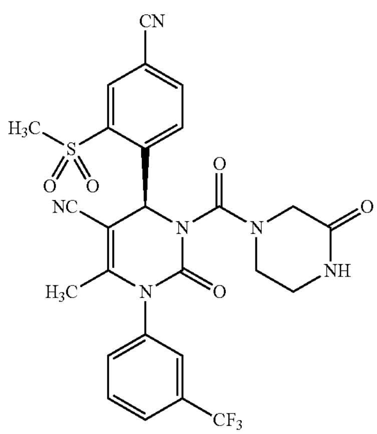 [SMILES: CC1=C(C#N)[C@@H](c2ccc(C#N)cc2S(C)(=O)=O)N(C(=O)N2CCNC(=O)C2)C(=O)N1c1cccc(C(F)(F)F)c1] | MS (ESIpos): m/z = 587 (M + H)⁺; R$_t$ = 1.89 min |
| 77 | 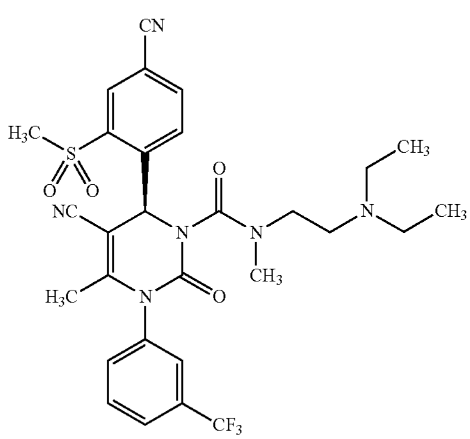 [SMILES: CCN(CC)CCN(C)C(=O)N1C(=O)N(c2cccc(C(F)(F)F)c2)C(C)=C(C#N)[C@H]1c1ccc(C#N)cc1S(C)(=O)=O] | MS (ESIpos): m/z = 617 (M + H)⁺; R$_t$ = 1.56 min |

TABLE 1-continued
| Example No. | Structure | LC/MS data (Method 7) |
|---|---|---|
| 78 | 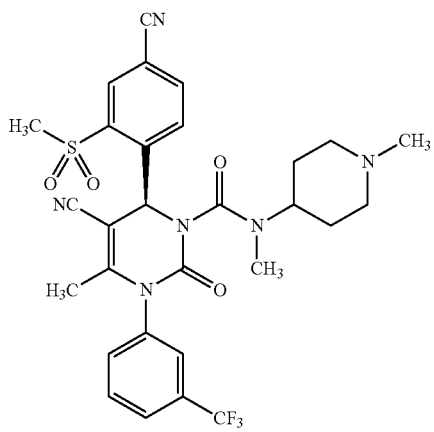 | MS (ESIpos): m/z = 615 (M + H)⁺; R_t = 1.54 min |
| 79 | 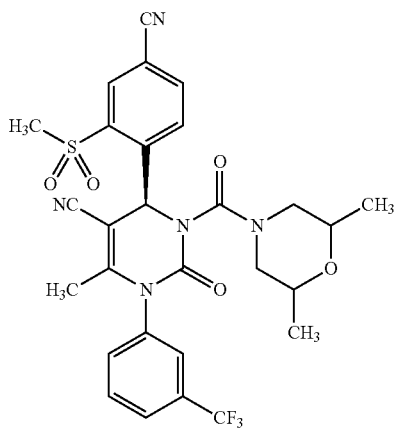 | MS (ESIpos): m/z = 602 (M + H)⁺; R_t = 2.17 min |
| 80 | 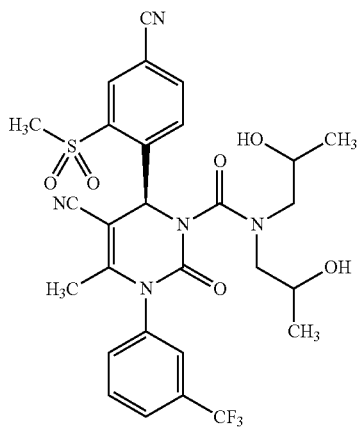 [SMILES: CC1=C(C#N)[C@@H](c2ccc(C#N)cc2S(C)(=O)=O)N(C(=O)N(CC(C)O)CC(C)O)C(=O)N1c1cccc(C(F)(F)F)c1] | MS (ESIpos): m/z = 620 (M + H)⁺; R_t = 2.00 min |

TABLE 1-continued

| Example No. | Structure | LC/MS data (Method 7) |
|---|---|---|
| 81 | 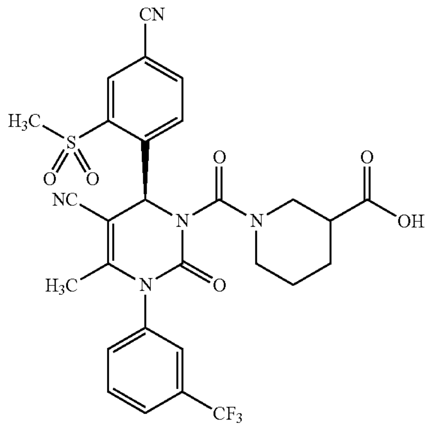 [SMILES: CC1=C(C#N)[C@@H](c2ccc(C#N)cc2S(C)(=O)=O)N(C(=O)N2CCCC(C(=O)O)C2)C(=O)N1c1cccc(C(F)(F)F)c1] | MS (ESIpos): m/z = 616 (M + H)⁺; R_t = 2.03 min |
| 82 | 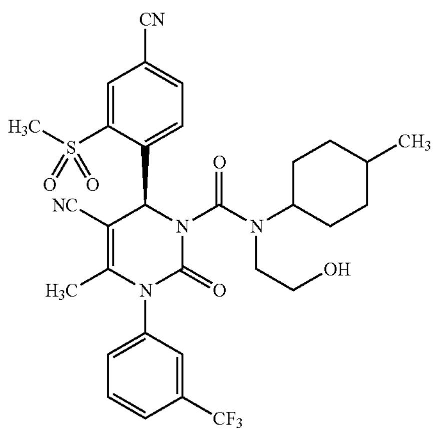 | MS (ESIpos): m/z = 644 (M + H)⁺; R_t = 2.25 min |
| 83 | 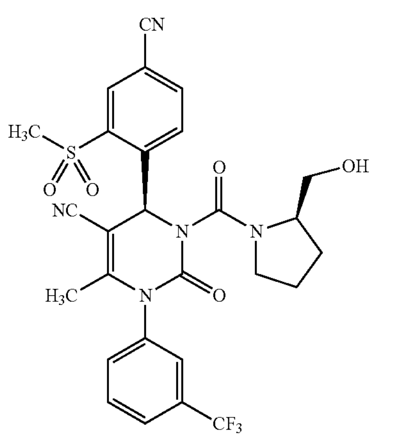 [SMILES: CC1=C(C#N)[C@@H](c2ccc(C#N)cc2S(C)(=O)=O)N(C(=O)N2CCC[C@@H]2CO)C(=O)N1c1cccc(C(F)(F)F)c1] | MS (ESIpos): m/z = 588 (M + H)⁺; R_t = 2.03 min |

TABLE 1-continued

| Example No. | Structure | LC/MS data (Method 7) |
|---|---|---|
| 84 | 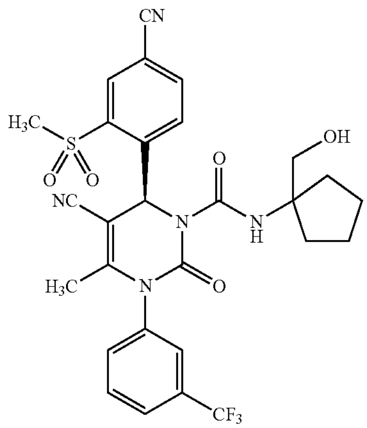 [SMILES: CC1=C(C#N)[C@@H](c2ccc(C#N)cc2S(C)(=O)=O)N(C(=O)NC2(CO)CCCC2)C(=O)N1c1cccc(C(F)(F)F)c1] | MS (ESIpos): m/z = 602 (M + H)+; Rt = 2.19 min |
| 85 | 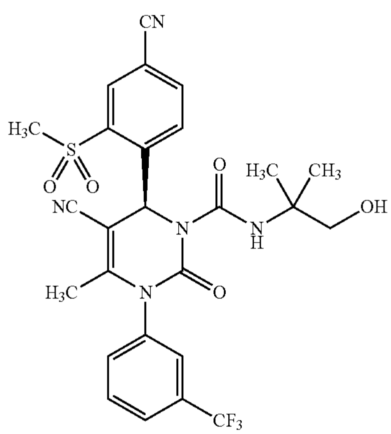 [SMILES: CC1=C(C#N)[C@@H](c2ccc(C#N)cc2S(C)(=O)=O)N(C(=O)NC(C)(C)CO)C(=O)N1c1cccc(C(F)(F)F)c1] | MS (ESIpos): m/z = 576 (M + H)+; Rt = 2.12 min |
| 86 | 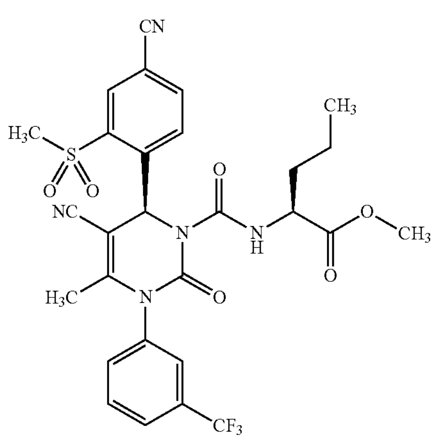 | MS (ESIpos): m/z = 618 (M + H)+; Rt = 2.31 min |

TABLE 1-continued

| Example No. | Structure | LC/MS data (Method 7) |
|---|---|---|
| 87 | 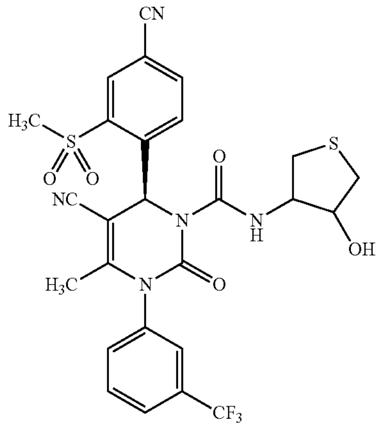 | MS (ESIpos): m/z = 606 (M + H)⁺; $R_t$ = 2.13 min |
| 88 | 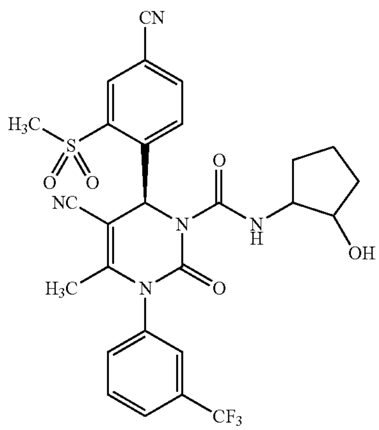 [SMILES: CC1=C(C#N)[C@@H](c2ccc(C#N)cc2S(C)(=O)=O)N(C(=O)NC2CCCC2O)C(=O)N1c1cccc(C(F)(F)F)c1] | MS (ESIpos): m/z = 588 (M + H)⁺; $R_t$ = 2.14 min |
| 89 | 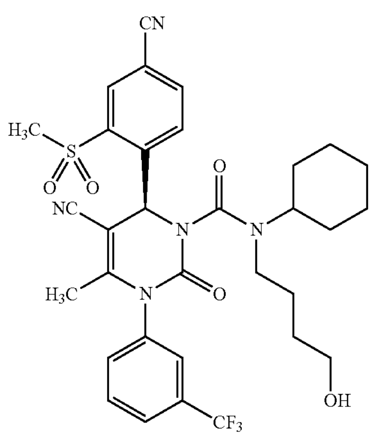 [SMILES: CC1=C(C#N)[C@@H](c2ccc(C#N)cc2S(C)(=O)=O)N(C(=O)N(CCCCO)C2CCCCC2)C(=O)N1c1cccc(C(F)(F)F)c1] | MS (ESIpos): m/z = 658 (M + H)⁺; $R_t$ = 2.21 min |

General Procedure 3: Synthesis of N-sulfonyldihydropyrimidinone derivatives Under argon, 35.4 mg (0.077 mmol) of (4S)-4-[4-cyano-2-(methylsulfonyl)phenyl]-6-methyl-2-oxo-1-[3-(trifluoromethyl)phenyl]-1,2,3,4-tetrahydropyrimidine-5-carbonitrile (Example 6) were dissolved in 0.4 ml of THF, 4.6 mg (0.192 mmol) of sodium hydride were added at 0° C. and the mixture was stirred at room temperature for 20 min. A solution of 0.0924 mmol of the appropriate sulfonyl chloride in 0.2 ml of THF was then added, and the mixture was stirred at room temperature for a further 30 min. 50 mg (0.93 mmol) of ammonium chloride were then added, and the THF was evaporated in a vacuum centrifuge. The crude product was taken up in 0.5 ml of DMSO and filtered, and the filtrate was purified by preparative HPLC/MS (Method 7). The exemplary embodiments shown in table 2 below were prepared according to the General Procedure 3:

TABLE 2

| Example No. | Structure | LC/MS data (Method 7) |
|---|---|---|
| 90 | (structure) | MS (ESIpos): m/z = 632 (M + H)+; R$_t$ = 2.17 min |
| 91 | (structure) | MS (ESIpos): m/z = 619 (M + H)+; R$_t$ = 2.26 min |
| 92 | (structure) | MS (ESIpos): m/z = 619 (M + H)+; R$_t$ = 1.88 min |

TABLE 2-continued
| Example No. | Structure | LC/MS data (Method 7) |
|---|---|---|
| 93 | 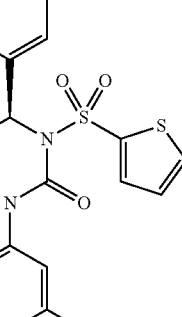 | MS (ESIpos): m/z = 621 (M + H)+; R$_t$ = 2.24 min |
| 94 | 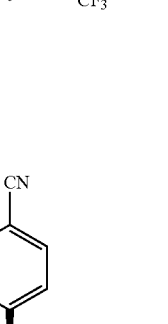 | MS (ESIpos): m/z = 645 (M + H)+; R$_t$ = 2.28 min |
| 95 | 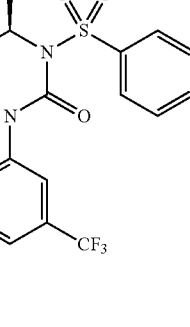 | MS (ESIpos): m/z = 657 (M + H)+; R$_t$ = 2.37 min |

TABLE 2-continued

| Example No. | Structure | LC/MS data (Method 7) |
|---|---|---|
| 96 | 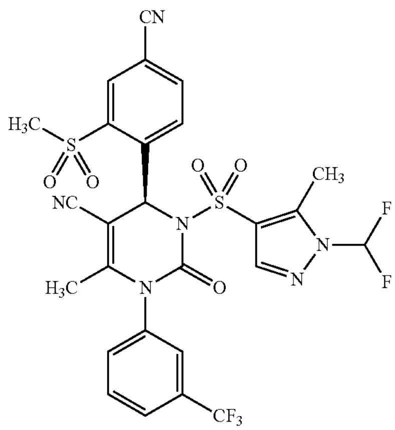 [SMILES: CC1=C(C#N)[C@@H](c2ccc(C#N)cc2S(C)(=O)=O)N(S(=O)(=O)c2cnn(C(F)F)c2C)C(=O)N1c1cccc(C(F)(F)F)c1] | MS (ESIpos): m/z = 655 (M + H)+; R$_t$ = 2.21 min |
| 97 | 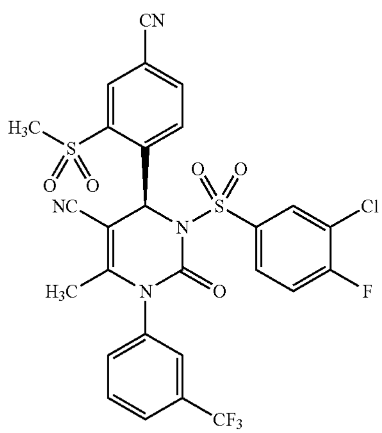 [SMILES: CC1=C(C#N)[C@@H](c2ccc(C#N)cc2S(C)(=O)=O)N(S(=O)(=O)c2ccc(F)c(Cl)c2)C(=O)N1c1cccc(C(F)(F)F)c1] | MS (ESIpos): m/z = 654 (M + H)+; R$_t$ = 2.30 min |
| 98 | 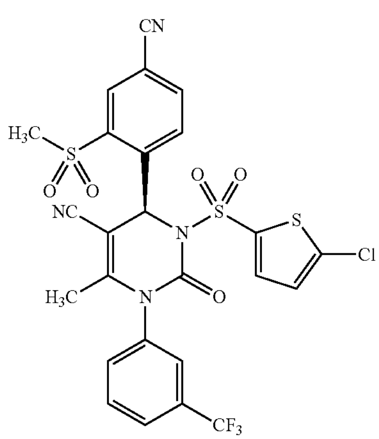 [SMILES: CC1=C(C#N)[C@@H](c2ccc(C#N)cc2S(C)(=O)=O)N(S(=O)(=O)c2ccc(Cl)s2)C(=O)N1c1cccc(C(F)(F)F)c1] | MS (ESIpos): m/z = 642 (M + H)+; R$_t$ = 2.29 min |

TABLE 2-continued

| Example No. | Structure | LC/MS data (Method 7) |
|---|---|---|
| 99 | 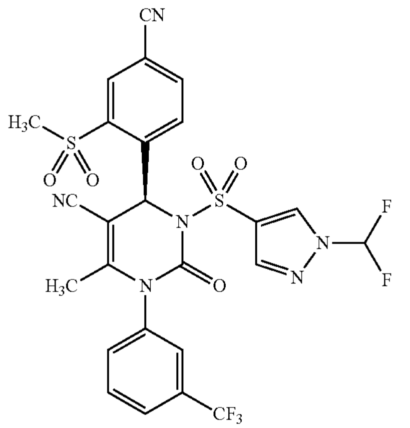 [SMILES: CC1=C(C#N)[C@@H](c2ccc(C#N)cc2S(C)(=O)=O)N(S(=O)(=O)c2cnn(C(F)F)c2)C(=O)N1c1cccc(C(F)(F)F)c1] | MS (ESIpos): m/z = 641 (M + H)⁺; R_t = 2.18 min |
| 100 | 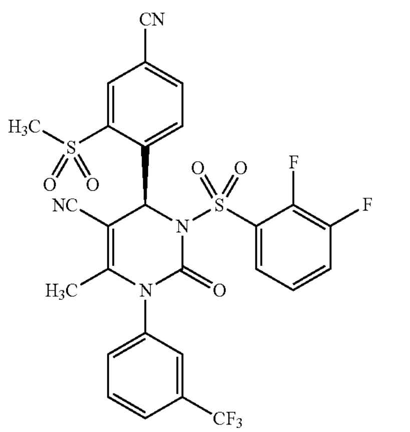 [SMILES: CC1=C(C#N)[C@@H](c2ccc(C#N)cc2S(C)(=O)=O)N(S(=O)(=O)c2cccc(F)c2F)C(=O)N1c1cccc(C(F)(F)F)c1] | MS (ESIpos): m/z = 637 (M + H)⁺; R_t = 2.23 min |
| 101 | 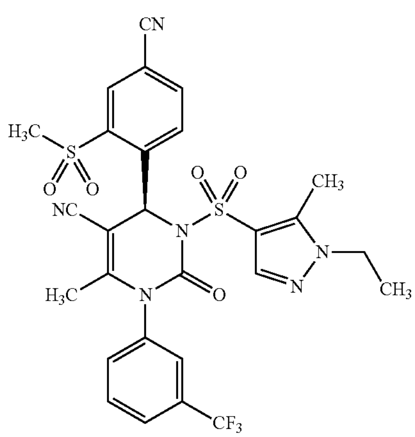 [SMILES: CCn1ncc(S(=O)(=O)N2C(=O)N(c3cccc(C(F)(F)F)c3)C(C)=C(C#N)[C@H]2c2ccc(C#N)cc2S(C)(=O)=O)c1C] | MS (ESIpos): m/z = 633 (M + H)⁺; R_t = 2.16 min |

TABLE 2-continued
| Example No. | Structure | LC/MS data (Method 7) |
|---|---|---|
| 102 | 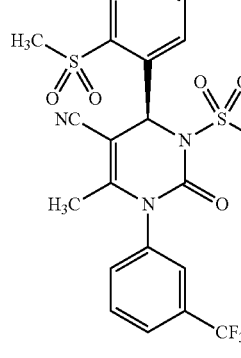 | MS (ESIpos): m/z = 631 (M + H)+; R$_t$ = 2.23 min |
| 103 | 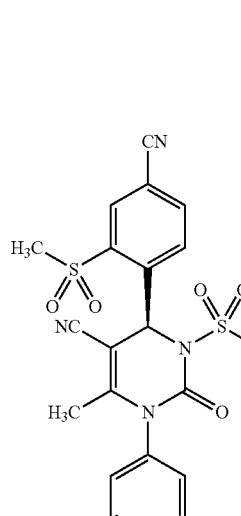 | MS (ESIpos): m/z = 626 (M + H)+; R$_t$ = 2.17 |
| 104 | 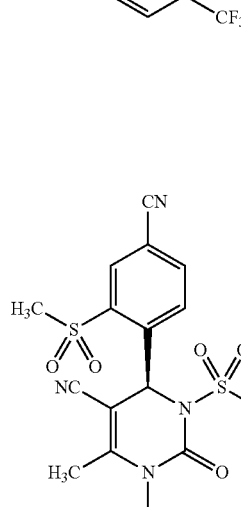 | MS (ESIpos): m/z = 621 (M + H)+; R$_t$ = 2.33 min |

TABLE 2-continued

| Example No. | Structure | LC/MS data (Method 7) |
|---|---|---|
| 105 | 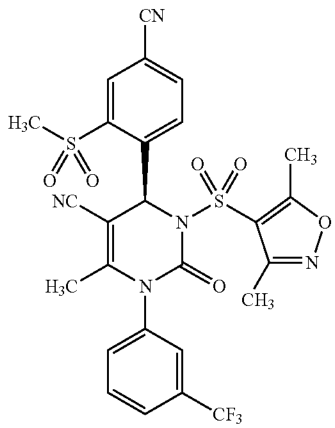 [SMILES: CC1=C(C#N)[C@@H](c2ccc(C#N)cc2S(C)(=O)=O)N(S(=O)(=O)c2c(C)noc2C)C(=O)N1c1cccc(C(F)(F)F)c1] | MS (ESIpos): m/z = 620 (M + H)⁺; R_t = 2.23 min |
| 106 | 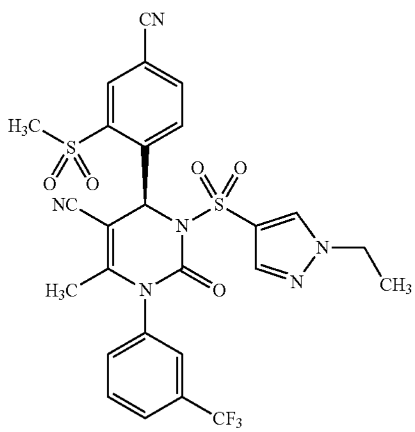 [SMILES: CCn1cc(S(=O)(=O)N2C(=O)N(c3cccc(C(F)(F)F)c3)C(C)=C(C#N)[C@H]2c2ccc(C#N)cc2S(C)(=O)=O)cn1] | MS (ESIpos): m/z = 619 (M + H)⁺; R_t = 2.16 min |
| 107 | 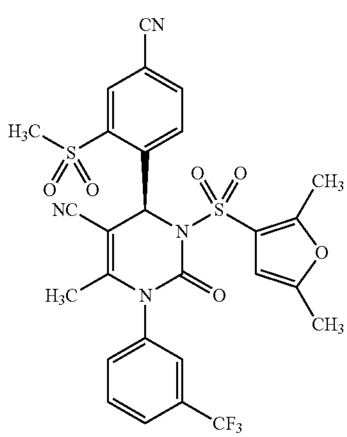 [SMILES: CC1=C(C#N)[C@@H](c2ccc(C#N)cc2S(C)(=O)=O)N(S(=O)(=O)c2cc(C)oc2C)C(=O)N1c1cccc(C(F)(F)F)c1] | MS (ESIpos): m/z = 619 (M + H)⁺; R_t = 2.27 min |

TABLE 2-continued

| Example No. | Structure | LC/MS data (Method 7) |
|---|---|---|
| 108 | 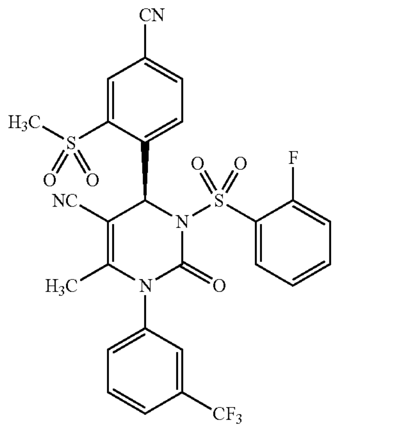 [SMILES: CC1=C(C#N)[C@@H](c2ccc(C#N)cc2S(C)(=O)=O)N(S(=O)(=O)c2ccccc2F)C(=O)N1c1cccc(C(F)(F)F)c1] | MS (ESIpos): m/z = 619 (M + H)⁺; R_t = 2.21 min |
| 109 | 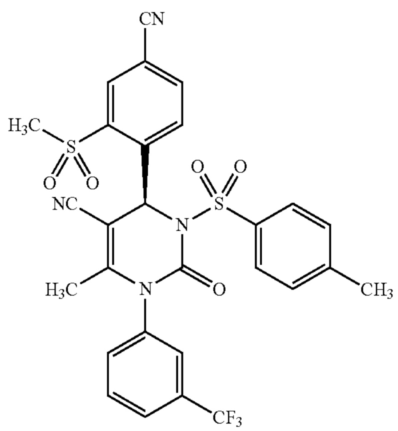 | MS (ESIpos): m/z = 615 (M + H)⁺; R_t = 2.27 min |
| 110 | 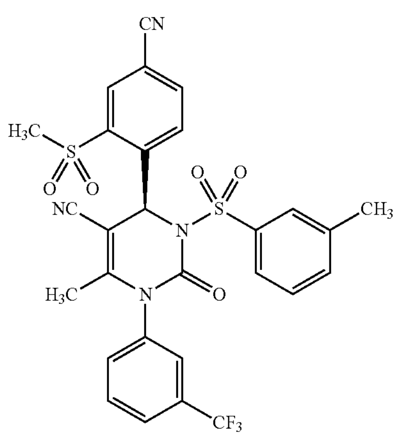 | MS (ESIpos): m/z = 615 (M + H)⁺; R_t = 2.26 min |

TABLE 2-continued

| Example No. | Structure | LC/MS data (Method 7) |
|---|---|---|
| 111 | 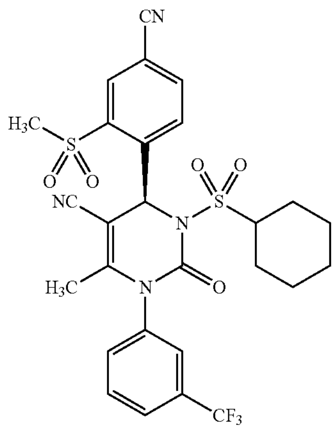 [SMILES: CC1=C(C#N)[C@@H](c2ccc(C#N)cc2S(C)(=O)=O)N(S(=O)(=O)C2CCCCC2)C(=O)N1c1cccc(C(F)(F)F)c1] | MS (ESIpos): m/z = 607 (M + H)$^+$; R$_t$ = 2.28 min |
| 112 | 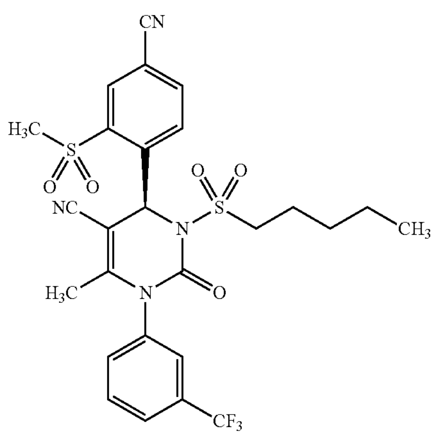 [SMILES: CCCCCS(=O)(=O)N1C(=O)N(c2cccc(C(F)(F)F)c2)C(C)=C(C#N)[C@H]1c1ccc(C#N)cc1S(C)(=O)=O] | MS (ESIpos): m/z = 594 (M + H)$^+$; R$_t$ = 2.28 min |
| 113 | 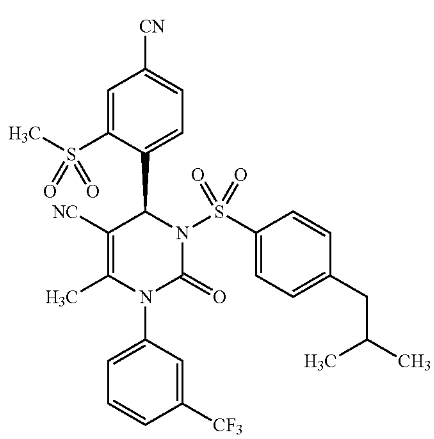 [SMILES: CC1=C(C#N)[C@@H](c2ccc(C#N)cc2S(C)(=O)=O)N(S(=O)(=O)c2ccc(CC(C)C)cc2)C(=O)N1c1cccc(C(F)(F)F)c1] | MS (ESIpos): m/z = 657 (M + H)$^+$; R$_t$ = 2.38 min |

TABLE 2-continued

| Example No. | Structure | LC/MS data (Method 7) |
|---|---|---|
| 114 | 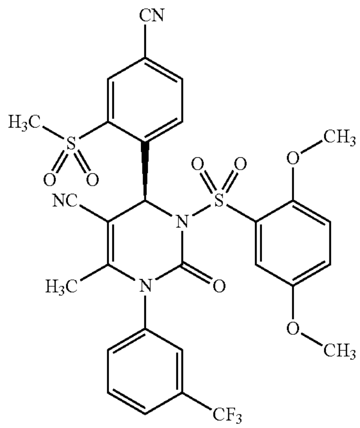 | MS (ESIpos): m/z = 661 (M + H)+; R_t = 2.22 min |

Example 115

(rac)-Ethyl 4-[4-cyano-2-(methylsulfonyl)phenyl]-6-methyl-2-oxo-1-[3-(trifluoromethyl)phenyl]-1,2,3,4-tetrahydropyrimidine-5-carboxylate

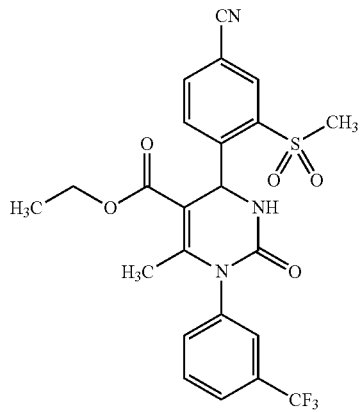 [SMILES: CCOC(=O)C1=C(C)N(c2cccc(C(F)(F)F)c2)C(=O)NC1c1ccc(C#N)cc1S(C)(=O)=O]

The reaction was carried out under argon. Triethyl phosphate (4.18 g, 22.9 mmol) and diphosphorus pentoxide (2.17 g, 15.3 mmol) were stirred at 50° C. overnight. The mixture was then diluted with methyl tert-butyl ether (60 ml), and 4-formyl-3-(methylsulfonyl)benzonitrile (4.00 g, 19.1 mmol; Example 4A), 1-[3-(trifluoromethyl)phenyl]urea (3.90 g, 19.1 mmol) and ethyl acetoacetate (3.73 g, 28.7 mmol) were then added. The mixture was stirred under reflux overnight. The precipitate formed was filtered off with suction and washed with diethyl ether (300 ml). Since the reaction had not entirely gone to completion, once more triethyl phosphate (5.36 g, 29.4 mmol) and diphosphorus pentoxide (2.71 g, 19.1 mmol) were stirred at 50° C. overnight and then stirred with the solid isolated beforehand and methyl tert-butyl ether (25 ml) under reflux for a further night. The precipitate formed was again filtered off with suction and washed with diethyl ether. This gave 5.93 g (61% of theory) of the target compound.

HPLC (Method 2): R_t=4.56 min.

MS (DCI/NH_3): m/z=508.1 [M+H]+, 525 [M+NH_4]+

$^1$H-NMR (400 MHz, DMSO-d_6): δ=0.94 (t, 3H), 2.13 (s, 3H), 3.50 (s, 3H), 3.89-4.02 (q, 2H), 6.41 (s, 1H), 7.25 (s, 1H), 7.68-7.90 (m, 4H), 8.09 (d, 1H), 8.26 (d, 1H), 8.39 (s, 1H).

Example 116

(4S)-3-(Cyanomethyl)-4-[4-cyano-2-(methylsulfonyl)phenyl]-6-methyl-2-oxo-1-[3-(trifluoromethyl)phenyl]-1,2,3,4-tetrahydropyrimidine-5-carbonitrile

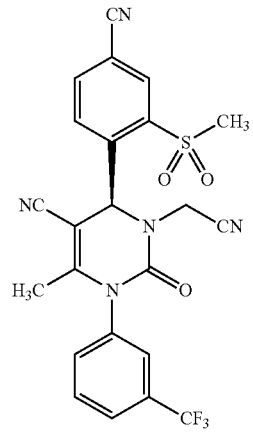 [SMILES: CC1=C(C#N)[C@@H](c2ccc(C#N)cc2S(C)(=O)=O)N(CC#N)C(=O)N1c1cccc(C(F)(F)F)c1]

The reaction was carried out under argon. (4S)-4-[4-Cyano-2-(methylsulfonyl)phenyl]-6-methyl-2-oxo-1-[3-(trifluoromethyl)phenyl]-1,2,3,4-tetrahydropyrimidine-5-carbonitrile (115 mg, 250 μmol) was initially charged in THF (1 ml) at 0° C., sodium hydride (14 mg, 350 μmol; 1.4 eq.) was added and the mixture was stirred for 20 min. After addition of bromoacetonitrile (50 mg, 376 μmol; 1.5 eq.), the mixture was stirred at RT for 120 min. The reaction mixture was then purified directly by preparative HPLC (column: Gromsil, C-18 5 μm; mobile phase: acetonitrile/water+0.1% TFA 10:90→75:25). This gave the title compound as a colorless solid (85 mg, 68% of theory).

LC-MS (Method 6): R_t=2.39 min; MS (ESIpos): m/z (%)=500.1 (100) [M+H]+; MS (ESIneg): m/z (%)=498.0 (100) [M−H]−

$^1$H-NMR (400 MHz, DMSO-d_6): δ=1.84 (s, 3H), 3.56 (s, 3H), 4.20 (d, 1H), 4.30 (d, 1H), 6.60 (s, 1H), 7.70-8.50 (m, 7H).

Example 117

(4S)-4-[4-Cyano-2-(methylsulfonyl)phenyl]-3-(4-cyanophenyl)-6-methyl-2-oxo-1-[3-(trifluoromethyl)phenyl]-1,2,3,4-tetrahydropyrimidine-5-carbonitrile

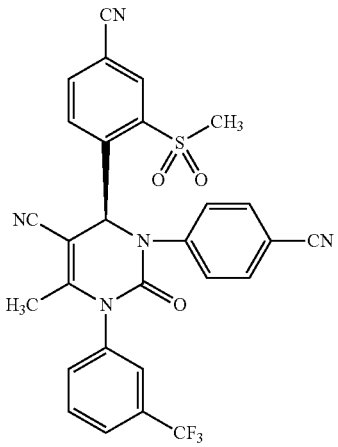 [SMILES: CC1=C(C#N)[C@@H](c2ccc(C#N)cc2S(C)(=O)=O)N(c2ccc(C#N)cc2)C(=O)N1c1cccc(C(F)(F)F)c1]

The reaction was carried out under argon. (4S)-4-[4-Cyano-2-(methylsulfonyl)phenyl]-6-methyl-2-oxo-1-[3-(trifluoromethyl)phenyl]-1,2,3,4-tetrahydropyrimidine-5-carbonitrile (100 mg, 217 µmol), 4-cyanophenylboronic acid (127.7 mg, 869 µmol; 4 eq.), copper(II) acetate (158 mg, 869 µmol; 4 eq.) and 4 Å molecular sieve (500 mg) were initially charged in dichloromethane (5 ml), pyridine (281 µl; 16 eq.) and triethylamine (121 µl; 4 eq.) were added and the mixture was subsequently stirred at RT for 4 days. The reaction mixture was then filtered through kieselguhr which was then repeatedly washed with methanol, and the filtrate was concentrated under reduced pressure. The crude product was purified by preparative
HPLC (column: Gromsil, C-18 5 µm; mobile phase: acetonitrile/water+0.1% TFA 10:90→80:20). This gave the title compound as a colorless solid (25 mg, 19.5% of theory).

LC-MS (Method 10): $R_t$=2.34 min; MS (ESIpos): m/z (%)=562.0 (100) [M+H]$^+$; MS (ESIneg): m/z (%)=416.1 (100), 560.2 (50) [M−H]$^-$ $^1$H-NMR (400 MHz, DMSO-d$_6$): δ=1.90 (s, 3H), 3.00 (s, 3H), 7.10 (s, 1H), 7.40 (m, 2H), 7.70-8.70 (m, 9H).

Example 118

(4S)-4-[4-Cyano-2-(methylsulfonyl)phenyl]-6-methyl-2-oxo-1,3-bis[3-(trifluoromethyl)phenyl]-1,2,3,4-tetrahydropyrimidine-5-carbonitrile

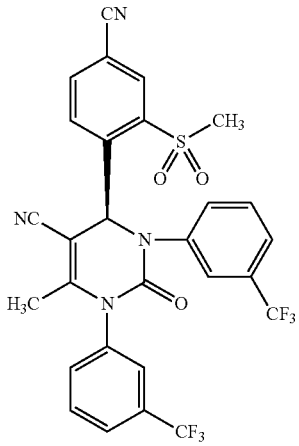 [SMILES: CC1=C(C#N)[C@@H](c2ccc(C#N)cc2S(C)(=O)=O)N(c2cccc(C(F)(F)F)c2)C(=O)N1c1cccc(C(F)(F)F)c1]

The reaction was carried out under argon. (4S)-4-[4-Cyano-2-(methylsulfonyl)phenyl]-6-methyl-2-oxo-1-[3-(trifluoromethyl)phenyl]-1,2,3,4-tetrahydropyrimidine-5-carbonitrile (100 mg, 217 µmol), 3-(trifluoromethyl)phenylboronic acid (165 mg, 869 µmol; 4 eq.), copper(II) acetate (158 mg, 869 µmol; 4 eq.) and 4 Å molecular sieve (500 mg) were initially charged in dichloromethane (5 ml), pyridine (281 µl; 16 eq.) and triethylamine (121 µl; 4 eq.) were added and the mixture was subsequently stirred at RT for 20 h. The reaction mixture was then filtered through kieselguhr which was then washed repeatedly with methanol, and the filtrate was concentrated under reduced pressure. The crude product was purified by preparative HPLC (Column: Gromsil, C-18 5 µm; mobile phase: acetonitrile/water+0.1% TFA 10:90→90:10). This gave the title compound as a colorless solid (34 mg, 26% of theory).

LC-MS (Method 4): $R_t$=1.39 min; MS (ESIpos): m/z (%)=605.0 (100) [M+H]$^+$ $^1$H-NMR (400 MHz, DMSO-d$_6$): δ=1.90 (s, 3H), 3.00 (s, 3H), 7.10 (s, 1H), 7.30 (m, 1H), 7.50 (m, 1H), 7.60 (m, 1H), 7.70 (m, 1H), 7.70-8.70 (m, 7H).

Example 119

(4S)-4-[4-Cyano-2-(methylsulfonyl)phenyl]-6-methyl-3-[(4-methylphenyl)sulfonyl]-2-oxo-1-[3-(trifluoromethyl)phenyl]-1,2,3,4-tetrahydropyrimidine-5-carbonitrile

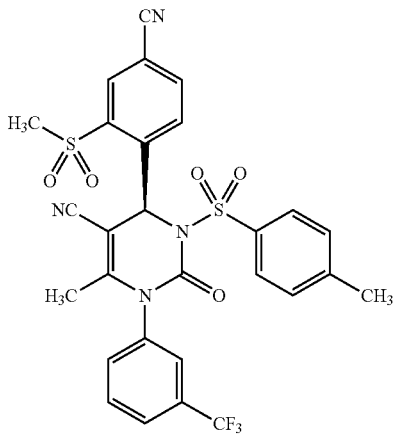

The reaction was carried out under argon. (4S)-4-[4-Cyano-2-(methylsulfonyl)phenyl]-6-methyl-2-oxo-1-[3-(trifluoromethyl)phenyl]-1,2,3,4-tetrahydropyrimidine-5-carbonitrile (278 mg, 604 µmol) was initially charged in dry THF (6 ml), and sodium hydride (60% in mineral oil; 34 mg, 845 µmol; 1.4 eq.) was added at 0° C. The mixture was warmed to RT and stirred for 20 min. A solution of p-toluenesulfonyl chloride (161 mg, 845 µmol; 1.4 eq.) in THF (~2 ml) was then slowly added dropwise. After a reaction time of 16 h, the reaction mixture was concentrated and the crude product was purified by preparative HPLC (column: Gromsil C-18 10 µm; mobile phase: acetonitrile/water+0.1% TFA 10:90→90:10). This gave the title compound as a colorless solid (358 mg, 96% of theory).

LC-MS (Method 4): $R_t$=1.38 min; MS (ESIpos): m/z (%)=615.2 (100) [M+H]$^+$

¹H-NMR (400 MHz, DMSO-d₆): δ=1.75 (s, 3H), 2.40 (s, 3H), 3.50 (s, 3H), 7.30-7.40 (m, 4H), 7.60 (s, 1H), 7.70 (m, 2H), 7.85-7.90 (m, 2H), 8.13 (m, 1H), 8.25 (m, 1H), 8.65 (s, 1H).

Example 120

Benzyl 5-cyano-6-[4-cyano-2-(methylsulfonyl)phenyl]-4-methyl-2-oxo-3-[3-(trifluoromethyl)phenyl]-3,6-dihydropyrimidine-1(2H)-carboxylate

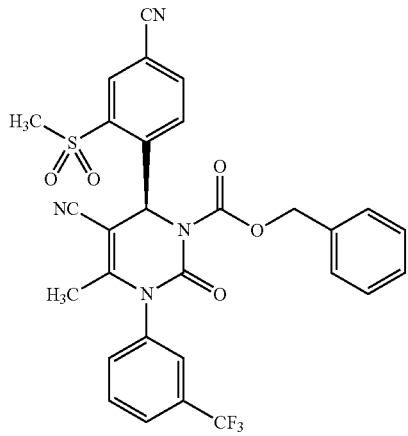 [SMILES: CC1=C(C#N)[C@@H](c2ccc(C#N)cc2S(C)(=O)=O)N(C(=O)OCc2ccccc2)C(=O)N1c1cccc(C(F)(F)F)c1]

The reaction was carried out under argon. (4S)-4-[4-Cyano-2-(methylsulfonyl)phenyl]-6-methyl-2-oxo-1-[3-(trifluoromethyl)phenyl]-1,2,3,4-tetrahydropyrimidine-5-carbonitrile (115 mg, 250 μmol) was initially charged in dry THF (3 ml), and sodium hydride (60% in mineral oil; 14 mg, 350 μmol; 1.4 eq.) was added at 0° C. The mixture was warmed to RT and stirred for 20 min. A solution of benzyl chloroformate (60 mg, 350 μmol; 1.4 eq.) in THF (1 ml) was then slowly added dropwise. After a reaction time of 1.5 h, the reaction mixture was concentrated and the crude product was purified by preparative HPLC (column: Gromsil C-18 10 μm; mobile phase: acetonitrile/water+0.1% TFA 10:90→90:10). This gave the title compound as a colorless solid (68 mg, 46% of theory).

LC-MS (Method 9): R$_t$=1.22 min; MS (ESIpos): m/z (%)=595 (10) [M+H]⁺; MS (ESIneg): m/z (%)=416.2 (100), 593.4 (50) [M−H]⁻

¹H-NMR (400 MHz, DMSO-d₆): δ=1.80 (s, 3H), 3.45 (s, 3H), 5.20 (s, 2H), 7.15 (m, 1H), 7.25-7.30 (m, 5H), 7.75-7.90 (m, 3H), 8.05 (br. s, 2H), 8.30 (dd, 1H), 8.50 (d, 1H).

Example 121

(4S)-4-[4-Cyano-2-(methylsulfonyl)phenyl]-3-[2-(diethylamino)ethyl]-6-methyl-2-oxo-1-[3-(trifluoromethyl)phenyl]-1,2,3,4-tetrahydropyrimidine-5-carbonitrile trifluoroacetate

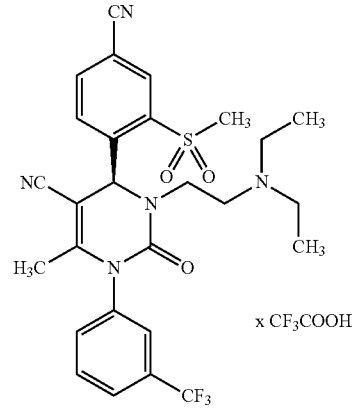 [SMILES: CCN(CC)CCN1C(=O)N(c2cccc(C(F)(F)F)c2)C(C)=C(C#N)[C@H]1c1ccc(C#N)cc1S(C)(=O)=O]

The reaction was carried out under argon. (4S)-4-[4-Cyano-2-(methylsulfonyl)phenyl]-6-methyl-2-oxo-1-[3-(trifluoromethyl)phenyl]-1,2,3,4-tetrahydropyrimidine-5-carbonitrile (100 mg, 217 μmol) was initially charged in dry THF (5 ml), sodium hydride (60% in mineral oil; 22 mg, 543 μmol; 2.5 eq.) was added at 0° C. and the mixture was stirred for 20 min. 2-Bromo-N,N-diethylethanamine hydrobromide (85 mg, 326 μmol; 1.5 eq.) was then added, and the mixture was stirred at RT for 90 minutes. The reaction was then added to saturated sodium chloride solution (50 ml) and extracted with ethyl acetate (3×30 ml). The combined organic phases were dried over solid sodium sulfate, filtered and concentrated under reduced pressure. The crude product was purified by preparative HPLC (column: Gromsil C-18 10 μm; mobile phase: acetonitrile/water+0.1% TFA 10:90→75:25). The title compound was obtained as a colorless solid (112 mg, 77% of theory).

LC-MS (Method 5): R$_t$=1.34 min; MS (ESIpos): m/z (%)=560.2 (100) [M+H]⁺; MS (ESIneg): m/z (%)=558.3 (100) [M−H]⁻

¹H-NMR (400 MHz, DMSO-d₆): δ=1.12 (t, 6H), 1.85 (s, 3H), 3.10 (br. m, 6H), 3.30 (m, 1H), 3.55 (s, 3H), 3.70 (m, 1H), 6.55 (s, 1H), 7.70-8.40 (m, 6H), 8.51 (s, 1H), 9.10 (br. s, 1H).

Example 122

Allyl (4S)-4-[4-cyano-2-(methylsulfonyl)phenyl]-3,6-dimethyl-2-oxo-1-[3-(trifluoromethyl)phenyl]-1,2,3,4-tetrahydropyrimidine-5-carboxylate

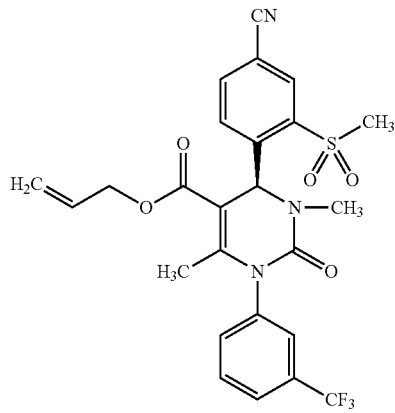 [SMILES: C=CCOC(=O)C1=C(C)N(c2cccc(C(F)(F)F)c2)C(=O)N(C)[C@@H]1c1ccc(C#N)cc1S(C)(=O)=O]

The reaction was carried out under argon. Allyl (4S)-4-[4-cyano-2-(methylsulfonyl)phenyl]-6-methyl-2-oxo-1-[3-(trifluoromethyl)phenyl]-1,2,3,4-tetrahydropyrimidine-5-carboxylate (260 mg, 0.5 mmol) was initially charged in THF (10 ml) at −78° C., and a 1 M solution of lithium hexamethyldisilazide (LiHMDS) in THF (0.6 ml; 1.2 eq.) was added. After 20 min of stirring, iodomethane (355 mg; 5 eq.) was added, and the mixture was stirred with gradual warming from −78° C. to RT for 16 h. The reaction mixture was then concentrated, and the residue was subjected to flash chromatography on silica gel (mobile phase: cyclohexane→cyclohexane/ethyl acetate 55:45). This gave the title compound as a solid (157 mg, 59% of theory).

LC-MS (Method 5): $R_t$=2.30 min; MS (ESIpos): m/z (%)=534.1 (100) [M+H]$^+$; MS (ESIneg): m/z (%)=532.1 (100) [M−H]$^−$.

Example 123

4-(4S)-3,6-Dimethyl-2,5-dioxo-1-[3-(trifluoromethyl)phenyl]-2,3,4,5,6,7-hexahydro-1H-pyrrolo[3,4-d]pyrimidin-4-yl-3-(methylsulfonyl)benzonitrile

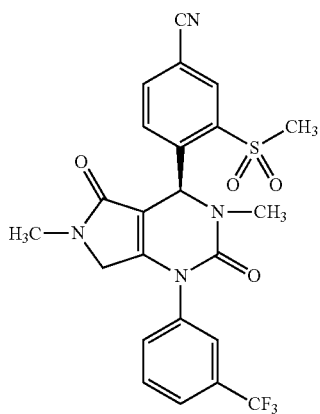

Under an argon protective gas atmosphere, a 1 M solution of methylamine in THF (20.7 ml, 20.7 mmol, 20 eq.) was added to 2,3-dibromopropyl (4S)-6-(bromomethyl)-4-[4-cyano-2-(methylsulfonyl)phenyl]-3-methyl-2-oxo-1-[3-(trifluoromethyl)phenyl]-1,2,3,4-tetrahydropyrimidine-5-carboxylate (801 mg, 1.04 mmol), and the mixture was stirred initially at RT for 2 h and then at 5° C. for a further 16 h. The reaction mixture was then concentrated under reduced pressure, and the crude product was purified by preparative HPLC (column: Gromsil C-18 10 μm; mobile phase: acetonitrile/water+0.1% TFA 10:90→75:25). This gave the title compound as a solid (314 mg, 60% of theory).

LC-MS (Method 5): $R_t$=1.82 min; MS (ESIpos): m/z (%)=505.1 (100) [M+H]$^+$; MS (ESIneg): m/z (%)=503.1 (100) [M−H]$^−$ $^1$H-NMR (400 MHz, DMSO-$d_6$): δ=2.70 (2s, 6H), 3.70 (s, 3H), 3.90 (m, 2H), 6.60 (s, 1H), 7.80 (m, 1H), 7.90 (m, 2H), 8.00 (br. s, 1H), 8.20 (m, 1H), 8.25 (m, 1H), 8.40 (m, 1H).

Example 124

Allyl (rac)-4-[4-cyano-2-(ethylsulfonyl)phenyl]-6-methyl-2-oxo-1-[3-(trifluoromethyl)phenyl]-1,2,3,4-tetrahydropyrimidine-5-carboxylate

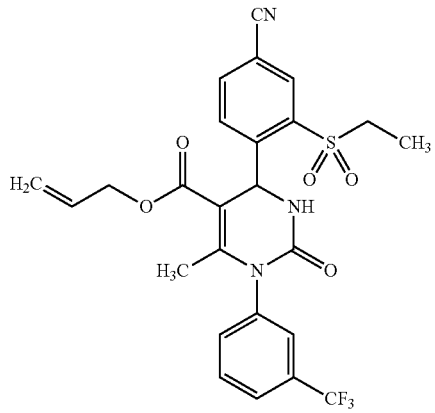 [SMILES: C=CCOC(=O)C1=C(C)N(c2cccc(C(F)(F)F)c2)C(=O)NC1c1ccc(C#N)cc1S(=O)(=O)CC]

The reaction was carried out under argon. Triethyl phosphate (0.718 g, 3.9 mmol) and diphosphorus pentoxide (0.511 g) were stirred at 40° C. overnight. The mixture was then diluted with MTBE (30 ml), and 4-formyl-3-(ethylsulfonyl)benzonitrile (0.88 g, 3.94 mmol), 1-[3-(trifluoromethyl)phenyl]urea (0.805 g, 3.94 mmol) and allyl acetoacetate (0.841 g, 5.91 mmol; 1.5 eq.) were added. The mixture was then stirred under reflux for 4 h. The reaction mixture was then concentrated by distillative removal of MTBE and subsequently heated at 90° C. for a further 2 h. For work-up, residual solvent was removed under reduced pressure, and the residue was suspended in MTBE (20 ml) and then filtered off with suction. The solid was washed with MTBE (10 ml). This gave 1.34 g (42% of theory) of the title compound.

LC-MS (Method 4): $R_t$=1.33 min; MS (ESIpos): m/z (%)=534.1 (100) [M+H]$^+$ $^1$H-NMR (400 MHz, DMSO-$d_6$): δ=1.20 (t, 3H), 2.15 (s, 3H), 3.54 (m, 2H), 4.45 (m, 2H), 4.95 (d, 1H), 5.05 (d, 1H), 5.70 (m, 1H), 6.25 (d, 1H), 7.00 (d, 1H), 7.70-7.85 (m, 4H), 8.10 (br. d, 1H), 8.30 (m, 1H), 8.35 (s, 1H).

Example 125

(rac)-4-[4-Cyano-2-(ethylsulfonyl)phenyl]-6-methyl-2-oxo-1-[3-(trifluoromethyl)phenyl]-1,2,3,4-tetrahydropyrimidine-5-carboxamide

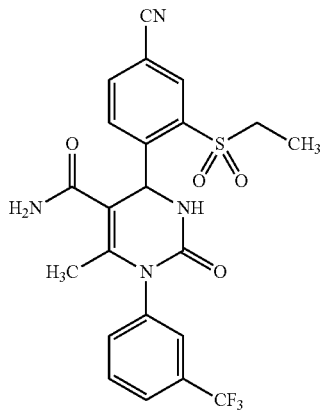 [SMILES: CCS(=O)(=O)c1cc(C#N)ccc1C1NC(=O)N(c2cccc(C(F)(F)F)c2)C(C)=C1C(N)=O]

The reaction was carried out under argon. (rac)-4-[4-Cyano-2-(ethylsulfonyl)phenyl]-6-methyl-2-oxo-1-[3-(trifluoromethyl)phenyl]-1,2,3,4-tetrahydropyrimidine-5-carboxylic acid (1100 mg, 2.29 mmol) and HATU (2 eq., 1695 mg, 4.5 mmol) were initially charged in dry DMF (28 ml) at 0° C., and a 0.5 M solution of ammonia in dioxane (6 eq., 23.6 ml, 13.4 mmol) and DIEA (2 eq., 576 mg, 4.5 mmol) were added after brief stirring (20 min). The mixture was stirred at RT for 3 h (HPLC control). The reaction mixture was then diluted with ethyl acetate (200 ml). The organic phase was washed successively with saturated sodium bicarbonate solution (50 ml), 10% strength citric acid (3×50 ml) and saturated sodium chloride solution (50 ml), dried over solid sodium sulfate, filtered and concentrated. The residue was subjected to flash chromatography on silica gel (mobile phase: dichloromethane→dichloromethane/methanol 50:3). This gave a colorless solid (1050 mg, 96% of theory).

LC-MS (Method 5): $R_t$=1.57 min; MS (ESIpos): m/z (%)=493.0 (100) [M+H]$^+$; MS (ESIneg): m/z (%)=448.1 (100), 491.1 (90) [M–H]$^-$ $^1$H-NMR (400 MHz, DMSO-$d_6$): δ=1.16 (t, 3H), 1.80 (s, 3H), 3.57 (m, 2H), 6.25 (s, 1H), 7.20 (m, 1H), 7.30 (br. s, 1H), 7.45 (br. s, 1H), 7.65-7.80 (m, 4H), 8.10 (d, 1H), 8.25 (s, 1H), 8.35 (dd, 1H).

Example 126

(rac)-4-[4-Cyano-2-(ethylsulfonyl)phenyl]-6-methyl-2-oxo-1-[3-(trifluoromethyl)phenyl]-1,2,3,4-tetrahydropyrimidine-5-carbonitrile

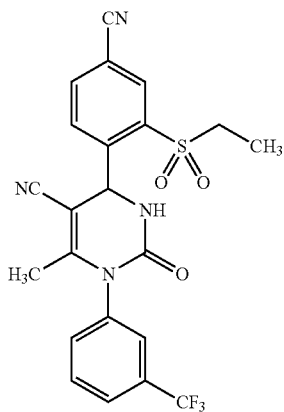

The reaction was carried out under argon. (rac)-4-[4-Cyano-2-(ethylsulfonyl)phenyl]-6-methyl-2-oxo-1-[3-(trifluoromethyl)phenyl]-1,2,3,4-tetrahydropyrimidine-5-carboxamide (1000 mg, 2.03 mmol) was initially charged in dry THF (50 ml), methoxycarbonylsulfamoyltriethylammonium hydroxide (Burgess reagent; 726 mg, 3.046 mmol) was added and the mixture was stirred at RT. After 75 min, HPLC control showed complete conversion. Water (20 ml) was then added, the reaction mixture was concentrated and the residue was taken up in ethyl acetate (200 ml).

The organic phase was washed with saturated sodium chloride solution (3×50 ml), dried over solid sodium sulfate, filtered and concentrated. The residue was subjected to flash chromatography on silica gel (mobile phase: cyclohexane→cyclohexane/ethyl acetate 2:3). The title compound was obtained as a colorless solid (890 mg, 92% of theory).

LC-MS (Method 6): $R_t$=2.34 min; MS (ESIpos): m/z (%)=475.0 (100) [M+H]$^+$; MS (ESIneg): m/z (%)=473.1 (100) [M–H]$^-$ $^1$H-NMR (400 MHz, DMSO-$d_6$): δ=1.20 (t, 3H), 1.80 (s, 3H), 3.45 (m, 2H), 6.35 (s, 1H), 7.70-7.85 (m, 3H), 7.95 (br. s, 1H), 8.30-8.40 (m, 4H).

Example 127

(4S)-4-[4-Cyano-2-(ethylsulfonyl)phenyl]-6-methyl-2-oxo-1-[3-(trifluoromethyl)phenyl]-1,2,3,4-tetrahydropyrimidine-5-carbonitrile

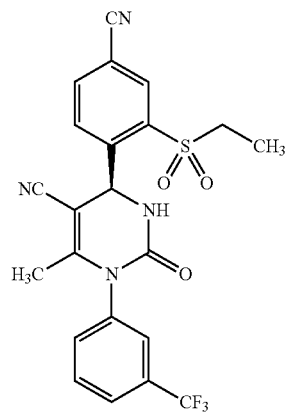 [SMILES: CCS(=O)(=O)c1cc(C#N)ccc1[C@H]1NC(=O)N(c2cccc(C(F)(F)F)c2)C(C)=C1C#N]

(rac)-4-[4-Cyano-2-(ethylsulfonyl)phenyl]-6-methyl-2-oxo-1-[3-(trifluoromethyl)phenyl]-1,2,3,4-tetrahydropyrimidine-5-carbonitrile (0.83 g) was separated into the enantiomers by preparative HPLC chromatography on a chiral phase [column: chiral silica gel phase based on the selector poly(N-methacryloyl-D-leucinedicyclopropylmethylamide); column dimensions: 670 mm×40 mm; sample preparation: solution in ethyl acetate (30 ml); injection volume: 6.1 ml; mobile phase: isohexane/ethyl acetate 3:7; flow rate 50 ml/min; temperature: 24° C.; detection: 260 nm]. This gave 0.379 g (89% of theory; >99.9% ee) of the 4S enantiomers. The enantiomeric excess (ee value) was determined chromatographically [column: chiral silica gel phase based on the selector poly(N-methacryloyl-D-leucinedicyclopropylmethylamide); column dimensions: 250 mm×4.6 mm; mobile phase: isohexane/ethyl acetate 1:1; flow rate: 2 ml/min; detection: 260 nm; $R_t$=4.26 min (4R enantiomer: $R_t$=8.87 min)].

LC-MS (Method 4): $R_t$=1.18 min; MS (ESIpos): m/z (%)=475.1 (100) [M+H]$^+$.

For the $^1$H-NMR data, see the racemic compound (Example 126).

Example 128

(4S)-4-[4-Cyano-2-(ethylsulfonyl)phenyl]-3,6-dimethyl-2-oxo-1-[3-(trifluoromethyl)phenyl]-1,2,3,4-tetrahydropyrimidine-5-carbonitrile

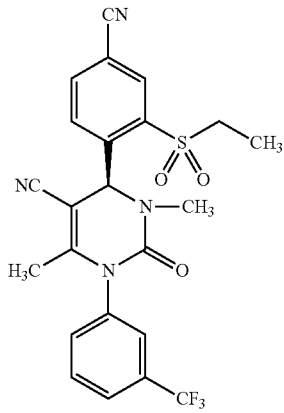

The reaction was carried out under argon. (4S)-4-[4-Cyano-2-(ethylsulfonyl)phenyl]-6-methyl-2-oxo-1-[3-(trifluoromethyl)phenyl]-1,2,3,4-tetrahydropyrimidine-5-carbonitrile (71.2 mg, 0.15 mmol) was initially charged in absolute THF (6 ml), and a 1 M solution of lithium hexamethyldisilazide (LiHMDS) in THF (180 µl; 1.2 eq.) was added at −78° C. After 20 min of stirring, iodomethane (47 µl; 5 eq.) was added, and the mixture was stirred with gradual warming from −78° C. to RT for 60 h. The reaction mixture was then purified directly by preparative HPLC (column: Gromsil, C-18 10 µm; mobile phase: acetonitrile/water+0.1% TFA 10:90→80:20). This gave the title compound as a colorless solid (60 mg, 82% of theory).

LC-MS (Method 6): $R_t$=2.42 min; MS (ESIpos): m/z (%)=489.0 (100) [M+H]$^+$; MS (ESIneg): m/z (%)=487.0 (100) [M−H]$^−$ $^1$H-NMR (400 MHz, DMSO-d$_6$): δ=1.20 (t, 3H), 1.80 (s, 3H), 2.68 (s, 3H), 3.55 (m, 2H), 6.45 (s, 1H), 7.70-8.05 (m, 4H), 8.40 (m, 3H).

Example 129

(4S)-4-[4-Cyano-2-(ethylsulfonyl)phenyl]-6-methyl-3-(methylsulfonyl)-2-oxo-1-[3-(trifluoromethyl)phenyl]-1,2,3,4-tetrahydropyrimidine-5-carbonitrile

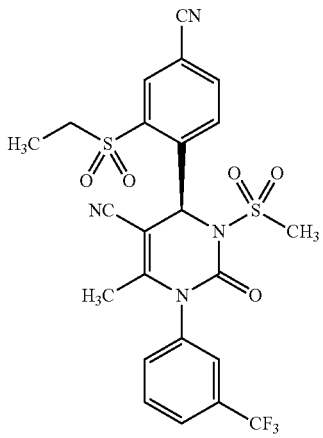 [SMILES: CCS(=O)(=O)c1cc(C#N)ccc1[C@@H]1C(C#N)=C(C)N(c2cccc(C(F)(F)F)c2)C(=O)N1S(C)(=O)=O]

The reaction was carried out under argon. (4S)-4-[4-Cyano-2-(ethylsulfonyl)phenyl]-6-methyl-2-oxo-1-[3-(trifluoromethyl)phenyl]-1,2,3,4-tetrahydropyrimidine-5-carbonitrile (71.2 mg, 150 µmol) was initially charged in dry THF (3 ml), and sodium hydride (60% in mineral oil; 8.4 mg, 210 µmol; 1.4 eq.) was added at 0° C. The mixture was warmed to RT and stirred for 20 min. A solution of methanesulfonyl chloride (24.1 mg, 210 µmol; 1.4 eq.) in THF (1 ml) was then slowly added dropwise.

After a reaction time of 20 h, the reaction mixture was concentrated and the crude product was purified by preparative HPLC (column: Gromsil C-18 10 µm; mobile phase: acetonitrile/water+0.1% TFA 10:90→80:20). This gave the title compound as a colorless solid (70 mg, 84% of theory).

LC-MS (Method 6): $R_t$=2.42 min; MS (ESIpos): m/z (%)=553.0 (100) [M+H]$^+$ $^1$H-NMR (400 MHz, DMSO-d$_6$): δ=1.25 (t, 3H), 1.80 (s, 3H), 3.40 (s, 3H), 3.55 (m, 2H), 7.20 (s, 1H), 7.80-8.40 (m, 7H).

Example 130

Allyl (rac)-4-[4-cyano-2-((2-hydroxyethyl)sulfonyl)phenyl]-6-methyl-2-oxo-1-[3-(trifluoromethyl)phenyl]-1,2,3,4-tetrahydropyrimidine-5-carboxylate

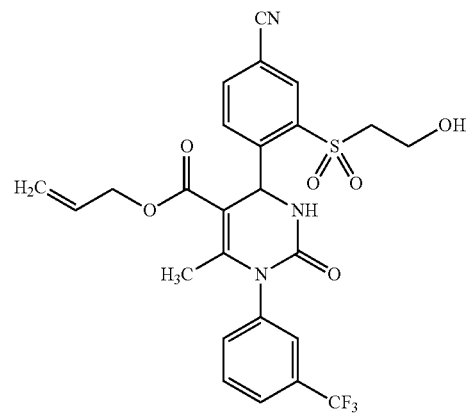 [SMILES: C=CCOC(=O)C1=C(C)N(c2cccc(C(F)(F)F)c2)C(=O)NC1c1ccc(C#N)cc1S(=O)(=O)CCO]

The reaction was carried out under argon. Triethyl phosphate (1.43 g, 7.9 mmol; 1.2 eq.) and diphosphorus pentoxide (0.745 g; 0.8 eq.) were stirred at 40° C. overnight. The mixture was then diluted with MTBE (35 ml), and 3-[(2-hydroxyethyl)sulfonyl]-4-formylbenzonitrile (1.57 g, 6.6 mmol), 1-[3-(trifluoromethyl)phenyl]urea (1.34 g, 6.6 mmol) and allyl acetoacetate (1.4 g, 9.84 mmol; 1.5 eq.) were added. The mixture was stirred under reflux for 2 h. The reaction mixture was then concentrated by distillative removal of MTBE and subsequently heated at 90° C. for a further 5 h. For work-up, residual solvent was removed under reduced pressure and the residue was taken up in ethyl acetate (250 ml). The organic phase was washed with saturated sodium chloride solution (3×50 ml), dried over solid sodium sulfate, filtered and concentrated under reduced pressure. The residue was subjected to flash chromatography on silica gel (mobile phase: cyclohexane→cyclohexane/ethyl acetate 2:3). The title compound was obtained as a colorless solid (1.22 g, 23% of theory).

LC-MS (Method 4): $R_t$=1.20 min; MS (ESIpos): m/z (%)=550.1 (100) [M+H]$^+$ $^1$H-NMR (400 MHz, DMSO-d$_6$): δ=2.15 (s, 3H), 3.54 (m, 2H), 3.85 (m, 2H), 4.45 (m, 2H), 5.00 (d, 1H), 5.05 (d, 1H), 5.15 (t, 1H), 5.70 (m, 1H), 6.30 (d, 1H), 7.05 (d, 1H), 7.70-7.85 (m, 4H), 8.10 (br. d, 1H), 8.25 (m, 1H), 8.35 (m, 1H).

Example 131

(rac)-4-[4-Cyano-2-((2-hydroxyethyl)sulfonyl)phenyl]-6-methyl-2-oxo-1-[3-(trifluoromethyl)phenyl]-1,2,3,4-tetrahydropyrimidine-5-carboxamide

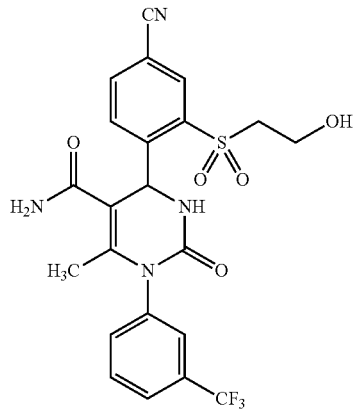 [SMILES: CC1=C(C(N)=O)C(c2ccc(C#N)cc2S(=O)(=O)CCO)NC(=O)N1c1cccc(C(F)(F)F)c1]

The reaction was carried out under argon. (rac)-4-[4-Cyano-2-((2-hydroxyethyl)sulfonyl)phenyl]-6-methyl-2-oxo-1-[3-(trifluoromethyl)phenyl]-1,2,3,4-tetrahydropyrimidine-5-carboxylic acid (910 mg, 1.79 mmol) and HATU (5 eq., 3396 mg, 8.9 mmol) were initially charged in dry DMF (20 ml) at 0° C., and ammonium chloride (5 eq., 478 mg, 8.9 mmol) and DIEA (10 eq., 2309 mg, 17.9 mmol) were added after brief stirring (20 min). The mixture was stirred at RT for 16 h (HPLC control) and then concentrated under reduced pressure. The crude product was purified by preparative HPLC (column: Gromsil C-18; mobile phase: acetonitrile/water+0.1% TFA 10:90→80:20). The title compound was obtained as a solid (740 mg, 81% of theory).

LC-MS (Method 6): $R_t$=1.84 min; MS (ESIpos): m/z (%)=509.1 (100) [M+H]$^+$; MS (ESIneg): m/z (%)=464.3 (100), 507.1 (50) [M−H]$^-$ $^1$H-NMR (400 MHz, DMSO-d$_6$): δ=1.80 (s, 3H), 3.70 (m, 4H), 6.30 (s, 1H), 7.10 (m, 1H), 7.25 (br. s, 1H), 7.45 (br. s, 1H), 7.65-7.80 (m, 4H), 8.10 (d, 1H), 8.30 (m, 2H).

Example 132

(rac)-4-[4-Cyano-2-((2-hydroxyethyl)sulfonyl)phenyl]-6-methyl-2-oxo-1-[3-(trifluoromethyl)phenyl]-1,2,3,4-tetrahydropyrimidine-5-carbonitrile

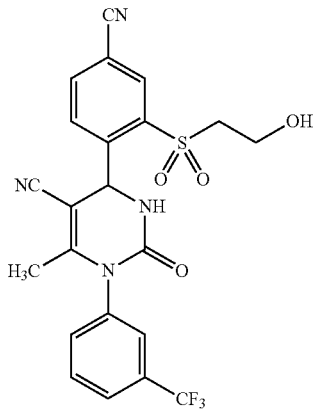 [SMILES: CC1=C(C#N)C(c2ccc(C#N)cc2S(=O)(=O)CCO)NC(=O)N1c1cccc(C(F)(F)F)c1]

The reaction was carried out under argon. 4-{2-[(2-{[tert-Butyl(dimethyl)silyl]oxy}ethyl)sulfonyl]-4-cyanophenyl}-6-methyl-2-oxo-1-[3-(trifluoromethyl)phenyl]-1,2,3,4-tetrahydropyrimidine-5-carbonitrile (550 mg, 0.909 mmol) was initially charged in dichloromethane (30 ml), trifluoroacetic acid (30 ml) was added and the mixture was stirred at RT for 5 h (HPLC control). The mixture was then concentrated without heating, and the residue was taken up in dichloromethane (200 ml). The organic phase was washed with saturated sodium bicarbonate solution (2×50 ml) and with saturated sodium chloride solution (50 ml), dried over solid sodium sulfate, filtered and concentrated under reduced pressure. The oil obtained was taken up in a little acetonitrile, water was added and the mixture was lyophilized. The title compound was obtained as a solid (450 mg, quant.).

LC-MS (Method 6): $R_t$=2.15 min; MS (ESIpos): m/z (%)=491.0 (100) [M+H]$^+$; MS (ESIneg): m/z (%)=446.0 (100), 489.0 (40) [M−H]$^-$.

Example 133

(4S)-4-[4-Cyano-2-((2-hydroxyethyl)sulfonyl)phenyl]-6-methyl-2-oxo-1-[3-(trifluoromethyl)phenyl]-1,2,3,4-tetrahydropyrimidine-5-carbonitrile

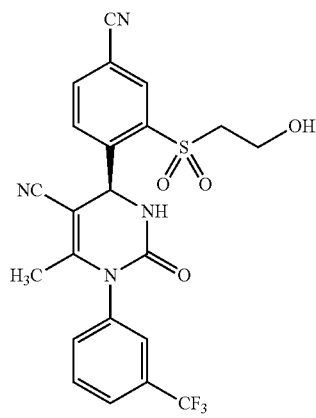

(rac)-4-[4-Cyano-2-((2-hydroxyethyl)sulfonyl)phenyl]-6-methyl-2-oxo-1-[3-(trifluoromethyl)phenyl]-1,2,3,4-tetrahydropyrimidine-5-carbonitrile (0.13 g) was separated into the enantiomers by preparative HPLC chromatography on a chiral phase [column: Daicel Chiralpak IC, 5 μm; column dimensions: 250 mm×20 mm; sample preparation: solution in methanol (10 ml); injection volume: 0.5 ml; mobile phase: MTBE/methanol 7:3; flow rate: 15 ml/min; temperature: 30° C.; detection: 220 nm]. This gave 0.042 g (65% of theory; >99.5% ee) of the 4S enantiomer. The enantiomeric excess (ee value) was determined chromatographically [column: Daicel Chiralpak IC, 5 μm; column dimensions: 250 mm×4.6 mm; mobile phase: MTBE/methanol 7:3; flow rate: 1 ml/min; detection: 220 nm; $R_t$=4.00 min (4R enantiomer: $R_t$=5.15 min)].

LC-MS (Method 5): $R_t$=1.72 min; MS (ESIpos): m/z (%)=491.1 (100) [M+H]$^+$; MS (ESIneg): m/z (%)=446.1 (100), 489.2 (30) [M−H]$^-$.

Example 134

Allyl (rac)-4-{4-cyano-2-[(1-methylethyl)sulfonyl]phenyl}-6-methyl-2-oxo-1-[3-(trifluoromethyl)phenyl]-1,2,3,4-tetrahydropyrimidine-5-carboxylate

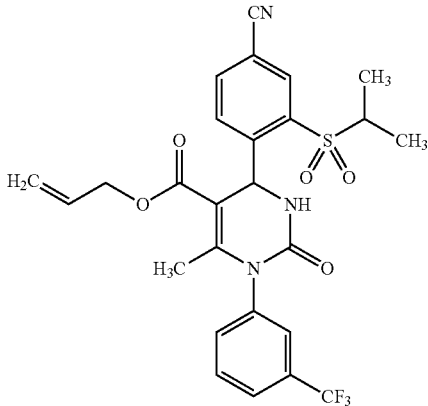 [SMILES: C=CCOC(=O)C1=C(C)N(c2cccc(C(F)(F)F)c2)C(=O)NC1c1ccc(C#N)cc1S(=O)(=O)C(C)C]

The reaction was carried out under argon. Triethyl phosphate (1.049 g, 5.76 mmol) and diphosphorus pentoxide (0.454 g) were stirred at 40° C. overnight. The mixture was then diluted with MTBE (25 ml), and 4-formyl-3-[(1-methylethyl)sulfonyl]benzonitrile (0.759 g, 3.2 mmol), 1-[3-(trifluoromethyl)phenyl]urea (0.653 g, 3.2 mmol) and allyl acetoacetate (0.682 g, 4.8 mmol; 1.5 eq.) were added. The mixture was stirred under reflux for 6 h. The reaction mixture was then concentrated by distillative removal of MTBE and subsequently heated at 90° C. for a further 2 h. For work-up, residual solvent was removed under reduced pressure and the residue was suspended in MTBE (20 ml) and then filtered off with suction. The solid was washed with MTBE (2×10 ml). This gave 1.25 g (48% of theory) of the title compound.

LC-MS (Method 4): $R_t$=1.37 min; MS (ESIpos): m/z (%)=548.1 (100) [M+H]$^+$ $^1$H-NMR (400 MHz, DMSO-d$_6$): δ=1.13 (d, 3H), 1.40 (d, 3H), 2.15 (s, 3H), 3.71 (m, 1H), 4.50 (m, 2H), 4.95 (d, 1H), 5.05 (d, 1H), 5.70 (m, 1H), 6.15 (d, 1H), 6.80 (d, 1H), 7.70-7.85 (m, 4H), 8.15 (br. d, 1H), 8.30 (m, 2H).

Example 135

(rac)-4-{4-Cyano-2-[(1-methylethyl)sulfonyl]phenyl}-6-methyl-2-oxo-1-[3-(trifluoromethyl)phenyl]-1,2,3,4-tetrahydropyrimidine-5-carboxamide

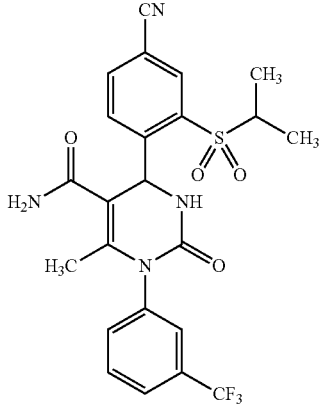 [SMILES: CC1=C(C(N)=O)C(c2ccc(C#N)cc2S(=O)(=O)C(C)C)NC(=O)N1c1cccc(C(F)(F)F)c1]

The reaction was carried out under argon. (rac)-4-{4-Cyano-2-[(1-methylethyl)sulfonyl]phenyl}-6-methyl-2-oxo-1-[3-(trifluoromethyl)phenyl]-1,2,3,4-tetrahydropyrimidine-5-carboxylic acid (1000 mg, 1.97 mmol) and HATU (3 eq., 2248 mg, 5.9 mmol) were initially charged in dry DMF (25 ml) at 0° C., and a 0.5 M solution of ammonia in dioxane (3 eq., 11.8 ml, 5.9 mmol) and DIEA (3 eq., 764 mg, 5.9 mmol) were added after brief stirring (20 min). The mixture was stirred at RT for 6 h (HPLC control) and then concentrated under reduced pressure. The crude product was purified by preparative HPLC (column: Gromsil C-18; mobile phase: acetonitrile/water+0.1% TFA 10:90→80:20). The title compound was obtained as a solid (750 mg, 75% of theory).

LC-MS (Method 5): $R_t$=1.61 min; MS (ESIpos): m/z (%)=507.2 (100) [M+H]$^+$; MS (ESIneg): m/z (%)=505.2 (100) [M−H]$^-$ $^1$H-NMR (400 MHz, DMSO-d$_6$): δ=1.07 (d, 3H), 1.35 (d, 3H), 1.80 (s, 3H), 3.85 (m, 1H), 6.20 (s, 1H), 7.05 (d, 1H), 7.30 (br. s, 1H), 7.45 (br. s, 1H), 7.65-7.80 (m, 4H), 8.15 (d, 1H), 8.25 (d, 1H), 8.35 (dd, 1H).

Example 136

(rac)-4-{4-Cyano-2-[(1-methylethyl)sulfonyl]phenyl}-6-methyl-2-oxo-1-[3-(trifluoromethyl)phenyl]-1,2,3,4-tetrahydropyrimidine-5-carbonitrile

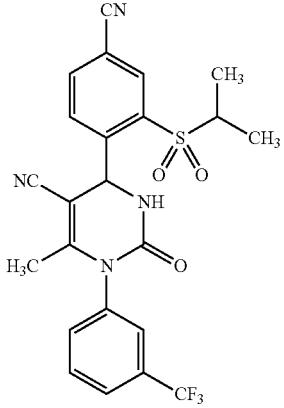 [SMILES: CC1=C(C#N)C(c2ccc(C#N)cc2S(=O)(=O)C(C)C)NC(=O)N1c1cccc(C(F)(F)F)c1]

The reaction was carried out under argon. (rac)-4-{4-Cyano-2-[(1-methylethyl)sulfonyl]phenyl}-6-methyl-2-oxo-1-[3-(trifluoromethyl)phenyl]-1,2,3,4-tetrahydropyrimidine-5-carboxamide (730 mg, 1.44 mmol) was initially charged in dry THF (35 ml), methoxycarbonylsulfamoyltriethylammonium hydroxide (Burgess reagent; 687 mg, 2.88 mmol; 2 eq.) was added and the mixture was stirred at RT. After 75 min, HPLC control showed complete conversion. Water (20 ml) was then added, the reaction mixture was concentrated and the residue was taken up in ethyl acetate (200 ml). The organic phase was washed with saturated sodium chloride solution (3×30 ml), dried over solid sodium sulfate, filtered and concentrated. The residue was subjected to flash chromatography on silica gel (mobile phase: cyclohexane→cyclohexane/ethyl acetate 1:1). The title compound was obtained as a colorless solid (700 mg, 99% of theory).

LC-MS (Method 4): $R_t$=1.22 min; MS (ESIpos): m/z (%)=489.1 (100) [M+H]$^+$ $^1$H-NMR (400 MHz, DMSO-d$_6$): δ=1.20 (d, 3H), 1.30 (d, 3H), 1.80 (s, 3H), 3.55 (m, 1H), 6.30 (s, 1H), 7.70-7.85 (m, 3H), 7.95 (br. s, 1H), 8.30-8.40 (m, 4H).

Example 137

(4S)-4-{4-Cyano-2-[(1-methylethyl)sulfonyl]phenyl}-6-methyl-2-oxo-1-[3-(trifluoromethyl)phenyl]-1,2,3,4-tetrahydropyrimidine-5-carbonitrile

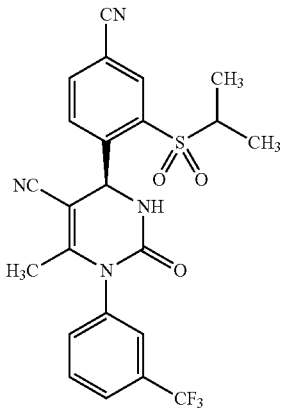

(rac)-4-{4-Cyano-2-[(1-methylethyl)sulfonyl]phenyl}-6-methyl-2-oxo-1-[3-(trifluoromethyl)phenyl]-1,2,3,4-tetrahydropyrimidine-5-carbonitrile (0.70 g) was separated into the enantiomers by preparative HPLC chromatography on a chiral phase [column: Daicel Chiralpak IC, 5 µm; column dimensions: 250 mm×20 mm; sample preparation: solution in methanol/acetonitrile (1:6, 35 ml); injection volume: 0.5 ml; mobile phase: MTBE/methanol 7:3; flow rate: 15 ml/min; temperature: 30° C.; detection: 220 nm]. This gave 0.334 g (95% of theory; >98.5% ee) of the 4S enantiomer.

The enantiomeric excess (ee value) was determined chromatographically [column: Daicel Chiralpak IA, 5 µm; column dimensions: 250 mm×4.6 mm; mobile phase: MTBE/acetonitrile 7:3; flow rate: 1 ml/min; detection: 220 nm; $R_t$=3.46 min (4R enantiomer: $R_t$=4.905 min)].

LC-MS (Method 5): $R_t$=1.97 min; MS (ESIpos): m/z (%)=489.2 (100) [M+H]$^+$; MS (ESIneg): m/z (%)=444.2 (100), 487.2 (70) [M−H]$^-$.

For the $^1$H-NMR data, see the racemic compound (Example 136).

Example 138

Allyl (rac)-4-[4-cyano-2-(phenylsulfonyl)phenyl]-6-methyl-2-oxo-1-[3-(trifluoromethyl)phenyl]-1,2,3,4-tetrahydropyrimidine-5-carboxylate

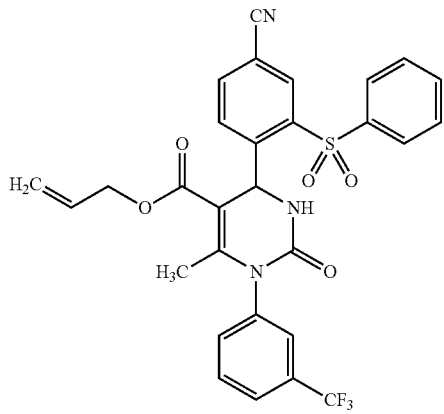 [SMILES: C=CCOC(=O)C1=C(C)N(c2cccc(C(F)(F)F)c2)C(=O)NC1c1ccc(C#N)cc1S(=O)(=O)c1ccccc1]

The reaction was carried out under argon. Triethyl phosphate (172 mg, 0.947 mmol) and diphosphorus pentoxide (90 mg) were stirred at 40° C. overnight. The mixture was then diluted with MTBE (9.5 ml), and 4-formyl-3-(phenylsulfonyl)benzonitrile (214 mg, 0.789 mmol), 1-[3-(trifluoromethyl)phenyl]urea (0.161 g, 0.789 mmol) and allyl acetoacetate (0.168 g, 1.18 mmol; 1.5 eq.) were added. The mixture was stirred under reflux for 16 h. The reaction mixture was then concentrated by distillative removal of MTBE and subsequently heated at 90° C. for a further 2 h. For work-up, residual solvent was removed under reduced pressure and the residue was taken up in ethyl acetate (150 ml). The organic phase was washed with saturated sodium chloride solution (2×30 ml), dried over solid sodium sulfate, filtered and concentrated under reduced pressure. The crude product was purified by preparative HPLC (column: Gromsil C-18; mobile phase: acetonitrile/water+0.1% TFA 10:90→90:10). The title compound was obtained as a solid (230 mg, 33% of theory).

LC-MS (Method 4): $R_t$=1.40 min; MS (ESIpos): m/z (%)=582.1 (100) [M+H]$^+$ $^1$H-NMR (400 MHz, DMSO-d$_6$): δ=2.10 (s, 3H), 3.45 (m, 1H), 4.10 (m, 1H), 4.50 (m, 2H), 4.75 (d, 1H), 5.15 (m, 1H), 6.15 (d, 1H), 6.95 (d, 1H), 7.65-7.80 (m, 7H), 8.05 (br. d, 1H), 8.15 (d, 2H), 8.25 (dd, 1H), 8.60 (d, 1H).

Example 139

(rac)-4-{4-Cyano-2-[phenylsulfonyl]phenyl}-6-methyl-2-oxo-1-[3-(trifluoromethyl)phenyl]-1,2,3,4-tetrahydropyrimidine-5-carboxamide

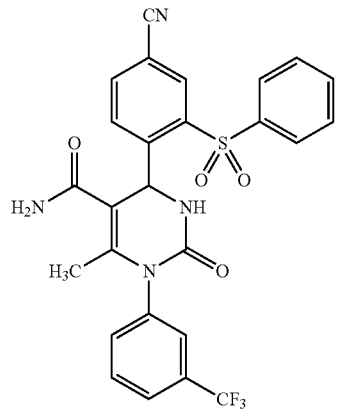 [SMILES: CC1=C(C(N)=O)C(c2ccc(C#N)cc2S(=O)(=O)c2ccccc2)NC(=O)N1c1cccc(C(F)(F)F)c1]

The reaction was carried out under argon. (rac)-4-{4-Cyano-2-[phenylsulfonyl]phenyl}-6-methyl-2-oxo-1-[3-(trifluoromethyl)phenyl]-1,2,3,4-tetrahydropyrimidine-5-carboxylic acid (166 mg, 0.307 mmol) and HATU (5 eq., 583 mg, 1.53 mmol) were initially charged in dry DMF (3.5 ml) at 0° C., and ammonium chloride (5 eq., 82 mg, 1.53 mmol) [alternatively: 1.23 ml of a 0.5 M solution of ammonia in dioxane] and DIEA (10 eq., 369 mg, 3.07 mmol) were added after brief stirring (20 minutes). The mixture was stirred at RT for 6 h (HPLC control) and then concentrated under reduced pressure. The crude product was purified by preparative HPLC (column: Gromsil C-18; mobile phase: acetonitrile/water+0.1% TFA 10:90→90:10). This gave the title compound as a solid (147 mg, 89% of theory).

LC-MS (Method 6): $R_t$=2.18 min; MS (ESIpos): m/z (%)=541.0 (100) [M+H]$^+$ $^1$H-NMR (400 MHz, DMSO-d$_6$): δ=1.75 (s, 3H), 6.20 (s, 1H), 6.85 (d, 1H), 7.05 (br. s, 1H), 7.30 (br. s, 1H), 7.60-7.80 (m, 7H), 8.15 (m, 3H), 8.25 (d, 1H), 8.55 (s, 1H).

Example 140

(rac)-4-{4-Cyano-2-[phenylsulfonyl]phenyl}-6-methyl-2-oxo-1-[3-(trifluoromethyl)phenyl]-1,2,3,4-tetrahydropyrimidine-5-carbonitrile

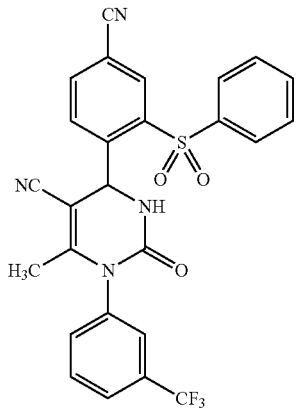 [SMILES: CC1=C(C#N)C(c2ccc(C#N)cc2S(=O)(=O)c2ccccc2)NC(=O)N1c1cccc(C(F)(F)F)c1]

The reaction was carried out under argon. (rac)-4-{4-Cyano-2-[phenylsulfonyl]phenyl}-6-methyl-2-oxo-1-[3-(trifluoromethyl)phenyl]-1,2,3,4-tetrahydropyrimidine-5-carboxamide (137 mg, 253 µmol) was initially charged in dry THF (8 ml), methoxycarbonylsulfamoyltriethylammonium hydroxide (Burgess reagent; 121 mg, 507 µmol; 2 eq.) was added and the mixture was stirred at RT for 8 h (HPLC control). The reaction mixture was then concentrated under reduced pressure, and the residue was purified by preparative HPLC (column: Gromsil C-18; mobile phase: acetonitrile/water+0.1% TFA 10:90→90:10). This gave the title compound as a solid (106 mg, 80% of theory).

LC-MS (Method 5): $R_t$=2.07 min; MS (ESIpos): m/z (%)=523.1 (100) [M+H]$^+$; MS (ESIneg): m/z (%)=478.1 (100), 521.2 (20) [M−H]$^−$ $^1$H-NMR (400 MHz, DMSO-d$_6$): δ=1.75 (s, 3H), 6.35 (s, 1H), 7.65-8.35 (m, 12H), 8.60 (s, 1H).

Example 141

(4S)-4-{4-Cyano-2-[phenylsulfonyl]phenyl}-6-methyl-2-oxo-1-[3-(trifluoromethyl)phenyl]-1,2,3,4-tetrahydropyrimidine-5-carbonitrile

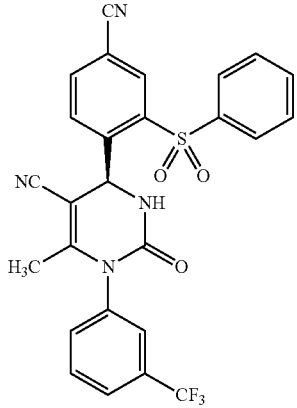 [SMILES: CC1=C(C#N)[C@@H](c2ccc(C#N)cc2S(=O)(=O)c2ccccc2)NC(=O)N1c1cccc(C(F)(F)F)c1]

(rac)-4-{4-Cyano-2-[phenylsulfonyl]phenyl}-6-methyl-2-oxo-1-[3-(trifluoromethyl)phenyl]-1,2,3,4-tetrahydropyrimidine-5-carbonitrile (90 mg) was separated into the enantiomers by preparative HPLC chromatography on a chiral phase [column: Daicel Chiralpak IC, 5 µm; column dimensions: 250 mm×20 mm; sample preparation: solution in methanol/acetonitrile (1:1, 18 ml); mobile phase: MTBE/methanol 7:3; flow rate: 15 ml/min; temperature: 30° C.; detection: 220 nm]. This gave 39 mg (87% of theory; >97.5% ee) of the 4S enantiomer.

The enantiomeric excess (ee value) was determined chromatographically [column: Daicel Chiralpak IA, 5 µm; column dimensions: 250 mm×4.6 mm; mobile phase: MTBE/methanol 7:3; flow rate: 1 ml/min; detection: 220 nm; $R_t$=3.49 min (4R enantiomer: $R_t$=5.95 min)].

LC-MS (Method 6): $R_t$=2.53 min; MS (ESIpos): m/z (%)=523.2 (100) [M+H]$^+$; MS (ESIneg): m/z (%)=478.1 (100), 521.2 (20) [M−H]$^−$.

For the $^1$H-NMR data, see the racemic compound (Example 140).

Example 142

2-Hydroxyethyl (4S)-4-[4-cyano-2-(methylsulfonyl)phenyl]-6-methyl-2-oxo-1-[3-(trifluoromethyl)phenyl]-1,2,3,4-tetrahydropyrimidine-5-carboxylate

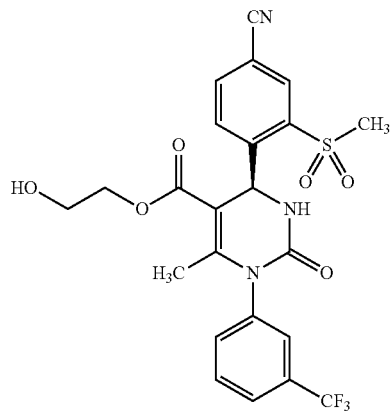 [SMILES: CC1=C(C(=O)OCCO)[C@@H](c2ccc(C#N)cc2S(C)(=O)=O)NC(=O)N1c1cccc(C(F)(F)F)c1]

The reaction was carried out under argon. (4S)-4-[4-Cyano-2-(methylsulfonyl)phenyl]-6-methyl-2-oxo-1-[3-(trifluoromethyl)phenyl]-1,2,3,4-tetrahydropyrimidine-5-carboxylic acid (170 mg, 355 µmol; Example 5A) was initially charged in dry DMF (4 ml), 2-bromoethanol (177 mg, 1.42 mmol; 4 eq.) and triethylamine (72 mg, 709 µmol; 2 eq.) were added and the mixture was stirred at 70° C. for 10 h. The reaction mixture was then concentrated under reduced pressure, and the residue was taken up in ethyl acetate (50 ml). The organic phase was washed with saturated sodium bicarbonate solution (2×20 ml) and saturated sodium chloride solution (20 ml), dried over solid sodium sulfate, filtered and concentrated under reduced pressure. The crude product was purified by preparative HPLC (column: Gromsil C-18; mobile phase: acetonitrile/water+0.1% TFA 10:90→90:10). This gave the title compound as a solid (175 mg, 94% of theory).

LC-MS (Method 5): $R_t$=1.74 min; MS (ESIpos): m/z (%)=524.1 (100) [M+H]$^+$; MS (ESIneg): m/z (%)=522.2 (100) [M−H]$^−$ $^1$H-NMR (400 MHz, DMSO-d$_6$): δ=2.15 (s, 3H), 3.35 (m, 2H), 3.50 (s, 3H), 3.90 (m, 1H), 4.00 (m, 1H), 4.65 (br. s, 1H), 6.30 (s, 1H), 7.10 (d, 1H), 7.70-7.85 (m, 4H), 8.10 (br. d, 1H), 8.25 (dd, 1H), 8.35 (d, 1H).

Example 143

Allyl (4S)-4-[4-cyano-2-(methylsulfonyl)phenyl]-6-methyl-3-(methylsulfonyl)-2-oxo-1-[3-(trifluoromethyl)phenyl]-1,2,3,4-tetrahydropyrim idine-5-carboxylate

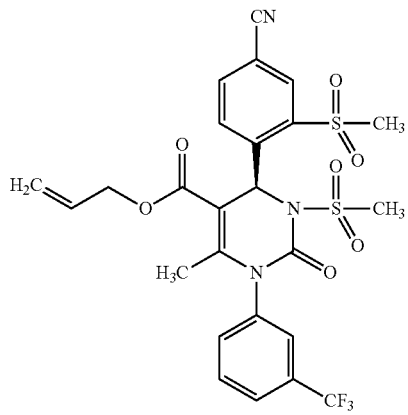 [SMILES: C=CCOC(=O)C1=C(C)N(c2cccc(C(F)(F)F)c2)C(=O)N(S(C)(=O)=O)[C@@H]1c1ccc(C#N)cc1S(C)(=O)=O]

The reaction was carried out under argon. Allyl (4S)-4-[4-cyano-2-(methylsulfonyl)phenyl]-6-methyl-2-oxo-1-[3-(trifluoromethyl)phenyl]-1,2,3,4-tetrahydropyrimidine-5-carboxylate (260 mg, 500 μmol) was initially charged in dry THF (10 ml), and sodium hydride (60% in mineral oil; 28 mg, 700 μmol; 1.4 eq.) was added at 0° C. The mixture was warmed to RT and stirred for 20 min. A solution of methanesulfonyl chloride (80 mg, 700 μmol; 1.4 eq.) in THF (2 ml) was then slowly added dropwise. After a reaction time of 20 h, the reaction mixture was concentrated and the residue was subjected to flash chromatogrphy on silica gel (mobile phase: cyclohexane→cyclohexane/ethyl acetate 55:45). The title compound was obtained as a colorless solid (288 mg, 96% of theory).

LC-MS (Method 5): $R_f$=2.24 min; MS (ESIpos): m/z (%)=540.1 (100), 598.1 (40) [M+H]$^+$; MS (ESIneg): m/z (%)=475.1 (80), 596.1 (100) [M−H]$^−$.

Example 144

2-Hydroxyethyl (4S)-4-[4-cyano-2-(methylsulfonyl)phenyl]-6-methyl-3-(methylsulfonyl)-2-oxo-1-[3-(trifluoromethyl)phenyl]-1,2,3,4-tetrahydropyrimidine-5-carboxylate

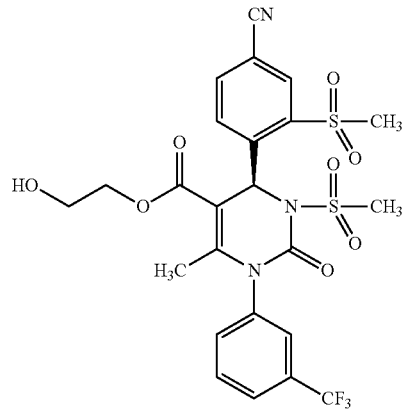 [SMILES: CC1=C(C(=O)OCCO)[C@@H](c2ccc(C#N)cc2S(C)(=O)=O)N(S(C)(=O)=O)C(=O)N1c1cccc(C(F)(F)F)c1]

The reaction was carried out under argon. (4S)-4-[4-Cyano-2-(methylsulfonyl)phenyl]-6-methyl-3-(methylsulfonyl)-2-oxo-1-[3-(trifluoromethyl)phenyl]-1,2,3,4-tetrahydropyrimidine-5-carboxylic acid (84 mg, 150 μmol) was initially charged in dry DMF (2 ml), 2-bromoethanol (75 mg, 600 μmol; 4 eq.) and triethylamine (31 mg, 300 μmol; 2 eq.) were added and the mixture was stirred at 70° C. for 8 h. The reaction mixture was then concentrated under reduced pressure, and the residue was taken up in ethyl acetate (50 ml). The organic phase was washed with saturated sodium bicarbonate solution (2×20 ml) and saturated sodium chloride solution (20 ml), dried over solid sodium sulfate, filtered and concentrated under reduced pressure. The crude product was subjected to flash chromatography on silica gel (mobile phase: cyclohexane→cyclohexane/ethyl acetate 1:3). The title compound was obtained as a colorless solid (56 mg, 62% of theory).

LC-MS (Method 4): $R_f$=1.13 min; MS (ESIpos): m/z (%)=539.9 (100), 602 (20) [M+H]$^+$; MS (ESIneg): m/z (%)=479.0 (100), 600.0 (80) [M−H]$^−$ $^1$H-NMR (400 MHz, DMSO-d$_6$): δ=1.75 (s, 3H), 3.40 (s, 3H), 3.50 (m, 2H), 4.05 (m, 2H), 4.65 (t, 1H), 7.30 (s, 1H), 7.75-7.90 (m, 3H), 8.05 (m, 2H), 8.25 (dd, 1H), 8.50 (d, 1H) [a methyl signal was obscured by the solvent peak].

Example 145

Allyl (4S)-4-[4-cyano-2-(methylsulfonyl)phenyl]-3,6-dimethyl-2-oxo-1-[3-(trifluoromethyl)phenyl]-1,2,3,4-tetrahydropyrimidine-5-carboxylate

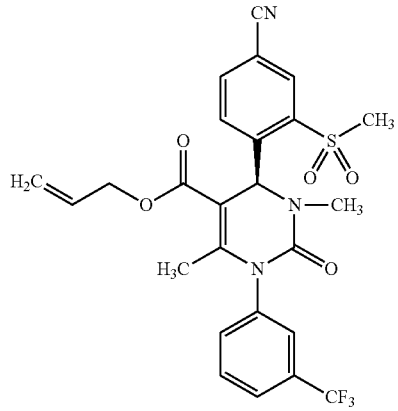 [SMILES: C=CCOC(=O)C1=C(C)N(c2cccc(C(F)(F)F)c2)C(=O)N(C)[C@@H]1c1ccc(C#N)cc1S(C)(=O)=O]

The reaction was carried out under argon. Allyl (4S)-4-[4-cyano-2-(methylsulfonyl)phenyl]-6-methyl-2-oxo-1-[3-(trifluoromethyl)phenyl]-1,2,3,4-tetrahydropyrimidine-5-carboxylate (260 mg, 0.5 mmol) was initially charged in absolute THF (10 ml), and a 1 M solution of lithium hexamethyldisilazide (LiHMDS) in THF (0.6 ml, 600 μmol; 1.2 eq.) was added at −78° C. After 20 min of stirring, iodomethane (355 mg, 2.5 mmol; 5 eq.) was added, and the mixture was stirred for 16 h with gradual warming from −78° C. to RT. The reaction mixture was then concentrated under reduced pressure, and the residue was subjected to flash chromatography on silica gel (mobile phase: cyclohexane→cyclohexane/ethyl acetate 55:45). The title compound was obtained as a colorless solid (157 mg, 59% of theory).

LC-MS (Method 5): $R_t$=2.30 min; MS (ESIpos): m/z (%)=534.1 (100) [M+H]$^+$; MS (ESIneg): m/z (%)=532.2 (100) [M−H]$^-$.

Example 146

2-Hydroxyethyl (4S)-4-[4-cyano-2-(methylsulfonyl) phenyl]-3,6-dimethyl-2-oxo-1-[3-(trifluoromethyl) phenyl]-1,2,3,4-tetrahydropyrimidine-5-carboxylate

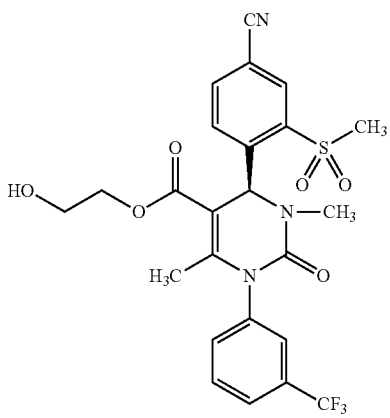 [SMILES: CC1=C(C(=O)OCCO)[C@@H](c2ccc(C#N)cc2S(C)(=O)=O)N(C)C(=O)N1c1cccc(C(F)(F)F)c1]

The reaction was carried out under argon. (4S)-4-[4-Cyano-2-(methylsulfonyl)phenyl]-3,6-dimethyl-2-oxo-1-[3-(trifluoromethyl)phenyl]-1,2,3,4-tetrahydropyrimidine-5-carboxylic acid (74 mg, 150 μmol) was initially charged in dry DMF (2 ml), 2-bromoethanol (75 mg, 600 μmol; 4 eq.) and triethylamine (31 mg, 300 μmol; 2 eq.) were added and the mixture was stirred at 70° C. for 8 h. The reaction mixture was then concentrated under reduced pressure, and the residue was taken up in ethyl acetate (50 ml). The organic phase was washed with saturated sodium bicarbonate solution (2×20 ml) and saturated sodium chloride solution (20 ml), dried over solid sodium sulfate, filtered and concentrated under reduced pressure. The crude product was subjected to flash chromatography on silica gel (mobile phase: cyclohexane→cyclohexane/ethyl acetate 1:3). The product-containing fractions were combined and concentrated, the residue was taken up in a little acetonitrile, water was added and the mixture was lyophilized. The title compound was obtained as a colorless solid (63 mg, 78% of theory).

LC-MS (Method 4): $R_t$=1.13 min; MS (ESIpos): m/z (%)=538.1 (100) [M+H]$^+$; MS (ESIneg): m/z (%)=536.2 (100) [M−H]$^-$ $^1$H-NMR (400 MHz, DMSO-d$_6$): δ=2.05 (s, 3H), 2.75 (s, 3H), 3.50 (m, 2H), 3.55 (s, 3H), 4.05 (m, 2H), 4.70 (t, 1H), 6.75 (s, 1H), 7.70-7.85 (m, 3H), 7.95 (br. s, 1H), 8.15 (br. d, 1H), 8.25 (dd, 1H), 8.50 (d, 1H).

Example 147

(4S)-4-{4-Cyano-2-[methylsulfinyl]phenyl}-6-methyl-3-(methyl sulfonyl)-2-oxo-1-[3-(trifluoromethyl)phenyl]-1,2,3,4-tetrahydropyrimidine-5-carbonitrile

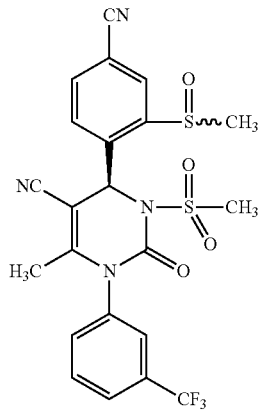

The reaction was carried out under argon. (4S)-4-{4-Cyano-2-[methylsulfinyl]phenyl}-6-methyl-2-oxo-1-[3-(trifluoromethyl)phenyl]-1,2,3,4-tetrahydropyrimidine-5-carbonitrile (444 mg, 1 mmol) was initially charged in dry THF (10 ml), and sodium hydride (60% in mineral oil; 56 mg, 1.4 mmol; 1.4 eq.) was added at 0° C. The mixture was warmed to RT and stirred for 20 min. A solution of methanesulfonyl chloride (160 mg, 1.4 mmol; 1.4 eq.) in THF (5 ml) was then slowly added dropwise. After a reaction time of 16 h, ammonium chloride solution (50 ml) was added to the reaction mixture, and the mixture was extracted with ethyl acetate (3×30 ml). The combined organic phases were dried over sodium sulfate, filtered and concentrated under reduced pressure. The residue was purified by preparative HPLC (column: Gromsil C-18; mobile phase: acetonitrile/water+0.1% TFA 10:90→80:20). This gave the title compound as a solid (210 mg, 40% of theory).

LC-MS (Method 4): $R_t$=1.15 min; MS (ESIpos): m/z (%)=523.0 (100) [M+H]$^+$; MS (ESIneg): m/z (%)=441.1 (100), 521.0 (100) [M−H]$^-$ $^1$H-NMR (400 MHz, DMSO-d$_6$): δ=1.80 (s, 3H), 2.70 (s, 3H), 3.30 (s, 3H), 6.75 (s, 1H), 7.70-8.32 (m, 6H), 8.50 (s, 1H).

Example 148

(4S)-4-{4-Cyano-2-[(cyclobutylmethyl)sulfonyl] phenyl}-3,6-dimethyl-2-oxo-1-[3-(trifluoromethyl) phenyl]-1,2,3,4-tetrahydropyrimidine-5-carbonitrile

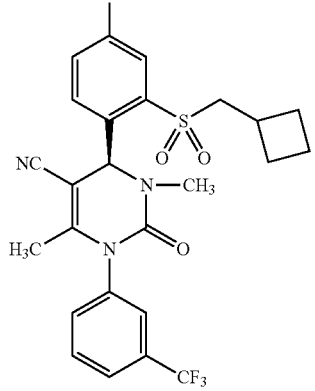

The reaction was carried out under argon. Sodium 5-cyano-2-{(4S)-5-cyano-3,6-dimethyl-2-oxo-1-[3-(trifluoromethyl)phenyl]-1,2,3,4-tetrahydropyrimidin-4-yl}benzenesulfinate (150 mg, 101 µmol; purity 32%) was suspended in DMF (1 ml). 1-(Bromomethyl)cyclobutane (164.1 mg) was then added, and the mixture was heated in a closed tube at 110° C. for 72 h. The mixture was then filtered, and the filtrate was concentrated under reduced pressure. The residue was purified by preparative HPLC (column: Gromsil C-18 10 µm; mobile phase: acetonitrile/water+0.1% TFA 10:90→90:10). The title compound was obtained as a solid (40.2 mg, 75% of theory).

LC-MS (Method 4): $R_t$=1.42 min; MS (ESIpos): m/z (%)=529.3 (100) [M+H]$^+$; MS (ESIneg): m/z (%)=527.3 (100) [M−H]$^−$ $^1$H-NMR (400 MHz, DMSO-d$_6$): δ=1.76-2.10 (m, 9H), 2.65 (s, 3H), 2.70 (m, 1H), 3.65 (dd, 1H), 3.75 (dd, 1H), 6.45 (s, 1H), 7.70-8.40 (m, 7H).

Example 149

(4S)-4-{4-Cyano-2-[(cyclopropylmethyl)sulfonyl]phenyl}-3,6-dimethyl-2-oxo-1-[3-(trifluoromethyl)phenyl]-1,2,3,4-tetrahydropyrimidine-5-carbonitrile

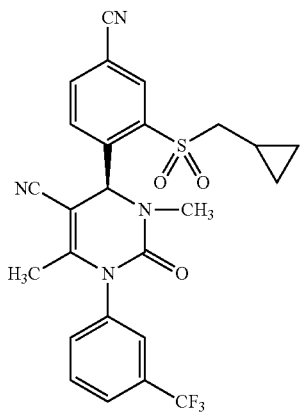 [SMILES: CC1=C(C#N)[C@@H](c2ccc(C#N)cc2S(=O)(=O)CC2CC2)N(C)C(=O)N1c1cccc(C(F)(F)F)c1]

The reaction was carried out under argon. Sodium 5-cyano-2-{(4S)-5-cyano-3,6-dimethyl-2-oxo-1-[3-(trifluoromethyl)phenyl]-1,2,3,4-tetrahydropyrimidin-4-yl}benzenesulfinate (100 mg, 67 µmol; purity 32%) was suspended in DMF (2000 µl). 1-(Bromomethyl)cyclopropane (278 mg, 2.06 mmol) was then added, and the mixture was heated in a closed tube at 130° C. overnight. Molecular sieve (4 Å), potassium iodide (110 mg, 0.66 mmol) and more 1-(bromomethyl)cyclopropane (89 mg, 0.66 mmol) were then added, and the reaction mixture was once more heated in a closed tube at 100° C. for 6 h. The mixture was then filtered, and the filtrate was concentrated under reduced pressure. The residue was purified by preparative HPLC (column: Gromsil C-18 10 µm; mobile phase: acetonitrile/water+0.1% TFA 10:90→90:10). The title compound was obtained as a solid (16.2 mg, 44% of theory).

LC-MS (Method 9): $R_t$=1.16 min; MS (ESIpos): m/z (%)=515.2 (100) [M+H]$^+$; MS (ESIneg): m/z (%)=513.2 (80) [M−H]$^−$ $^1$H-NMR (400 MHz, DMSO-d$_6$): δ=0.20 (m, 1H), 0.30 (m, 1H), 0.50 (m, 1H), 0.60 (m, 1H), 1.00 (m, 1H), 1.80 (s, 3H), 2.70 (s, 3H), 3.45 (dd, 1H), 3.60 (dd, 1H), 6.50 (s, 1H), 7.75-8.45 (m, 7H).

Example 150

(4S)-4-{4-Cyano-2-[(3,3,3-trifluoropropyl)sulfonyl]phenyl}-3,6-dimethyl-2-oxo-1-[3-(trifluoromethyl)phenyl]-1,2,3,4-tetrahydropyrimidine-5-carbonitrile

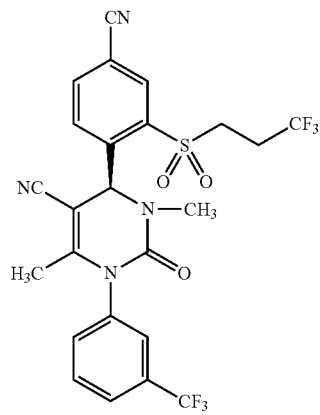 [SMILES: CC1=C(C#N)[C@@H](c2ccc(C#N)cc2S(=O)(=O)CCC(F)(F)F)N(C)C(=O)N1c1cccc(C(F)(F)F)c1]

The reaction was carried out under argon. Sodium 5-cyano-2-{(4S)-5-cyano-3,6-dimethyl-2-oxo-1-[3-(trifluoromethyl)phenyl]-1,2,3,4-tetrahydropyrimidin-4-yl}benzenesulfinate (66 mg, 44 µmol; purity 32%) was suspended in DMF (600 µl). 1,1,1-Trifluoro-3-iodopropane (144 mg, 643 µmol; 14.6 eq.) was then added, and the mixture was heated in a closed tube at 120° C. overnight. The mixture was then filtered, and the filtrate was concentrated under reduced pressure. The residue was purified by preparative HPLC (column: Gromsil C-18 10 µm; mobile phase: acetonitrile/water+0.1% TFA 10:90→90:10). The title compound was obtained as a solid (7.4 mg, 30% of theory).

LC-MS (Method 9): $R_t$=1.18 min; MS (ESIpos): m/z (%)=557.2 (100) [M+H]$^+$; MS (ESIneg): m/z (%)=555.2 (80) [M−H]$^−$ $^1$H-NMR (400 MHz, DMSO-d$_6$): δ=1.80 (s, 3H), 2.70 (s, 3H), 2.80 (m, 2H), 3.90 (t, 2H), 6.45 (s, 1H), 7.65-8.40 (br. m, 5H), 8.45 (m, 1H), 8.55 (s, 1H).

Example 151

(4S)-4-{4-Cyano-2-[(trifluoromethyl)sulfonyl]phenyl}-3,6-dimethyl-2-oxo-1-[3-(trifluoromethyl)phenyl]-1,2,3,4-tetrahydropyrimidine-5-carbonitrile

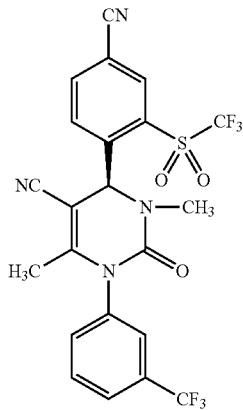 [SMILES: CC1=C(C#N)[C@@H](c2ccc(C#N)cc2S(=O)(=O)C(F)(F)F)N(C)C(=O)N1c1cccc(C(F)(F)F)c1]

The reaction was carried out under argon. Tris(dimethylamino)sulfonium difluorotrimethylsilicate (TASF; 18.4 mg, 66.7 µmol; 1.1 eq.) and (trifluoromethyl)trimethylsilane (2 M solution in THF, 60.6 µl, 121 µmol) were initially charged in THF (1.45 ml) at 0° C. 5-Cyano-2-{(4S)-5-cyano-3,6-dimethyl-2-oxo-1-[3-(trifluoromethyl)phenyl]-1,2,3,4-tetrahydropyrimidin-4-yl}benzenesulfonyl chloride (30 mg, 60.6 µmol) was added, and the mixture was stirred at RT overnight. More tris(dimethylamino)sulfonium difluorotrimethylsilicate (TASF; 16.7 mg, 60.6 µmol; 1.0 eq.) and (trifluoromethyl)trimethylsilane (2 M solution in THF, 65 µl, 130 µmol) were then added at 0° C., and the mixture was again stirred for 15 h with gradual warming to RT. The mixture was then filtered, and the filtrate was concentrated under reduced pressure. The residue was purified by preparative HPLC (column: Gromsil C-18 10 µm; mobile phase: acetonitrile/water+0.1% TFA 10:90→90:10). The title compound was obtained as a solid (3.3 mg, 10% of theory).

LC-MS (Method 9): $R_t$=1.19 min; MS (ESIpos): m/z (%)=529.2 (100) $[M+H]^+$; MS (ESIneg): m/z (%)=527.1 (80) $[M-H]^-$.

$^1$H-NMR (400 MHz, DMSO-$d_6$): δ=1.80 (s, 3H), 2.65 (s, 3H), 6.25 (s, 1H), 7.75-8.55 (m, 5H), 8.65 (dd, 1H), 8.80 (s, 1H).

Example 152

(4S)-4-[2-(Benzylsulfonyl)-4-cyanophenyl]-3,6-dimethyl-2-oxo-1-[3-(trifluoromethyl)phenyl]-1,2,3,4-tetrahydropyrimidine-5-carbonitrile

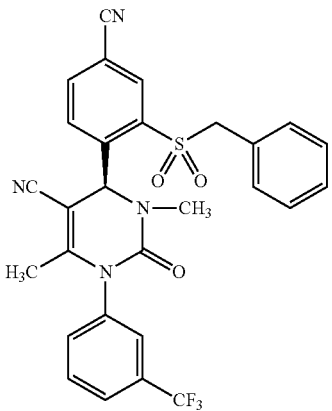 [SMILES: CC1=C(C#N)[C@@H](c2ccc(C#N)cc2S(=O)(=O)Cc2ccccc2)N(C)C(=O)N1c1cccc(C(F)(F)F)c1]

The reaction was carried out under argon. Sodium 5-cyano-2-{(4S)-5-cyano-3,6-dimethyl-2-oxo-1-[3-(trifluoromethyl)phenyl]-1,2,3,4-tetrahydropyrimidin-4-yl}benzenesulfinate (150 mg, 101 µmol; purity 32%) was suspended in DMF (1 ml). Benzyl bromide (173 mg, 1.01 mmol; 10 eq.) was then added, and the mixture was heated in a closed tube at 110° C. for 24 h. Molecular sieve (4 Å), potassium iodide (110 mg, 0.66 mmol) and further benzyl bromide (173 mg, 1.01 mmol; 10 eq.) were then added, and the reaction mixture was again heated in a closed tube at 100° C. for 6 h. The mixture was then filtered, and the filtrate was concentrated under reduced pressure. The residue was purified by preparative HPLC (column: Gromsil C-18 10 µm; mobile phase: acetonitrile/water+0.1% TFA 10:90→90:10). The title compound was obtained as a solid (49.3 mg, 89% of theory).

LC-MS (Method 9): $R_t$=1.22 min; MS (ESIpos): m/z (%)=551.3 (100) $[M+H]^+$; MS (ESIneg): m/z (%)=549.2 (100) $[M-H]^-$ $^1$H-NMR (400 MHz, DMSO-$d_6$): δ=1.80 (s, 3H), 2.45 (s, 3H), 4.90 (q, 2H), 6.55 (s, 1H), 7.30-7.40 (m, 5H), 7.70-8.40 (m, 7H).

Example 153

(4S)-4-{4-Cyano-2-[(2-methoxyethyl)sulfonyl]phenyl}-3,6-dimethyl-2-oxo-1-[3-(trifluoromethyl)phenyl]-1,2,3,4-tetrahydropyrimidine-5-carbonitrile

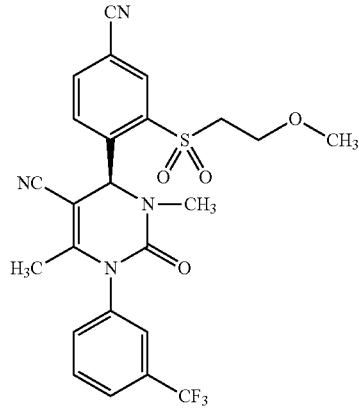

The reaction was carried out under argon. Sodium 5-cyano-2-{(4S)-5-cyano-3,6-dimethyl-2-oxo-1-[3-(trifluoromethyl)phenyl]-1,2,3,4-tetrahydropyrimidin-4-yl}benzenesulfinate (100 mg, 73 µmol; purity 32%) was suspended in DMF (0.5 ml). 2-Bromoethyl methyl ether (148 mg, 1.06 mmol) was then added, and the mixture was heated in a closed tube at 115° C. for 15 h. The mixture was then filtered, and the filtrate was concentrated under reduced pressure. The residue was purified by preparative HPLC (column: Gromsil C-18 10 µm; mobile phase: acetonitrile/water+0.1% TFA 10:90→90:10). The title compound was obtained as a solid (27.3 mg, 73% of theory).

LC-MS (Method 9): $R_t$=1.11 min; MS (ESIpos): m/z (%)=519.2 (100) $[M+H]^+$; MS (ESIneg): m/z (%)=517.2 (100) $[M-H]^-$ $^1$H-NMR (400 MHz, DMSO-$d_6$): δ=1.80 (s, 3H), 2.70 (s, 3H), 3.15 (s, 3H), 3.70-3.87 (m, 4H), 6.45 (s, 1H), 7.30-8.40 (m, 6H), 8.45 (m, 1H).

Example 154

(4S)-4-{4-Cyano-2-[(1,3-thiazol-4-ylmethyl)sulfonyl]phenyl}-3,6-dimethyl-2-oxo-1-[3-(trifluoromethyl)phenyl]-1,2,3,4-tetrahydropyrimidine-5-carbonitrile

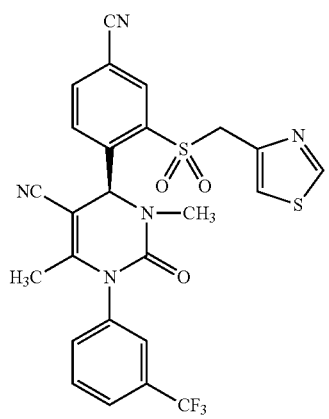 [SMILES: CC1=C(C#N)[C@@H](c2ccc(C#N)cc2S(=O)(=O)Cc2cscn2)N(C)C(=O)N1c1cccc(C(F)(F)F)c1]

The reaction was carried out under argon. 4-(Chloromethyl)thiazole hydrochloride (86 mg, 505 µmol; 5.0 eq.), sodium 5-cyano-2-{(4S)-5-cyano-3,6-dimethyl-2-oxo-1-[3-(trifluoromethyl)phenyl]-1,2,3,4-tetrahydropyrimidin-4-yl}benzenesulfinate (150 mg, 101 µmol; purity 32%), potassium carbonate (77 mg, 556 µmol; 5.5 eq.), potassium iodide (84 mg, 505 µmol; 5.0 eq.) and 18-crown-6 (13.4 mg, 51 µmol; 0.5 eq.) were suspended in DMF (3 ml). The mixture was then heated in a closed tube at 110° C. for 15 h. Molecular sieve (4 Å), potassium iodide (84 mg, 505 µmol; 5.0 eq.) and further 4-(chloromethyl)thiazole hydrochloride (86 mg, 505 µmol; 5.0 eq.) were then added, and the reaction mixture was again heated in a closed tube at 100° C. for 2 h. The mixture was then filtered, and the filtrate was concentrated under reduced pressure. The residue was purified by preparative HPLC (column: Gromsil C-18 10 µm; mobile phase: acetonitrile/water+0.1% TFA 10:90→90:10). The title compound was obtained as a solid (37 mg, 66% of theory). LC-MS (Method 4): $R_t$=1.25 min; MS (ESIpos): m/z (%)=558.1 (100) [M+H]$^+$; MS (ESIneg): m/z (%)=492.3 (100), 557.0 (100) [M-H]

$^1$H-NMR (400 MHz, DMSO-d$_6$): δ=1.80 (s, 3H), 2.60 (s, 3H), 5.15 (m, 2H), 6.50 (s, 1H), 7.70-8.40 (br. m, 8H), 9.0 (s, 1H).

Example 155

(4S)-4-[2-(Cyclobutylsulfonyl)-4-cyanophenyl]-3,6-dimethyl-2-oxo-1-[3-(trifluoromethyl)phenyl]-1,2,3,4-tetrahydropyrimidine-5-carbonitrile

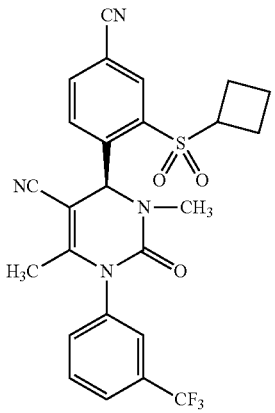 [SMILES: CC1=C(C#N)[C@@H](c2ccc(C#N)cc2S(=O)(=O)C2CCC2)N(C)C(=O)N1c1cccc(C(F)(F)F)c1]

Under argon, sodium 5-cyano-2-{(4S)-5-cyano-3,6-dimethyl-2-oxo-1-[3-(trifluoromethyl)phenyl]-1,2,3,4-tetrahydropyrimidin-4-yl}benzenesulfinate (150 mg, 65 µmol; purity about 21%) was suspended in a pressure-proof glass tube in DMF (1 ml). Molecular sieve (4 Å, 20 mg) and bromocyclobutane (100 µl, 1088 µmol, 16.7 eq.) were added. The sealed tube was heated at 115° C. for 15 h. The reaction mixture was then filtered, and the filtrate was concentrated under reduced pressure. The residue was purified by preparative HPLC (Gromsil C18 column; mobile phase: acetonitrile/water+0.1% TFA). After lyophilization, the title compound was obtained as a solid (15.5 mg, purity according to LC-MS 90%, 41% of theory).

LC-MS (Method 9): $R_t$=1.20 min; MS (ESIpos): m/z (%)=515.3 (100) [M+H]$^+$; MS (ESIneg): m/z (%)=513.2 (100) [M-H]$^-$.

Example 156

(4S)-4-{4-Cyano-2-[(trifluoromethyl)sulfanyl]phenyl}-3,6-dimethyl-2-oxo-1-[3-(trifluoromethyl)phenyl]-1,2,3,4-tetrahydropyrimidine-5-carbonitrile

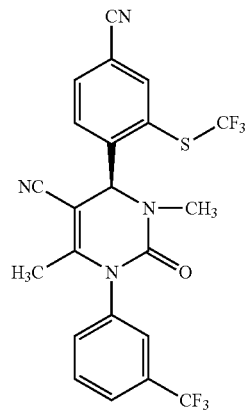 [SMILES: CC1=C(C#N)[C@@H](c2ccc(C#N)cc2SC(F)(F)F)N(C)C(=O)N1c1cccc(C(F)(F)F)c1]

Under argon, (4S)-4-(4-cyano-2-sulfanylphenyl)-3,6-dimethyl-2-oxo-1-[3-(trifluoromethyl)phenyl]-1,2,3,4-tetrahydropyrimidine-5-carbonitrile (45 mg, purity 50%, 53 µmol) was dissolved in dichloromethane (1 ml). At -78° C., 3,3-dimethyl-1-(trifluoromethyl)-1,3-dihydro-1λ$^3$,2-benziodoxole (26 mg, 79 µmol; 1.5 eq.) was added, and the mixture was stirred for 2 h. The reaction solution was then concentrated under reduced pressure, and the residue was purified by preparative HPLC (Kromasil C18 column, 20×50 mm; mobile phase: acetonitrile/water+0.1% TFA). After lyophilization, the title compound was obtained as a solid (11.4 mg, 44% of theory).

LC-MS (Method 9): $R_t$=1.24 min; MS (ESIpos): m/z (%)=497.3 (100) [M+H]$^+$; MS (ESIneg): m/z (%)=495.2 (100) [M-H]$^-$ $^1$H-NMR (400 MHz, DMSO-d$_6$): δ=1.75 (s, 3H), 2.70 (s, 3H), 6.00 (s, 1H), 7.75 (m, 2H), 7.85 (m, 2H), 8.05 (br. s, 1H), 8.25 (m, 1H), 8.45 (s, 1H).

B. ASSESSMENT OF THE PHARMACOLOGICAL ACTIVITY

The pharmacological effect of the compounds of the invention can be shown in the assays described below:

Abbreviations

AMC 7-amido-4-methylcoumarin
BNP brain natriuretic peptide
BSA bovine serum albumin
HEPES N-(2-hydroxyethyl)piperazine-N'-2-ethanesulfonic acid
HNE humane neutrophil elastase
IC inhibitory concentration
MeOSuc methoxysuccinyl
NADP nicotinamide adenine dinucleotide phosphate
v/v volume to volume ratio (of a solution)
w/v weight to volume ratio (of a solution)

B-1. In Vitro HNE Inhibition Assay

The potency of the compounds of the invention is ascertained in an in vitro inhibition assay. The HNE-mediated amidolytic cleavage of a suitable peptide substrate leads in this connection to an increase in the fluorescent light. The signal intensity of the fluorescent light is directly proportional to the enzyme activity. The effective concentration of a test compound at which half the enzyme is inhibited (50% signal intensity of the fluorescent light) is indicated as $IC_{50}$.

Procedure:

Enzyme (80 µM HNE; from Serva, Heidelberg) and substrate (20 µM MeOSuc-Ala-Ala-Pro-Val-AMC; from Bachem, Weil am Rhein) are incubated in an assay volume of in total 50 µl of assay buffer (0.1 M HEPES pH 7.4, 0.5 M NaCl, 0.1% w/v BSA, 1% v/v DMSO) in a 384-well microtiter plate in the presence and absence of the test substance at 37° C. for 2 hours. The intensity of the fluorescent light from the assay mixtures is measured (Ex. 380 nm, Em. 460 nm). The $IC_{50}$ values are determined by plotting the intensity of the fluorescent light against the active substance concentration.

Representative $IC_{50}$ values for the compounds of the invention at an HNE concentration of 80 pM are shown in table A below:

TABLE A

Inhibition of human neutrophil elastase (HNE)

| Exemplary embodiment No. | $IC_{50}$ [nM] |
|---|---|
| 2 | 10.0 |
| 6 | 0.5 |
| 10 | <0.3 |
| 12 | <0.3 |
| 14 | <0.3 |
| 18 | <0.3 |
| 20 | 1.9 |
| 22 | 0.45 |
| 27 | <0.3 |
| 32 | <0.3 |
| 33 | <0.3 |
| 36 | <0.3 |
| 41 | <0.3 |
| 43 (Diastereomer 1) | 0.3 |
| 50 | 1.6 |
| 51 | <0.3 |
| 55 | <0.3 |
| 69 | 0.9 |
| 80 | <0.3 |
| 85 | <0.3 |
| 91 | <0.3 |
| 96 | <0.3 |
| 103 | <0.3 |
| 116 | <0.3 |
| 120 | <0.3 |
| 128 | <0.3 |
| 132 | 1.1 |
| 141 | <0.3 |
| 144 | <0.3 |

B-2. Animal Model of Pulmonary Arterial Hypertension

The monocrotaline-induced pulmonary hypertension in rats is a widely used animal model of pulmonary arterial hypertension. The pyrrolizidine alkaloid monocrotaline is metabolized after subcutaneous injection to the toxic monocrotalinepyrrole in the liver and leads within a few days to endothelial damage in the pulmonary circulation, followed by a remodeling of the small pulmonary arteries (media hypertrophy, de novo muscularization). A single subcutaneous injection is sufficient to induce pronounced pulmonary hypertension in rats within 4 weeks [Cowan et al., Nature Med. 6, 698-702 (2000)].

Male Sprague-Dawley rats are used for the model. On day 0, the animals receive a subcutaneous injection of 60 mg/kg monocrotaline. Treatment of the animals begins no earlier than 14 days after the monocrotaline injection and extends over a period of at least 14 days. At the end of the study, the animals undergo hemodynamic investigations, and the arterial and central venous oxygen saturation are determined. For the hemodynamic measurement, the rats are initially anesthetized with pentobarbital (60 mg/kg). The animals are then tracheotomized and artificially ventilated (rate: 60 breaths/min; inspiration to expiration ratio: 50:50; positive end-expiratory pressure: 1 cm $H_2O$; tidal volume: 10 ml/kg of body weight; $FIO_2$: 0.5). The anesthesia is maintained by isoflurane inhalation anesthesia. The systemic blood pressure is determined in the left carotid artery using a Millar microtip catheter. A polyethylene catheter is advanced through the right jugular vein into the right ventricle to determine the right ventricular pressure. The cardiac output is determined by thermodilution. Following the hemodynamics, the heart is removed and the ratio of right to left ventricle including septum is determined. In addition, plasma samples are obtained to determine biomarkers (for example proBNP) and plasma substance levels.

B-3. Animal Model of Acute Lung Failure

Elastase-induced lung failure in mice, rats or hamsters is a widely used animal model of acute lung failure (also: "acute lung injury", "acute respiratory distress syndrome") [Tremblay et al., Chest 121, 582-588 (2002); Kuraki et al., Am. J. Resp. Crit. Care Med. 166, 596-500 (2002)]. The animals are treated 1 hour prior to orotracheal instillation of human neutrophil elastase (HNE). 2 hours after orotracheal HNE instillation, a bronchoalveolar lavage is carried out, and the hemoglobin content and the differential cell picture of the lavage are determined.

B-4. Animal Model of Pulmonary Emphysema

Elastase-induced pulmonary emphysema in mice, rats or hamsters is a widely used animal model of pulmonary emphysema [Sawada et al., Exp. Lung Res. 33, 277-288 (2007)]. The animals receive an orotracheal instillation of porcine pancreas elastase. The treatment of the animals starts at the day of the instillation of the porcine pancreas elastase and extends over a period of 3 weeks. At the end of the study, the pulmonary compliance is determined, and an alveolar morphometry is carried out.

B-5. CYP Inhibition Assay

The ability of substances to be able to inhibit CYP1A2, CYP2C9, CYP2D6 and CYP3A4 in humans is investigated with pooled human liver microsomes as enzyme source in the presence of standard substrates (see below) which form CYP-specific metabolites. The inhibitory effects are investigated with six different concentrations of the test compounds [2.8, 5.6, 8.3, 16.7, 20 (or 25) and 50 µM], compared with the extent of the CYP-specific metabolite formation of the standard substrates in the absence of the test compounds, and the corresponding $IC_{50}$ values are calculated. A standard inhibitor which specifically inhibits a single CYP isoform is always included in the incubation in order to make the results comparable between different series.

Procedure:

Incubation of phenacetin, diclofenac, tolbutamide, dextromethorphan or midazolam with human liver microsomes in the presence of in each case six different concentrations of a test compound (as potential inhibitor) is carried out on a work station (Tecan, Genesis, Crailsheim, Germany). Standard incubation mixtures comprise 1.3 mM NADP, 3.3 mM $MgCl_2 \times 6\ H_2O$, 3.3 mM glucose 6-phosphate, glucose 6-phosphate dehydrogenase (0.4 U/ml) and 100 mM phosphate buffer (pH 7.4) in a total volume of 200 μl. Test compounds are preferably dissolved in acetonitrile. 96-well plates are incubated with pooled human liver microsomes at 37° C. for a defined time. The reactions are stopped by adding 100 μl of acetonitrile in which a suitable internal standard is always present. Precipitated proteins are removed by centrifugation, and the supernatants are combined and analyzed by LC-MS/MS.

B-6. Hepatocyte Assay to Determine the Metabolic Stability

The metabolic stability of test compounds in the presence of hepatocytes is determined by incubating the compounds with low concentrations (preferably below or around 1 μM) and with low cell counts (preferably $1*10^6$ cells/ml) in order to ensure as far as possible linear kinetic conditions in the experiment. Seven samples of the incubation solution are taken in a fixed time pattern for the LD-MS analysis in order to determine the half-life (i.e. the degradation) of the compound in each case. Various clearance parameters (CL) and $F_{max}$ values are calculated from this half-life (see below).

The Cl and $F_{max}$ values represent a measure of the phase 1 and phase 2 metabolism of the compounds in the hepatocytes. In order to minimize the influence of the organic solvent on the enzymes in the incubation mixtures, this concentration is generally limited to 1% (acetonitrile) or 0.1% (DMSO).

A cell count for hepatocytes in the liver of $1.1*10^8$ cells/g of liver is used for calculation for all species and breeds. CL parameters calculated on the basis of half-lives extending substantially beyond the incubation time (normally 90 minutes) can be regarded only as rough guidelines.

The calculated parameters and their meaning are:

| | |
|---|---|
| $F_{max}$ well-stirred [%] | maximum possible bioavailability after oral administration |
| Calculation: | $(1 - CL_{blood}$ well-stirred/QH$) * 100$ |
| $CL_{blood}$ well-stirred [L/(h*kg)] | calculated blood clearance (well stirred model) |
| Calculation: | $(QH * CL'_{intrinsic})/(QH + CL'_{intrinsic})$ |
| $CL'_{intrinsic}$ [ml/(min*kg)] | maximum ability of the liver (of the hepatocytes) to metabolize a compound (on the assumption that the hepatic blood flow is not rate-limiting) |
| Calculation: | $CL'_{intrinsic, apparent} *$ species-specific hepatocyte count [$1.1 * 10^8$/g of liver] * species-specific liver weight [g/kg] |
| $CL'_{intrinsic, apparent}$ [ml/(min*mg)] | normalizes the elimination constant by dividing it by the hepatocyte cell count x (x * $10^6$/ml) employed |
| Calculation: | $k_{el}$ [1/min]/(cell count [x * $10^6$]/incubation volume [ml]) |

(QH = species-specific hepatic blood flow).

Representative values for the compounds according to the invention from this assay after incubation of the compounds with rat hepatocytes are shown in Table B below:

TABLE B calculated blood clearance and bioavailability after incubation with rat hepatocytes

| Exemplary embodiment No. | $CL_{blood}$ [L/(h*kg)] | $F_{max}$ [%] |
|---|---|---|
| 5 | 0.0 | 100 |
| 6 | 0.2 | 96 |
| 10 | 1.5 | 65 |
| 12 | 1.7 | 59 |
| 22 | 0.2 | 95 |
| 25 | 0.3 | 93 |
| 27 | 0.4 | 91 |
| 29 | 0.4 | 90 |
| 31 | 0.4 | 91 |
| 32 | 0.1 | 97 |
| 33 | 0.6 | 87 |
| 36 | 0.4 | 89 |
| 38 | 0.2 | 96 |

TABLE B-continued calculated blood clearance and bioavailability after incubation with rat hepatocytes

| Exemplary embodiment No. | $CL_{blood}$ [L/(h*kg)] | $F_{max}$ [%] |
|---|---|---|
| 43 (diastereomer 1) | 1.3 | 69 |
| 91 | 0.7 | 83 |
| 92 | 0.7 | 83 |
| 116 | 0.4 | 91 |
| 117 | 0.1 | 97 |
| 118 | 0.6 | 86 |
| 123 | 1.0 | 75 |
| 127 | 0.2 | 94 |
| 128 | 0.9 | 78 |
| 129 | 0.9 | 79 |
| 144 | 1.2 | 72 |

C. EXEMPLARY EMBODIMENTS OF PHARMACEUTICAL COMPOSITIONS

The compounds of the invention can be converted into pharmaceutical preparations in the following ways:

Tablet:

Composition:

100 mg of the compound of the invention, 50 mg of lactose (monohydrate), 50 mg of corn starch (native), 10 mg of polyvinylpyrrolidone (PVP 25) (from BASF, Ludwigshafen, Germany) and 2 mg of magnesium stearate.

Tablet weight 212 mg, diameter 8 mm, radius of curvature 12 mm.

Production:

The mixture of compound of the invention, lactose and starch is granulated with a 5% strength solution (m/m) of the PVP in water. The granules are mixed with the magnesium stearate for 5 minutes after drying. This mixture is compressed with a conventional tablet press (see above for format of the tablet). A guideline compressive force for the compression is 15 kN.

Suspension which can be Administered Orally:

Composition:

1000 mg of the compound of the invention, 1000 mg of ethanol (96%), 400 mg of Rhodigel® (xanthan gum from FMC, Pennsylvania, USA) and 99 g of water. 10 ml of oral suspension correspond to a single dose of 100 mg of the compound of the invention.

Production:

The Rhodigel is suspended in ethanol, and the compound of the invention is added to the suspension. The water is added while stirring. The mixture is stirred for about 6 h until the swelling of the Rhodigel is complete.

Solution which can be Administered Orally:
Composition:

500 mg of the compound of the invention, 2.5 g of polysorbate and 97 g of polyethylene glycol 400.20 g of oral solution correspond to a single dose of 100 mg of the compound according to the invention.

Production:

The compound of the invention is suspended in the mixture of polyethylene glycol and polysorbate with stirring. The stirring process is continued until the compound according to the invention has completely dissolved.

i.v. Solution:

The compound of the invention is dissolved in a concentration below the saturation solubility in a physiologically tolerated solvent (e.g. isotonic saline solution, 5% glucose solution and/or 30% PEG 400 solution). The solution is sterilized by filtration and used to fill sterile and pyrogen-free injection containers.

The invention claimed is:

1. A method for the treatment of pulmonary arterial hypertension (PAH) and of pulmonary hypertension (PH) associated with chronic obstructive pulmonary disease (COPD), of chronic-obstructive pulmonary diseases (COPD), of acute lung injury (ALI), of acute respiratory distress syndrome (ARDS), of pulmonary emphysema, of alpha-1 antitrypsin deficiency (AATD), of cystic fibrosis (CF) and of bronchiectasia, comprising administering an effective amount of a compound of formula (I) to a human or animal in need thereof, wherein the compound of formula (I) is:

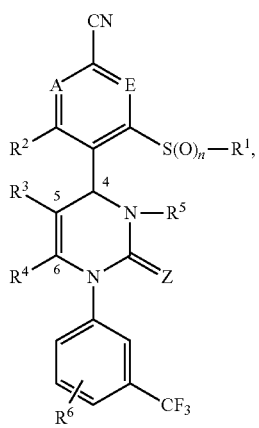

in which

A and E both represent C—$R^7$ or one of the two ring members A and E represents N and the other represents C—$R^7$, in which $R^7$ represents in each case hydrogen, fluorine or chlorine, Z represents O or S, n represents the number 0, 1 or 2, $R^1$ represents $(C_1-C_6)$-alkyl which may be substituted by hydroxyl, $(C_1-C_4)$-alkoxy, amino, mono- or di-$(C_1-C_4)$-alkylamino, hydroxycarbonyl, aminocarbonyl, $(C_3-C_6)$-cycloalkyl, phenyl or 5- or 6-membered heteroaryl or up to five times by fluorine, or represents $(C_2-C_6)$-alkenyl, $(C_3-C_6)$-cycloalkyl, phenyl or 5- or 6-membered heteroaryl, where the $(C_3-C_6)$-cycloalkyl groups mentioned may be substituted up to two times by identical or different substituents from the group consisting of $(C_1-C_4)$-alkyl, hydroxyl and $(C_1-C_4)$-alkoxy and the phenyl and heteroaryl groups mentioned may be substituted up to two times by identical or different substituents from the group consisting of fluorine, chlorine, cyano, $(C_1-C_4)$-alkyl, difluoromethyl, trifluoromethyl, $(C_1-C_4)$-alkoxy, difluoromethoxy and trifluoromethoxy, $R^2$ represents hydrogen, fluorine or chlorine, $R^3$ represents cyano or a group of the formula —C(=O)—$R^8$, —C(=O)—O—$R^8$, —C(=O)—$NH_2$ or —C(=O)—NH—$R^8$, in which $R^8$ represents $(C_1-C_6)$-alkyl, $(C_3-C_6)$-alkenyl or $(C_3-C_6)$-cycloalkyl, where $(C_1-C_6)$-alkyl and $(C_3-C_6)$-cycloalkyl for their part may be substituted up to two times by identical or different substituents from the group consisting of hydroxyl, $(C_1-C_4)$-alkoxy, hydroxycarbonyl, $(C_1-C_4)$-alkoxycarbonyl, amino, mono- and di-$(C_1-C_4)$-alkylamino and in $(C_1-C_6)$-alkyl and $(C_3-C_6)$-cycloalkyl in each case one $CH_2$ group may be replaced by an oxygen atom, if this results in a chemically stable compound, $R^4$ represents methyl or ethyl or $R^3$ and $R^4$ are attached to one another and together form a fused group of the formula

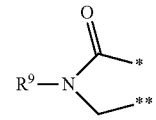

in which

* denotes the point of attachment to the 5-position, shown in formula (I), of the dihydropyrimidine ring and

** denotes the point of attachment to the 6-position, shown in formula (I), of the dihydropyrimidine ring and $R^9$ represents hydrogen, $(C_1-C_6)$-alkyl or $(C_3-C_6)$-cycloalkyl, where $(C_1-C_6)$-alkyl may be substituted by hydroxyl, $(C_1-C_4)$-alkoxy, aminocarbonyl, aminocarbonylamino, $(C_1-C_4)$-acylamino or $(C_3-C_6)$-cycloalkyl, $R^5$ represents hydrogen or $(C_1-C_6)$-alkyl which may be substituted by cyano, hydroxyl, $(C_1-C_4)$-alkoxy, amino, mono- or di-$(C_1-C_4)$-alkylamino or $(C_3-C_6)$-cycloalkyl or up to three times by fluorine, or represents phenyl, pyridyl or pyrimidinyl, where phenyl, pyridyl and pyrimidinyl for their part may be substituted up to two times by identical or different substituents from the group consisting of fluorine, chlorine, cyano, $(C_1-C_4)$-alkyl, trifluoromethyl, $(C_1-C_4)$-alkoxy and trifluoromethoxy, or $R^5$ represents a group of the formula —C(=O)—O—$R^{10}$, -$L^1$-C(=O)—O—$R^{11}$, -$L^2$-C(=O)—$NR^{12}R^{13}$, -$L^2$-$SO_2$—$NR^{12}R^{13}$, -$L^2$-C(=O)—$NR^{14}$—$NR^{12}R^{13}$ or -$L^2$-$SO_2$—$R^{15}$, in which $L^1$ represents $(C_1-C_6)$-alkanediyl, $L^2$ represents a bond or $(C_1-C_6)$-alkanediyl, $R^{10}$ represents $(C_1-C_6)$-alkyl which may be substituted by $(C_3-C_6)$-cycloalkyl or phenyl, $R^{11}$ represents hydrogen or $(C_1-C_6)$-alkyl which may be substituted by $(C_3-C_6)$-cycloalkyl or phenyl, $R^{12}$ and $R^{13}$ are identical or different and independently of one another represent hydrogen, $(C_1-C_6)$-alkyl, $(C_3-C_6)$-cycloalkyl or 4- to 6-membered heterocyclyl, where $(C_1-C_6)$-alkyl, $(C_3-C_6)$-cycloalkyl and 4- to 6-membered heterocyclyl for their part may be substituted up to two times by identical or different substituents from the group consisting of fluorine, hydroxyl, $(C_1-C_4)$-alkoxy, oxo, amino, mono- or di-$(C_1-C_4)$-alkylamino, hydroxycarbonyl, $(C_1-C_4)$-alkoxycarbonyl and aminocarbonyl and in $(C_1-C_6)$-alkyl a $CH_2$ group may be replaced by an oxygen atom, if this results in a chemically stable compound, and $(C_3-C_6)$-cycloalkyl and 4- to 6-membered heterocyclyl may additionally be substituted up to two times by identical or different $(C_1-C_4)$-alkyl radicals, which for their part may be substituted by hydroxyl, $(C_1-C_4)$-alkoxy or hydroxycarbonyl, or $R^{12}$ and $R^{13}$ together with the nitrogen atom to which they are attached form a 4- to 6-membered heterocycle which may contain a further ring heteroatom from the group consisting of N, O, S, SO and $SO_2$ and which may be substituted up to two times by identical or different substituents from the group consisting of $(C_1-C_4)$-alkyl, hydroxyl, $(C_1-C_4)$-alkoxy, oxo, amino, mono- or di-$(C_1-C_4)$-alkylamino, hydroxycarbonyl, aminocarbonyl, $(C_3-C_6)$-cycloalkyl, 4- to 6-membered heterocyclyl and 5- or 6-membered heteroaryl, where $(C_1-C_4)$-alkyl for its part may be substituted by hydroxyl, $(C_1-C_4)$-alkoxy or hydroxycarbonyl, $R^{14}$ represents hydrogen or $(C_1-C_4)$-alkyl and $R^{15}$ represents $(C_1-C_6)$-alkyl, $(C_3-C_6)$-cycloalkyl, phenyl or 5- or 6-membered heteroaryl, where $(C_1-C_6)$-alkyl may be substituted by chlorine, hydroxyl, $(C_1-C_4)$-alkoxy, mono- or di-$(C_1-C_4)$-alkylamino or $(C_3-C_6)$-cycloalkyl or up to three times by fluorine and phenyl and 5- or 6-membered heteroaryl for their part may be substituted up to two times by identical or different substituents from the group consisting of fluorine, chlorine, cyano, $(C_1-C_4)$-alkyl, difluoromethyl, trifluoromethyl, $(C_1-C_4)$-alkoxy and trifluoromethoxy, and $R^6$ represents hydrogen, fluorine or chlorine, or a physiologically acceptable salt thereof.

2. The method of claim 1, wherein in the compound of formula (I),

A and E both represent C—$R^7$ or one of the two ring members A and E represents N and the other represents C—$R^7$, in which $R^7$ represents in each case hydrogen, fluorine or chlorine, Z represents O or S, n represents the number 0, 1 or 2, $R^1$ represents $(C_1-C_6)$-alkyl which may be substituted by hydroxyl, $(C_1-C_4)$-alkoxy, amino, mono- or di-$(C_1-C_4)$-alkylamino, hydroxycarbonyl, aminocarbonyl, $(C_3-C_6)$-cycloalkyl or phenyl, or represents $(C_2-C_6)$-alkenyl, $(C_3-C_6)$-cycloalkyl or phenyl, where the $(C_3-C_6)$-cycloalkyl groups mentioned may be substituted up to two times by identical or different substituents from the group consisting of $(C_1-C_4)$-alkyl, hydroxyl and $(C_1-C_4)$-alkoxy and the phenyl groups mentioned may be substituted up to two times by identical or different substituents from the group consisting of fluorine, chlorine, cyano, $(C_1-C_4)$-alkyl, difluoromethyl, trifluoromethyl, $(C_1-C_4)$-alkoxy, difluoromethoxy and trifluoromethoxy, $R^2$ represents hydrogen, fluorine or chlorine, $R^3$ represents cyano or a group of the formula —C(=O)—$R^8$, —C(=O)—O—$R^8$, —C(=O)—$NH_2$ or —C(=O)—NH—$R^8$, in which $R^8$ represents $(C_1-C_6)$-alkyl, $(C_3-C_6)$-alkenyl or $(C_3-C_6)$-cycloalkyl, where $(C_1-C_6)$-alkyl and $(C_3-C_6)$-cycloalkyl for their part may be substituted up to two times by identical or different substituents from the group consisting of hydroxyl, $(C_1-C_4)$-alkoxy, hydroxycarbonyl, $(C_1-C_4)$-alkoxycarbonyl, amino, mono- and di-$(C_1-C_4)$-alkylamino and in $(C_1-C_6)$-alkyl and $(C_3-C_6)$-cycloalkyl in each case one $CH_2$ group may be replaced by an oxygen atom, if this results in a chemically stable compound, $R^4$ represents methyl or ethyl or $R^3$ and $R^4$ are attached to one another and together form a fused group of the formula

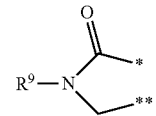

in which

* denotes the point of attachment to the 5-position, shown in formula (I), of the dihydropyrimidine ring and

** denotes the point of attachment to the 6-position, shown in formula (I), of the dihydropyrimidine ring and $R^9$ represents hydrogen, $(C_1-C_6)$-alkyl or $(C_3-C_6)$-cycloalkyl, where $(C_1-C_6)$-alkyl may be substituted by hydroxyl, $(C_1-C_4)$-alkoxy, aminocarbonyl, $(C_1-C_4)$-acylamino or $(C_3-C_6)$-cycloalkyl, $R^5$ represents hydrogen or $(C_1-C_6)$-alkyl which may be substituted up to three times by fluorine, or represents phenyl, pyridyl or pyrimidinyl, where phenyl, pyridyl and pyrimidinyl for their part may be substituted up to two times by identical or different substituents from the group consisting of fluorine, chlorine, cyano, $(C_1-C_4)$-alkyl, trifluoromethyl, $(C_1-C_4)$-alkoxy and trifluoromethoxy, or $R^5$ represents a group of the formula —C(=O)—O—$R^{10}$, -$L^1$-C(=O)—O—$R^{11}$, -$L^2$-C(=O)—$NR^{12}R^{13}$, -$L^2$-$SO_2$—$NR^{12}R^{13}$, -$L^2$-C(=O)—$NR^{14}$—$NR^{12}R^{13}$ or -$L^2$-$SO_2$—$R^{15}$, in which $L^1$ represents $(C_1-C_6)$-alkanediyl, $L^2$ represents a bond or $(C_1-C_6)$-alkanediyl, $R^{10}$ represents $(C_1-C_6)$-alkyl, $R^{11}$ represents hydrogen or $(C_1-C_6)$-alkyl, $R^{12}$ and $R^{13}$ are identical or different and independently of one another represent hydrogen, $(C_1-C_6)$-alkyl, $(C_3-C_6)$-cycloalkyl or 4- to 6-membered heterocyclyl, where ($C_1$-$C_6$)-alkyl, ($C_3$-$C_6$)-cycloalkyl and 4- to 6-membered heterocyclyl for their part may be substituted up to two times by identical or different substituents from the group consisting of fluorine, hydroxyl, ($C_1$-$C_4$)-alkoxy, oxo, amino, mono- or di-($C_1$-$C_4$)-alkylamino, hydroxycarbonyl, ($C_1$-$C_4$)-alkoxycarbonyl and aminocarbonyl and in ($C_1$-$C_6$)-alkyl a $CH_2$ group may be replaced by an oxygen atom, if this results in a chemically stable compound, or $R^{12}$ and $R^{13}$ together with the nitrogen atom to which they are attached form a 4- to 6-membered heterocycle which may contain a further ring heteroatom from the group consisting of N, O, S, SO and $SO_2$ and may be substituted up to two times by identical or different substituents from the group consisting of ($C_1$-$C_4$)-alkyl, hydroxyl, ($C_1$-$C_4$)— alkoxy, oxo, amino, mono- and di-($C_1$-$C_4$)-alkylamino, where ($C_1$-$C_4$)-alkyl for its part may be substituted by hydroxyl or ($C_1$-$C_4$)-alkoxy, $R^{14}$ represents hydrogen or ($C_1$-$C_4$)-alkyl and $R^{15}$ represents ($C_1$-$C_6$)-alkyl, ($C_3$-$C_6$)-cycloalkyl, phenyl or 5- or 6-membered heteroaryl, where ($C_1$-$C_6$)-alkyl may be substituted by fluorine, chlorine, hydroxyl, ($C_1$-$C_4$)-alkoxy, mono- or di-($C_1$-$C_4$)-alkylamino and phenyl and 5- or 6-membered heteroaryl for their part may be substituted up to two times by identical or different substituents from the group consisting of fluorine, chlorine, cyano, ($C_1$-$C_4$)-alkyl, trifluoromethyl, ($C_1$-$C_4$)-alkoxy and trifluoromethoxy, and $R^6$ represents hydrogen, fluorine or chlorine, or a physiologically acceptable salt thereof.

3. The method of claim 1, wherein in the compound of formula (I),

A and E both represent CH,

Z represents O, n represents the number 0 or 2, $R^1$ represents ($C_1$-$C_4$)-alkyl which may be substituted by hydroxyl, ($C_1$-$C_4$)-alkoxy, hydroxycarbonyl, aminocarbonyl, ($C_3$-$C_6$)-cycloalkyl, phenyl or 5-membered heteroaryl or up to three times by fluorine, or represents ($C_3$-$C_6$)-cycloalkyl, phenyl or 5-membered heteroaryl, where the phenyl and heteroaryl groups mentioned may be substituted up to two times by identical or different substituents from the group consisting of fluorine, chlorine, cyano, methyl, trifluoromethyl, methoxy and trifluoromethoxy, $R^2$ represents hydrogen, $R^3$ represents cyano, acetyl or (2-hydroxyethoxy)carbonyl, $R^4$ represents methyl or $R^3$ and $R^4$ are attached to one another and together form a fused group of the formula

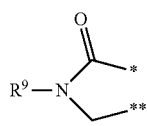

in which

* denotes the point of attachment to the 5-position, shown in formula (I), of the dihydropyrimidine ring and

** denotes the point of attachment to the 6-position, shown in formula (I), of the dihydropyrimidine ring and $R^9$ represents hydrogen, ($C_1$-$C_4$)-alkyl or ($C_3$-$C_6$)-cycloalkyl, where ($C_1$-$C_4$)-alkyl may be substituted by hydroxyl or ($C_1$-$C_4$)-alkoxy, $R^5$ represents hydrogen or ($C_1$-$C_4$)-alkyl which may be substituted by cyano or di-($C_1$-$C_4$)-alkylamino, or represents a group of the formula -$L^2$-C(=O)—$NR^{12}R^{13}$, -$L^2$-C(=O)—NH—$NR^{12}R^{13}$ or -$L^2$-$SO_2$—$R^{15}$, in which $L^2$ represents a bond, —$CH_2$—, —$CH_2CH_2$— or —CH($CH_3$)—, $R^{12}$ represents hydrogen or ($C_1$-$C_4$)-alkyl which may be substituted by hydroxyl or ($C_1$-$C_4$)-alkoxy, $R^{13}$ represents hydrogen, ($C_1$-$C_6$)-alkyl or ($C_3$-$C_6$)-cycloalkyl, where ($C_1$-$C_6$)-alkyl may be substituted up to two times by identical or different substituents from the group consisting of hydroxyl, ($C_1$-$C_4$)-alkoxy, hydroxycarbonyl, ($C_1$-$C_4$)-alkoxycarbonyl and aminocarbonyl and in ($C_1$-$C_6$)-alkyl a $CH_2$ group may be replaced by an oxygen atom, if this results in a chemically stable compound, or $R^{12}$ and $R^{13}$ together with the nitrogen atom to which they are attached form a 5- or 6-membered heterocycle which may contain a further ring heteroatom from the group consisting of N, O and S and may be substituted by ($C_1$-$C_4$)-alkyl, hydroxyl, ($C_1$-$C_4$)-alkoxy, oxo, hydroxycarbonyl, aminocarbonyl, 4- to 6-membered heterocyclyl or 5- or 6-membered heteroaryl, where ($C_1$-$C_4$)-alkyl for its part may be substituted by hydroxyl, ($C_1$-$C_4$)-alkoxy or hydroxycarbonyl, and $R^{15}$ represents ($C_1$-$C_4$)-alkyl, ($C_3$-$C_6$)-cycloalkyl or phenyl, where ($C_1$-$C_4$)-alkyl may be substituted by ($C_3$-$C_6$)-cycloalkyl and phenyl may be substituted up to two times by identical or different substituents from the group consisting of fluorine, chlorine, cyano, methyl, trifluoromethyl, methoxy and trifluoromethoxy, and $R^6$ represents hydrogen or fluorine, or a physiologically acceptable salt thereof.

4. The method of claim 1, wherein in the compound of the formula (I),

A and E both represent CH,

Z represents O, n represents the number 0 or 2, $R^1$ represents ($C_1$-$C_4$)-alkyl which may be substituted by hydroxyl, ($C_1$-$C_4$)-alkoxy, hydroxycarbonyl, aminocarbonyl, ($C_3$-$C_6$)-cycloalkyl or phenyl, or represents ($C_3$-$C_6$)-cycloalkyl or phenyl, where the phenyl groups mentioned may be substituted up to two times by identical or different substituents from the group consisting of fluorine, chlorine, cyano, methyl, trifluoromethyl, methoxy and trifluoromethoxy, $R^2$ represents hydrogen, $R^3$ represents cyano or acetyl, $R^4$ represents methyl or $R^3$ and $R^4$ are attached to one another and together form a fused group of the formula in which
* denotes the point of attachment to the 5-position, shown in formula (I), of the dihydropyrimidine ring
and
** denotes the point of attachment to the 6-position, shown in the formula (I), of the dihydropyrimidine ring
and
$R^9$ represents hydrogen, $(C_1-C_4)$-alkyl or $(C_3-C_6)$-cycloalkyl,
where $(C_1-C_4)$-alkyl may be substituted by hydroxyl or $(C_1-C_4)$-alkoxy,
$R^5$ represents hydrogen, $(C_1-C_4)$-alkyl or a group of the formula $-L^2-C(=O)-NR^{12}R^{13}$, $-L^2-C(=O)-NH-NR^{12}R^{13}$ or $-L^2-SO_2-R^{15}$, in which
$L^2$ represents a bond, $-CH_2-$, $-CH_2CH_2-$ or $-CH(CH_3)-$,
$R^{12}$ represents hydrogen or $(C_1-C_4)$-alkyl which may be substituted by hydroxyl or $(C_1-C_4)$-alkoxy,
$R^{13}$ represents hydrogen, $(C_1-C_6)$-alkyl or $(C_3-C_6)$-cycloalkyl,
where $(C_1-C_6)$-alkyl may be substituted up to two times by identical or different substituents from the group consisting of hydroxyl, $(C_1-C_4)$-alkoxy, hydroxycarbonyl, $(C_1-C_4)$-alkoxycarbonyl and aminocarbonyl and in $(C_1-C_6)$-alkyl a $CH_2$ group may be replaced by an oxygen atom, if this results in a chemically stable compound,
or
$R^{12}$ and $R^{13}$ together with the nitrogen atom to which they are attached form a 5- or 6-membered heterocycle which may contain a further ring heteroatom from the group consisting of N, O and S and may be substituted by $(C_1-C_4)$-alkyl, hydroxyl, $(C_1-C_4)$-alkoxy or oxo,
where $(C_1-C_4)$-alkyl for its part may be substituted by hydroxyl or $(C_1-C_4)$-alkoxy,
and
$R^{15}$ represents $(C_1-C_4)$-alkyl, $(C_3-C_6)$-cycloalkyl or phenyl,
where phenyl may be substituted up to two times by identical or different substituents from the group consisting of fluorine, chlorine, cyano, methyl, trifluoromethyl, methoxy and trifluoromethoxy,
and
$R^6$ represents hydrogen or fluorine,
or a physiologically acceptable salt thereof.

5. The method of claim 1, wherein in the compound of formula (I),
A and E both represent CH,
Z represents O,
n represents the number 2,
$R^1$ represents $(C_1-C_4)$-alkyl which may be substituted by hydroxyl, $(C_1-C_4)$-alkoxy, cyclopropyl, cyclobutyl or phenyl or up to three times by fluorine,
$R^2$ represents hydrogen,
$R^3$ represents cyano or (2-hydroxyethoxy)carbonyl,
$R^4$ represents methyl,
$R^5$ represents hydrogen, $(C_1-C_4)$-alkyl or a group of the formula $-L^2-C(=O)-NH-R^{13}$ or $-SO_2-R^{15}$, in which
$L^2$ represents a bond or $-CH_2-$, $R^{13}$ represents hydrogen or $(C_1-C_4)$-alkyl which may be substituted by hydroxyl or $(C_1-C_4)$-alkoxy, or $(C_3-C_6)$-cycloalkyl
and
$R^{15}$ represents $(C_1-C_4)$-alkyl or $(C_3-C_6)$-cycloalkyl,
and
$R^6$ represents hydrogen,
or a physiologically acceptable salt thereof.

6. The method of claim 1, wherein in compound of the formula (I)
A and E both represent CH,
Z represents O,
n represents the number 2,
$R^1$ represents $(C_1-C_4)$-alkyl which may be substituted by hydroxyl or $(C_1-C_4)$-alkoxy,
$R^2$ represents hydrogen,
$R^3$ represents cyano,
$R^4$ represents methyl,
$R^5$ represents hydrogen, $(C_1-C_4)$-alkyl or a group of the formula $-CH_2-C(=O)-NH-R^{13}$ or $-SO_2-R^{15}$, in which
$R^{13}$ represents hydrogen or $(C_1-C_4)$-alkyl which may be substituted by hydroxyl or $(C_1-C_4)$-alkoxy
and
$R^{15}$ represents $(C_1-C_4)$-alkyl or $(C_3-C_6)$-cycloalkyl,
and
$R^6$ represents hydrogen,
or a physiologically acceptable salt thereof.

7. The method of claim 1, wherein the compound of formula (I) is administered as a pharmaceutical composition comprising the compound of formula (I) and one or more inert non-toxic pharmaceutically acceptable auxiliaries.

8. The method of claim 7, wherein the pharmaceutical composition further comprises one or more further active compounds selected from the group consisting of a beta-adrenergic receptor agonist, and an anticholinergic.

9. The method of claim 1, wherein the compound of formula (I) has the configuration shown in formula (I-ent) at the 4-position of the dihydropyrimidine ring:

(I-ent)

in which A, E, Z, n, $R^1$, $R^2$, $R^3$, $R^4$, $R^5$, and $R^6$ each defined as given in claim 1.

10. The method of claim 1, wherein the compound of formula (I) is selected from the group consisting of:
4-{(4S)-5-acetyl-6-methyl-2-oxo-1-[3-(trifluoromethyl)phenyl]-1,2,3,4-tetrahydropyrimidin-4-yl}-3-(methylsulfonyl)benzonitrile;

(4S)-4-[4-cyano-2-(methylsulfonyl)phenyl]-6-methyl-2-oxo-1-[3-(trifluoromethyl)phenyl]-1,2,3,4-tetrahydropyrimidin-5-carbonitrile;

(6S)-5-cyano-6-[4-cyano-2-(methylsulfonyl)phenyl]-N-(2-hydroxyethyl)-4-methyl-2-oxo-3-[3-(trifluoromethyl)phenyl]-3,6-dihydropyrimidin-1(2H)-carboxamide;

(6S)-5-cyano-6-[4-cyano-2-(methylsulfonyl)phenyl]-N',N'-bis(2-hydroxyethyl)-4-methyl-2-oxo-3-[3-(trifluoromethyl)phenyl]-3,6-dihydropyrimidin-1(2H)-carbohydrazide;

(6S)-5-cyano-6-[4-cyano-2-(methylsulfonyl)phenyl]-N-[2-(2-hydroxyethoxy)ethyl]-4-methyl-2-oxo-3-[3-(trifluoromethyl)phenyl]-3,6-dihydropyrimidin-1(2H)-carboxamide;

(4S)-4-[4-cyano-2-(methylsulfonyl)phenyl]-3-{[(3S)-3-hydroxypyrrolidin-1-yl]carbonyl}-6-methyl-2-oxo-1-[3-(trifluoromethyl)phenyl]-1,2,3,4-tetrahydropyrimidin-5-carbonitrile;

(4S)-4-[4-cyano-2-(methylsulfonyl)phenyl]-3-{[4-(2-hydroxyethyl)piperazin-1-yl]-carbonyl}-6-methyl-2-oxo-1-[3-(trifluoromethyl)phenyl]-1,2,3,4-tetrahydropyrimidin-5-carbonitrile;

2-[(6S)-5-cyano-6-[4-cyano-2-(methylsulfonyl)phenyl]-4-methyl-2-oxo-3-[3-(trifluoromethyl)-phenyl]-3,6-dihydropyrimidin-1(2H)-yl]acetamide;

(4S)-4-[4-cyano-2-(methylsulfonyl)phenyl]-6-methyl-[3-(methylsulfonyl)-2-oxo-1,3-(trifluoro-methyl)phenyl]-1,2,3,4-tetrahydropyrimidin-5-carbonitrile;

(4S)-4-[4-cyano-2-(methylsulfonyl)phenyl]-6-methyl-3-(cyclopropylsulfonyl)-2-oxo-1-[3-(tri-fluoromethyl)phenyl]-1,2,3,4-tetrahydropyrimidin-5-carbonitrile;

(4S)-4-[4-cyano-2-(methylsulfonyl)phenyl]-3,6-dimethyl-2-oxo-1-[3-(trifluoromethyl)phenyl]-1,2,3,4-tetrahydropyrimidin-5-carbonitrile;

4-{(4S)-6-methyl-3-(methylsulfonyl)-2,5-dioxo-1-[3-(trifluoromethyl)phenyl]-2,3,4,5,6,7-hexahydro-1H-pyrrolo[3,4-d]pyrimidin-4-yl}-3-(methylsulfonyl)benzonitrile;

(4S)-4-[4-cyano-2-(methylsulfanyl)phenyl]-6-methyl-2-oxo-1-[3-(trifluoromethyl)phenyl]-1,2,3,4-tetrahydropyrimidin-5-carbonitrile;

(4S)-4-{4-cyano-2-[(S)-methylsulfinyl]phenyl}-6-methyl-2-oxo-1-[3-(trifluoromethyl)-phenyl]-1,2,3,4-tetrahydropyrimidin-5-carbonitrile;

(rac)-1-(2-{-4-[4-cyano-2-(methylsulfonyl)phenyl]-2,5-dioxo-1-[3-(trifluoromethyl)phenyl]-1,2,3,4,5,7-hexahydro-6H-pyrrolo[3,4-d]pyrimidin-6-yl}ethyl)urea;

(4S)-4-[4-cyano-2-(methylsulfonyl)phenyl]-3-[(3-hydroxyazetidin-1-yl)carbonyl]-6-methyl-2-oxo-1-[3-(trifluoromethyl)phenyl]-1,2,3,4-tetrahydropyrimidin-5-carbonitrile;

(4S)-3-[(3R)-3-aminopiperidin-1-yl]carbonyl-4-[4-cyano-2-(methylsulfonyl)phenyl]-6-methyl-2-oxo-1-[3-(trifluoromethyl)phenyl]-1,2,3,4-tetrahydropyrimidin-5-carbonitrile;

(4S)-4-[4-cyano-2-(methylsulfonyl)phenyl]-6-methyl-2-oxo-3-{[4-(pyridin-2-yl)piperazin-1-yl]-carbonyl}-1-[3-(trifluoromethyl)phenyl]-1,2,3,4-tetrahydropyrimidin-5-carbonitrile;

(6S)-5-cyano-6-[4-cyan-2-(methylsulfonyl)phenyl]-N,N-bis(2-hydroxypropyl)-4-methyl-2-oxo-3-[3-(trifluoromethyl)phenyl]-3,6-dihydropyrimidin-1(2H)-carboxamide;

(6S)-5-cyano-6-[4-cyan-2-(methylsulfonyl)phenyl]-N-(1-hydroxy-2-methylpropan-2-yl)-4-methyl-2-oxo-3-[(4-(trifluoromethyl)phenyl]-3,6-dihydropyrimidin-1(2H)-carboxamide;

(4S)-4-[4-cyano-2-(methylsulfonyl)phenyl]-3-[(4-fluorophenyl)sulfonyl]-6-methyl-2-oxo-1-[3-(trifluoromethyl)phenyl]-1,2,3,4-tetrahydropyrimidin-5-carbonitrile;

(4S)-4-[4-cyano-2-(methylsulfonyl)phenyl]-3-{[1-(difluoromethyl)-5-methyl-1H-pyrazol-4-yl]-sulfonyl}-6-methyl-2-oxo-1-[3-(trifluoromethyl)phenyl]-1,2,3,4-tetrahydropyrimidin-5-carbonitrile (4S)-4-[4-cyano-2-(methylsulfonyl)phenyl]-3-[(2-cyanphenyl)sulfonyl]-6-methyl-2-oxo-1-[3-(trifluoromethyl)phenyl]-1,2,3,4-tetrahydropyrimidin-5-carbonitrile;

(4S)-3-(cyanomethyl)-4-[4-cyano-2-(methylsulfonyl)phenyl]-6-methyl-2-oxo-1-[3-(trifluoro-methyl)phenyl]-1,2,3,4-tetrahydropyrimidin-5-carbonitrile;

benzyl 5-cyano-6-[4-cyano-2-(methylsulfonyl)phenyl]-4-methyl-2-oxo-3-[3-(trifluoromethyl)-phenyl]-3,6-dihydropyrimidin-1(2H)-carboxylate;

(4S)-4-[4-cyano-2-(ethylsulfonyl)phenyl]-3,6-dimethyl-2-oxo-1-[3-(trifluoromethyl)phenyl]-1,2,3,4-tetrahydropyrimidin-5-carbonitrile;

(rac)-4-[4-cyano-2-((2-hydroxyethyl)sulfonyl)phenyl]-6-methyl-2-oxo-1-[3-(trifluoromethyl)-phenyl]-1,2,3,4-tetrahydropyrimidin-5-carbonitrile;

(4S)-4-{4-cyano-2-[phenylsulfonyl]phenyl}-6-methyl-2-oxo-1-[3-(trifluoromethyl)phenyl]-1,2,3,4-tetrahydropyrimidin-5-carbonitrile; and 2-hydroxyethyl (4S)-4-[4-cyano-2-(methylsulfonyl)phenyl]-6-methyl-3-(methylsulfonyl)-2-oxo-1-[3-(trifluoromethyl)phenyl]-1,2,3,4-tetrahydropyrimidin-5-carboxylate;

or a physiologically acceptable salt thereof.

11. The method of claim 1 or 2, wherein the compound of formula (I) is selected from the group consisting of:

(4S)-4-[4-cyano-2-(methylsulfonyl)phenyl]-6-methyl-2-oxo-1-[3-(trifluoromethyl)phenyl]-1,2,3,4-tetrahydropyrimidin-5-carboxamide;

(4S)-4-[4-cyano-2-(methylsulfonyl)phenyl]-6-methyl-2-oxo-1-[3-(trifluoromethyl)phenyl]-1,2,3,4-tetrahydropyrimidin-5-carbonitrile;

(6S)-5-cyano-6-[4-cyano-2-(methylsulfonyl)phenyl]-N-(2-hydroxyethyl)-4-methyl-2-oxo-3-[3-[(trifluoromethyl)Phenyl]-3,6-dihydropyrimidin-1(2H)-carboxamide;

(6S)-5-cyano-6-[4-cyano-2-(methylsulfonyl)phenyl]-N',N'-bis(2-hydroxyethyl)-4-methyl-2-oxo-3-[3-(trifluoromethyl)phenyl]-3,6-dihydropyrimidin-1(2H)-carbohydrazide;

2-[(6S)-5-cyano-6-[4-cyano-2-(methylsulfonyl)phenyl]-4-methyl-2-oxo-3-[3-[(trifluoromethyl)phenyl]-3,6-dihydropyrimidin-1(2H)-yl]acetamide;

(4S)-4-[4-cyano-2-(methylsulfonyl)phenyl]-6-methyl-[2-oxo-3-[2-oxo-2-(3-oxopiperazin-1-yl)ethyl]-1,3-(trifluoromethyl)phenyl]-1,2,3,4-tetrahydropyrimidin-5-carbonitrile;

(4S)-4-[4-cyano-2-(methylsulfonyl)phenyl]-6-methyl-3-(methylsulfonyl)-2-oxo-1-[3-(trifluoro-methyl)phenyl]-1,2,3,4-tetrahydropyrimidin-5-carbonitrile;

(4S)-4-[4-cyano-2-(methylsulfonyl)phenyl]-6-methyl-3-{[2-(trifluoromethoxy)phenyl]sulfonyl}-2-oxo-1-[3-(trifluoromethyl)phenyl]-1,2,3,4-tetrahydropyrimidin-5-carbonitrile;

(4S)-4-[4-cyano-2-(methylsulfonyl)phenyl]-6-methyl-3-(ethylsulfonyl)-2-oxo-1-[3-(trifluoro-methyl)phenyl]-1,2,3,4-tetrahydropyrimidin-5-carbonitrile;

(4S)-4-[4-cyano-2-(methylsulfonyl)phenyl]-6-methyl-3-(cyclopropylsulfonyl)-2-oxo-1-[3-(tri-fluoromethyl)phenyl]-1,2,3,4-tetrahydropyrimidin-5-carbonitrile;

(4S)-4-[4-cyano-2-(methylsulfonyl)phenyl]-3,6-dimethyl-2-oxo-1-[3-(trifluoromethyl)phenyl]-1,2,3,4-tetrahydropyrimidin-5-carbonitrile;

4-{(4S)-6-methyl-3-(methylsulfonyl)-2,5-dioxo-1-[3-(trifluoromethyl)phenyl]-2,3,4,5,6,7-hexahydro-1H-pyrrolo[3,4-d]pyrimidin-4-yl}-3-(methylsulfonyl)benzonitrile;

(rac)-4-[4-cyano-2-(methylsulfonyl)phenyl]-N-(2-hydroxyethyl)-6-methyl-2,5-dioxo-1-[3-(tri-fluoromethyl)phenyl]-1,2,4,5,6,7-hexahydro-3H-pyrrolo[3,4-d]pyrimidin-3-carboxamide;

(4S)-4-{4-cyano-2-[(S)-methylsulfinyl]phenyl}-6-methyl-2-oxo-1-[3-(trifluoromethyl)phenyl]-1,2,3,4-tetrahydropyrimidin-5-carbonitrile;

(4S)-4-[4-cyano-2-(methylsulfonyl)phenyl]-3-[(4-fluorophenyl)sulfonyl]-6-methyl-2-oxo-1-[3-(trifluoromethyl)phenyl]-1,2,3,4-tetrahydropyrimidin-5-carbonitrile;

(4S)-4-[4-cyano-2-(methylsulfonyl)phenyl]-3-[(1,2-dimethyl-1H-imidazol-4-yl)sulfonyl]-6-methyl-2-oxo-1-[3-(trifluoromethyl)phenyl]-1,2,3,4-tetrahydropyrimidin-5-carbonitrile;

(4S)-3-(cyanomethyl)-4-[4-cyano-2-(methylsulfonyl)phenyl]-6-methyl-2-oxo-1-[3-(trifluoro-methyl)phenyl]-1,2,3,4-tetrahydropyrimidin-5-carbonitrile;

(4S)-4-[4-cyano-2-(methylsulfonyl)phenyl]-3-(4-cyanophenyl)-6-methyl-2-oxo-1-[3-(trifluoro-methyl)phenyl]-1,2,3,4-tetrahydropyrimidin-5-carbonitrile;

(4S)-4-[4-cyano-2-(methylsulfonyl)phenyl]-6-methyl-2-oxo-1,3-bis[3-(trifluoromethyl)phenyl]-1,2,3,4-tetrahydropyrimidin-5-carbonitrile;

4-(4S)-3,6-dimethyl-2,5-dioxo-1-[3-(trifluoromethyl)phenyl]-2,3,4,5,6,7-hexahydro-1H-pyrrolo[3,4-d]pyrimidin-4-yl-3-(methylsulfonyl)benzonitrile;

(4S)-4-[4-cyano-2-(ethylsulfonyl)phenyl]-6-methyl-2-oxo-1-[3-(trifluoromethyl)phenyl]-1,2,3,4-tetrahydropyrimidin-5-carbonitrile;

(4S)-4-[4-cyano-2-(ethylsulfonyl)phenyl]-3,6-dimethyl-2-oxo-1-[3-(trifluoromethyl)phenyl]-1,2,3,4-tetrahydropyrimidin-5-carbonitrile;

(4S)-4-[4-cyano-2-(ethylsulfonyl)phenyl]-6-methyl-3-(methylsulfonyl)-2-oxo-1-[3-(tri-fluoromethyl)phenyl]-1,2,3,4-tetrahydropyrimidin-5-carbonitrile; and 2-hydroxyethyl (4S)-4-[4-cyano-2-(methylsulfonyl)phenyl]-6-methyl-3-(methylsulfonyl)-2-oxo-1-[3-(trifluoromethyl)phenyl]-1,2,3,4-tetrahydropyrimidin-5-carboxylate;

or a physiologically acceptable salt thereof.

12. The method of claim 1, wherein the compound of formula (I) is (4S)-4-[4-cyano-2-(methylsulfonyl)phenyl]-3,6-dimethyl-2-oxo-1-[3-(trifluoromethyl)phenyl]-1,2,3,4-tetrahydropyrimidine-5-carbonitrile, or a physiologically acceptable salt thereof.

13. The method of claim 1, wherein the compound of formula (I) is (4S)-4-[4-cyano-2-(methylsulfonyl)phenyl]-6-methyl-3-(methylsulfonyl)-2-oxo-1-[3-(trifluoromethyl)phenyl]-1,2,3,4-tetrahydropyrimidine-5-carbonitrile, or a physiologically acceptable salt thereof.

14. The method of claim 1, wherein the compound of formula (I) is ((4S)-4-[4-cyano-2-(methylsulfonyl)phenyl]-6-methyl-2-oxo-1-[3-(trifluoromethyl)phenyl]-1,2,3,4-tetrahydropyrimidine-5-carbonitrile, or a physiologically acceptable salt thereof.

* * * * *